United States Patent
Lou et al.

(10) Patent No.: US 10,517,867 B2
(45) Date of Patent: Dec. 31, 2019

(54) POSACONAZOLE DERIVATIVE, PHARMACEUTICAL COMPOSITION AND USE THEREOF

(71) Applicants: WUHAN LL SCIENCE AND TECHNOLOGY DEVELOPMENT CO., LTD., Wuhan, Hubei (CN); WUHAN QR PHARMACEUTICALS CO., LTD., Wuhan, Hubei (CN)

(72) Inventors: Jun Lou, Hubei (CN); Penggao Yu, Hubei (CN); Li Liu, Hubei (CN); Hongwei Tang, Hubei (CN); Anxiao Zheng, Hubei (CN); Yongkai Chen, Hubei (CN); Chaodong Wang, Hubei (CN)

(73) Assignees: WUHAN LL SCIENCE AND TECHNOLOGY DEVELOPMENT CO., LTD., Wuhan (CN); WUHAN QR PHARMACEUTICALS CO., LTD., Wuhan (CN)

( * ) Notice: Subject to any disclaimer, the term of this patent is extended or adjusted under 35 U.S.C. 154(b) by 0 days.

(21) Appl. No.: 16/075,514

(22) PCT Filed: Jan. 26, 2017

(86) PCT No.: PCT/CN2017/072722
§ 371 (c)(1),
(2) Date: Aug. 3, 2018

(87) PCT Pub. No.: WO2017/133632
PCT Pub. Date: Aug. 10, 2017

(65) Prior Publication Data
US 2019/0038621 A1     Feb. 7, 2019

(30) Foreign Application Priority Data

Feb. 4, 2016  (CN) .......................... 2016 1 0079139

(51) Int. Cl.
| | |
|---|---|
| A61K 31/496 | (2006.01) |
| C07D 405/14 | (2006.01) |
| A61K 31/675 | (2006.01) |
| A61P 31/10 | (2006.01) |
| C07F 9/6558 | (2006.01) |
| A61K 31/133 | (2006.01) |
| C07H 5/04 | (2006.01) |

(52) U.S. Cl.
CPC .......... *A61K 31/496* (2013.01); *A61K 31/133* (2013.01); *A61K 31/675* (2013.01); *A61P 31/10* (2018.01); *C07D 405/14* (2013.01); *C07F 9/65586* (2013.01); *C07H 5/04* (2013.01); *Y02P 20/55* (2015.11)

(58) Field of Classification Search
CPC ..................................................... A61K 31/496
USPC ......................................................... 514/254
See application file for complete search history.

(56) References Cited

U.S. PATENT DOCUMENTS 6,376,548 B1    4/2002   Mulvihill et al.

FOREIGN PATENT DOCUMENTS

| CN | 1161038 A | 10/1997 |
|---|---|---|
| CN | 102958528 A | 3/2013 |
| CN | 105287403 A | 2/2016 |

*Primary Examiner* — Taofiq A Solola
(74) *Attorney, Agent, or Firm* — Novick, Kim & Lee, PLLC; Allen Xue

(57) ABSTRACT

The present disclosure provides a posaconazole derivative, a pharmaceutical composition and use thereof, which specifically include a compound represented by the following formula (I), a racemate, stereoisomer, tautomer, oxynitride, or a pharmaceutically acceptable salt thereof:

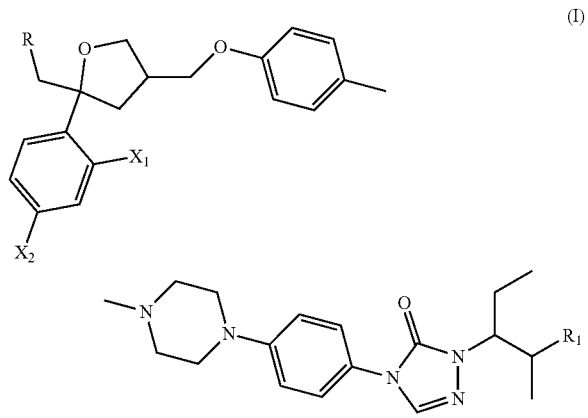

(I)

The compounds of the present disclosure have strong antifungal activity, high safety, and good water solubility, without the need for the addition of a cosolvent (such as hydroxypropyl-β-cyclodextrin, sulfobutyl ether-β-cyclodextrin, and the like) with potential safety risks. Furthermore, the formulation process of the compound could have less difficulty and less cost, and therefore can be used to prepare improved antifungal drugs.

19 Claims, No Drawings

POSACONAZOLE DERIVATIVE, PHARMACEUTICAL COMPOSITION AND USE THEREOF

CROSS REFERENCE TO RELATED APPLICATIONS

This application is a National Phase Application of PCT International Application No. PCT/CN2017/072722, filed on Jan. 26, 2017, which claims the priority of Chinese patent application No. 201610079139.9 filed on Feb. 4, 2016, the disclosure of which is incorporated herein in its entirety by reference.

TECHNICAL FIELD

The present disclosure relates to the technical field of antibiotic drugs, in particular to a class of posaconazole derivatives having antifungal activity and uses thereof.

BACKGROUND ART

Fungal infections are clinically common and frequently-occurring diseases. Said infections can be classified into superficial fungal infections and deep fungal infections. The superficial infections are caused by fungi invading skin, hair, finger (toe), and other body surface parts, and have high incidence and less harmful effects. Deep fungal infections are caused by *Candida, Aspergillus, Cryptococcus* and other fungi invading internal organs and deep tissues, and are of great harm.

In recent years, with the increasing number of immunosuppressed patients, the incidence of deep fungal infections has increased significantly. Fungal infections, especially deep fungal infections, are increasingly attracting widespread attention. However, at present, clinically applied antifungal drugs have serious side effects and are susceptible to drug resistance. Clinically existing antifungal drugs can be divided into organic acids, polyenes, azoles, allylamines, etc. according to their structures. Among them, azole antifungal drugs are a class of rapidly developing fully synthetic antifungal compounds. Currently, it has become the main medication for the treatment of deep and superficial fungal infections. Since the first anti-fungal effect of the first azole compound was reported in the middle of the last century, the first generation of triazoles such as fluconazole, itraconazole, and the second generation of triazole voriconazole gradually appeared in the field of antifungal treatment.

Posaconazole is a derivative of itraconazole. Its oral suspension was first marketed in Germany in 2005 and was approved by the FDA in 2006. It is clinically effective in treating systemic fungal infections caused by *Aspergillus* and *Candida* as well as oropharyngeal candidiasis. Posaconazole is currently approved in more than 70 countries and regions around the world, and is listed in more than 40 countries and regions including the United States and the European Union. However, the degree of absorption of oral suspensions is easily affected by factors such as food and gastrointestinal function, leading to large differences in pharmacokinetic parameters among individuals, fluctuations in blood drug concentration range, lower bioavailability and other issues. Posaconazole is a weakly alkaline, poorly water-soluble drug and is not easily developed into an injection form. Some immunosuppressed patients undergoing chemotherapy or organ transplantation have problems such as nausea, vomiting, and gastrointestinal discomfort, resulting in difficulty in oral administration and need to be administered by injection.

In order to solve the problem that posaconazole is difficult to develop into an injection preparation due to poor solubility, Patent Application No. 201180031488.9 of Merck Sharp & Dohme Ltd. discloses a formulation of intravenous infusion of poraconazole that is solubilized with substituted β-cyclodextrin, and an injectable formulation is prepared by solubilizing posaconazole with a substituted β-cyclodextrin in which an injectable formulation is prepared by solubilizing posaconazole with substituted β-cyclodextrin. The injection is currently approved for listing in the United States. Although the injection solves the problem that posaconazole is insoluble in water and achieves administration to patients who are inconvenient for oral administration, due to the addition of a large amount of sulfobutyl ether-β-cyclodextrin (SBE-β-CD) for solubilization, there is a potential safety risk, and preclinical toxicology studies have shown that sulfobutyl ether-β-cyclodextrin causes vacuolization of urethral epithelial cells and activates liver and lung macrophages. Clinical studies have shown that SBE-β-CD needs to be metabolized through the kidneys, which greatly increases the burden on the kidneys. The target patients for posaconazole injections are patients who have undergone bone marrow transplantation, chemotherapy, and other immunosuppression and fungal infections. Renal impairment is present in a significant proportion of patients, particularly in patients with moderate or severe renal insufficiency having lower glomerular filtration efficiency, resulting in accumulation of SBE-β-CD in the body with high safety risks. The use of excipient sulfobutyl ether-β-cyclodextrin greatly limits the clinical application of the drug. The instruction for posaconazole injection specifically states that the drug is not suitable for patients with moderate to severe renal impairment. Therefore, it is of great clinical value to improve the existing deficiencies in the prior art and increase the safety and drug applicability for renal injury patients.

Contents of the Present Disclosure

The present disclosure provides a compound represented by the following formula (I), a racemate, stereoisomer, tautomer, oxynitride, or a pharmaceutically acceptable salt thereof:

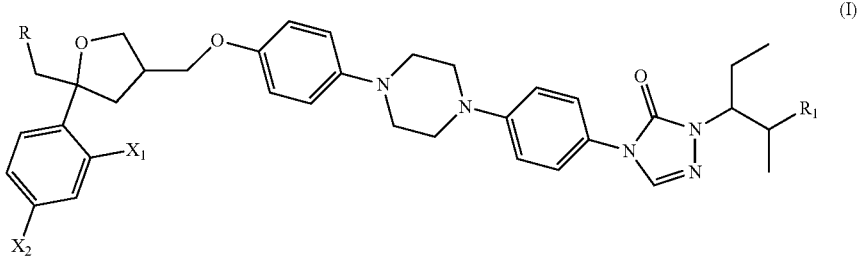

wherein, R is selected from unsubstituted or optionally substituted triazole groups, for example, from the following groups which are unsubstituted or optionally substituted with one or more $R_a$ or $R_b$:

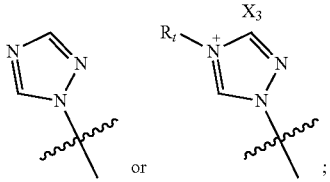

$R_t$ is selected from

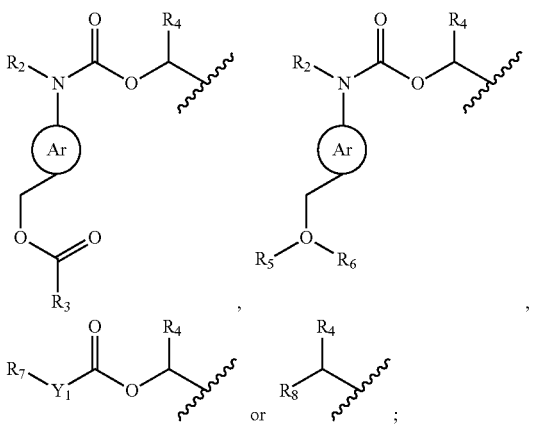

$X_1$ and $X_2$ are independently selected from F, Cl, Br, or I;

Each $X_3$ is independently selected from pharmaceutically acceptable anions;

$R_1$ is selected from OH or $R_h$; $R_h$ is a group that can be converted into a hydroxyl group in vivo, for example,

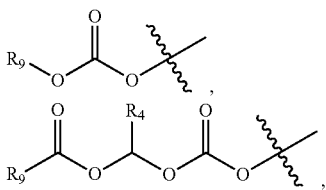

$O(O)CR_f$, —$OP(O)(OM_1)(OM_2)$, —$OS(O)_2OM_3$, or the following groups which are unsubstituted or optionally substituted with one or more $R_b$: $C_{1-40}$ alkyloxy, $C_{3-20}$ cycloalkyloxy, 3-20 membered heterocyclyloxy, $C_{6-20}$ aryloxy, or 5-20 membered heteroaryloxy;

$R_2$ and $R_4$ are independently selected from H, or $C_{1-40}$ alkyl which is unsubstituted or optionally substituted with one or more $R_a$;

$R_3$ is selected from $C_{1-40}$ alkyl which is unsubstituted or optionally substituted with one or more $R_b$;

$R_5$ and $R_6$ are independently selected from H, or the following groups which are unsubstituted or optionally substituted with one or more $R_m$: $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, or —$C(O)R_f$;

Ar is selected from the following groups which are unsubstituted or optionally substituted with one or more $R_c$: $C_{6-20}$ aryl, 5-20 membered heteroaryl, wherein the heteroaryl comprises 1-5 heteroatoms independently selected from N, O, and S;

$R_7$ is selected from the following groups which are unsubstituted or optionally substituted with one or more $R_c$: $C_{1-40}$ alkyl, $C_{3-20}$ cycloalkyl, 3-20 membered heterocyclyl, $C_{6-20}$ aryl, 5-20 membered heteroaryl, —$Y_2P(O)(OM_1)(OM_2)$, —$C(O)R_f$, or —$(CH_2CH_2O)_z$—$R_b$, wherein z is an integer of 1 or more, preferably an integer of 1 to 10;

$R_8$ is selected from H, or the following groups which are unsubstituted or optionally substituted with one or more $R_b$: $C_{1-40}$ alkyl, $C_{3-20}$ cycloalkyl, 3-20 membered heterocyclyl, $C_{6-20}$ aryl, 5-20 membered heteroaryl, $NR_dR_e$, —$CONR_dR_e$, —$C(O)Y_2R_f$, —$Y_2(O)CR_f$, —$Y_2P(O)(OM_1)(OM_2)$, or —$Y_2S(O)_2OM_3$;

$R_9$ is selected from the following groups which are unsubstituted or optionally substituted with one or more $R_b$: $R_{10}$—$Y_3$—$Y_4$—, $R_{11}$—$C(O)$—$Y_5$—$Y_6$—, $C_{1-40}$ alkyl, $C_{1-40}$ alkoxy, $C_{3-20}$ cycloalkyl, 3-20 membered heterocyclyl, $C_{6-20}$ aryl, 5-20 membered heteroaryl, —$Y_2$—$N(R_4)$—$C(=NH)$—$NH_2$, —$Y_3$—$N(R_2)$—$C(O)$—$Y_2$—$N(R_4)$—$C(=NH)$—$NH_2$, —$(CH_2CH_2O)_z$—H, wherein z is an integer of 1 or more, preferably an integer of 1 to 10;

$R_{10}$ and $R_{11}$ are independently selected from H, or the following groups which are unsubstituted or optionally substituted with one or more $R_b$: $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, —$Y_2P(O)(OM_1)(OM_2)$, or —$Y_2S(O)_2OM_3$.

$Y_1$, $Y_2$, $Y_3$, $Y_4$, $Y_5$, and $Y_6$ are independently selected from a chemical bond, —O—, —S— or the following groups which are unsubstituted or optionally substituted with one or more $R_a$: —NH—, $C_{1-40}$ alkyl, $C_{1-40}$ alkoxy, $C_{3-20}$ cycloalkyl, 3-20 membered heterocyclyl, $C_{6-20}$ aryl, 5-20 membered heteroaryl, or —$(CH_2CH_2O)_m$, wherein m is an integer of 0 or more, for example, an integer from 0 to 10.

Preferably, when two or more of $Y_1$, $Y_2$, $Y_3$, $Y_4$, $Y_5$ or $Y_6$ are adjacent, the adjacent groups are not chemical bonds at the same time;

Each $R_a$ is independently selected from H, $C_{1-40}$ alkyl, $C_{1-40}$ alkoxy, $C_{2-40}$ alkenyl, $C_{2-40}$ alkynyl, $C_{3-20}$ cycloalkyl, F, Cl, Br, I, OH, SH, CN, =O, $NR_dR_e$, —$C(O)Y_2R_f$, —$Y_2(O)CR_f$, —$CONR_dR_e$, —$Y_2P(O)(OM_1)(OM_2)$, or —$Y_2S(O)_2OM_3$.

Each $R_b$ is independently selected from H, F, Cl, Br, I, OH, SH, CN, or the following groups which are unsubstituted or optionally substituted with one or more $R_a$: $C_{1-40}$ alkyl, $C_{1-40}$ alkoxy, $C_{2-40}$ alkenyl, $C_{2-40}$ alkynyl, $C_{3-20}$ cycloalkyl, $C_{3-20}$ cycloalkyloxy, 3-20 membered heterocyclyl, 3-20 membered heterocyclyloxy, $C_{6-20}$ aryl, $C_{6-20}$ aryloxy, 5-20 membered heteroaryl, 5-20 membered heteroaryloxy, $NR_dR_e$, —$CONR_dR_e$, —$C(O)Y_2R_f$, —$Y_2(O)CR_f$, —$Y_2P(O)(OM_1)(OM_2)$, or —$Y_2S(O)_2OM_3$.

Each $R_c$ is independently selected from F, Cl, Br, I, OH, SH, CN or the following groups which are unsubstituted or optionally substituted with one or more $R_a$: $C_{1-40}$ alkyl, $C_{1-40}$ alkoxy, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, $NR_dR_e$, —$CONR_dR_e$, —$C(O)Y_2R_f$, —$Y_2(O)CR_f$, —$Y_2P(O)(OM_1)(OM_2)$, or —$Y_2S(O)_2OM_3$.

Each $R_d$ and $R_e$ are independently selected from H, or the following groups which are unsubstituted or optionally substituted with one or more $R_m$: $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, —$CONR_fR_g$, —$C(O)Y_2R_f$, —$Y_2(O)CR_f$, —$Y_2P(O)(OM_1)(OM_2)$, or —$Y_2S(O)_2OM_3$;

Each $R_f$ and $R_g$ are independently selected from H, or the following groups which are unsubstituted or optionally substituted with one or more $R_m$: $C_{1-40}$ alkyl, $C_{2-40}$ alkenyl, $C_{2-40}$ alkynyl, $C_{3-20}$ cycloalkyl, COOH, 3-20 membered heterocyclyl, $C_{6-20}$ aryl, 5-20 membered heteroaryl.

Each $R_m$ is independently selected from H, F, Cl, Br, I, OH, SH, CN, or the following groups which are unsubstituted or optionally substituted with one or more $R_a$: $C_{1-40}$ alkyl, $C_{1-40}$ alkoxy, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, $NR_dR_e$, —$CONR_dR_e$, —$C(O)Y_2R_f$, $Y_2(O)CR_f$, —$Y_2P(O)(OM_1)(OM_2)$, or —$Y_2S(O)_2OM_3$.

$M_1$, $M_2$, and $M_3$ are independently selected from H, or $C_{1-40}$ alkyl which is unsubstituted or optionally substituted with one or more $R_b$.

Provided that when R is

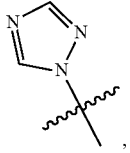

$R_1$ is not hydroxyl; and when $R_t$ is

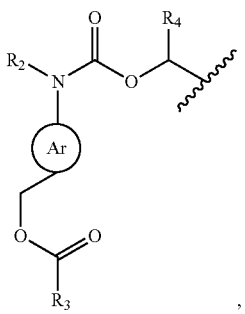

$R_3$ is not —$CH_2NHCH_3$;

wherein the heterocyclyl and heteroaryl independently from each other contain 1-5 heteroatoms independently selected from N, O, or S.

According to an embodiment of the present disclosure, wherein:

$X_1$ and $X_2$ are independently from each other selected from F, Cl, or Br;

$X_3$ can represent an acid ion generated by ionization of an inorganic acid or an organic acid;

The number of acid ions represented by $X_3$ is not particularly limited, for example, $X_3$ can represent a monovalent acid ion generated by ionization of an inorganic or organic acid;

Alternatively, when a plurality of cations are present in the structure of the compound of formula (I), $X_3$ can represent a plurality of monovalent acid ions generated by ionization of an inorganic acid or an organic acid, preferably 2 or 3 monovalent acid ions generated by ionization of an inorganic acid or an organic acid;

Alternatively, when a plurality of cations in the structure of the compound of formula (I) share one polyvalent acid ion, $X_3$ can also represent a part of the polyvalent acid ion, for example, ½, ⅓, ⅔ of the polyvalent acid ion;

Persons skilled in the art should understand that when there are multiple sulfonium ions in the compound of formula (I), $X_3$ can also represent a mixture of the monovalent acid ions, a mixture of the polyvalent acid ions, or a mixture of the monovalent acid ions and the polyvalent acid ions.

For example, $X_3$ can represent $Cl^-$, $Br^-$, $I^-$, $HSO_4^-$, $NO_3^-$, $½SO_4^{2-}$, $SO_4^{2-}$, $3/2SO_4^{2-}$, $H_2PO_4^-$, $½HPO_4^{2-}$, $3/2HPO_4^{2-}$, $⅓PO_4^{3-}$, $⅔PO_4^{3-}$, or $PO_4^{3-}$;

$R_2$ is selected from H, or $C_{1-40}$ alkyl (for example, methyl, ethyl, propyl, isopropyl, or tert-butyl) which is unsubstituted or optionally substituted with one or more $R_a$;

$R_3$ is selected from $C_{1-40}$ alkyl which is unsubstituted or optionally substituted with one or more $R_b$; for example, $R_3$ can be $C_{1-40}$ alkyl substituted with 1, 2, or 3 substituents independently selected from $C_{1-6}$ alkyl, —$NH_2$, —COOH, —OH, —$CONH_2$, $N(CH_3)_2$, $NH(CH_3)$, $NHCONH_2$, $(C_6H_4)$—OH, or $NH(CH_2)_kCH_3$;

As an example, $R_3$ can be —$(CH_2)_k$—$NH_2$, —$CH(NH_2)$—$(CH_2)_k$—COOH, $NH_2(CH_2)_kCH(NH_2)$, $CH_2CH(NH_2)COOH$, —$(CH_2)_k$—COOH, —$CH(NH_2)$—$(CH_2)_k$—NH—$CONH_2$, $CH(NH_2)$—$(CH_2)_k$—$CONH_2$, —$CH(NH_2)$—$(CH_2)_k$—OH, —$CH(NH_2)$—$(CH_2)_k$—$CH(OH)$—$CH_3$, —$CH(NH_2)$—$(CH_2)_k$—$(C_6H_4)$—OH, —$CH(NH_2)$—$(CH_2)_k$—NH—$(CH_2)_k$—$CH_3$, —$(CH_2)_k$—NH—$(CH_2)_k$—$CH_3$, —$(CH_2)_k$—$N(CH_3)_2$, wherein k is independently selected from an integer of 0 to 16, such as 0, 1, 2, 3, 4, 5, 6, 7, 8, 9, 10;

Ar can be selected from the following groups which are unsubstituted or optionally substituted with one or more $R_c$: $C_{6-10}$ aryl, 5-10 membered heteroaryl;

For example, Ar can be selected from pyridyl, phenyl, specifically

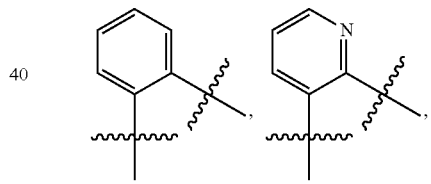

wherein the C atom at 2-position of the pyridyl is connected to N atom, and the C atom at 3-position is connected to methylene group.

According to an embodiment of the present disclosure, R can be selected from

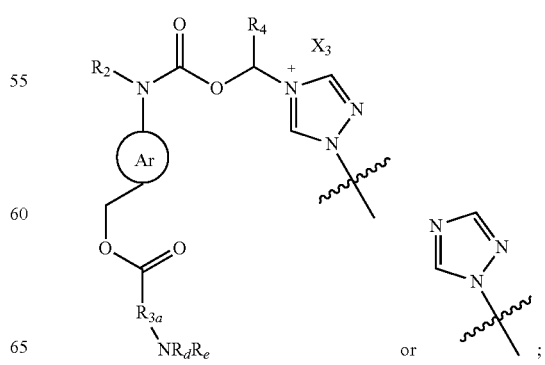

$R_{3a}$ can be selected from $C_{1-40}$ alkyl which is unsubstituted or optionally substituted with one or more $NR_dR_e$.

According to the present disclosure, the group that can be converted into a hydroxyl group in vivo can be an ester group that can be converted into a hydroxyl group in vivo, for example, an ester group that can be converted into a hydroxyl group in vivo by hydrolysis and/or enzymatic hydrolysis. The ester groups include polyether ester group, phosphate group, sulfate group, heterocyclic ester group, alkanoate group, alkenoate group, amino acid ester group, carbonate group, or acid ester group. As an example, the ester group can be phosphate group, amino acid ester group, carbonate group or acidic ester group.

The ester group can be structurally represented as a group produced by removing a group linked to an oxy group in the ester functional group, for example, a group represented by the following formula (H1) or (H2):

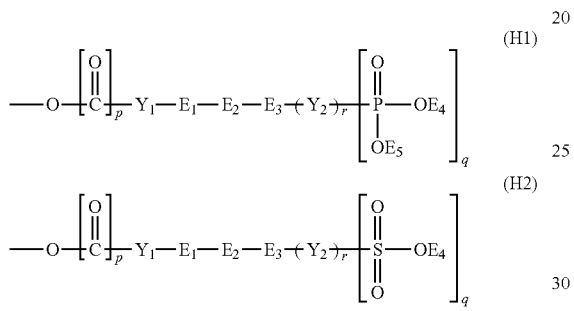

wherein p, q, and r are independently selected from 0 or 1;

$Y_1$ is selected from chemical bond or —O—;

$Y_2$ is selected from chemical bond, —O—, —S— or —NH— unsubstituted or optionally substituted with one or more $R_a$;

$E_1$ is selected from chemical bond, or $C_{1-40}$ alkyl which is unsubstituted or optionally substituted with one or more $R_c$;

$E_2$ is independently selected from chemical bond or —OC(O)—;

$E_3$ is independently selected from chemical bond, or the following groups which are unsubstituted or optionally substituted with one or more $R_c$: $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, or 5-20 membered heteroaryl; preferably from $C_{1-40}$ alkyl, $C_{6-20}$ aryl, $C_{6-20}$ arylalkyl, or 5-20 membered heteroaryl which are unsubstituted or independently substituted with one or more $R_c$, for example, —$(CH_2)_k$—, —$(CH_2)_k$—$(C_6H_4)$—, —$(CH_2CH_2O)_z$—, wherein k is an integer selected from 0 to 10; z is an integer of 1 or more, preferably an integer of 1 to 10;

Provided that $E_1$ and $E_3$ are not chemical bonds at the same time;

$E_4$ and $E_5$ are independently from each other selected from H, and the following groups which are unsubstituted or optionally substituted with one or more $R_c$: $C_{1-40}$ alkyl, 3-20 membered heterocyclyl, $C_{6-20}$ aryl, or 5-20 membered heteroaryl;

$R_c$ has the definition as described above.

As an example, the phosphate group according to the present disclosure can be, for example, a phosphate group represented by the following formula:

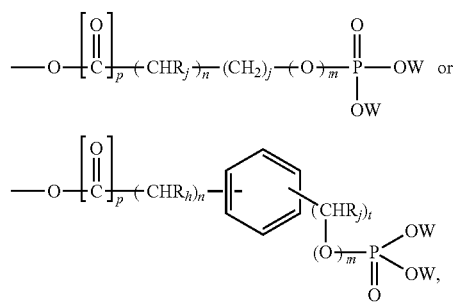

wherein p has the definition as described above;

Each $R_j$ is independently selected from H, OH, and $C_{1-40}$ alkyl which is unsubstituted or optionally substituted with one or more $R_a$, preferably OH;

t is an integer selected from 1 to 6, preferably 2 or 3;

n and j are independently selected from an integer of 0 to 4;

m is selected from 0 or 1;

Each W is independently selected from H, benzyl or

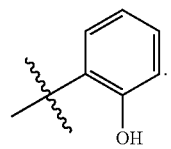 [SMILES: *c1ccccc1O]

As an example, the phosphate group can be selected from

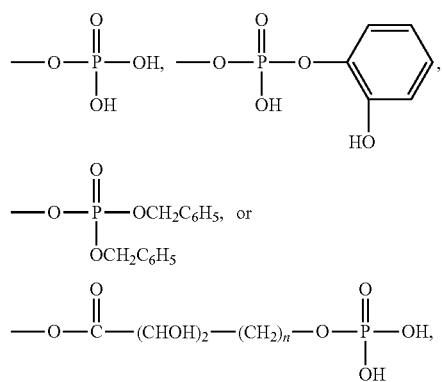

n is an integer selected from 0 to 5.

For example, $R_1$ can be

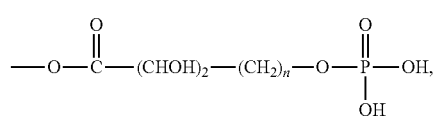

wherein n is 1, 2, or 3; as an example, when R is

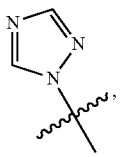

$R_1$ is

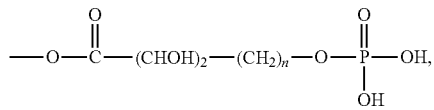

wherein n is 1.

The amino acid ester group of the present disclosure can be selected from amino acid ester groups, dipeptide ester group or polypeptide ester group, including but not limited to:

natural (L)-α-amino acid ester groups, such as glycine ester group (—OCOCH$_2$NH$_2$), L-alanine ester group, L-phenylalanine ester group, glycine ester group, L-leucine ester group, L-serine ester group, L-isoleucine ester group, L-valine ester group, L-glutamine ester group, L-asparagine ester group, L-threonine ester group, methyl glycine ester group, ornithine ester group, L-isoleucine ester group, and L-valine ester group;

Non-natural α-amino acid ester groups, such as —OC(O)CH(NH$_2$)(CH$_2$)$_3$CO$_2$H, —OC(O)CH(NH$_2$)(CH$_2$)$_2$NH$_2$, —OC(O)CH(NH$_2$)(CH$_2$)$_3$NH$_2$, or an α-aminoalkanoate group represented by the formula —OC(O)CH(NR$_{22}$R$_{23}$)R$_{24}$;

$R_{22}$ and $R_{23}$ is independently selected from H or C$_{1-40}$ alkyl which is unsubstituted or optionally substituted with one or more R$_a$, or alternatively R$_{22}$ and R$_{23}$ together with N can form 3-20 membered heterocyclyl or 5-20 membered heteroaryl which optionally contain O or S as a ring-forming atom, for example, 4-, 5-, or 6-membered heterocyclyl or heteroaryl;

$R_{24}$ is H or C$_{1-40}$ alkyl which is unsubstituted or optionally substituted with one or more R$_c$;

Each R$_c$ independently has the definition as described above; as an example, each R$_c$ is independently selected from CH$_3$, —OH, —CH$_2$OH, —CONH$_2$, —CH$_2$CONH$_2$, —(CH$_2$)$_2$CONH$_2$, —CH(CH$_3$)$_2$, —C(CH$_3$)$_3$, —CH(CH$_3$)C$_2$H$_5$, —COOH, —CH$_2$CO$_2$H, —(CH$_2$)$_2$CO$_2$H, —C$_6$H$_5$, or —CH$_2$C$_6$H$_5$.

Preferred amino acid ester groups are ester groups derived from the following natural a-amino acids: L-alanine, L-phenylalanine, glycine, L-leucine, L-serine, L-glutamine, L-asparagine, L-threonine, methylglycine, ornithine, L-isoleucine, and L-valine. Further preferred amino acid ester groups are glycine ester group —OCOCH$_2$NH$_2$, serine ester group —OCOCH(NH$_2$)CH$_2$OH, threonyl ester group —OCOCH(NH$_2$)CH(OH)CH$_3$, leucine ester group —OCOCH(NH$_2$)CH$_2$CH(CH$_3$)$_2$, isoleucyl ester group —OCOCH(NH$_2$)CH(CH$_3$)CH$_2$CH$_3$, orvaline ester group —OCOCH(NH$_2$)CH(CH$_3$)$_2$.

The acidic ester groups described herein can be selected from acidic ester groups represented by the following formula

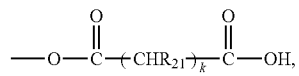

wherein $R_{21}$ is independently selected from H, OH, C$_{1-40}$ alkyl which is unsubstituted or optionally substituted with one or more R$_a$, preferably OH, and k has the definition as described above.

Preferred acidic ester groups include oxalate group, malonate group, succinate group, glutarate group and adipate group, and branched diacid ester groups, such as ester groups of

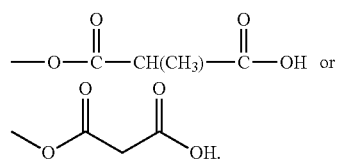

The alkanoate groups described herein can be selected from alkanoate groups that are unsubstituted or optionally substituted with hydroxy and/or ether group. Preferred alkanoate groups include C$_{2-12}$ alkanoate groups, such as C$_{2-4}$ alkanoate groups, that are unsubstituted or optionally substituted by hydroxy and/or ether group. As an example, the alkanoate group can be C$_1$-C$_8$ alkanoate group substituted with one hydroxy group and/or one C$_{1-6}$ alkoxy group.

The alkenoate groups described herein can be selected from alkenoate groups that are unsubstituted or optionally substituted with hydroxy and/or ether group. Preferred alkenoate group can be C$_{10-20}$ alkenoate group, including C$_{14-18}$ alkenoate group, such as cis-7-hexadecenoate group.

The carbonate groups described herein can be selected from unsubstituted or substituted alkoxycarbonyloxy groups, for example

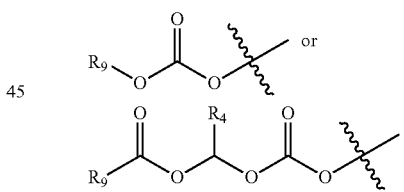

as defined above.

According to an embodiment of the present disclosure, R$_h$ can be selected from, for example,

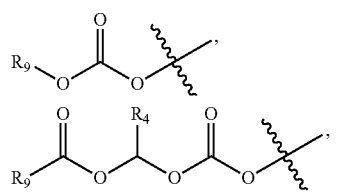

—O(O)CR$_f$, —OP(O)(OM$_1$)(OM$_2$), —OS(O)$_2$OM$_3$, or C$_{1-40}$ alkoxy which is unsubstituted or optionally substituted with one or more R$_b$;

According to an embodiment of the present disclosure, $R_h$ can be selected from, for example,

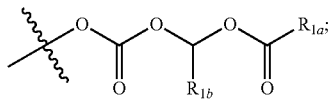

preferably, when R is

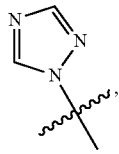

$R_h$ is

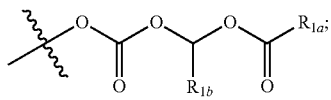

wherein, $R_{1a}$ can be selected from $C_{1-40}$ alkyl, $C_{6-20}$ aryl, $C_{6-20}$ arylalkyl, 5-20 membered heteroarylalkyl, and 5-20 membered heteroaryl which are unsubstituted or optionally substituted with one or more $C(O)OR_f$, —OP(O)(OM$_1$)(OM$_2$), —OS(O)$_2$OM$_3$; preferably, $R_{1a}$ is selected from —(CH$_2$)$_k$—C(O)OR$_f$, —(CH$_2$)$_k$—(C$_6$H$_4$)—C(O)OR$_f$, —(CH$_2$)$_z$—OP(O)(OM$_1$)(OM$_2$), —(CH$_2$)$_k$—(C$_6$H$_4$)—OP(O)(OM$_1$)(OM$_2$), —(CH$_2$)$_k$—(C$_6$H$_4$)—OS(O)$_2$OM$_3$, —(CH$_2$)$_z$—S(O)$_2$OM$_3$ k is an integer of 0-10; z and $R_f$ have definitions as described above;

$R_{1b}$ can be selected from H or $C_{1-40}$ alkyl, for example H, methyl, ethyl, or isopropyl;

$R_9$ is selected from the following groups which are unsubstituted or optionally substituted with one or more $R_b$: $R_{10}$—Y$_3$—Y$_4$—, $R_{11}$—C(O)—Y$_5$—Y$_6$—, $C_{1-40}$ alkyl, $C_{1-40}$ alkoxy, —Y$_2$—N(R$_4$)—C(=NH)—NH$_2$, —Y$_3$—N(R$_2$)—C(O)—Y$_2$—N(R$_4$)—C(=NH)—NH$_2$, —(CH$_2$CH$_2$O)$_z$—H, wherein z is 1, 2, 3, 4, 5, 6, 7, 8, 9 or 10;

$R_{10}$ and $R_{11}$ have the definitions as described above and can be, for example

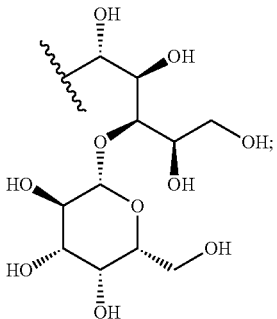

$R_f$ is selected from the following groups which are unsubstituted or optionally substituted with one or more $R_m$: $C_{1-40}$ alkyl, COOH, 3-20 membered heterocyclyl, $C_{6-20}$ aryl, or 5-20 membered heteroaryl;

Each $R_m$ is independently selected from H, F, Cl, Br, I, OH, SH, CN, or the following groups which are unsubstituted or optionally substituted with one or more $R_a$: $C_{1-40}$ alkyl, $C_{1-40}$ alkoxy, $C_{3-20}$ cycloalkyl, 3-20 membered heterocyclyl, $C_{6-20}$ aryl, 5-20 membered heteroaryl, NR$_d$R$_e$, —CONR$_d$R$_e$, C(O)Y$_2$R$_f$, Y$_2$(O)CR$_f$, —Y$_2$P(O)(OM$_1$)(OM$_2$), or —Y$_2$S(O)$_2$OM$_3$.

$M_1$, $M_2$, and $M_3$ can be selected from H, methyl, ethyl, or isopropyl.

As an example, $R_h$ can be selected from —OP(O)(OH)$_2$, —OS(O)$_2$OH, —OC(O)CH(OH)CH(OH)CH$_2$OP(O)(OH)$_2$, —OC(O)CH(NH$_2$)CH$_2$OH, —OC(O)OCH(CH$_3$)OC(O)CH$_2$CH$_2$COOH, —OC(O)OCH(CH$_3$)OC(O)CH$_2$COOH, —OC(O)OCH(CH$_3$)OC(O)COOH, —OC(O)OCH(CH$_3$)OC(O)C$_6$H$_4$COOH, —OC(O)OCH(CH$_3$)OC$_6$H$_3$(COOH)$_2$, —OC(O)OCH(CH$_3$)OC(O)CH$_2$CH$_2$CH$_3$, —OC(O)OCH(CH$_3$)OC(O)CH$_2$NH$_2$, —OC(O)OCH(CH$_3$)OC(O)CH$_2$NHCH$_3$, —OC(O)OCH(CH$_3$)OC(O)CH$_2$N(CH$_3$)P(O)(OH)$_2$, —OC(O)OCH(CH$_3$)OC(O)CH$_2$NHP(O)(OH)$_2$, —OC(O)OCH(CH$_3$)OC(O)CH$_2$N(CH$_3$)S(O)$_2$OH, —OC(O)OCH(CH$_3$)OC(O)CH$_2$NHS(O)$_2$OH, —OC(O)OCH(CH$_3$)OC(O)CH$_2$N(CH$_3$)$_2$, —OC(O)OCH$_2$CH$_2$OP(O)(OH)$_2$, —OC(O)O(CH$_2$CH$_2$O)$_2$P(O)(OH)$_2$, —OC(O)O—(CH$_2$CH$_2$O)$_3$—P(O)(OH)$_2$, —OC(O)OCH(CH$_3$)OC(O)CH$_2$OP(O)(OH)$_2$, —OC(O)OCH(CH$_3$)OC(O)C$_6$H$_5$OP(O)(OH)$_2$, —OC(O)OCH(CH$_3$)OC(O)CH$_2$C$_6$H$_5$OP(O)(OH)$_2$, —OC(O)OCH(CH$_3$)OC(O)CH$_2$C$_6$H$_5$OS(O)$_2$OH, —OC(O)OCH(CH$_3$)OC(O)CH$_2$NHC(=NH)NHP(O)(OH)$_2$, —OC(O)OCH(CH$_3$)OC(O)CH$_2$N(CH$_3$)C(=NH)NHP(O)(OH)$_2$, —OC(O)OCH(CH$_3$)OC(O)CH$_2$NHC(O)CH$_2$N(CH$_3$)C(=NH)NHP(O)(OH)$_2$, —OC(O)OCH(CH$_3$)OC(O)CH$_2$N(CH$_3$)CH$_2$OP(O)(OH)$_2$, —OC(O)OCH(CH$_3$)OC(O)CH$_2$N(CH$_3$)C(O)CH$_2$OP(O)(OH)$_2$, —OC(O)OCH(CH$_3$)OC(O)CH$_2$NHC(O)CH$_2$OP(O)(OH)$_2$, —OC(O)OCH(CH$_3$)OC(O)CH(OH)CH$_2$OP(O)(OH)$_2$, —OC(O)OCH[(CH$_2$)$_3$OS(O)$_2$OH]OC(O)CH$_2$N(CH$_3$)$_2$, —OC(O)OCH[(CH$_2$)$_3$OS(O)$_2$OH]OC(O)CH$_2$NHCH$_3$, OC(O)OCH[(CH$_2$)$_3$OP(O)(OH)$_2$]OC(O)CH$_2$N(CH$_3$)$_2$, —OCH(C$_2$H$_5$)OP(O)(OH)$_2$, —OCH(C$_6$H$_5$)OP(O)(OH)$_2$, —OC(O)OCH(CH$_3$)OC(O)—[CH(OH)]$_4$—CH$_2$OH, —OC(O)OCH(CH$_3$)OC(O)CH(COOH)$_2$,

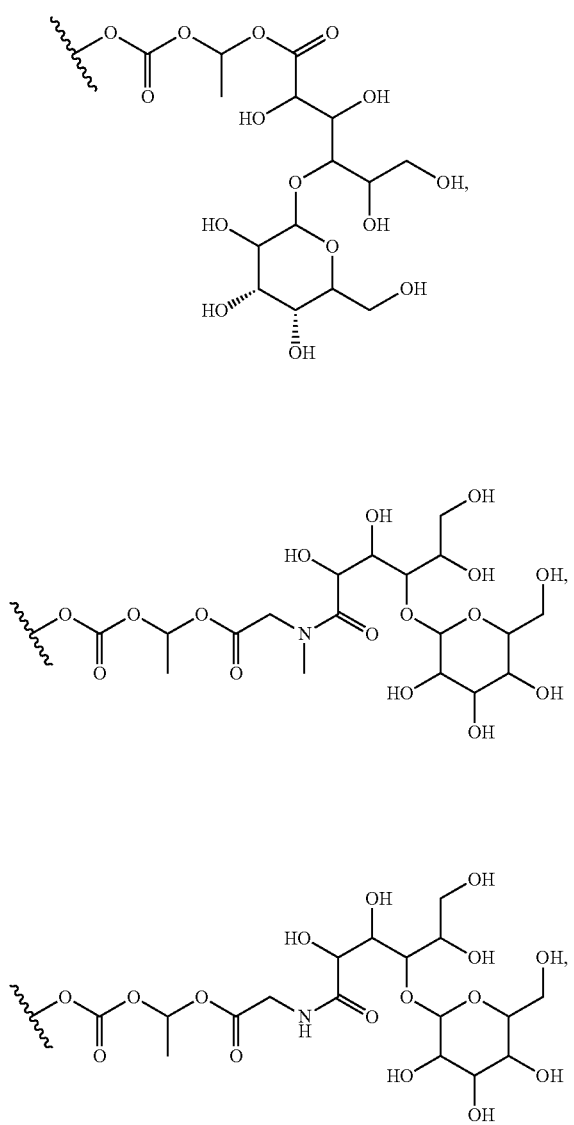

—OC(O)OCH(CH$_3$)OC(O)(CH$_2$)$_k$OP(O)(OH)$_2$, —OC(O)OCH$_2$OC(O)(CH$_2$)$_k$OP(O)(OH)$_2$, —OC(O)OCH(CH$_3$)OC(O)(CH$_2$)$_k$OS(O)$_2$OH, —OC(O)OCH$_2$OC(O)(CH$_2$)$_k$OS(O)$_2$OH, wherein each k independently has the definition as described above;

According to an embodiment of the present disclosure, the pharmaceutically acceptable salts of the compounds of formula (I) includes, but is not limited to:

alkali metal salts, alkaline earth metal salts, ammonium salts of compounds of formula (I), or salts of compounds of formula (I) formed with organic bases providing physiologically acceptable cations, for example salts of compounds of formula (I) formed with sodium ion, potassium ion, calcium ion, magnesium ion, N-methylglucosamine, dimethylglucosamine, ethylglucosamine, lysine, dicyclohexylamine, 1,6-hexamethylenediamine, ethanolamine, glycosamine, meglumine, sarcosine, serinol, trishydroxymethyl aminomethane, aminopropylene glycol, 1-amino-2,3,4-butanetriol. As an example, when 1, 2, or 3 of M$_1$, M$_2$, and M$_3$ is/are H, the pharmaceutically acceptable salts include, for example, the pharmaceutically acceptable salts of the present disclosure include, for example, salts formed from —OP(O)(OM$_1$)(OM$_2$), —P(O)(OM$_1$)(OM$_2$), —OS(O)$_2$OM$_3$, or —S(O)$_2$OM$_3$, with, for example, the above-mentioned sodium ion, potassium ion, ammonium ion, and the like;

or alternatively, acid addition salts of compounds of formula (I) with the following acids: inorganic acids such as hydrochloric acid, hydrofluoric acid, hydrobromic acid, hydroiodic acid, sulfuric acid, pyrosulfuric acid, phosphoric acid or nitric acid; organic acids such as formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxyl benzoyl) benzoic acid, camphoric acid, cinnamic acid, cyclopentane propionic acid, digluconic acid, 3-hydroxy-2-naphthoic acid, nicotinic acid, embonic acid, pectinic acid, persulfuric acid, 3-phenyl propionic acid, picric acid, pivalic acid, 2-hydroxyethanesulfonic acid, itaconic acid, sulfamic acid, trifluoromethanesulfonic acid, dodecyl sulfate, ethanesulfonic acid, benzenesulfonic acid, p-toluenesulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, gluconic acid, glycerophosphoric acid, aspartic acid, sulfosalicylic acid, hemisulfuric acid or thiocyanic acid.

Persons skilled in the art should understand that, if appropriate, the pharmaceutically acid addition salts of the compound of formula (I) include not only salts formed by 1 molecule of the compound of formula (I) with 1 molecule of acid, but also salts formed by several molecules of compound of formula (I) with 1 molecule of acid (e.g. hemisulfate), salts formed by 1 molecule of compound of formula (I) with several molecules of acid, and salts formed by several molecules of compound of formula (I) with several molecules of acid. Also, if appropriate, alkali metal salts, alkaline earth metal salts, ammonium salts of compounds of formula (I), or salts of compounds of formula (I) with organic bases that provide physiologically acceptable cations include not only salts formed by 1 molecule of compound of formula (I) with 1 cation, but also salts formed by several molecules of compound of formula (I) with 1 cation, and salts formed by 1 molecule of compound of formula (I) with several cations.

According to a preferred embodiment of the present disclosure, the compound of formula (I) can have the structure represented by the following formula (I'):

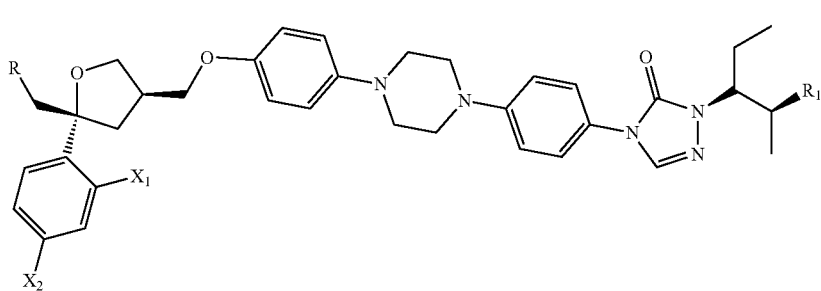
(I')
wherein, each group has the definition as described above.
As an example, the compound of formula (I) can be selected from the following compounds and pharmaceutically acceptable salts thereof:

| No. | Structure |
|-----|-----------|
| 0001 | 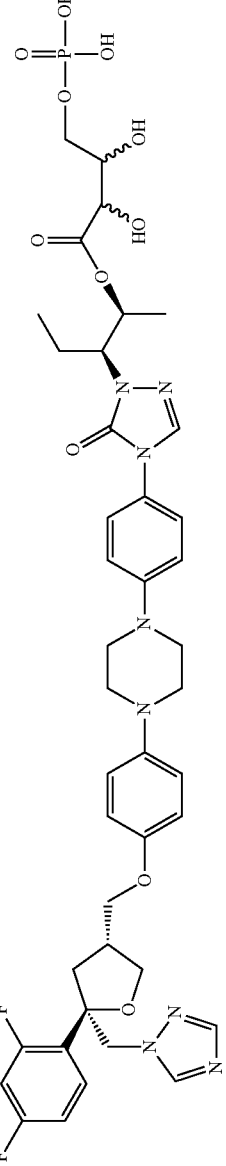 |
| 0002 | 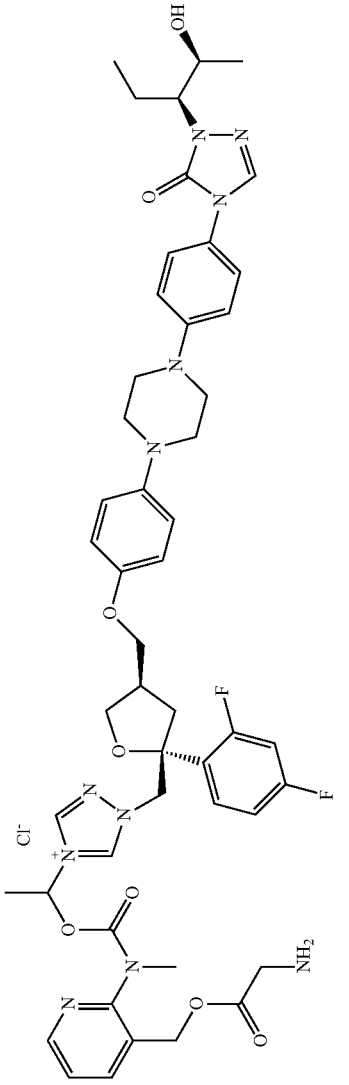 |
| 0003 | 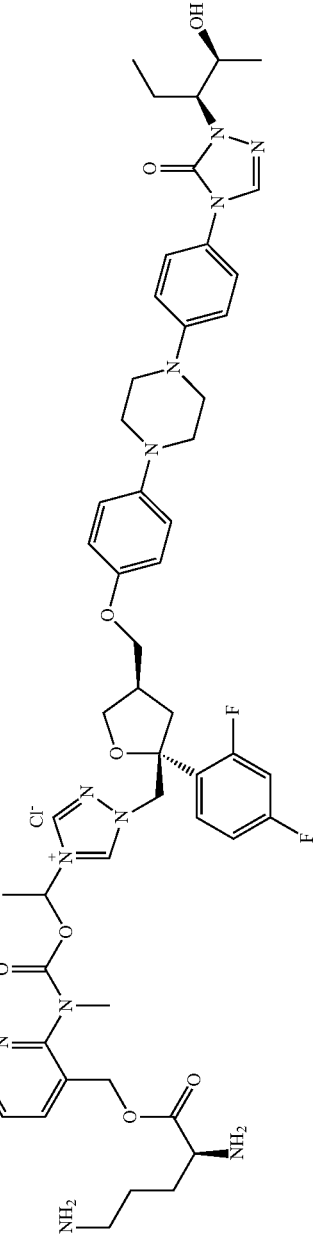 |

-continued
| No. | Structure |
|---|---|
| 0004 | 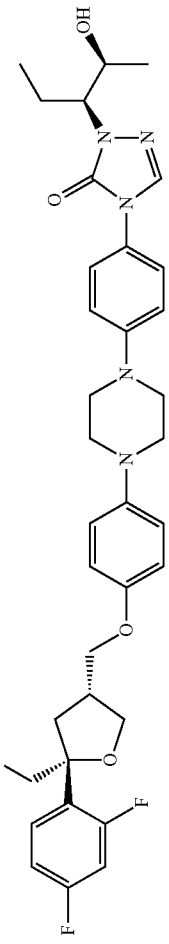 |
| 0005 | 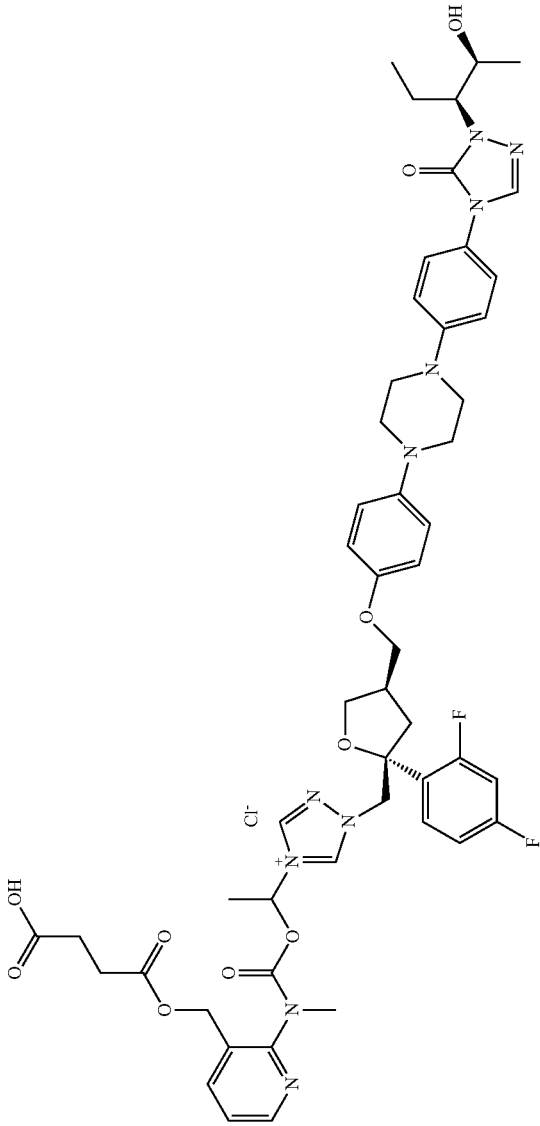 |

| No. | Structure |
|---|---|
| 0006 | 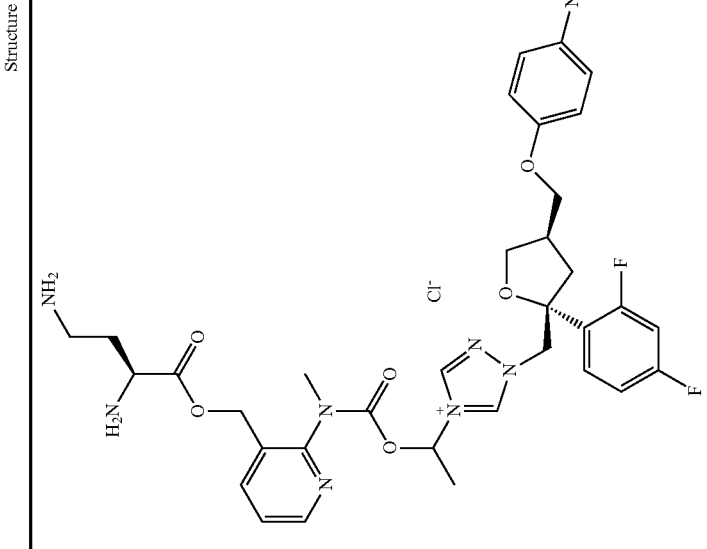 |
| 0007 | 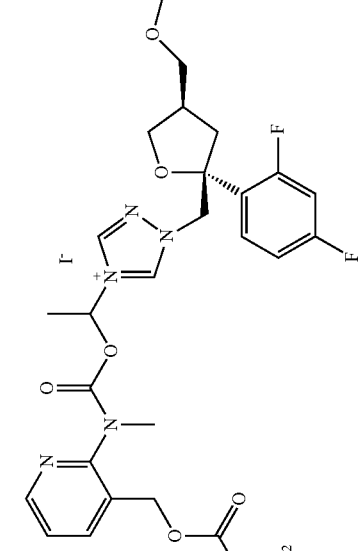 |

-continued
| No. | Structure |
|---|---|
| 0008 | 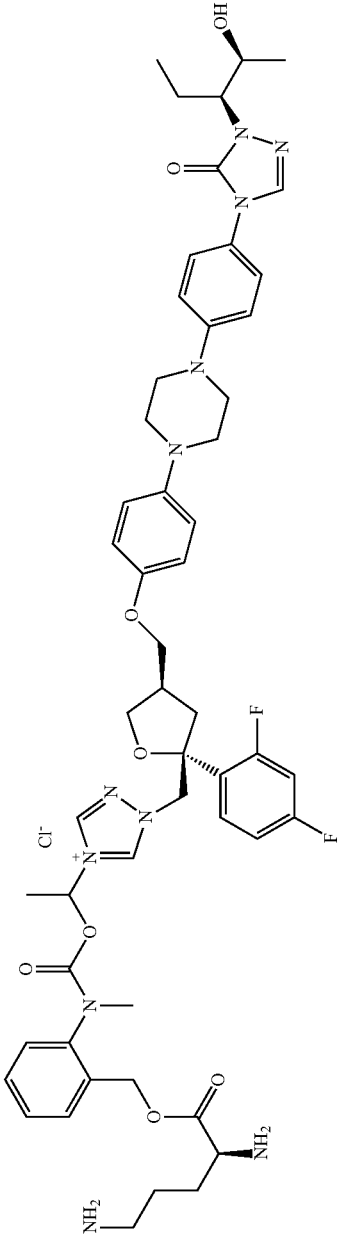 |
| 0009 | 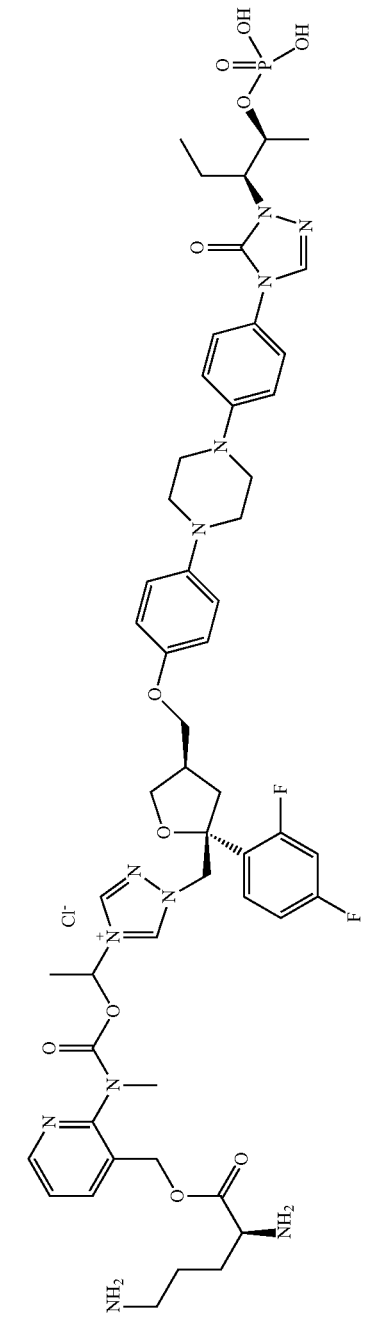 |
| 0010 | 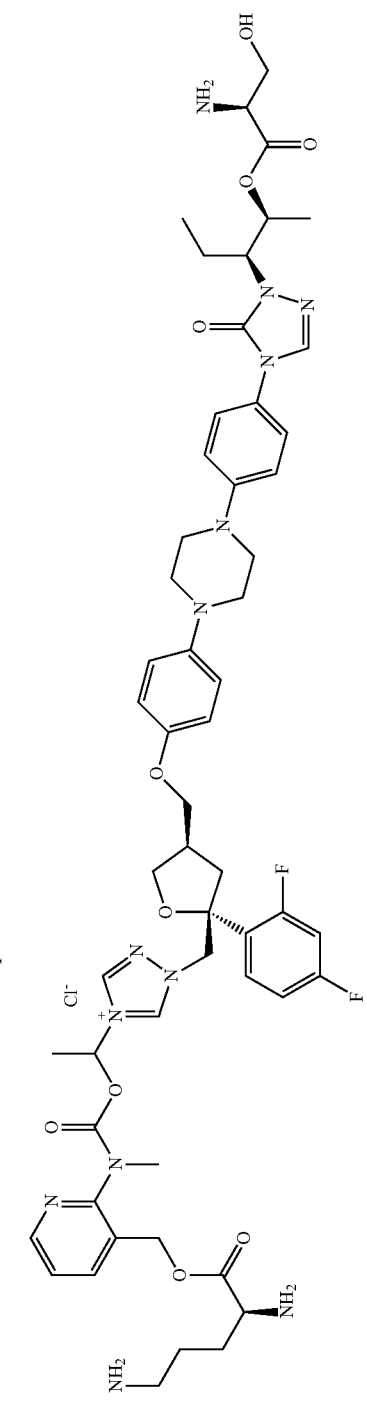 |

-continued
| No. | Structure |
|---|---|
| 0011 | 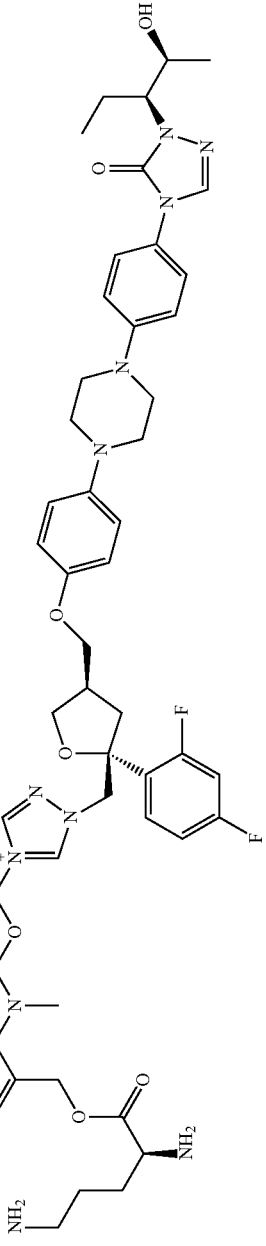 |
| 0012 | 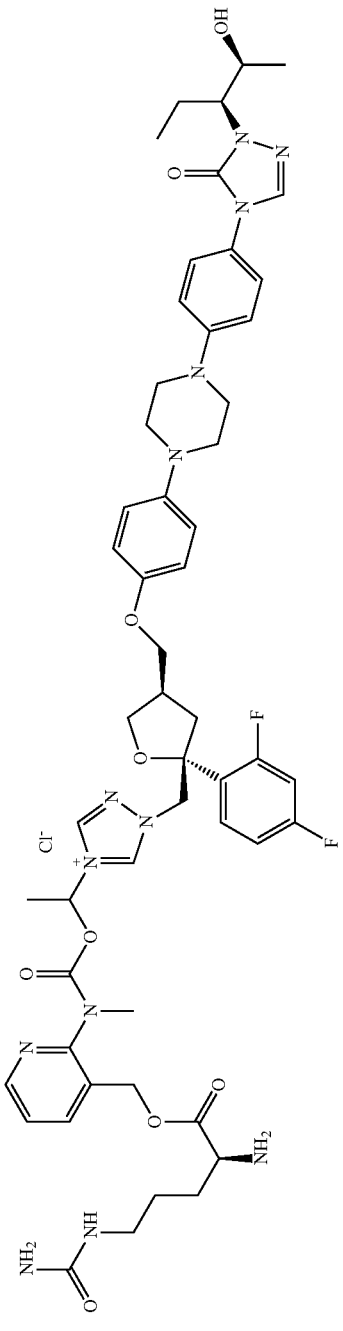 |
| 0013 | 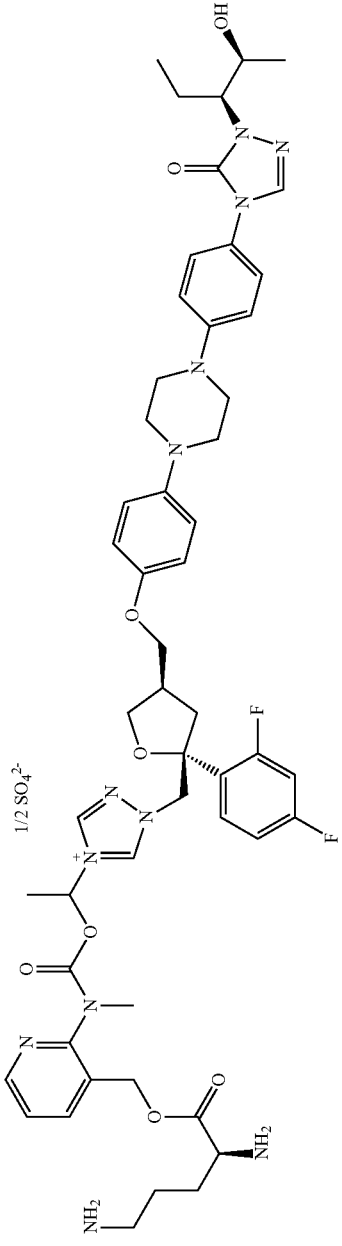 |

| No. | Structure |
|---|---|
| 0014 | (chemical structure with H₂PO₄⁻ counterion) |
| 0015 | (chemical structure with NO₃⁻ counterion) |
| 0016 | (chemical structure with Cl⁻ counterion) |

-continued

| No. | Structure |
|---|---|
| 0017 | 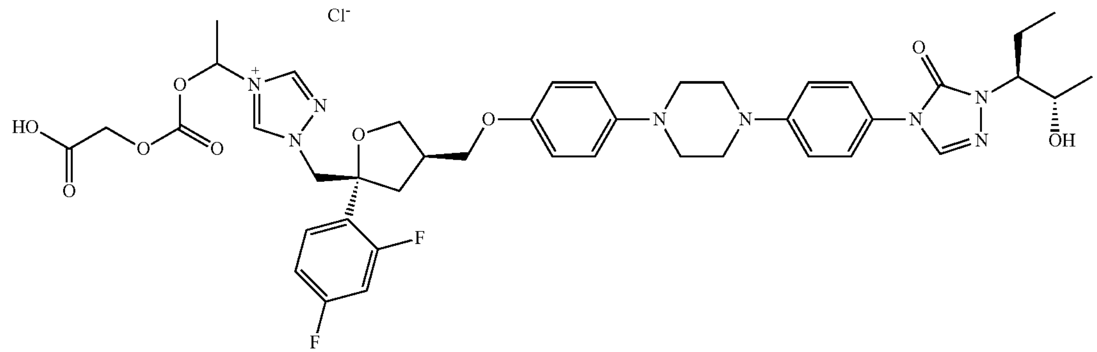 |
| 0018 | 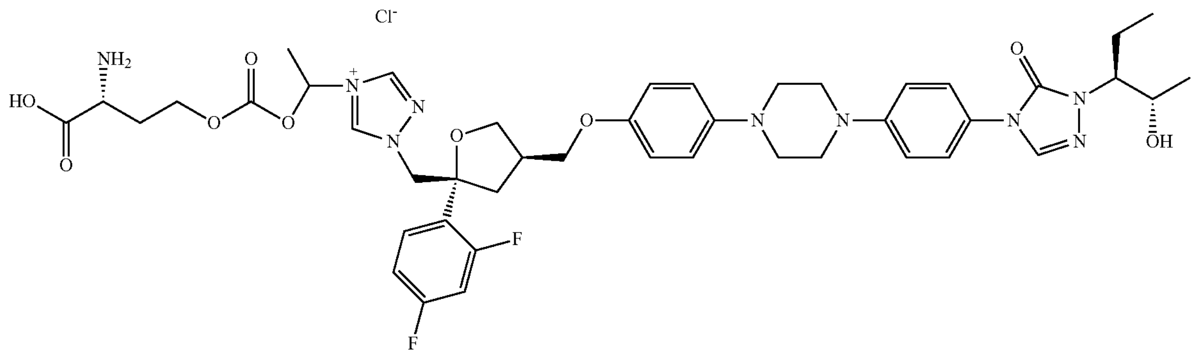 |
| 0019 | 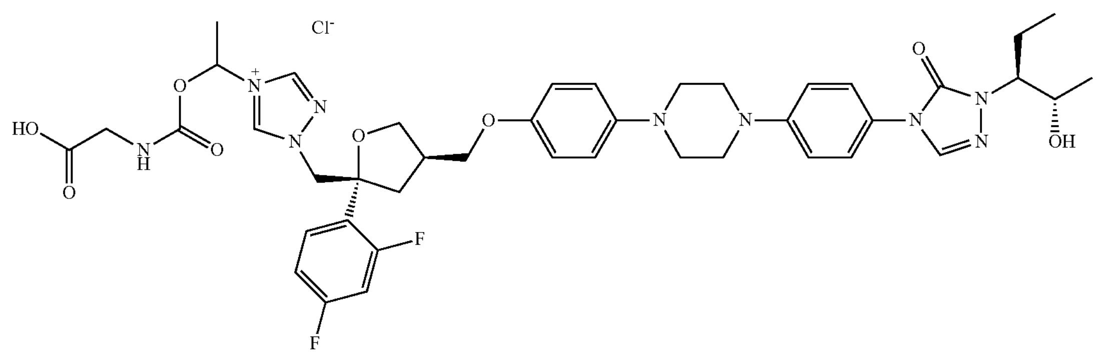 |

-continued
| No. | Structure |
|---|---|
| 0020 | 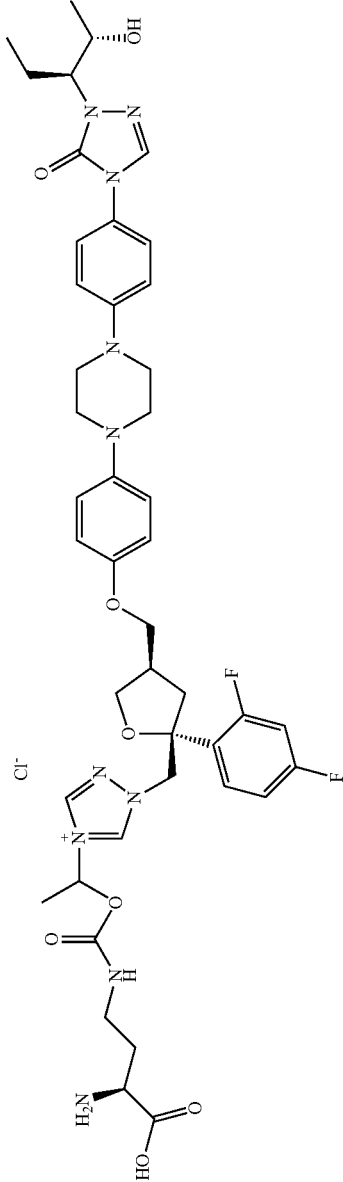 |
| 0021 | 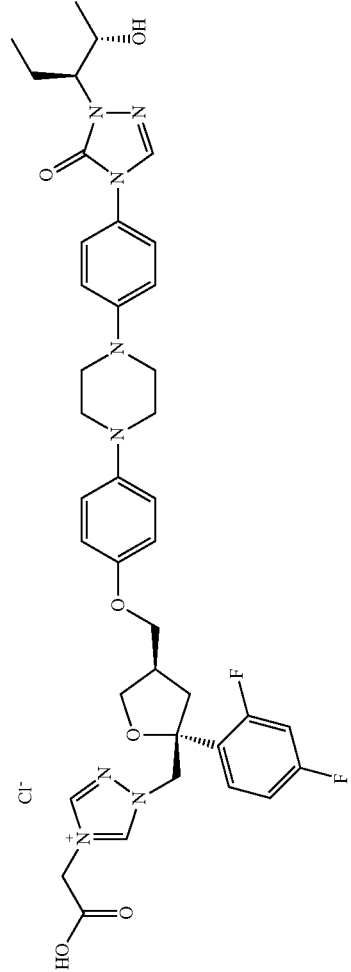 |
| 0022 | 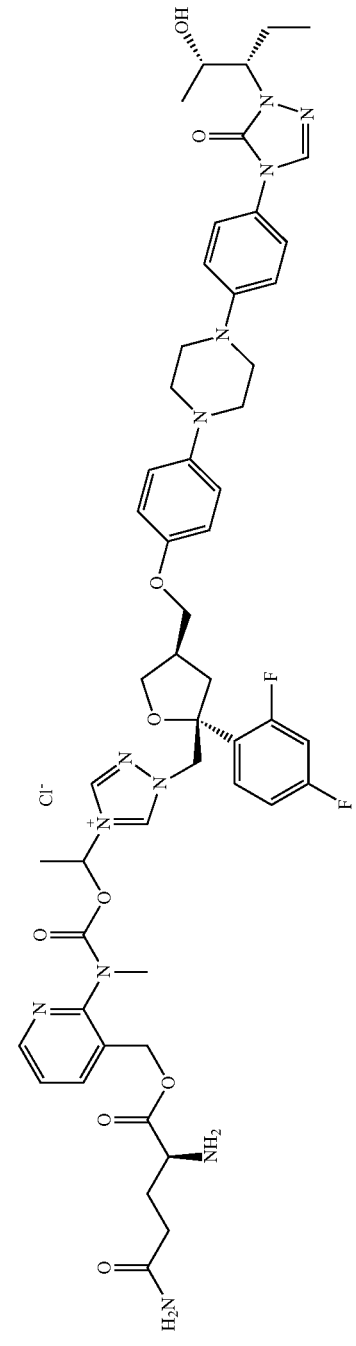 |

-continued
| No. | Structure |
|---|---|
| 0023 | 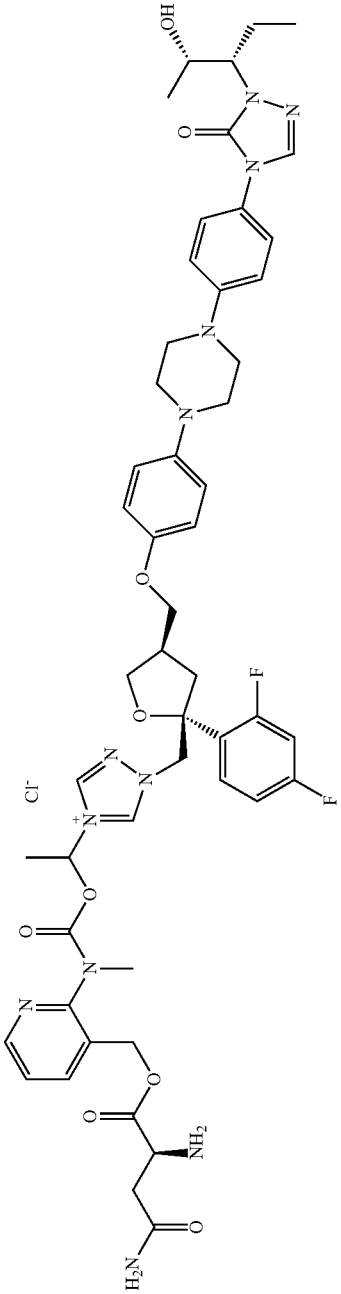 |
| 0024 | 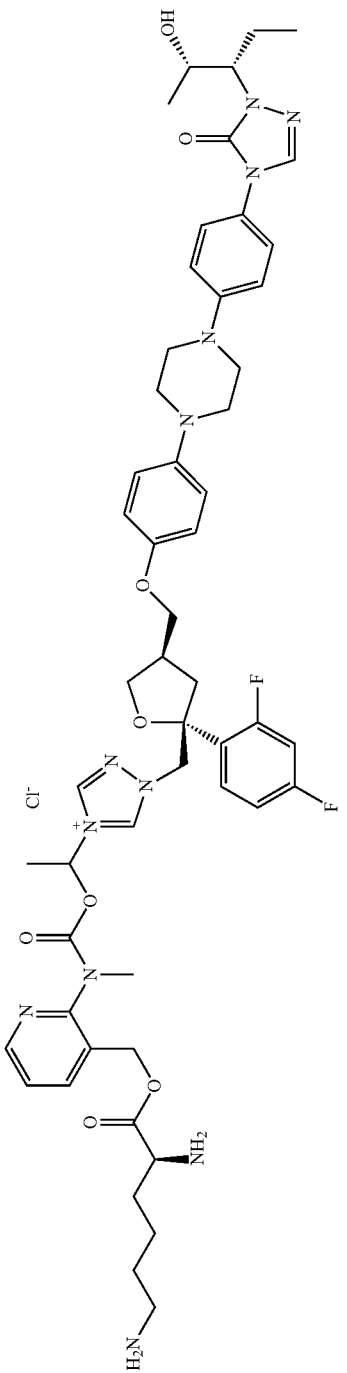 |
| 0025 | 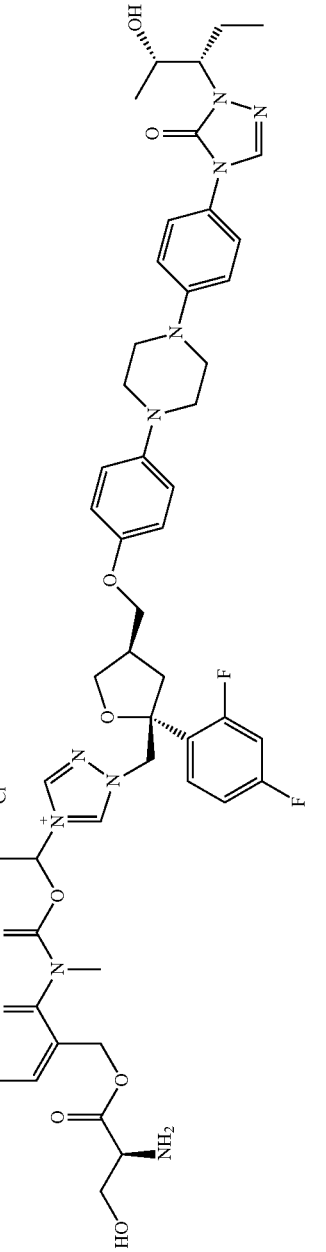 |

-continued
| No. | Structure |
|---|---|
| 0026 | 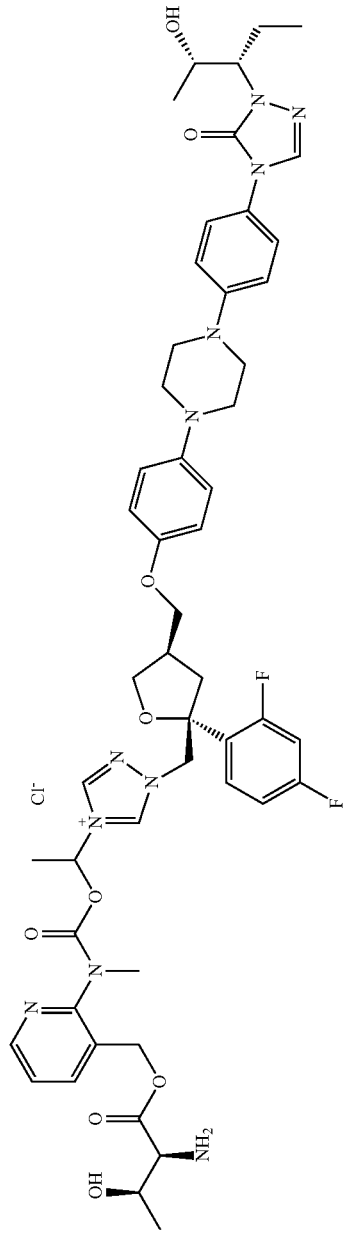 |
| 0027 | 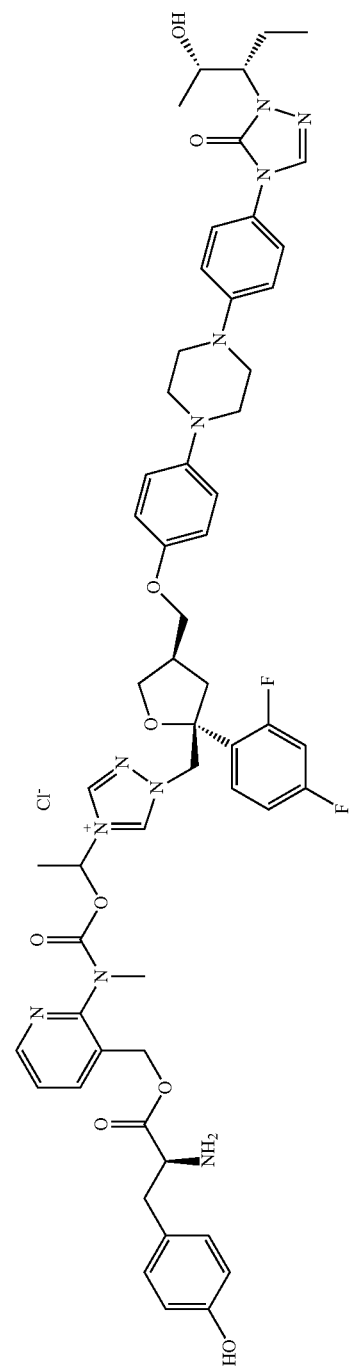 |

-continued
| No. | Structure |
|---|---|
| 0028 | 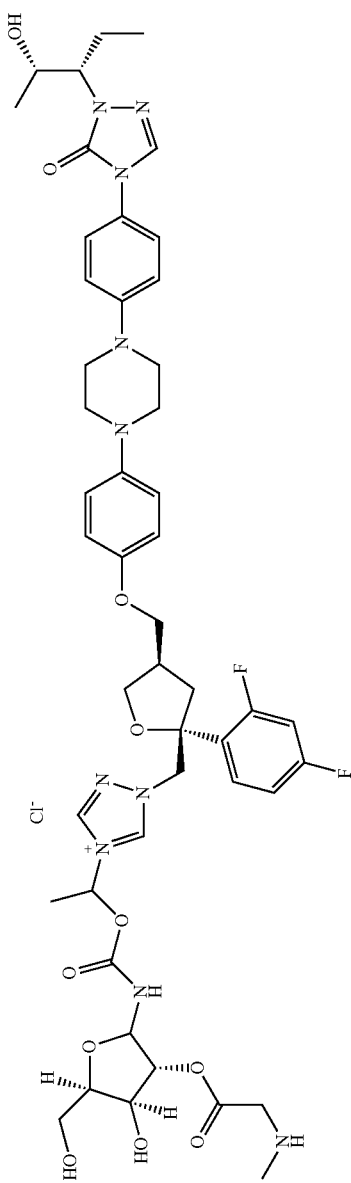 |
| 0029 | 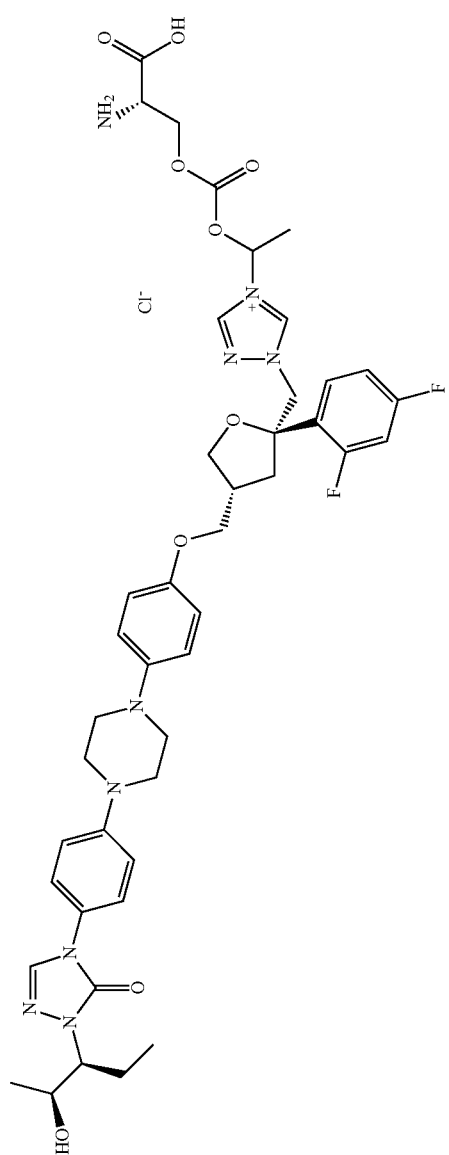 |

| No. | Structure |
|---|---|
| 0030 | 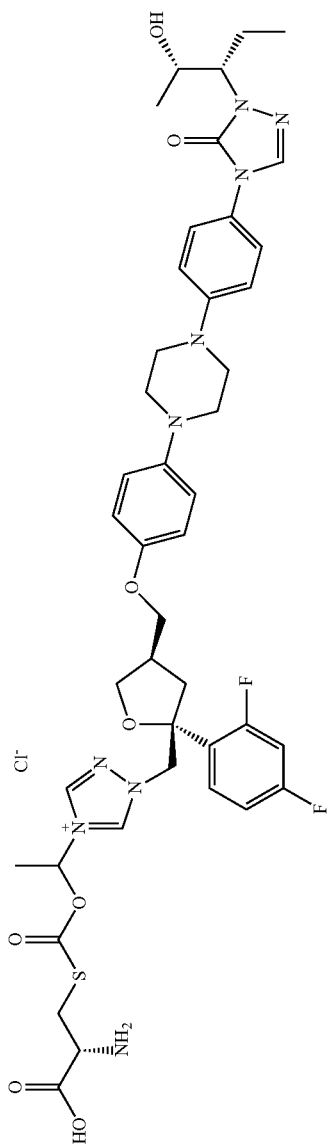 |
| 0031 | 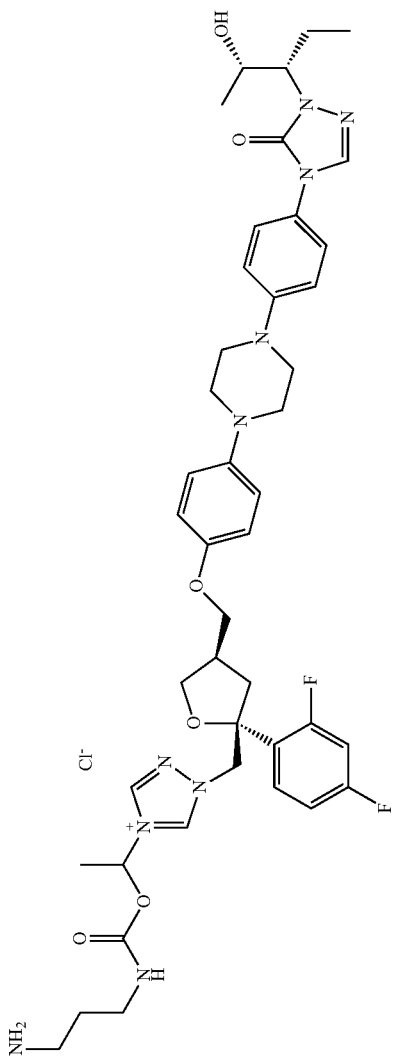 |

| No. | Structure |
|---|---|
| 0032 | 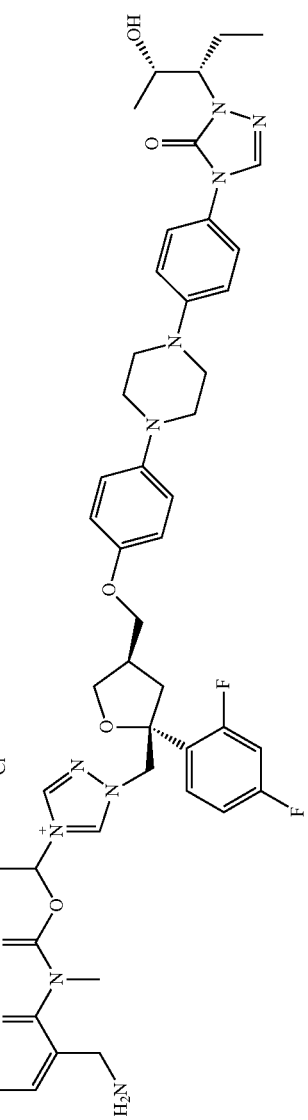 |
| 0033 | 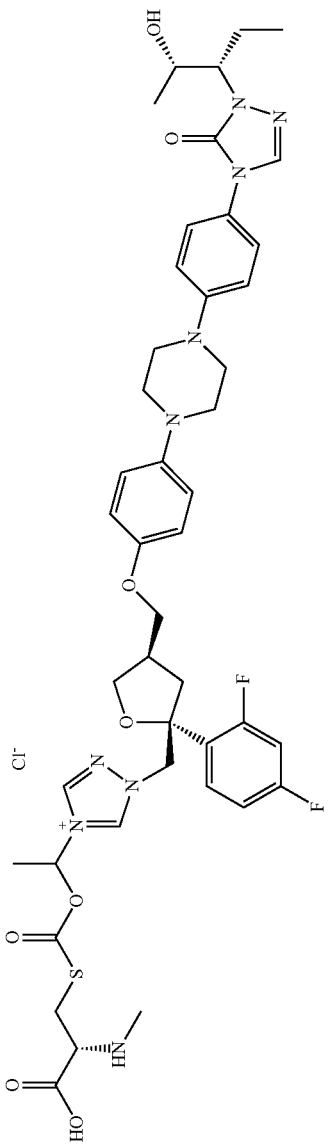 |
| 0034 | 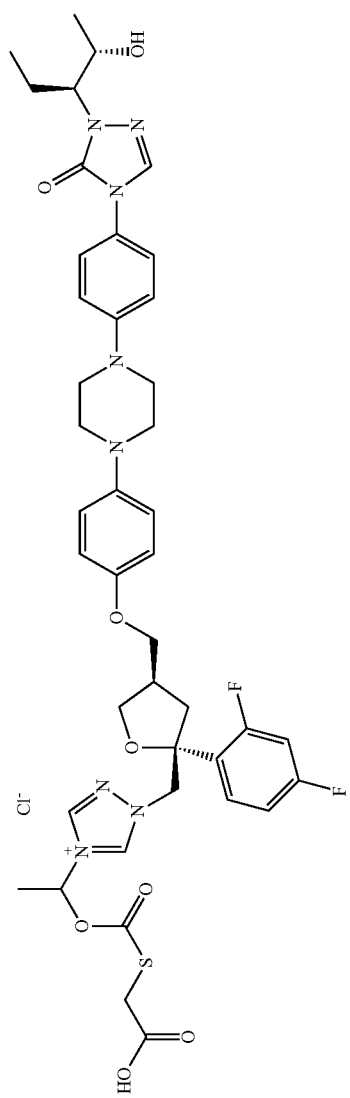 |

-continued
| No. | Structure |
|---|---|
| 0035 | 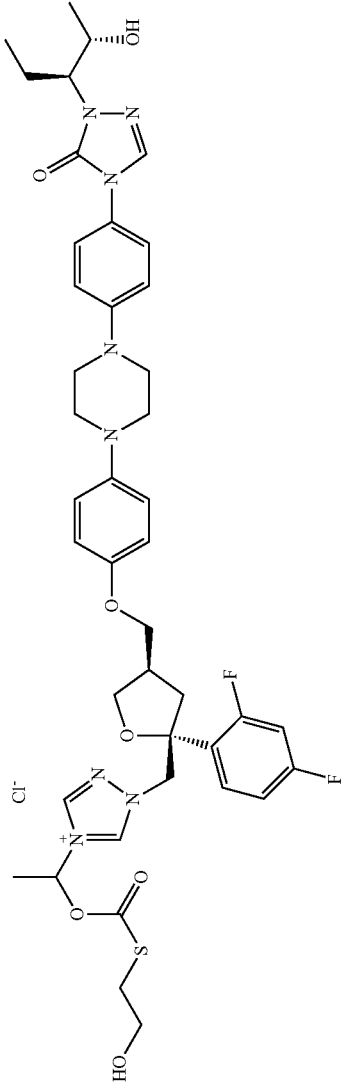 |
| 0036 | 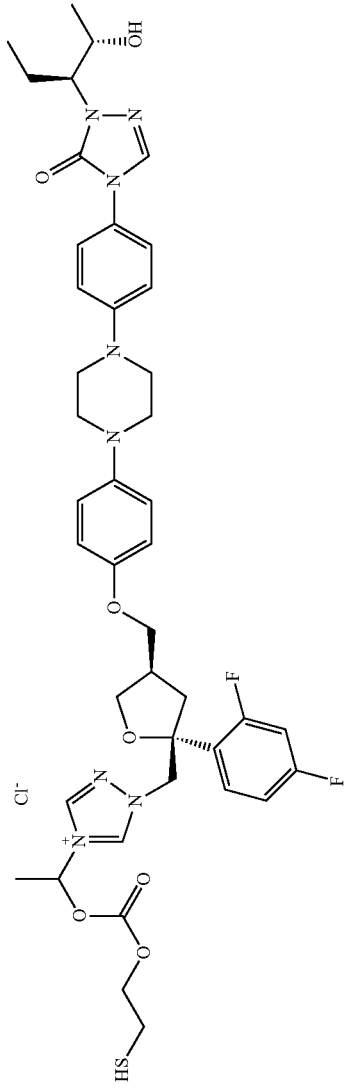 |
| 0037 | 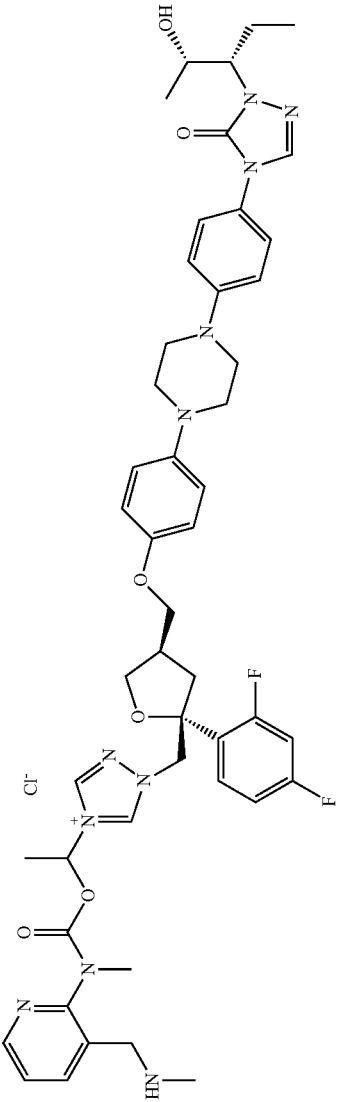 |

-continued

| No. | Structure |
|---|---|
| 0038 | 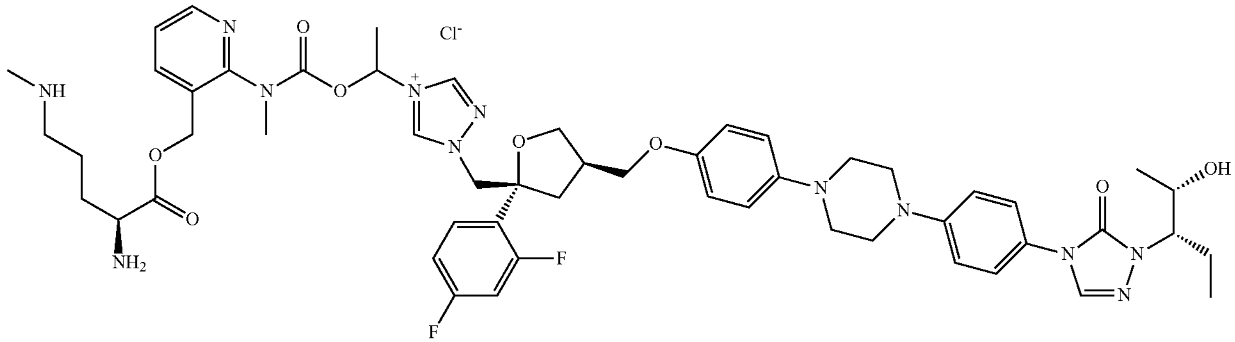 |
| 0039 | 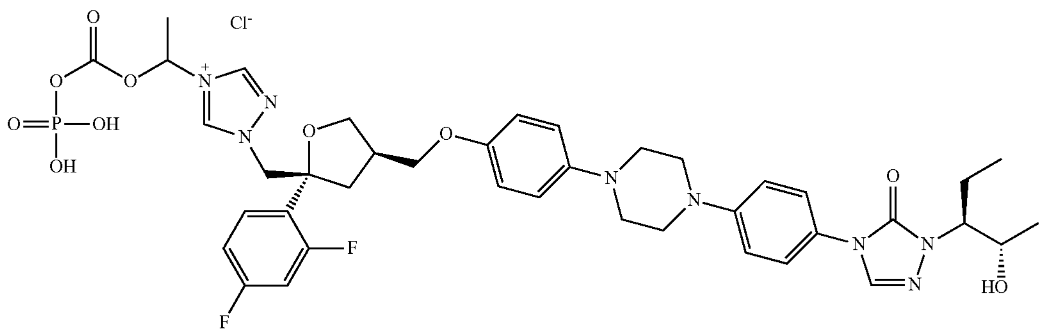 |
| 0040 | 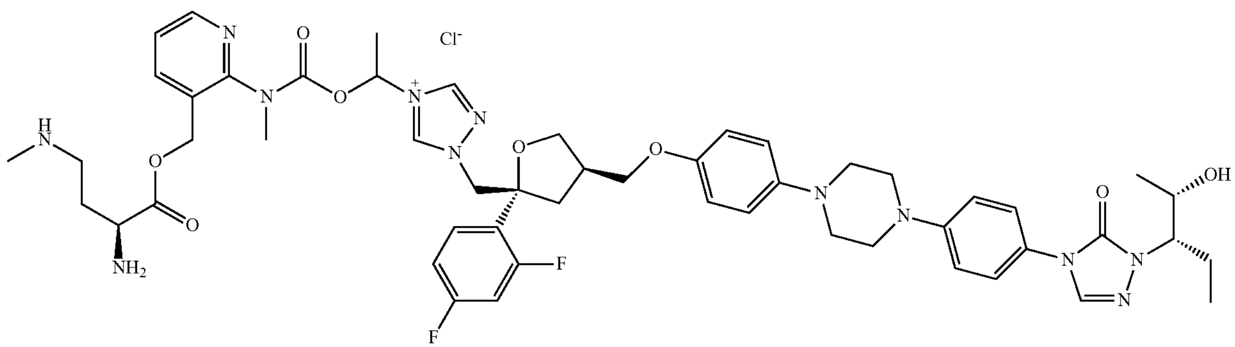 |

-continued

| No. | Structure |
|---|---|
| 0041 | 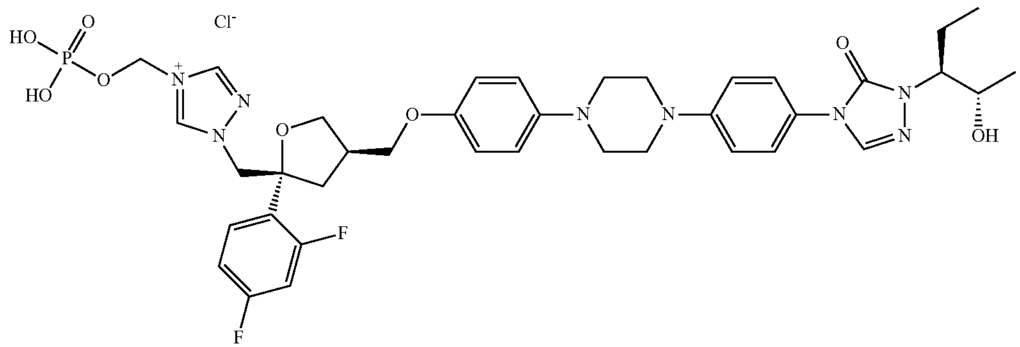 |
| 0042 | 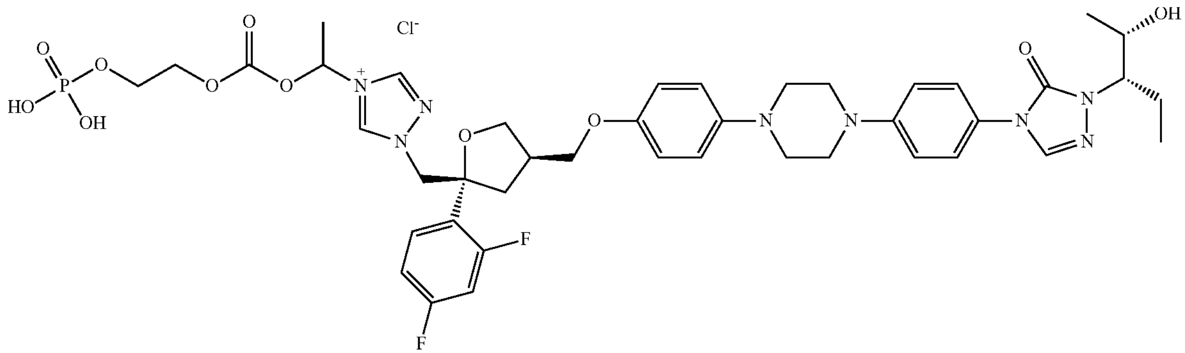 |
| 0043 | 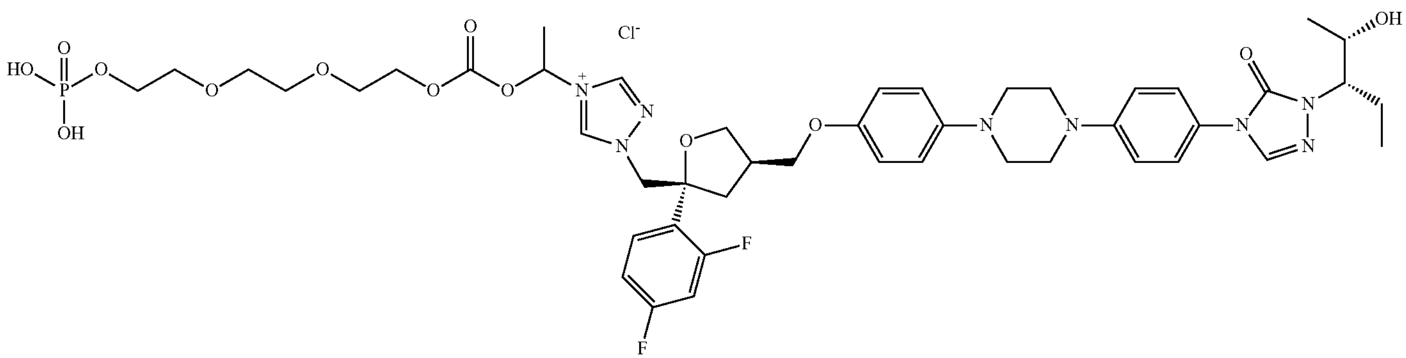 |

| No. | Structure |
|---|---|
| 0044 | 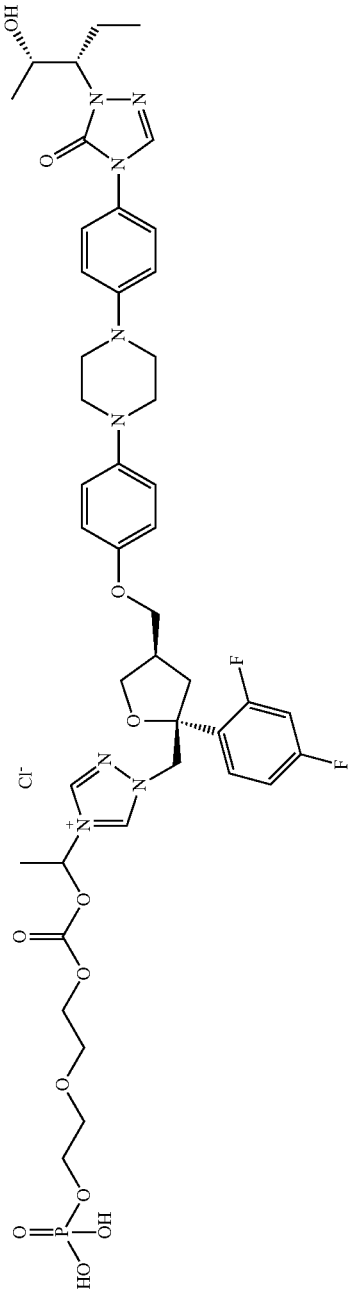 |
| 0045 | 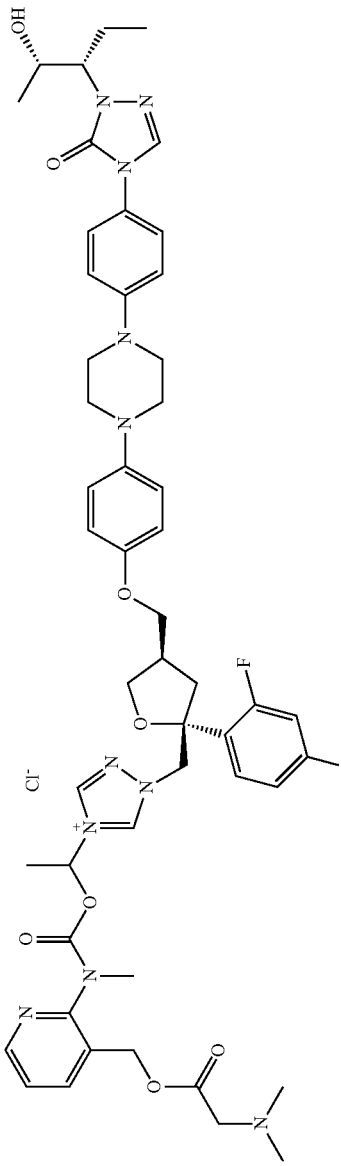 |
| 0046 | 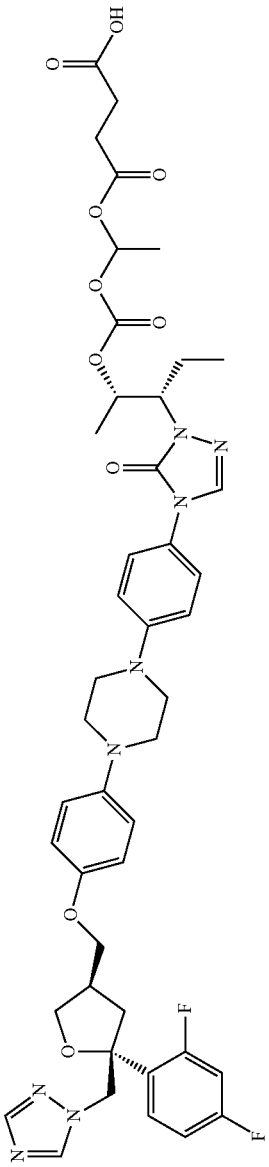 |

-continued
| No. | Structure |
|---|---|
| 0047 | 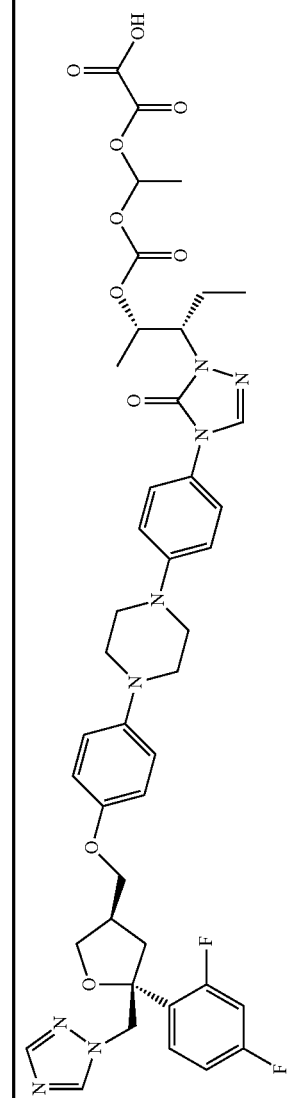 |
| 0048 | 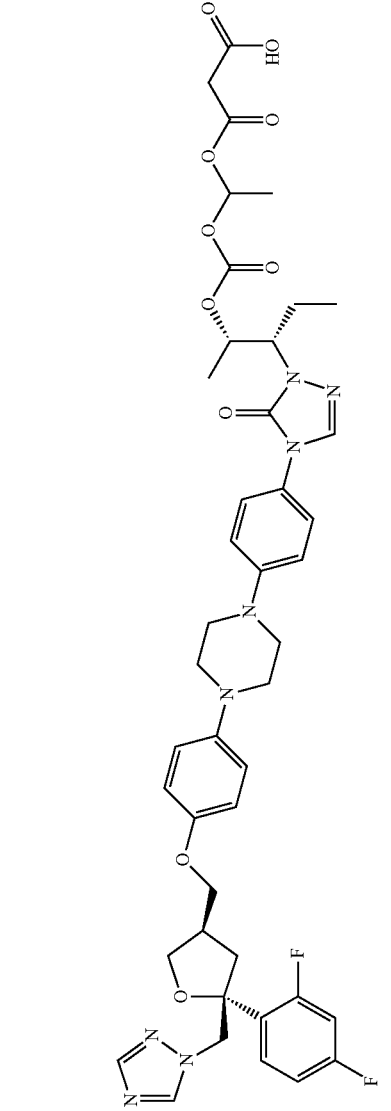 |
| 0049 | 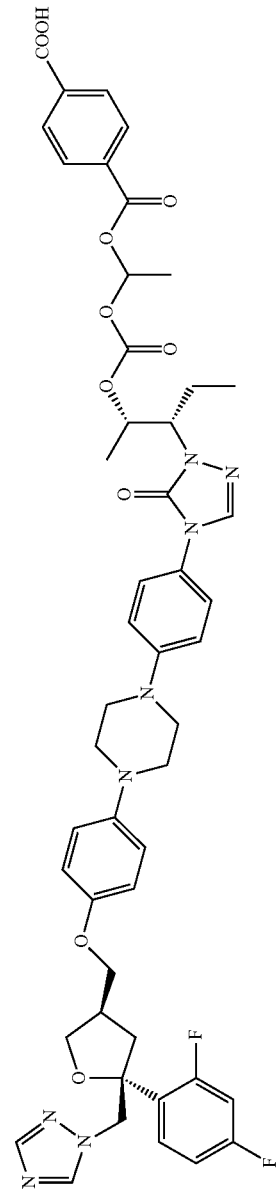 |

| No. | Structure |
|---|---|
| 0050 | 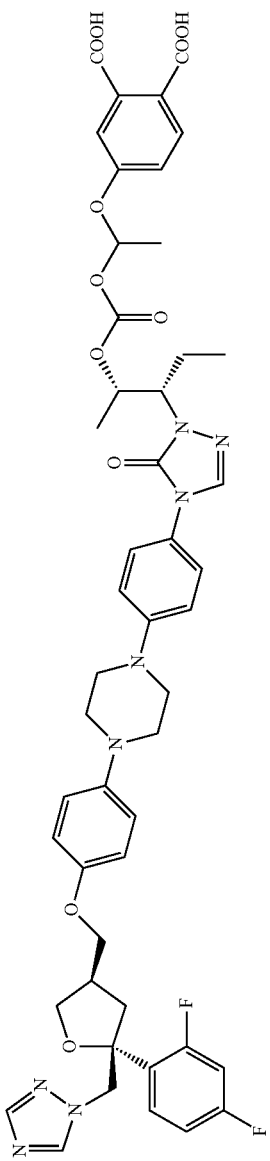 |
| 0051 | 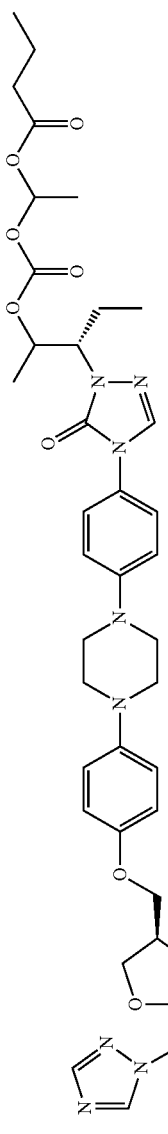 |
| 0052 | 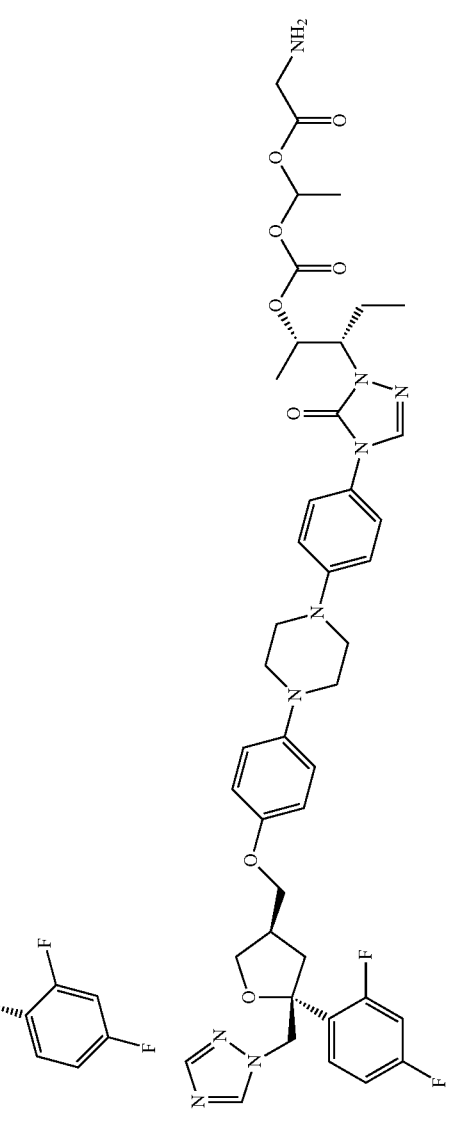 |

-continued
| No. | Structure |
|---|---|
| 0053 | 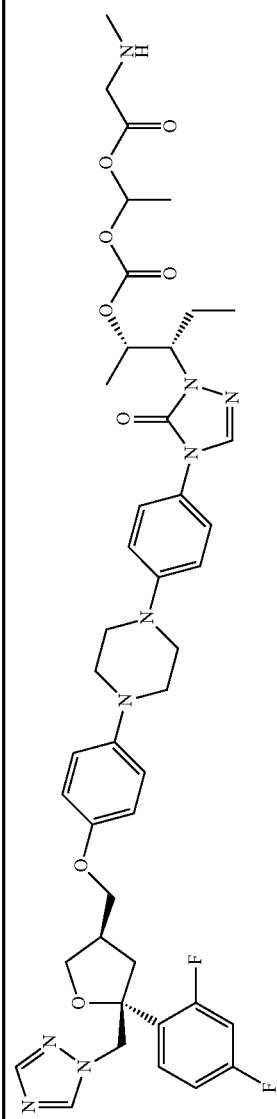 |
| 0054 | 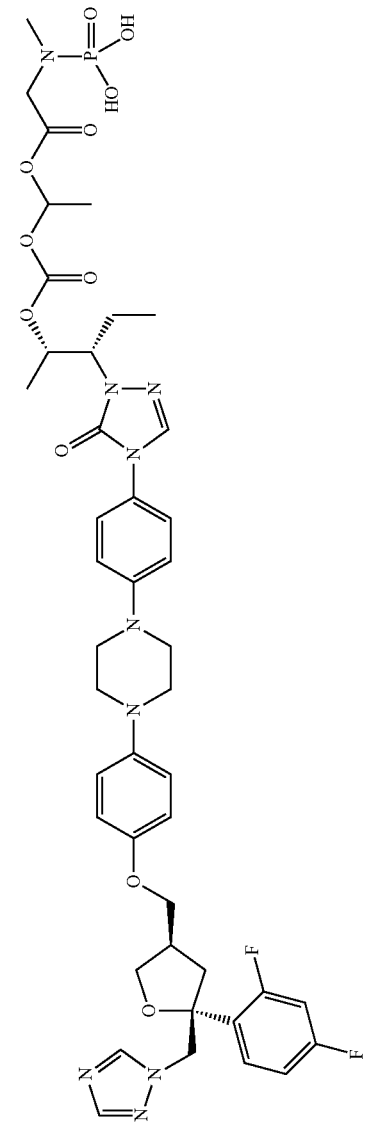 |
| 0055 | 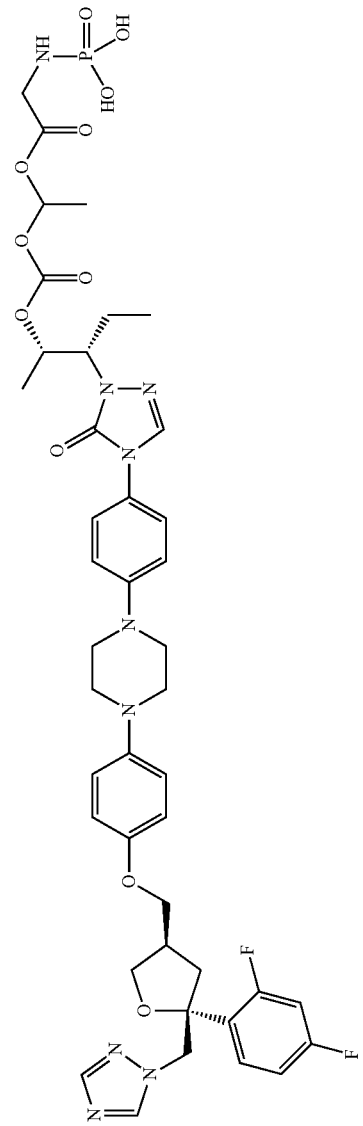 |

-continued
| No. | Structure |
|---|---|
| 0056 | 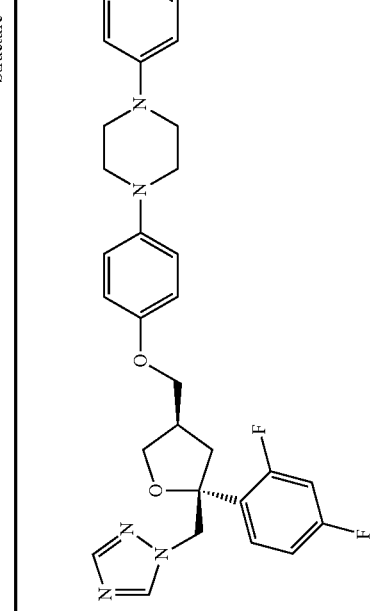 |
| 0057 | 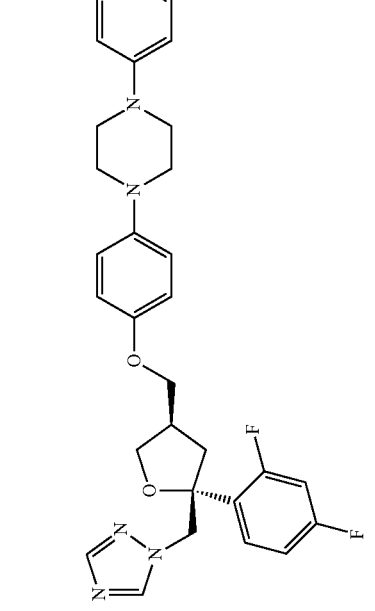 |
| 0058 | 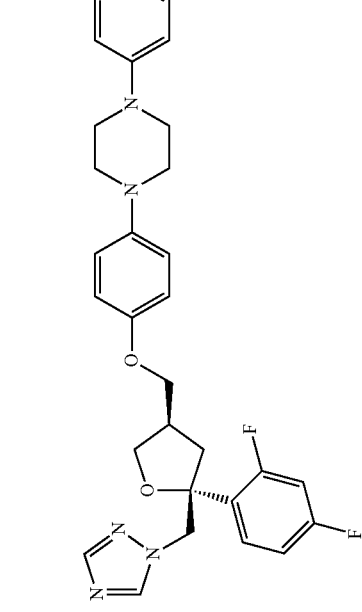 |

-continued
| No. | Structure |
|---|---|
| 0059 | 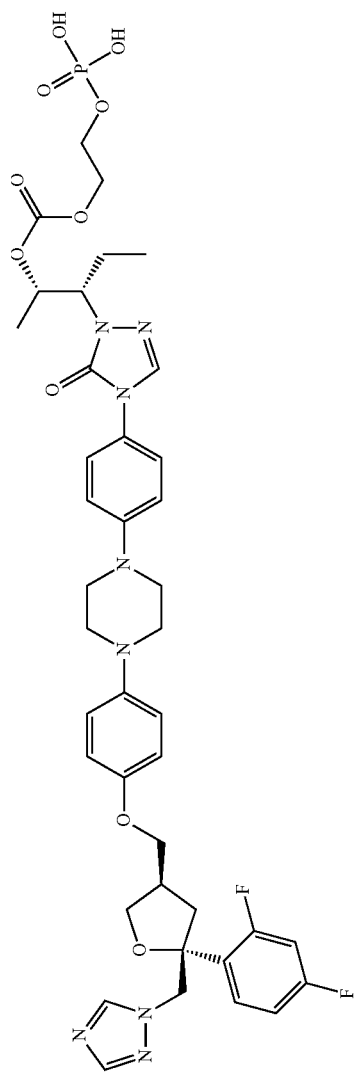 |
| 0060 | 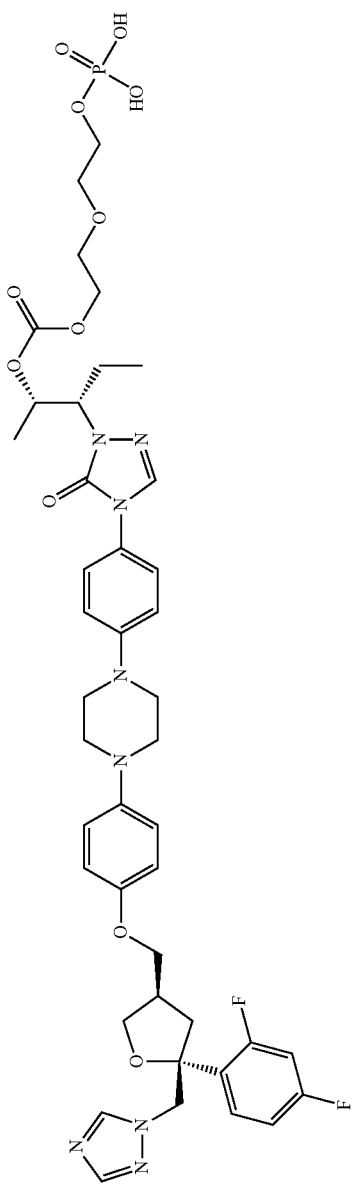 |

-continued
| No. | Structure |
|---|---|
| 0061 | 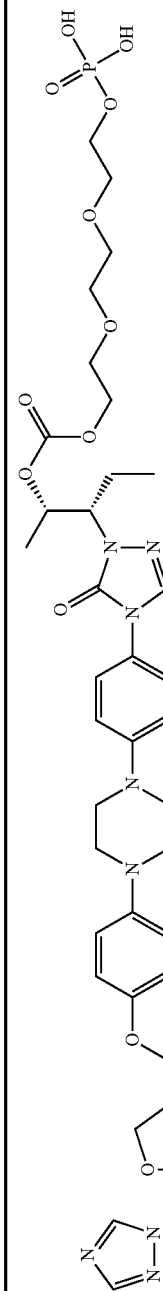 |
| 0062 | 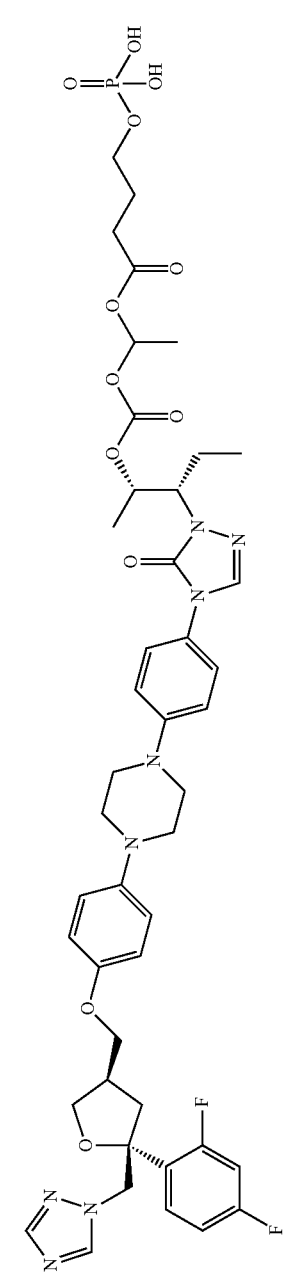 |
| 0063 | 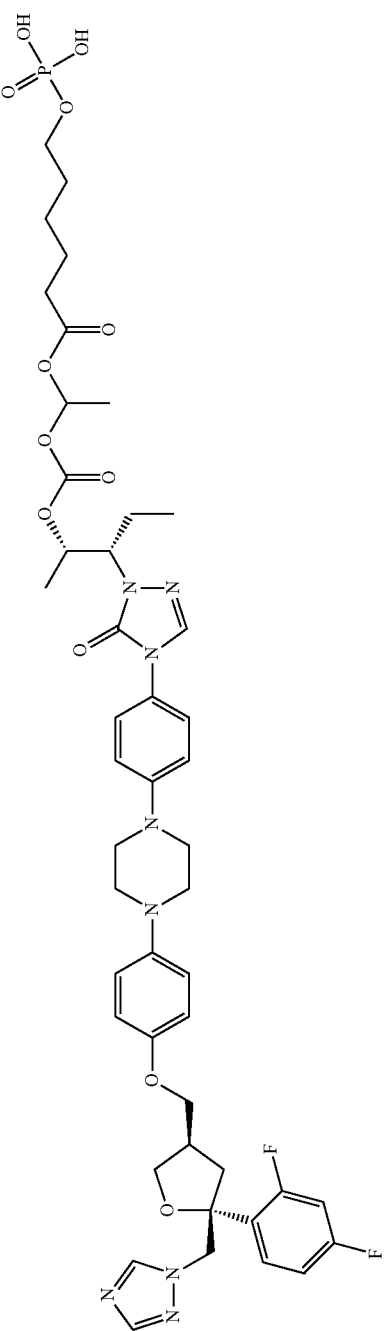 |

-continued
| No. | Structure |
|---|---|
| 0064 | 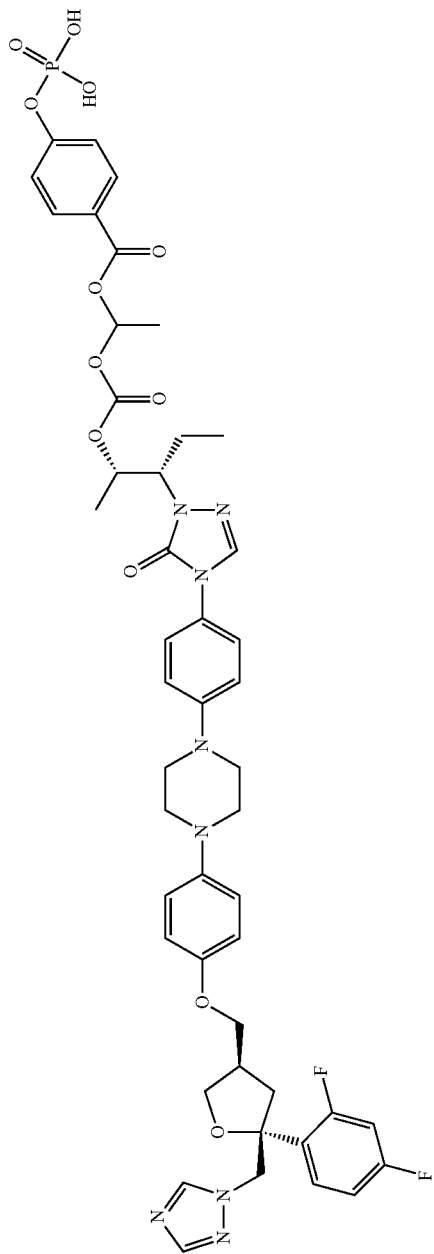 |
| 0065 | 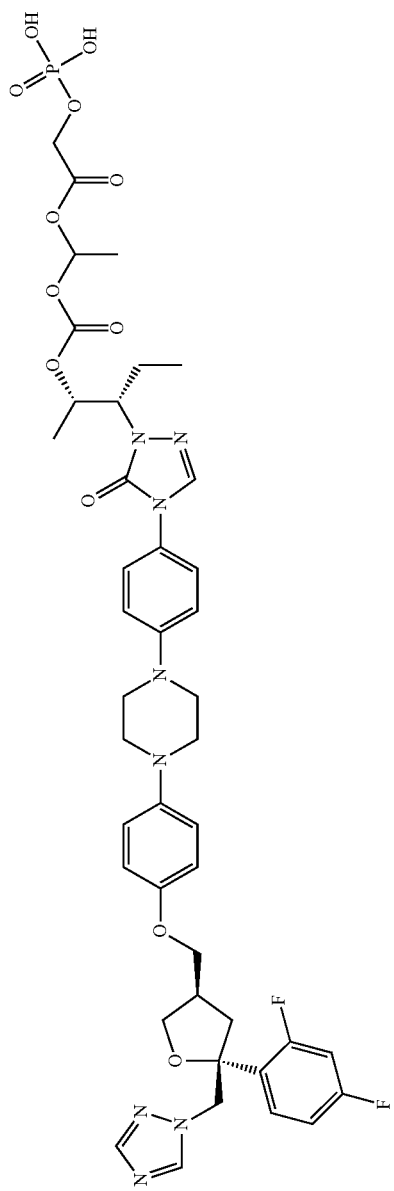 |

| No. | Structure |
|---|---|
| 0066 | 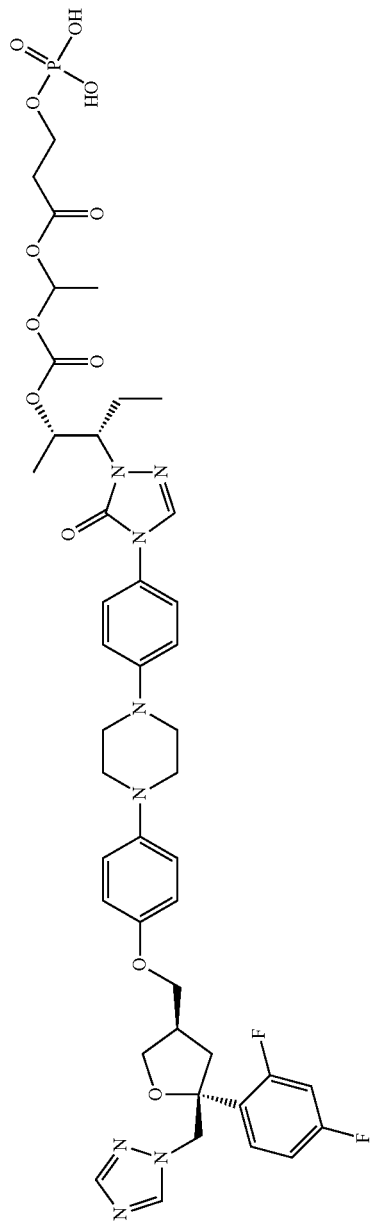 |
| 0067 | 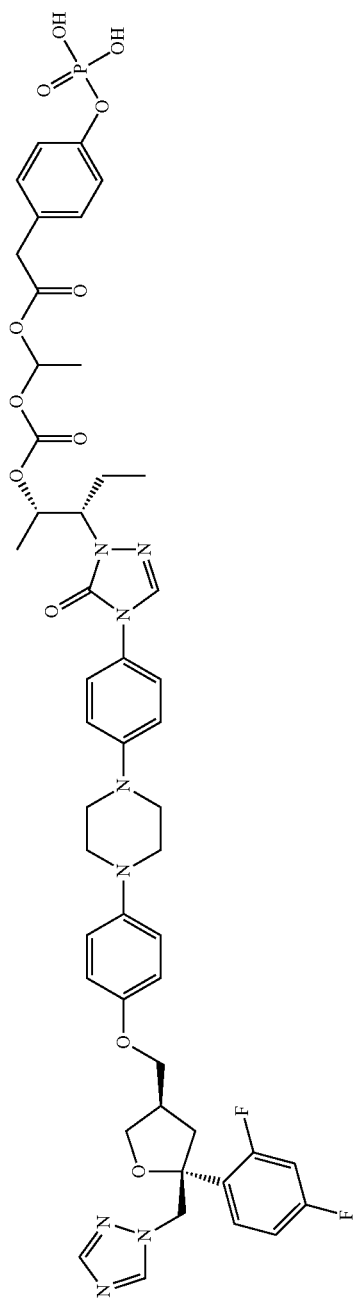 |

-continued
| No. | Structure |
|---|---|
| 0068 | 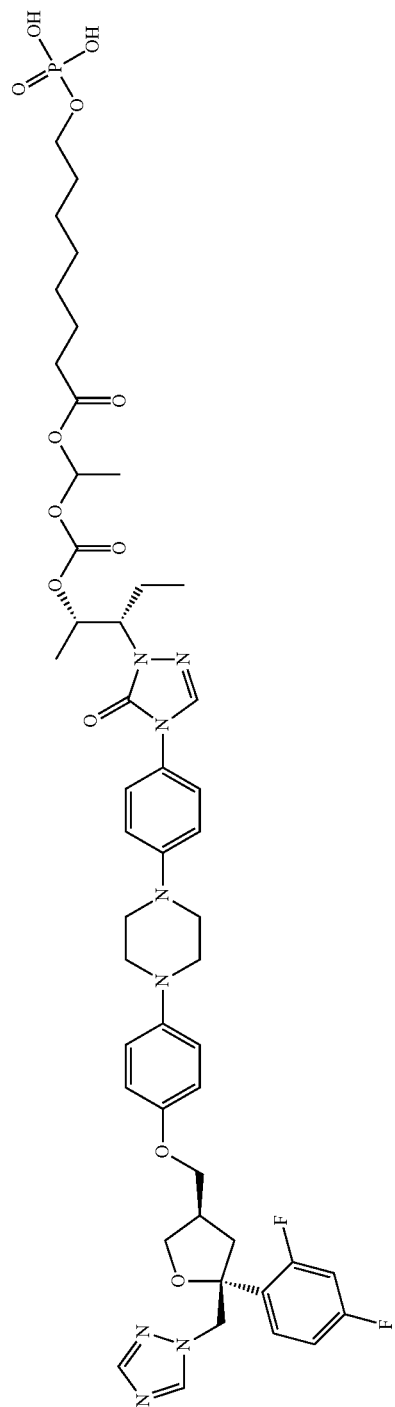 |
| 0069 | 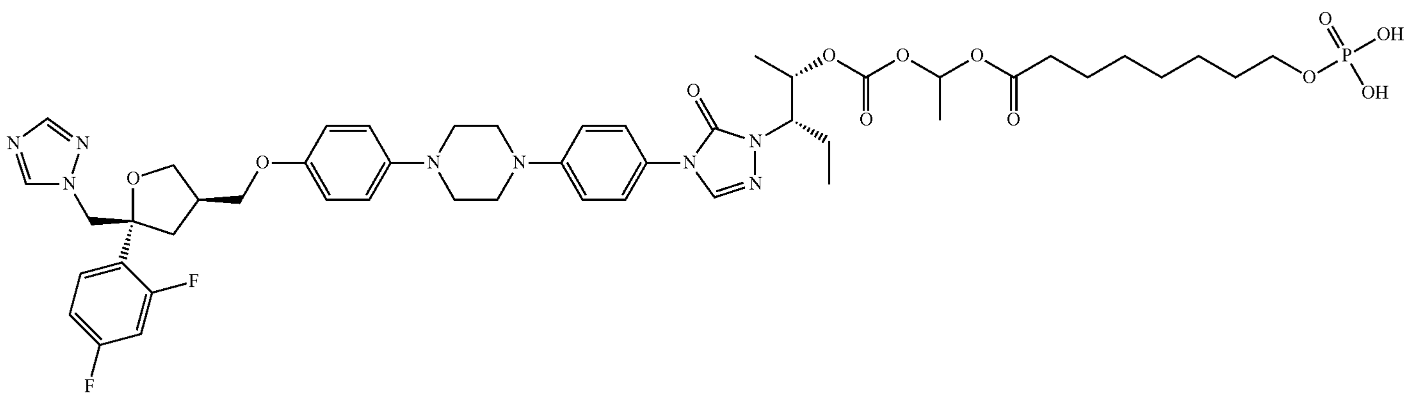 [SMILES: CC[C@@H]([C@H](C)OC(=O)OC(C)OC(=O)CCCCCCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |

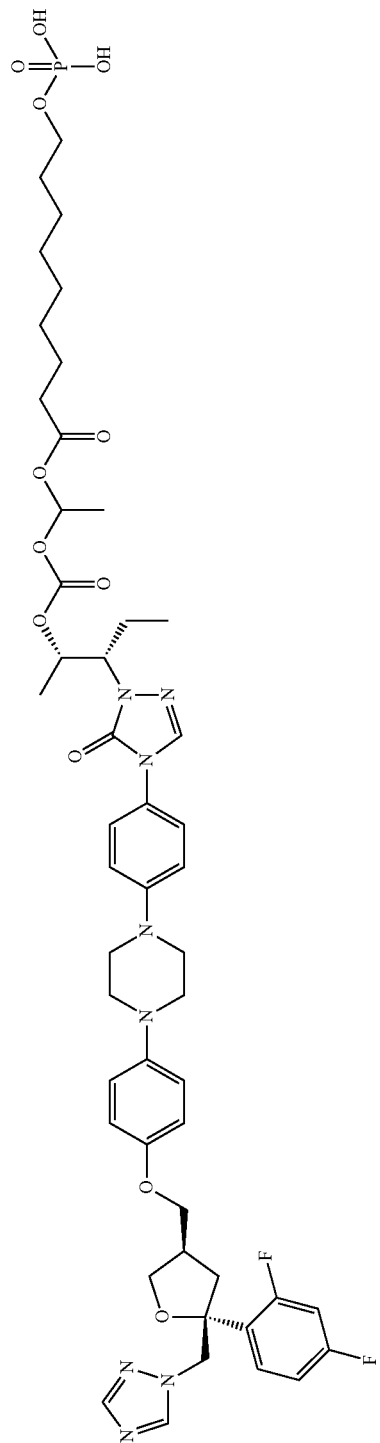

-continued
| No. | Structure |
|---|---|
| 0072 | 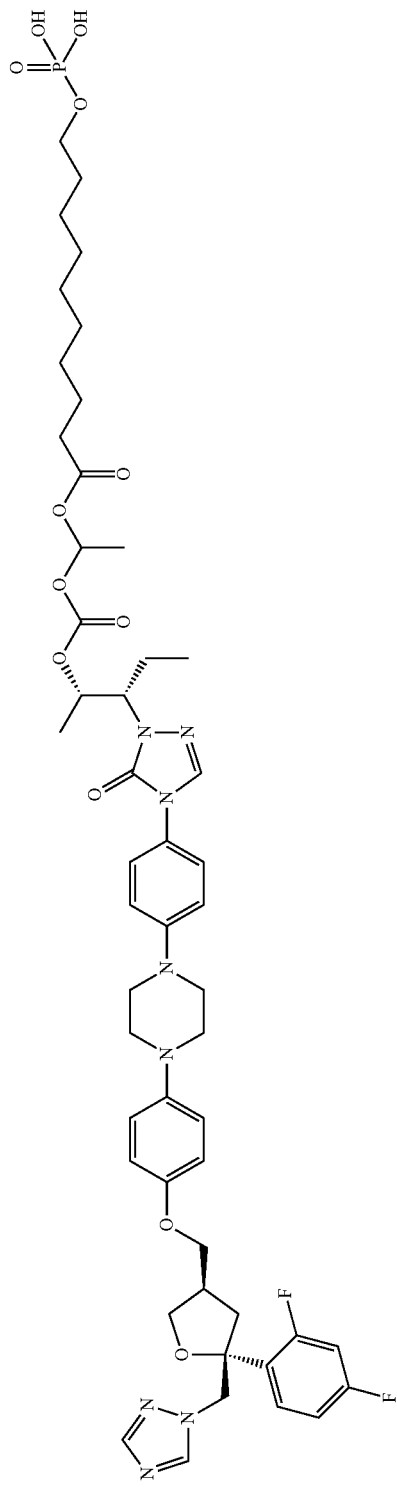 |
| 0073 | 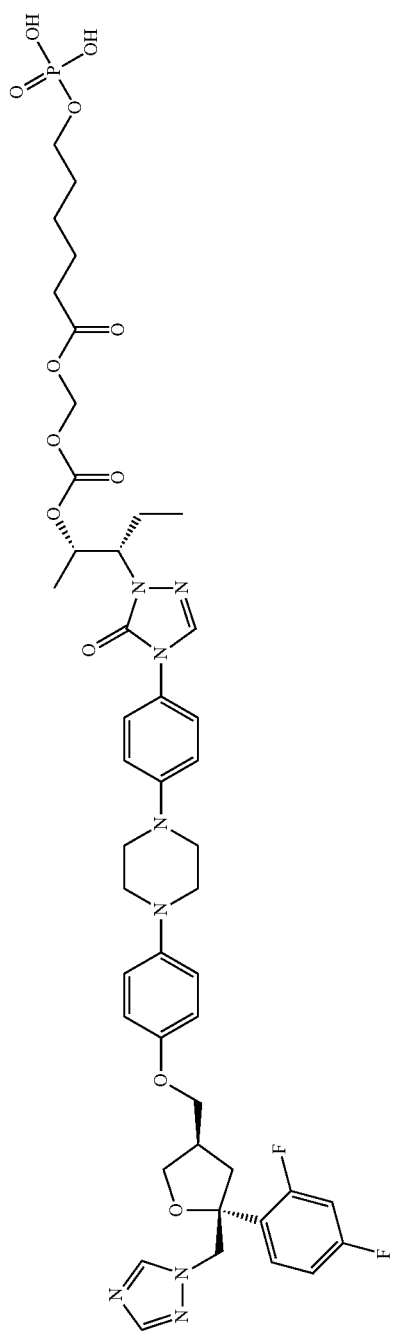 |

-continued
| No. | Structure |
|---|---|
| 0074 | 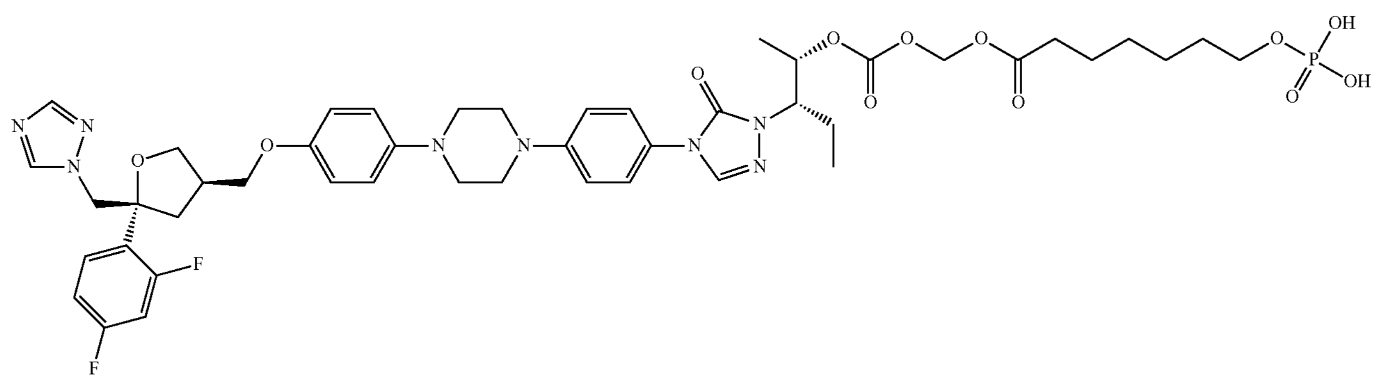 [SMILES: CC[C@@H]([C@H](C)OC(=O)OCOC(=O)CCCCCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0075 | 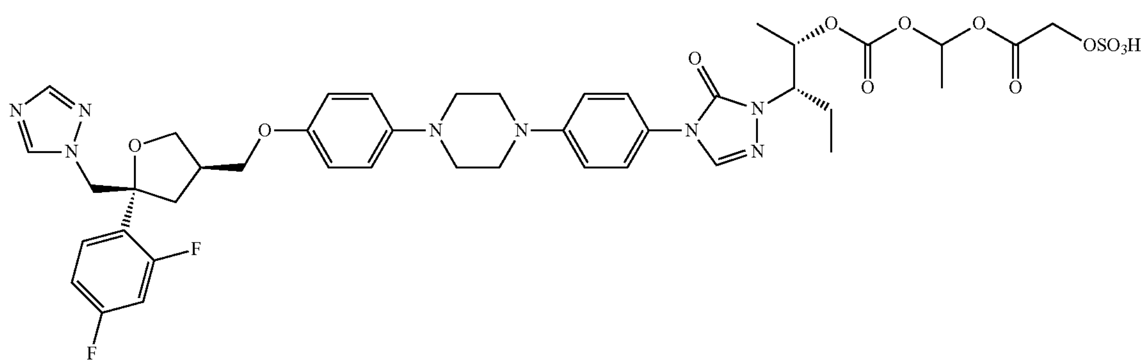 |
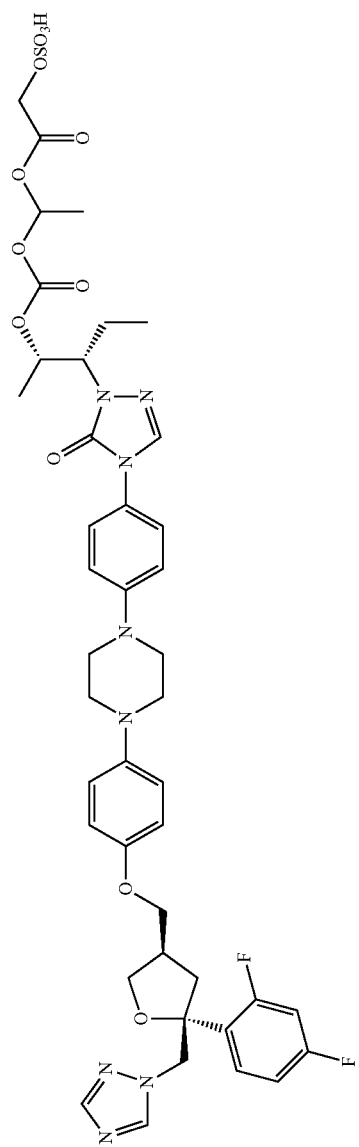

-continued
| No. | Structure |
|---|---|
| 0076 | 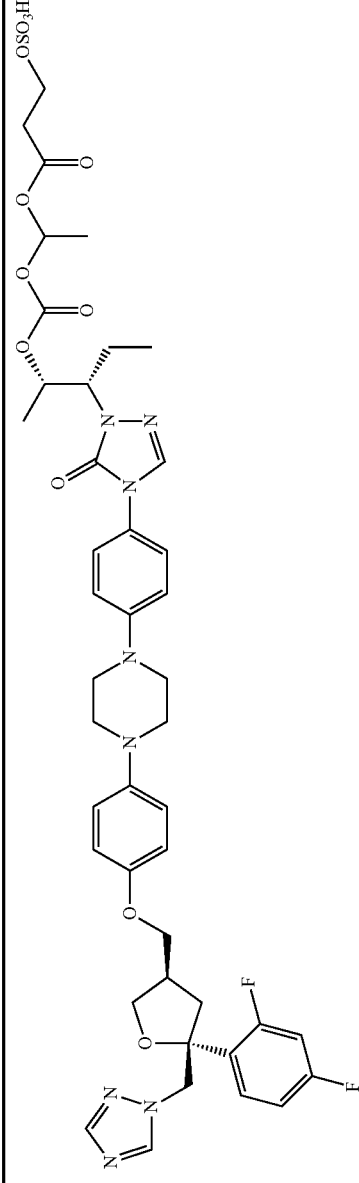 |
| 0077 | 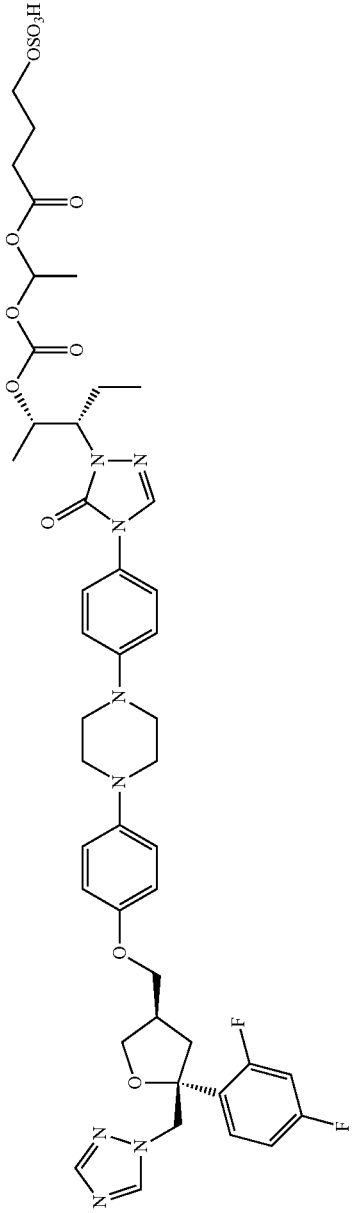 |
| 0078 | 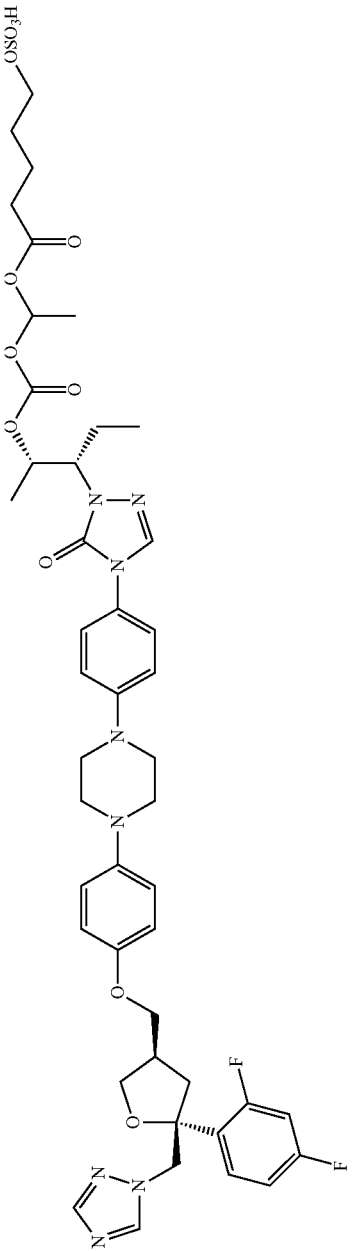 |

-continued
| No. | Structure |
|---|---|
| 0079 | 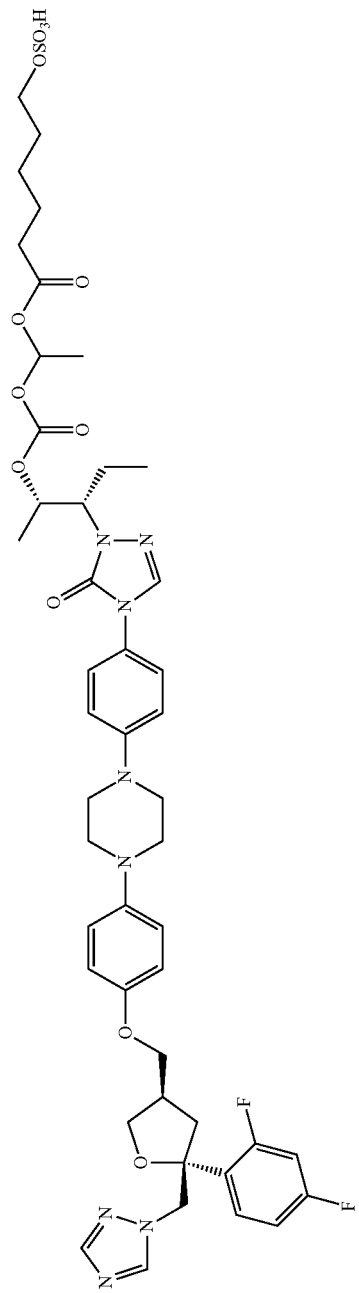 |
| 0080 | 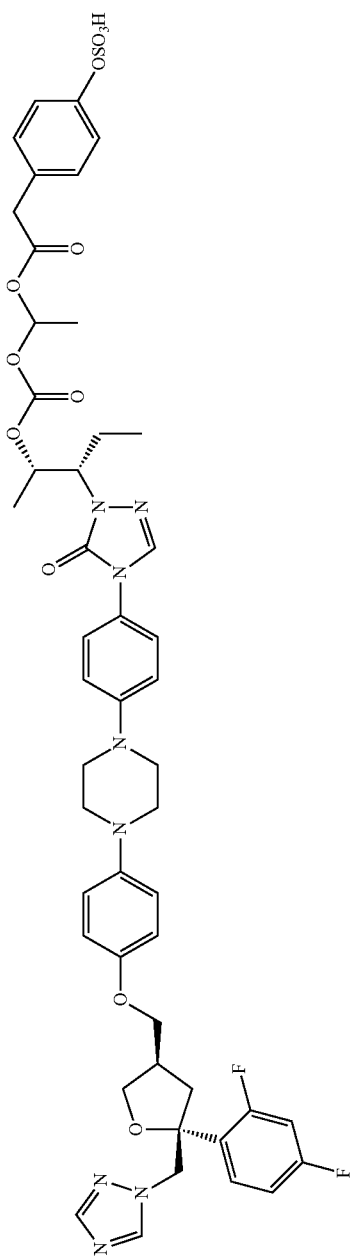 |

| No. | Structure |
|---|---|
| 0081 | (structure) |
| 0082 | (structure) |
| 0083 | (structure) |

| No. | Structure |
|---|---|
| 0084 | *(chemical structure)* |
| 0085 | *(chemical structure)* |

| No. | Structure |
|---|---|
| 0086 | 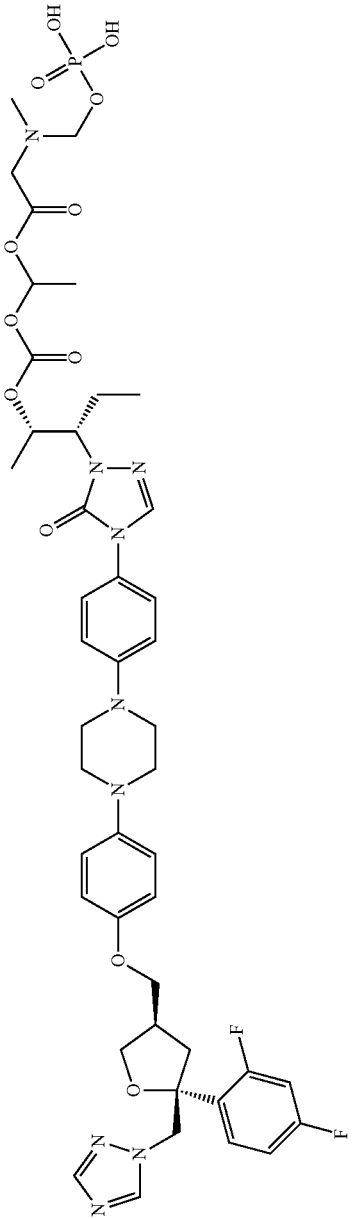 |
| 0087 | 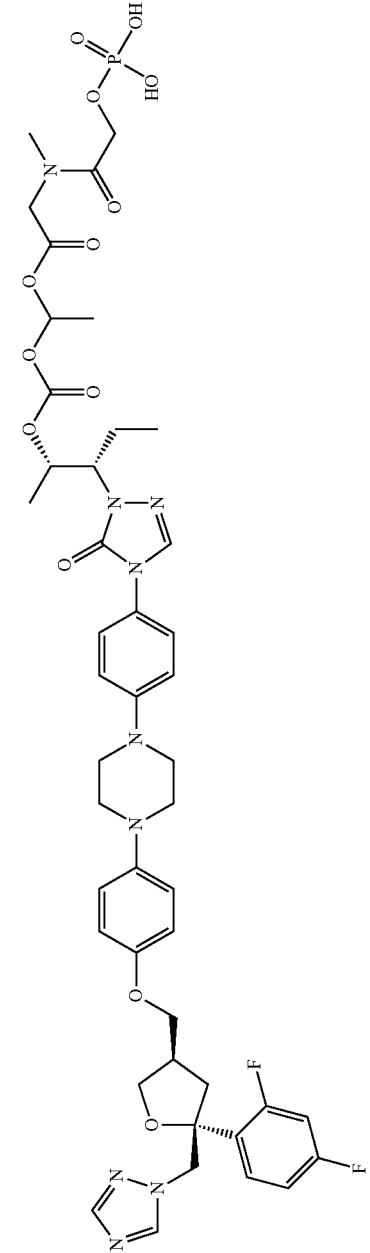 |
| 0088 | 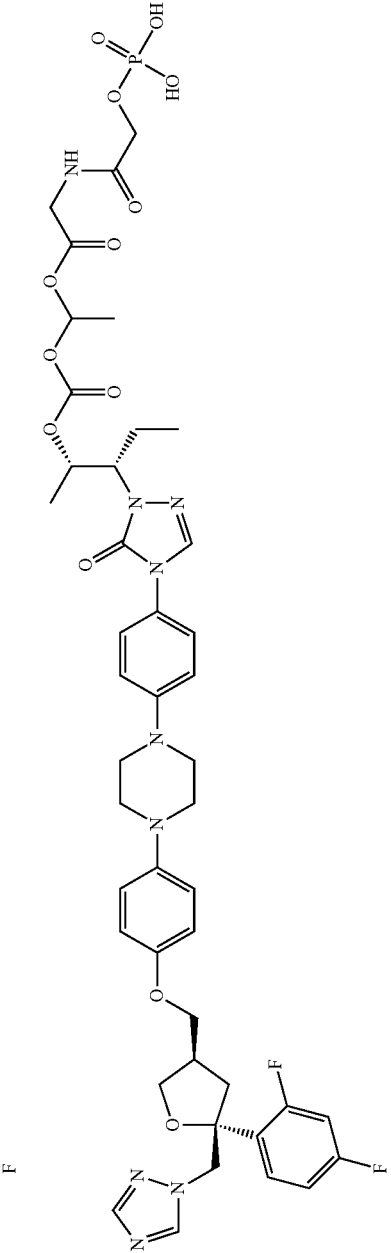 |

-continued
| No. | Structure |
|---|---|
| 0089 | 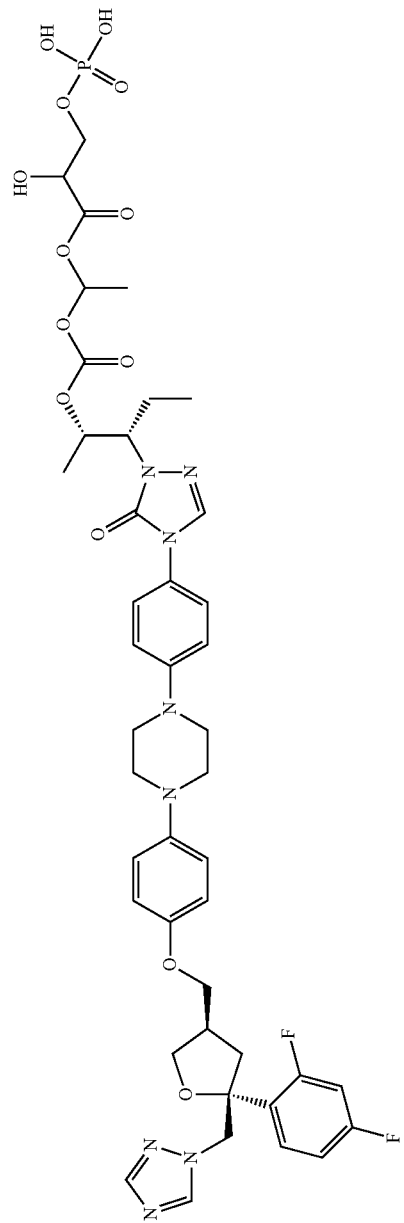 |
| 0090 | 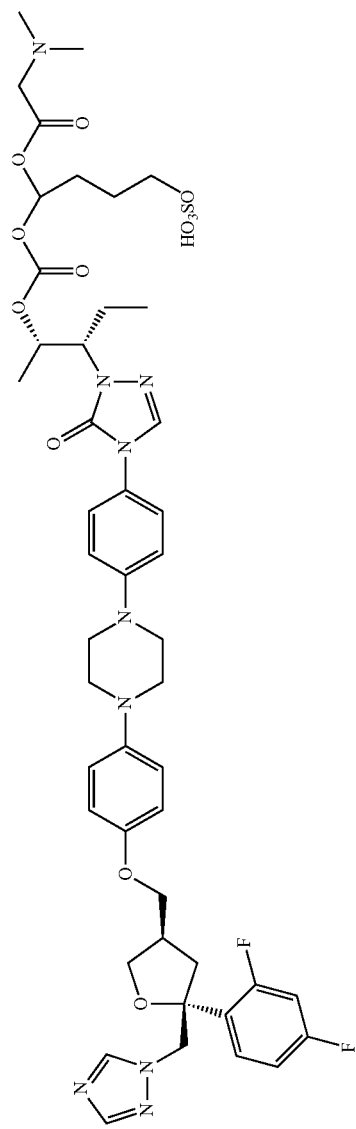 |

| No. | Structure |
|---|---|
| 0091 | 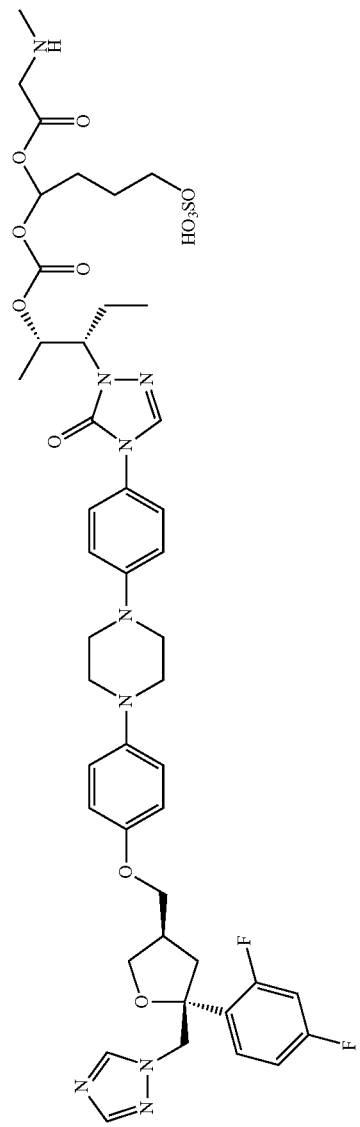 |
| 0092 | 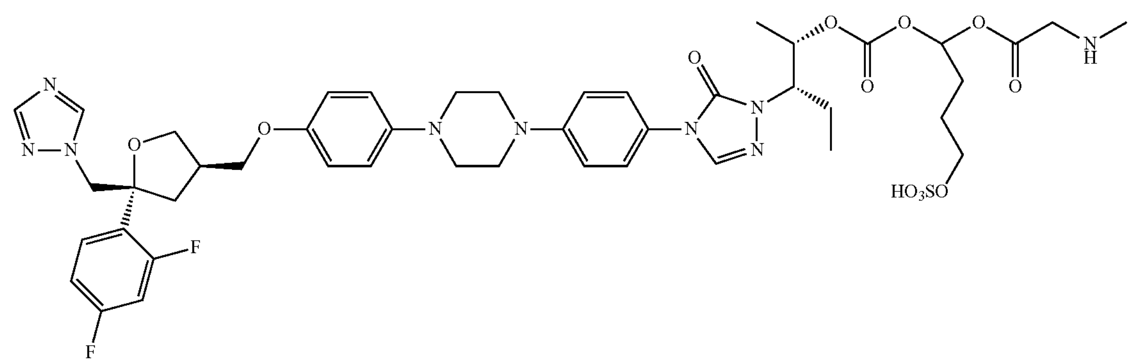 |

-continued
| No. | Structure |
|---|---|
| 0093 | 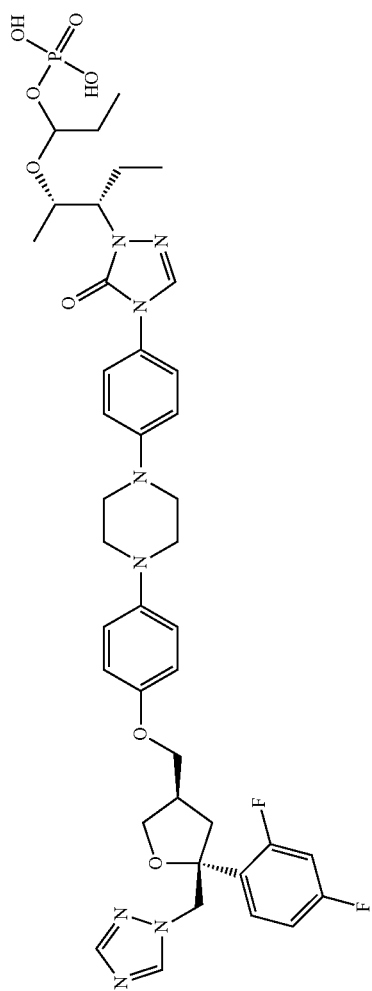 |
| 0094 | 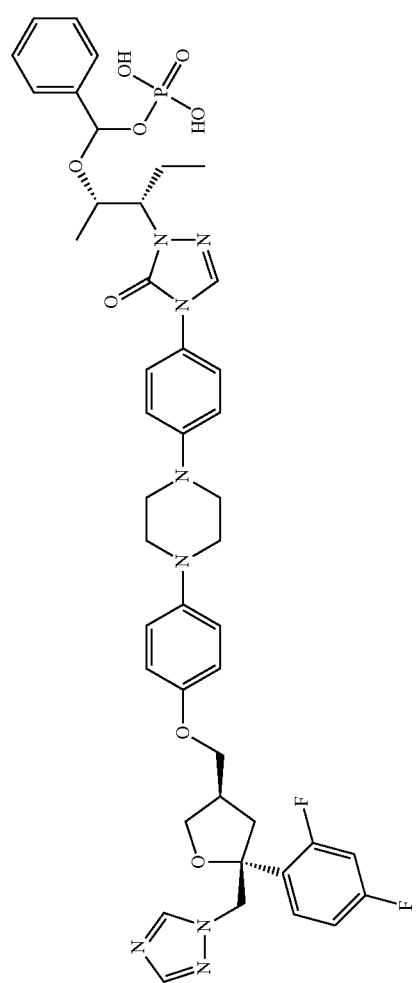 |

| No. | Structure |
|---|---|
| 0095 | 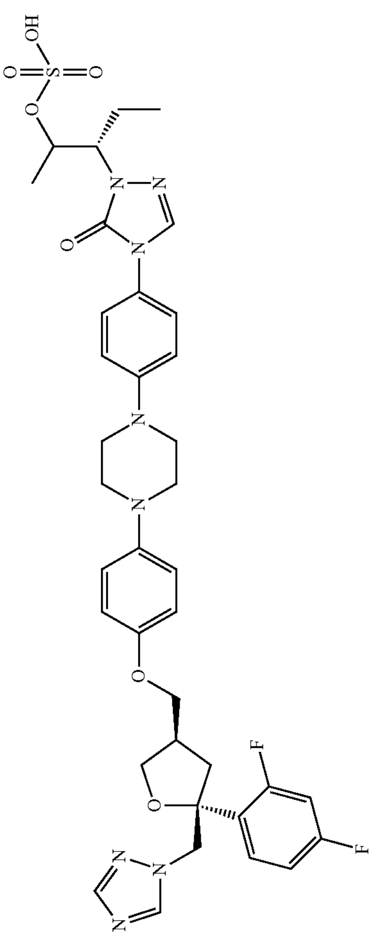 |
| 0096 | 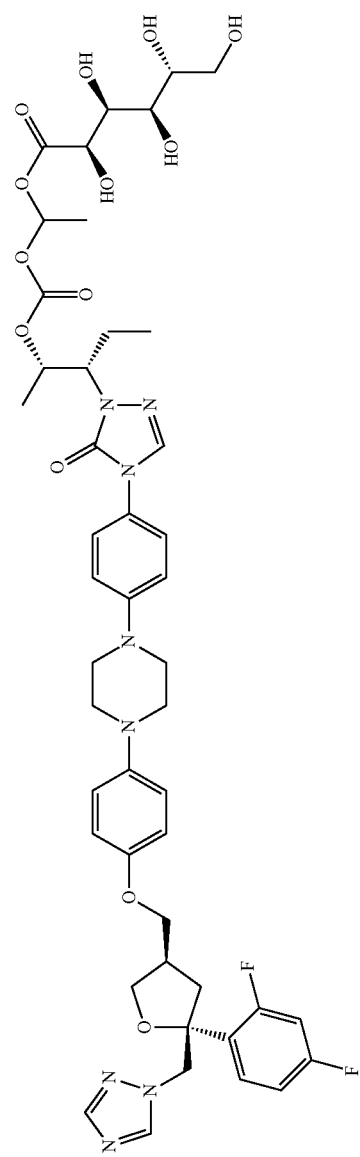 |

-continued
| No. | Structure |
|---|---|
| 0097 | 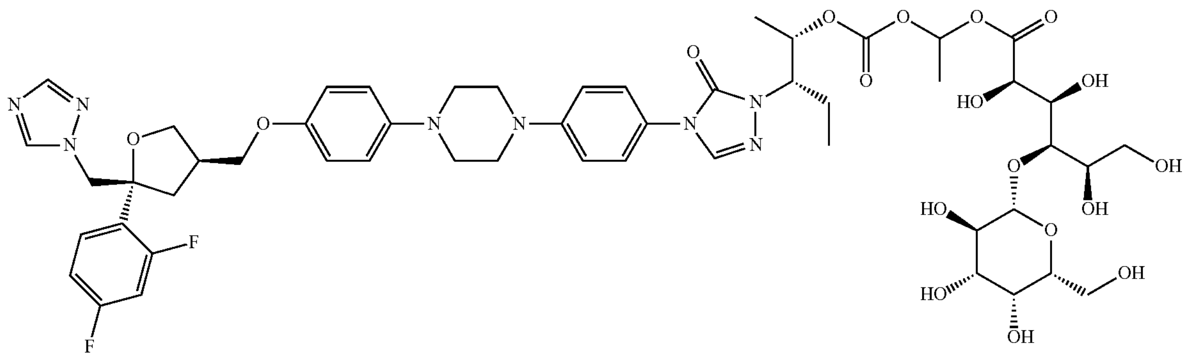 [SMILES: CC[C@@H]([C@H](C)OC(=O)OC(C)OC(=O)[C@H](O)[C@@H](O)[C@H](O[C@@H]1O[C@H](CO)[C@H](O)[C@H](O)[C@H]1O)[C@H](O)CO)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0098 | 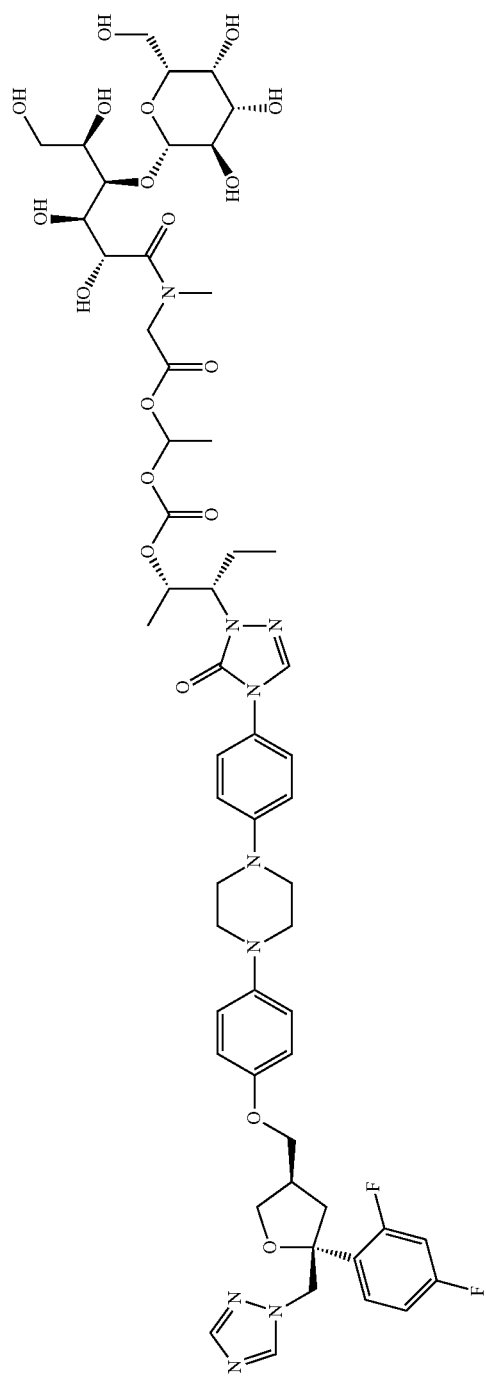 |

| No. | Structure |
|---|---|
| 0099 | *-continued* (chemical structure) |
| 0100 | (chemical structure) |

The pharmaceutically acceptable salts of the above compounds can be an acidic salt or a basic salt. For example, the salts can be hydrochloride, sulfate, nitrate, phosphate, or salts formed by the compounds with sodium ion, potassium ion, ammonium ion, or the like. Specifically, the salts can be listed as follows.

| No. | Structure formula |
|---|---|
| ST0001 | 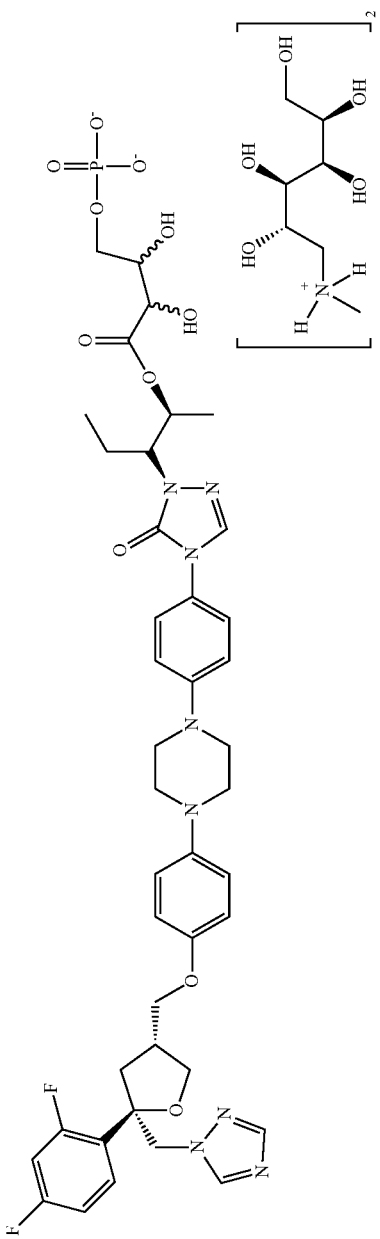 |
| ST0002 | 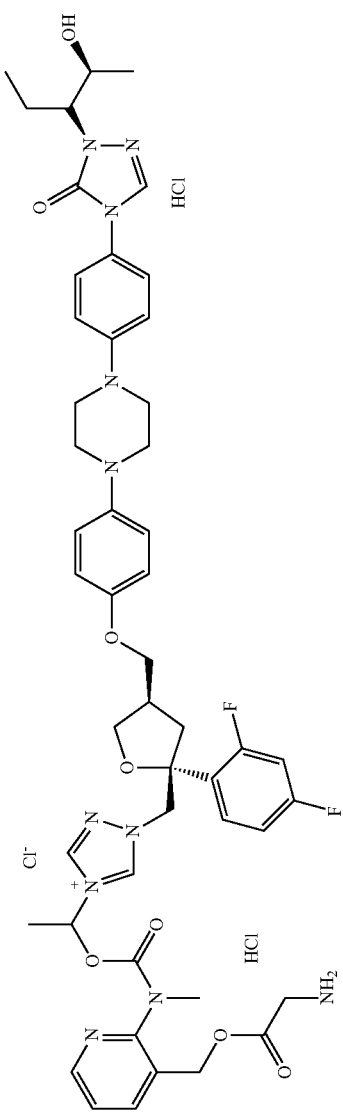 |

-continued
| No. | Structure formula |
|---|---|
| ST0003 | 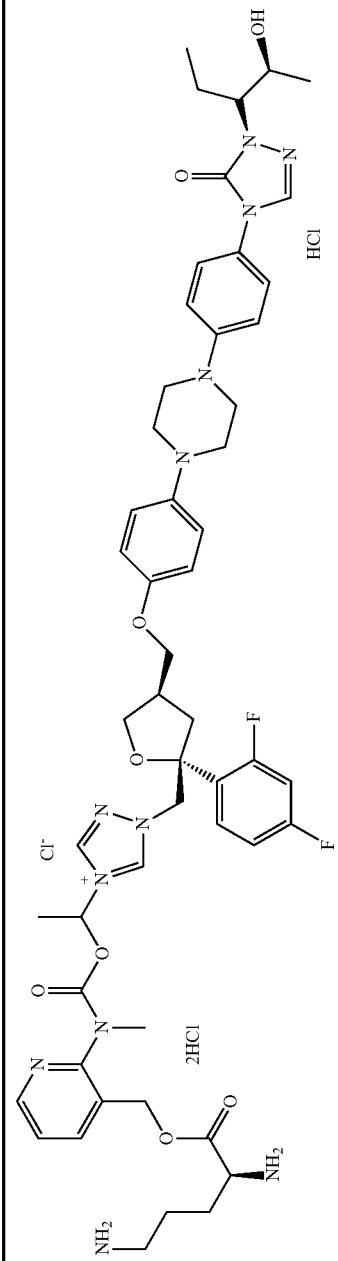 |
| ST0004 | 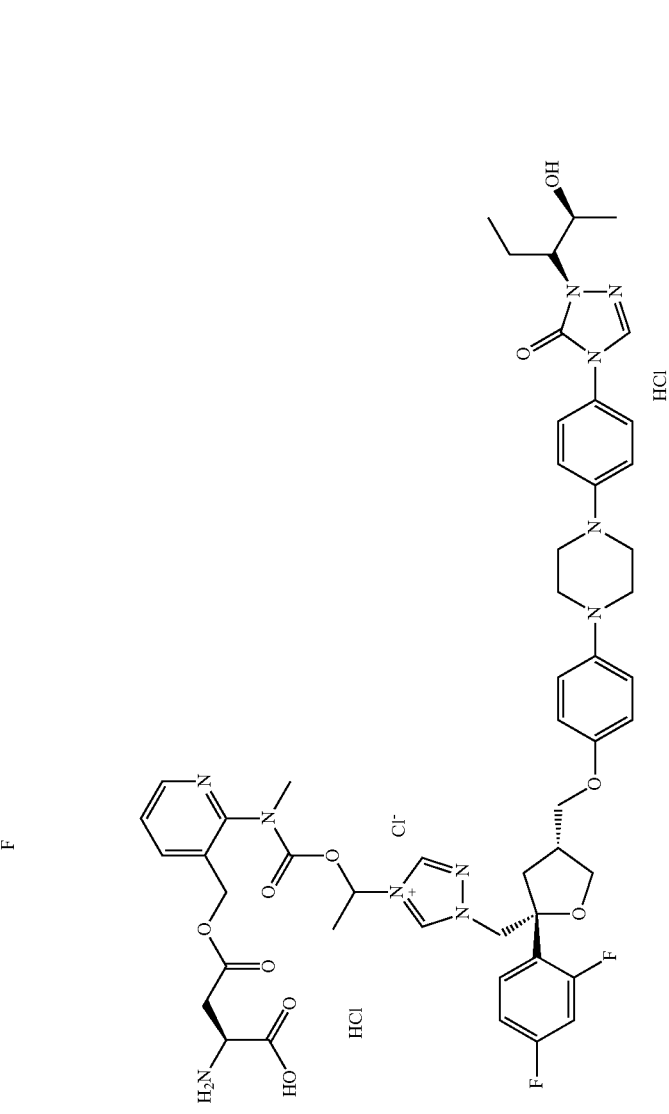 |

-continued
| No. | Structure formula |
|---|---|
| ST0005 | 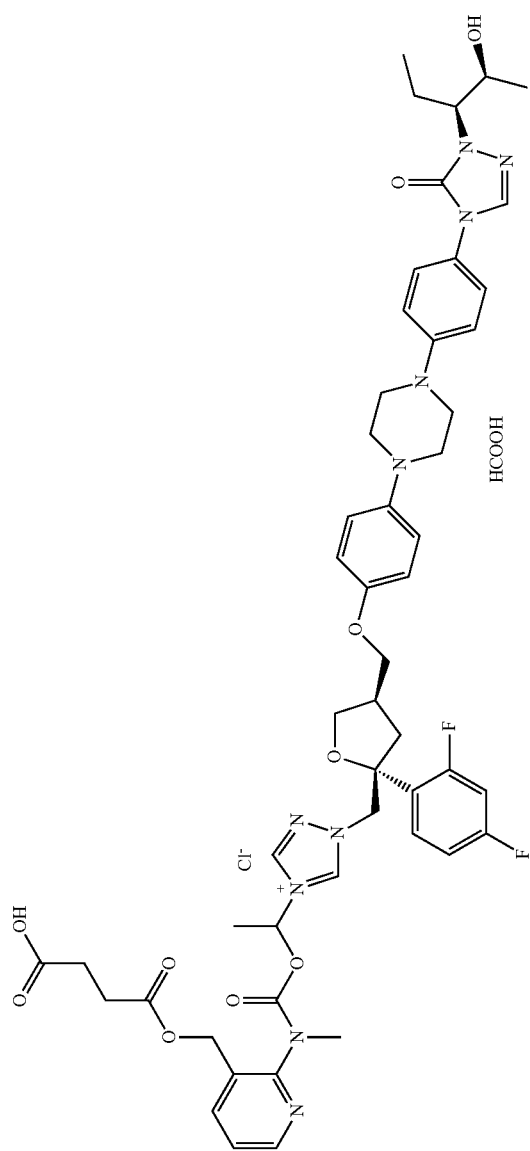 |

-continued
| No. | Structure formula |
|---|---|
| ST0006 | 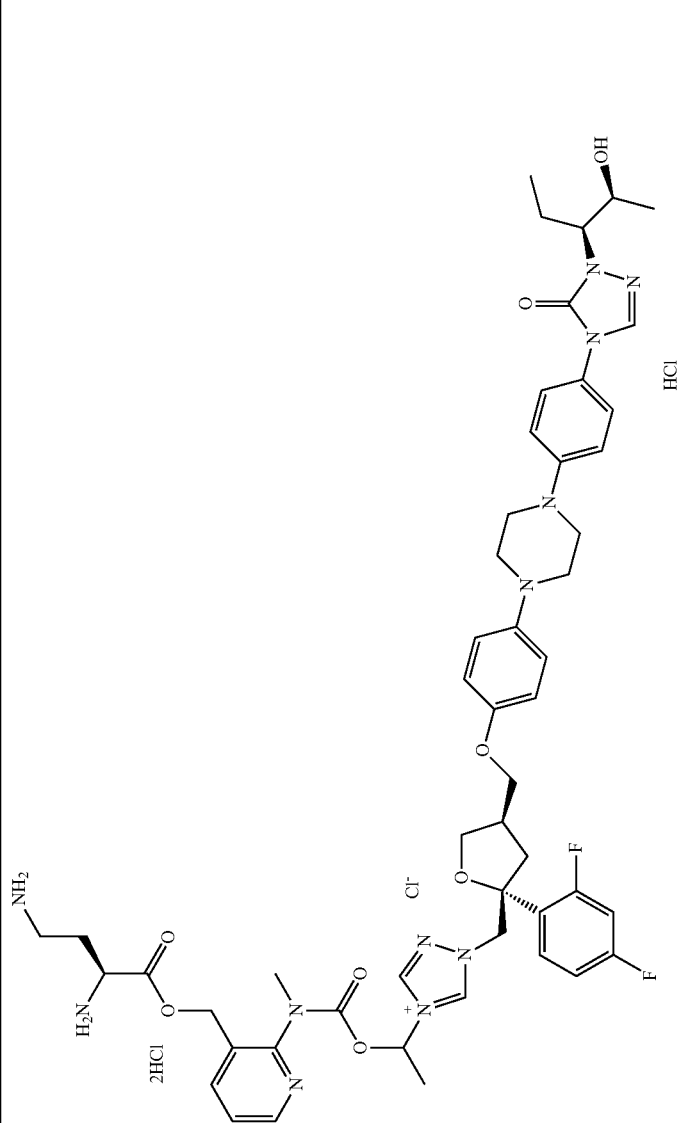 |
| ST0007 | 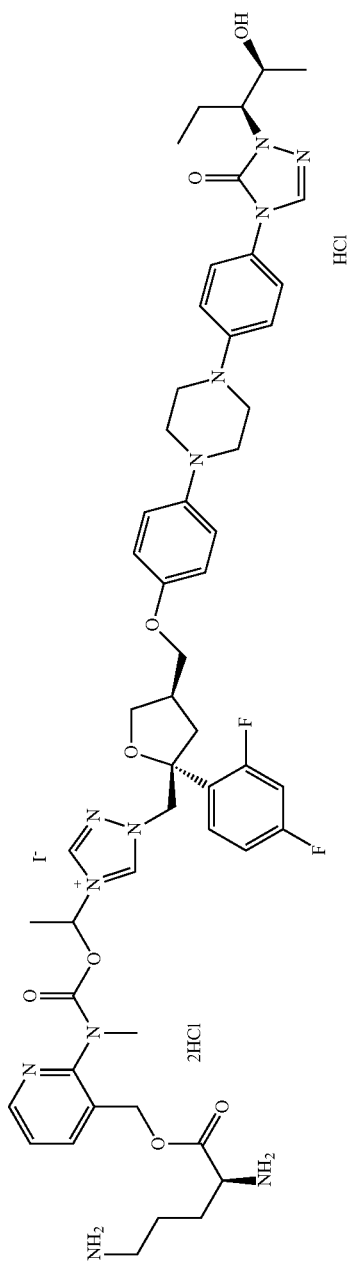 |

-continued

| No. | Structure formula |
|---|---|
| ST0008 | (structure) |
| ST0009 | (structure) |
| ST0010 | (structure) |

-continued

| No. | Structure formula |
|---|---|
| ST0011 | |
| ST0012 | |
| ST0013 | |

-continued
| No. | Structure formula |
|---|---|
| ST0014 | 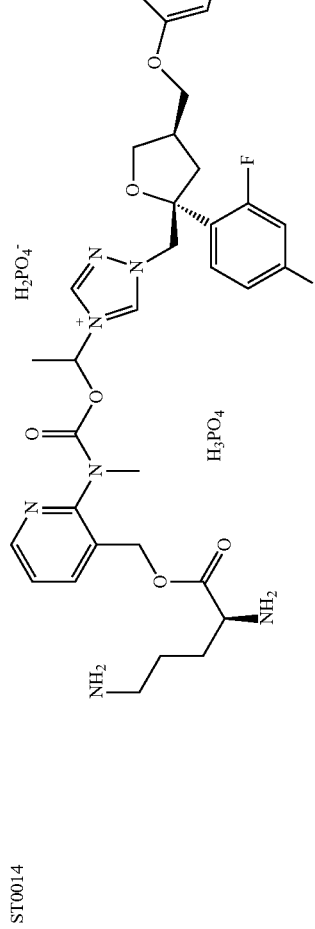 |
| ST0015 | 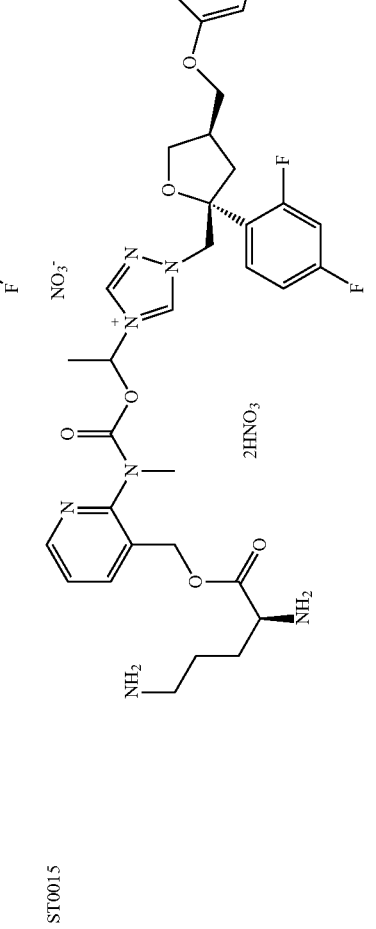 |
| ST0016 | 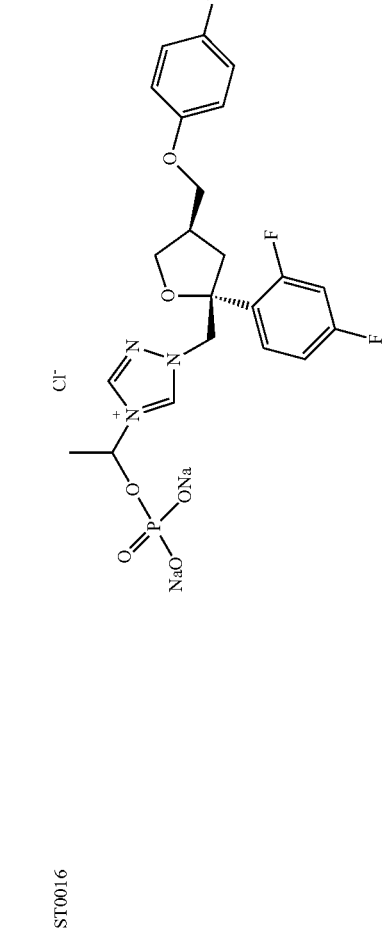 |

-continued
| No. | Structure formula |
|---|---|
| ST0017 | 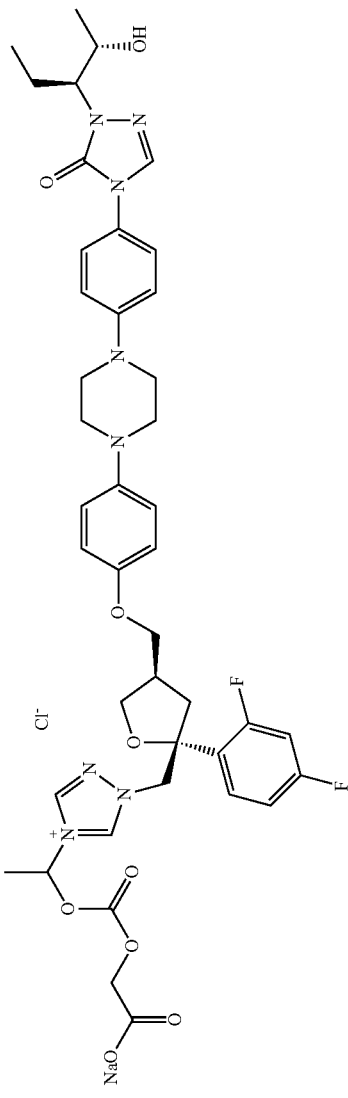 |
| ST0018 | |

| No. | Structure formula |
|---|---|
| ST0019 | 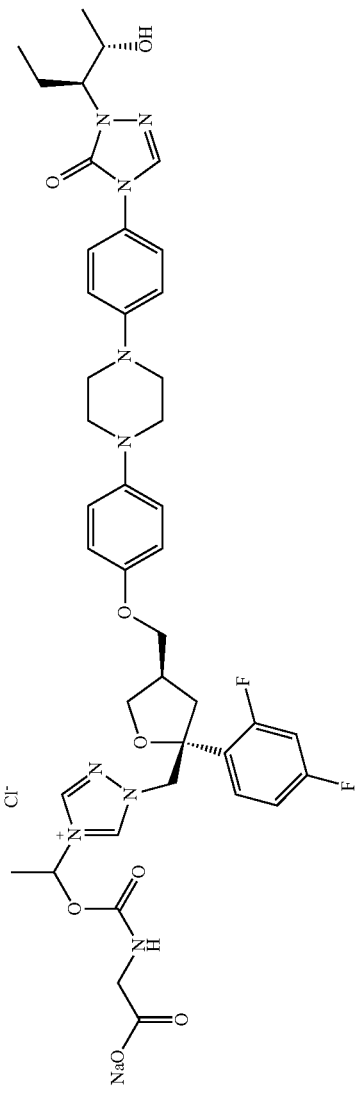 |
| ST0020 | 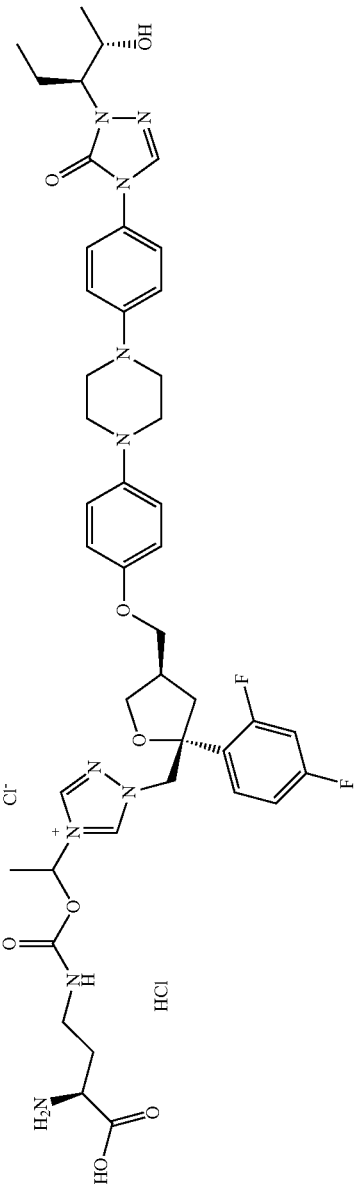 |

-continued
| No. | Structure formula |
|---|---|
| ST0021 | 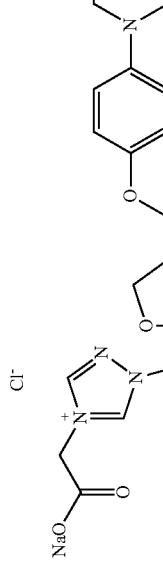 |
| ST0022 | 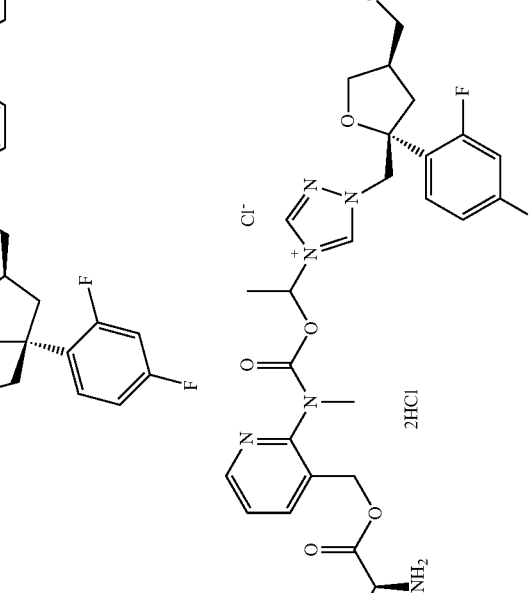 |
| ST0023 | 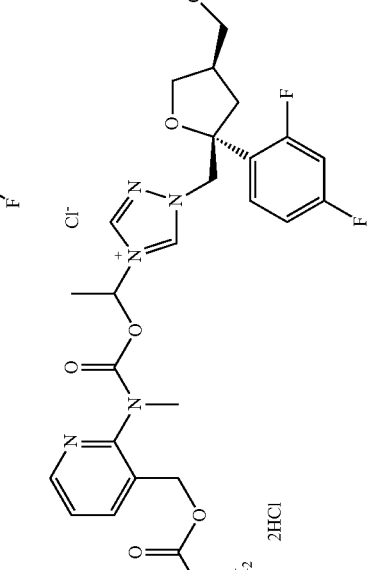 |

-continued

| No. | Structure formula |
|---|---|
| ST0024 | (structure, 3HCl) |
| ST0025 | (structure, 2HCl) |
| ST0026 | (structure, 2HCl) |

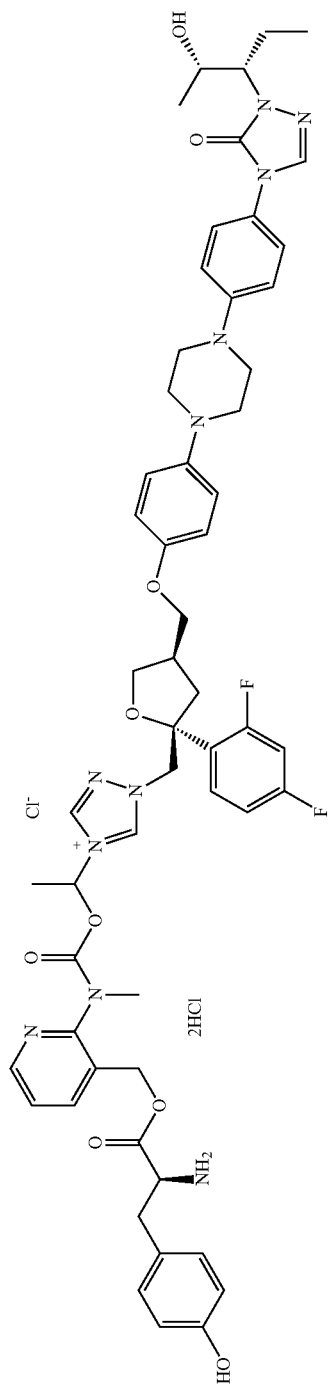

-continued

| No. | Structure formula |
|---|---|
| ST0029 | |
| ST0030 | |

-continued
| No. | Structure formula |
|---|---|
| ST0031 | 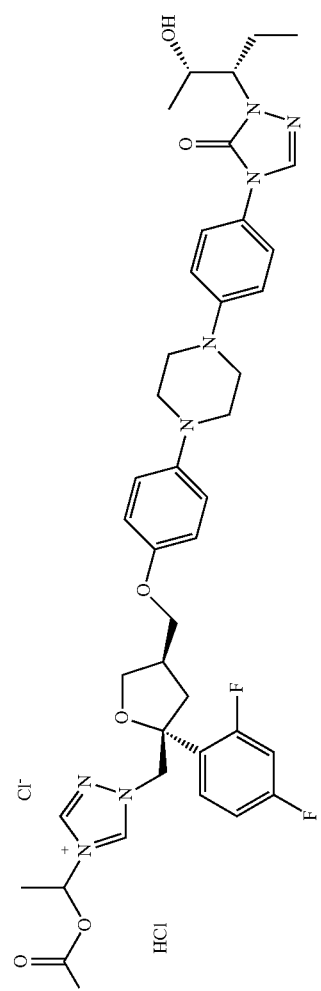 |
| ST0032 | 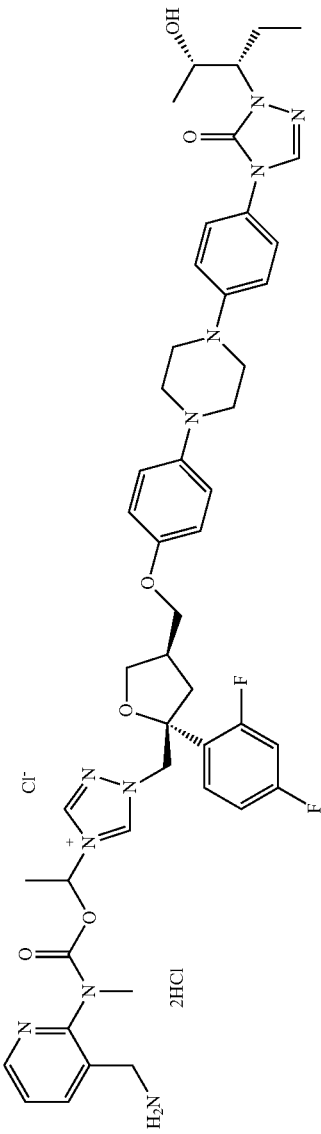 |
| ST0033 | 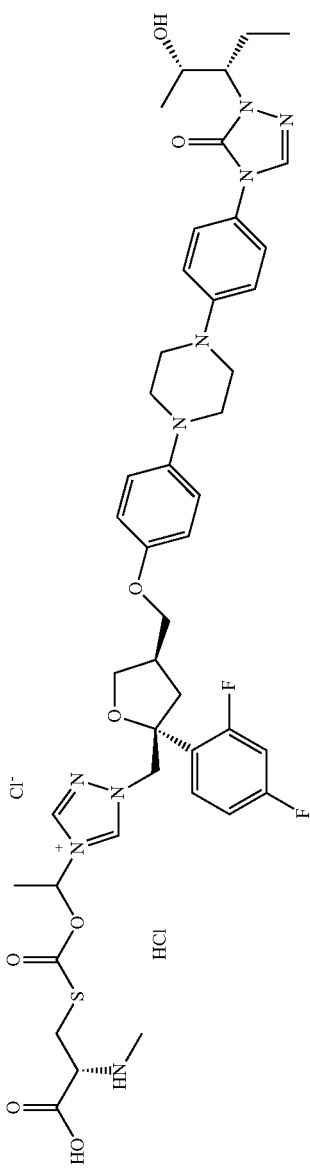 |

| No. | Structure formula |
|---|---|
| ST0034 | |
| ST0037 | |
| ST0038 | |

-continued

| No. | Structure formula |
|---|---|
| ST0039 | |
| ST0040 | 3HCl |
| ST0041 | |

-continued
| No. | Structure formula |
|---|---|
| ST0042 | 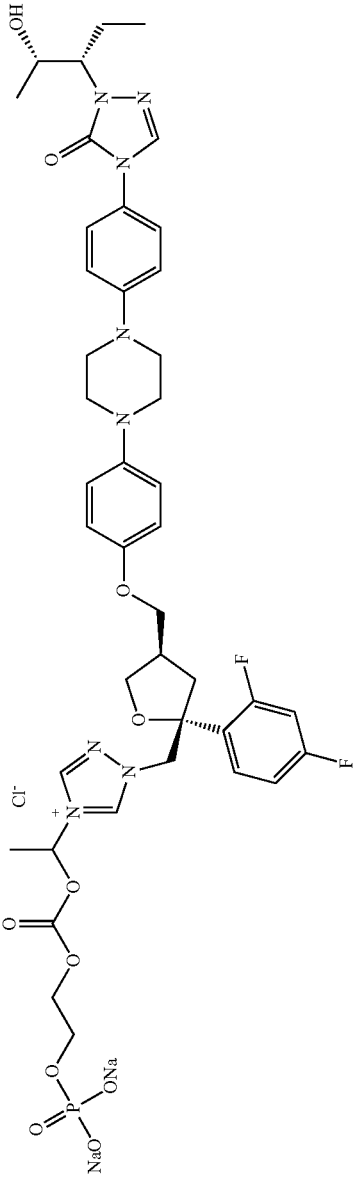 |
| ST0043 | 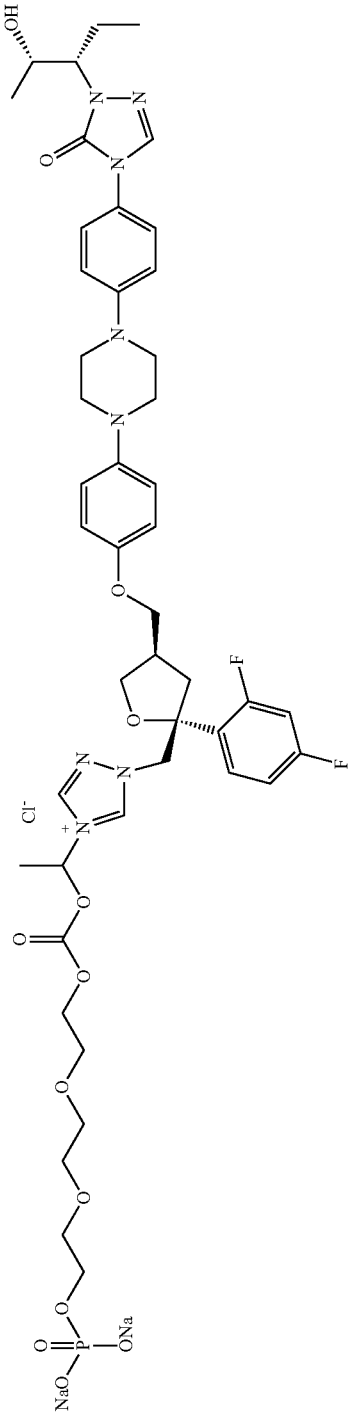 |

| No. | Structure formula |
|---|---|
| ST0044 | 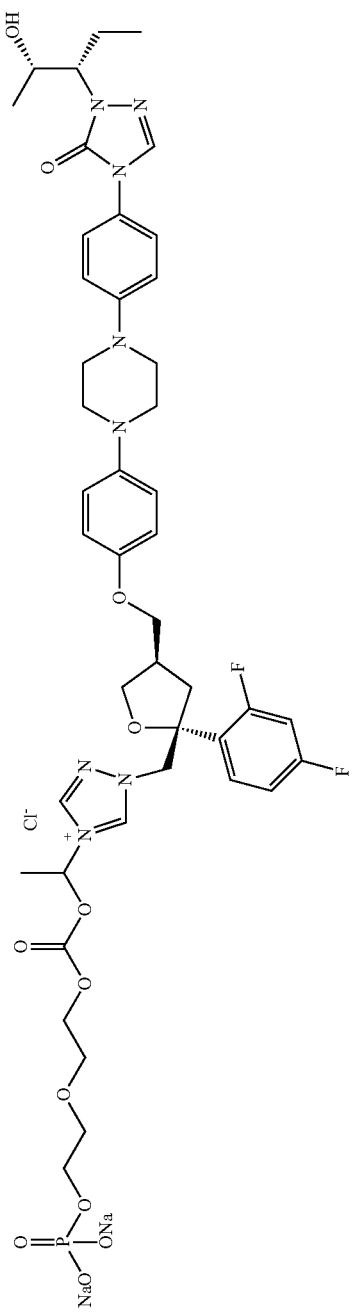 |
| ST0045 | 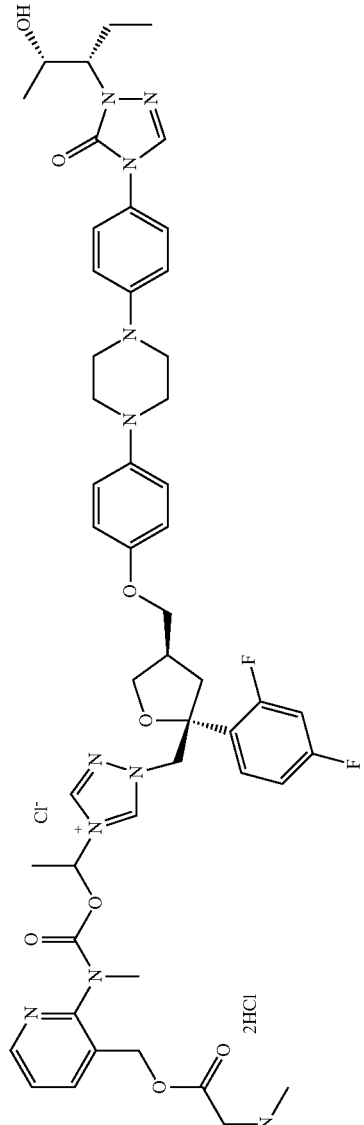 |
| ST0046 | 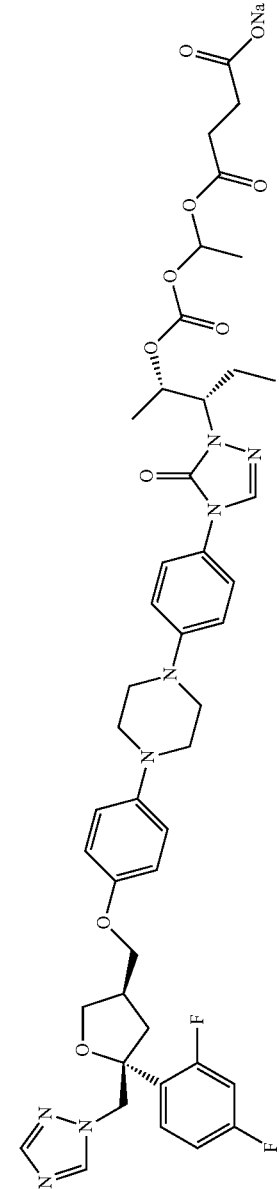 |

-continued
| No. | Structure formula |
|---|---|
| ST0047 | 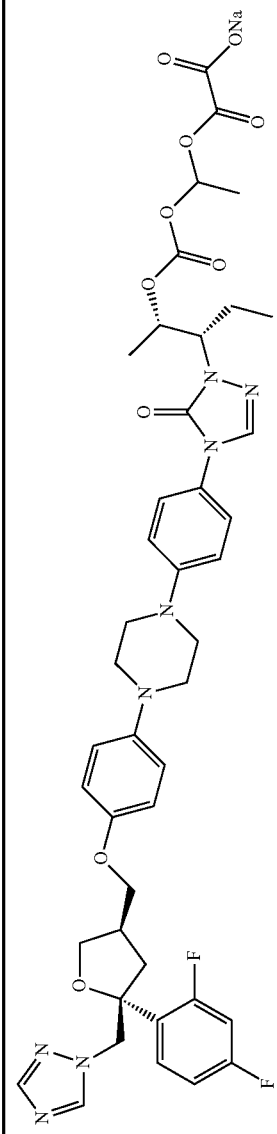 |
| ST0048 | 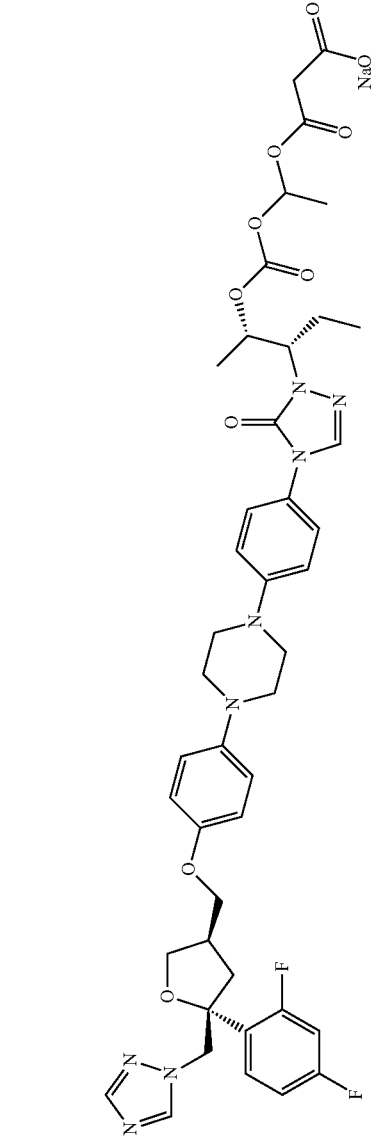 |
| ST0049 | 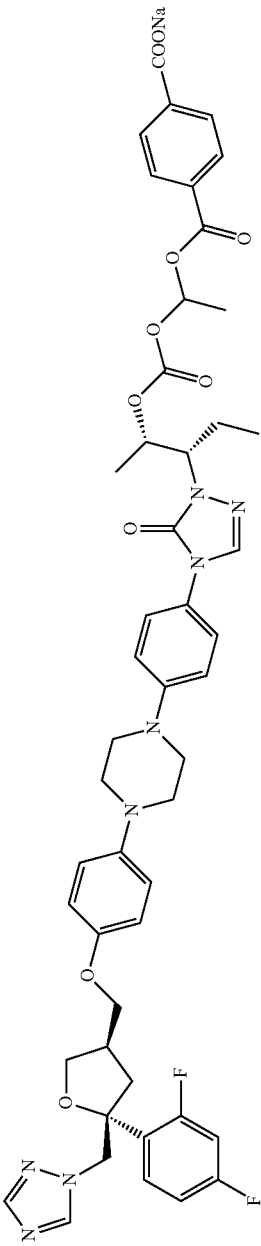 |

-continued
| No. | Structure formula |
|---|---|
| ST0050 | 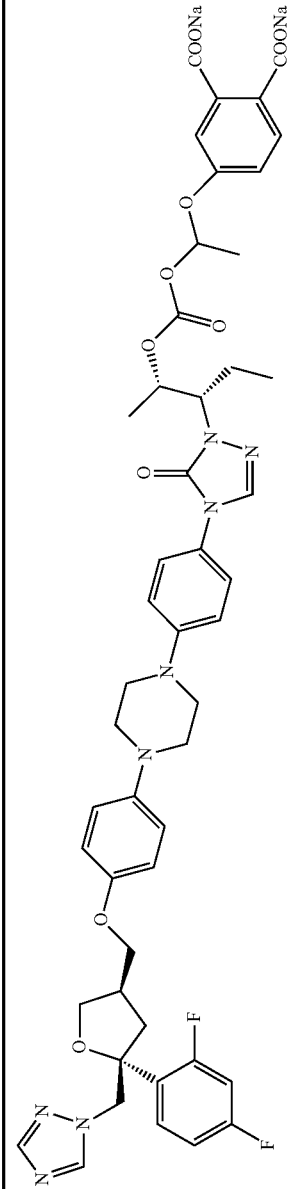 |
| ST0052 | 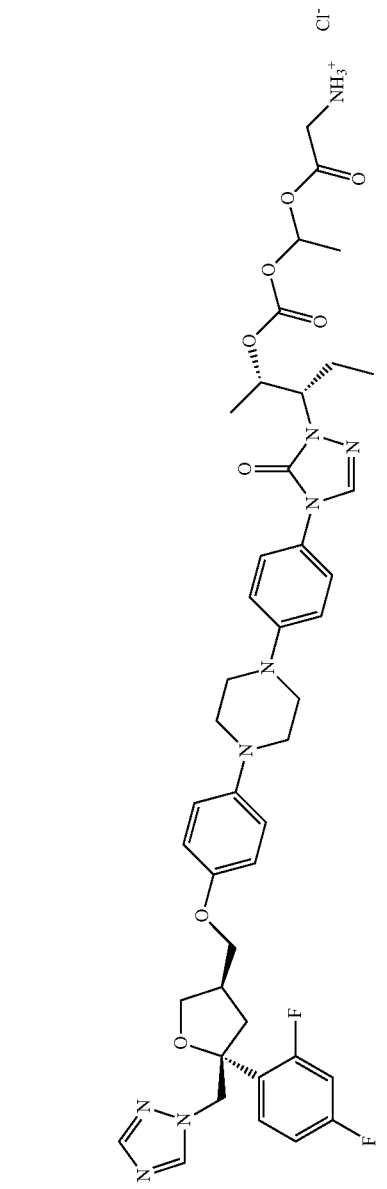 |
| ST0053 | 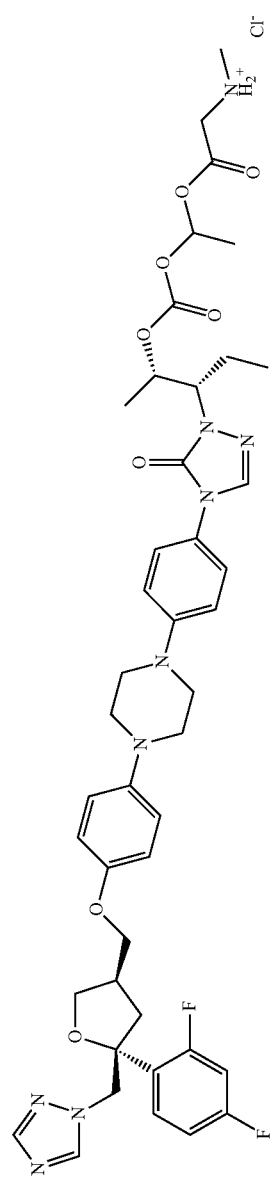 |

-continued

| No. | Structure formula |
|---|---|
| ST0054 | |
| ST0055 | |
| ST0056 | |

-continued
| No. | Structure formula |
|---|---|
| ST0057 | 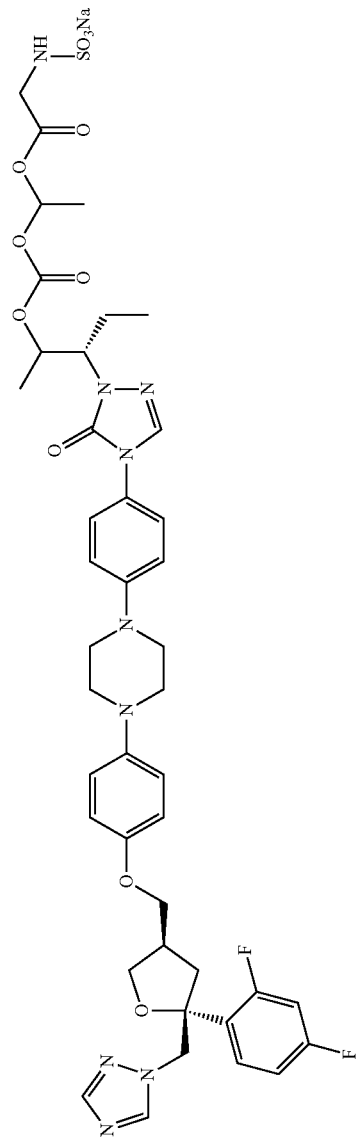 |
| ST0058 | |

| No. | Structure formula |
|---|---|
| ST0059 | 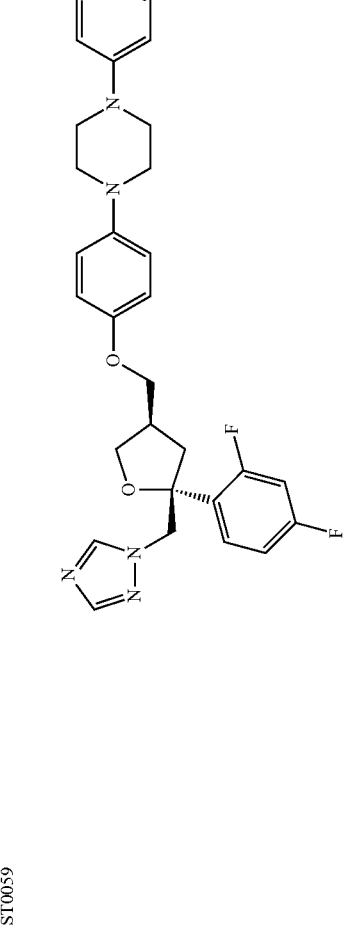 |
| ST0060 | 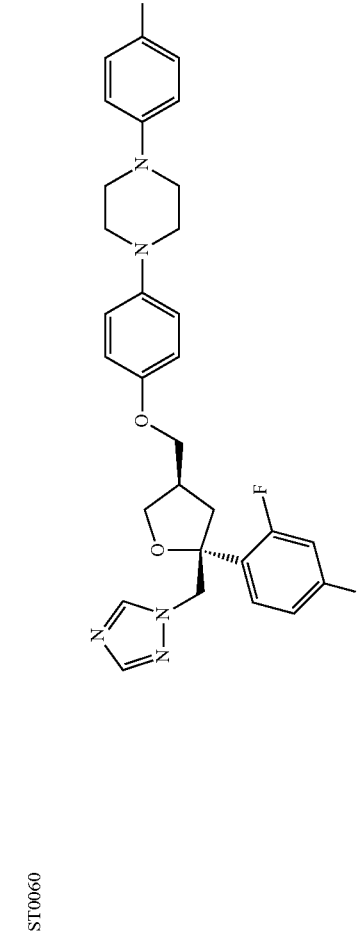 |
| ST0061 | 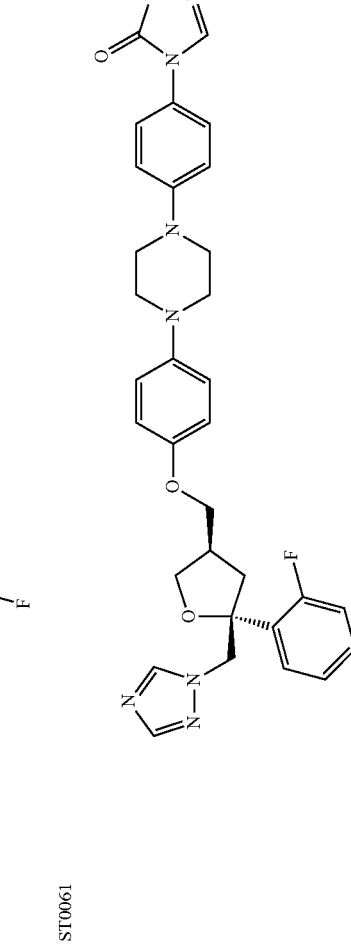 |

| No. | Structure formula |
|---|---|
| ST0062 | 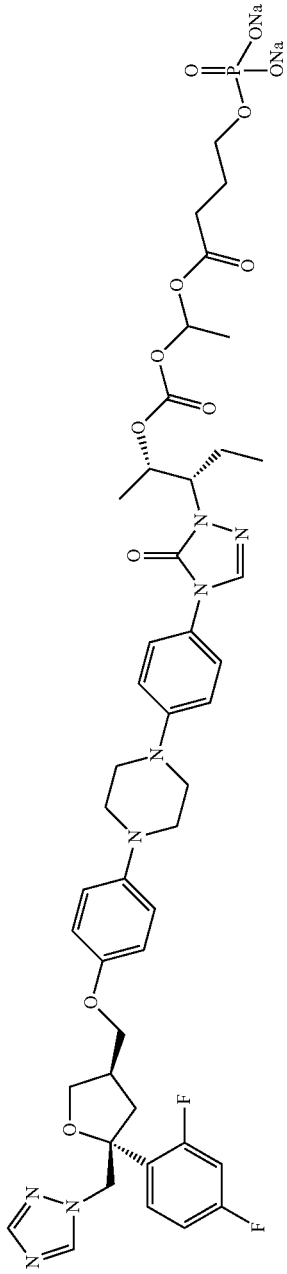 |
| ST0063 | 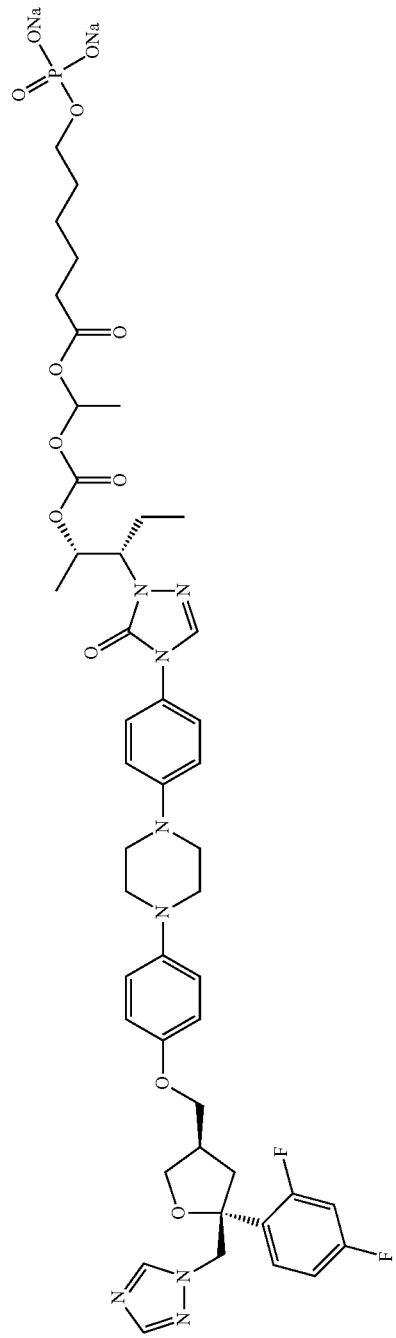 |

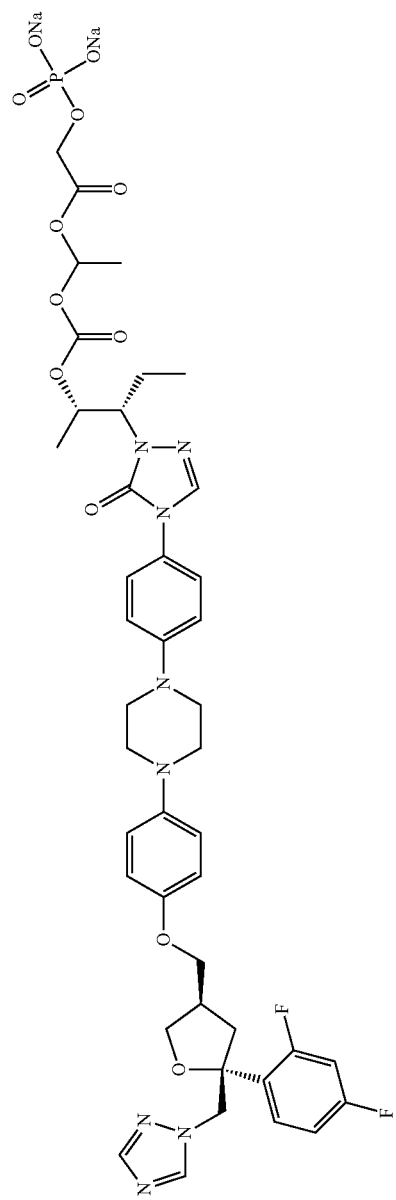

-continued
| No. | Structure formula |
|---|---|
| ST0066 | 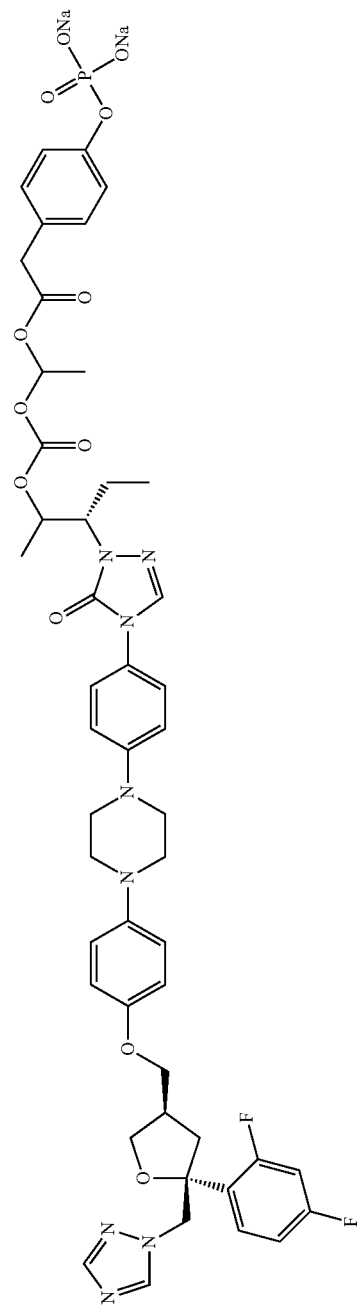 |
| ST0067 | |

-continued
| No. | Structure formula |
|---|---|
| ST0068 | 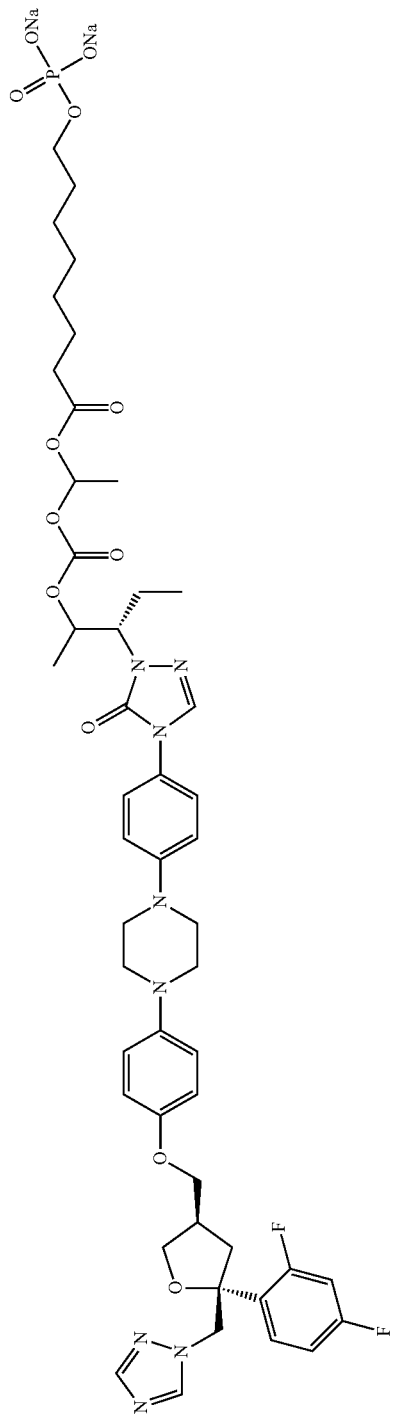 |
| ST0069 | |

-continued
| No. | Structure formula |
|---|---|
| ST0070 | 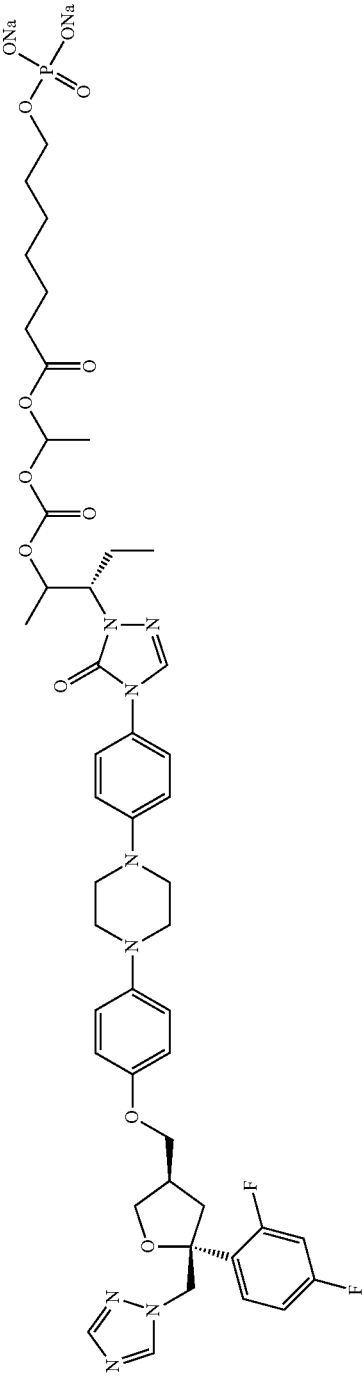 |
| ST0071 | 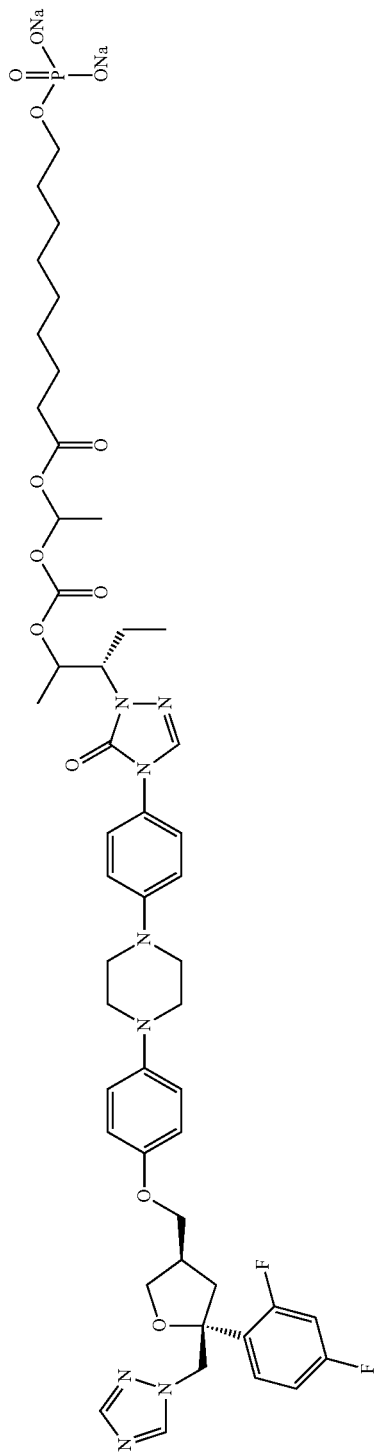 |

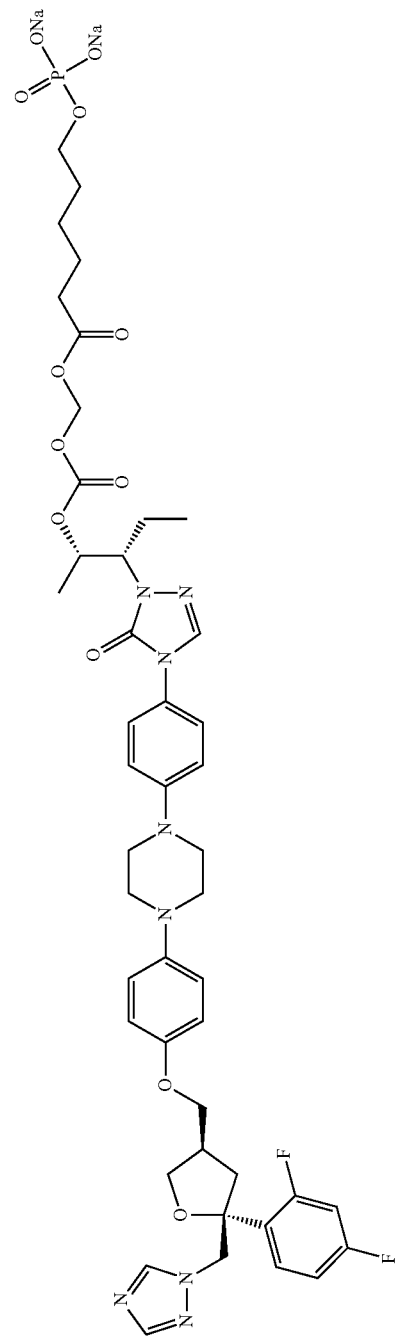

| No. | Structure formula |
|---|---|
| ST0074 | 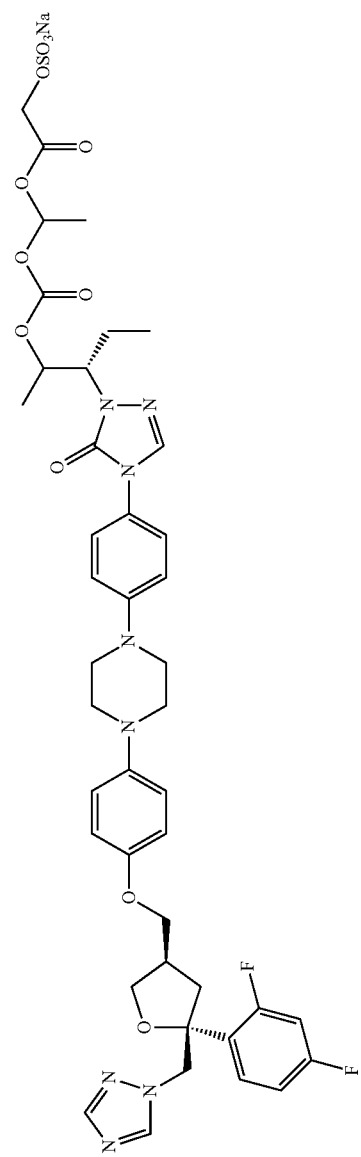 |
| ST0075 | |

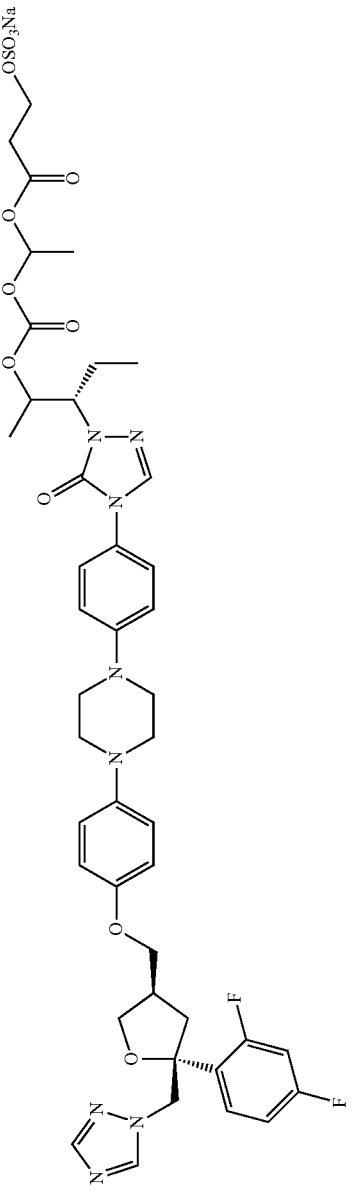

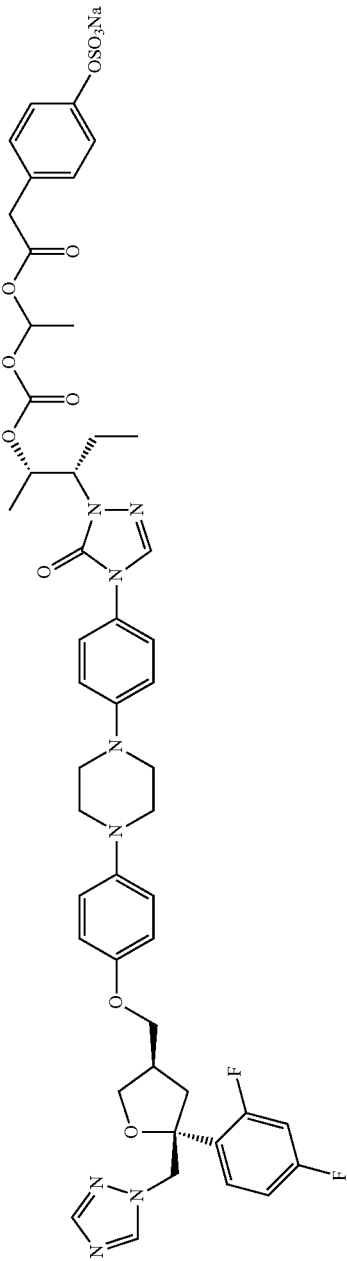

| No. | Structure formula |
|---|---|
| ST0082 | 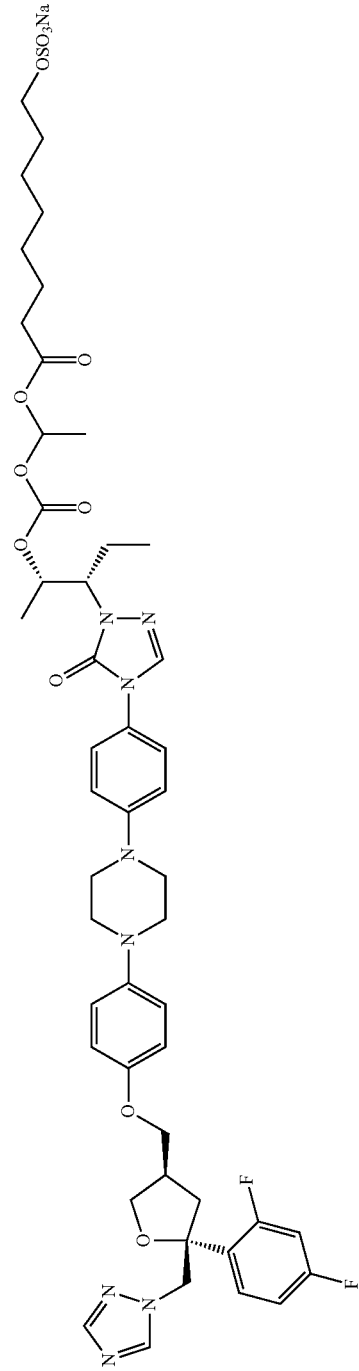 |
| ST0083 | 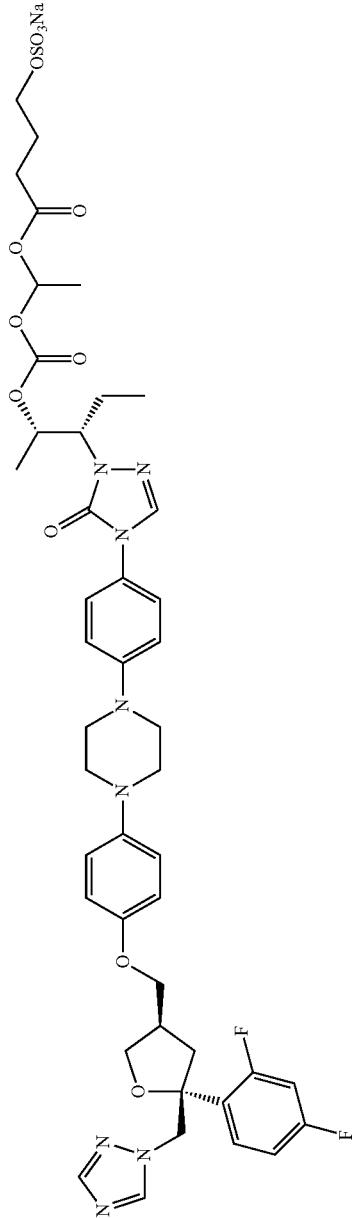 |

-continued
| No. | Structure formula |
|---|---|
| ST0084 | 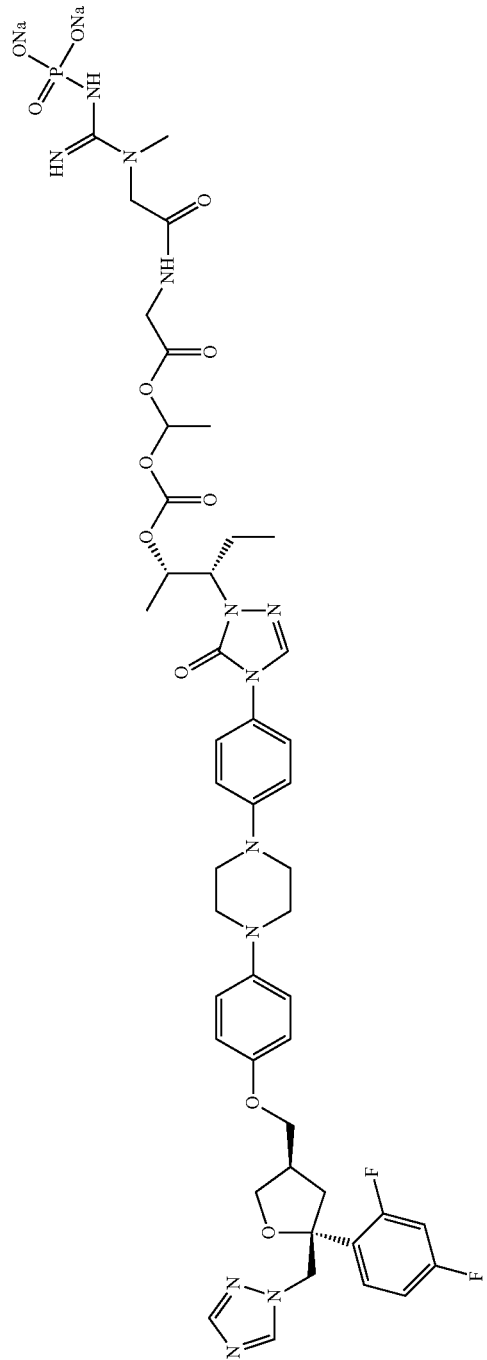 |
| ST0085 | |
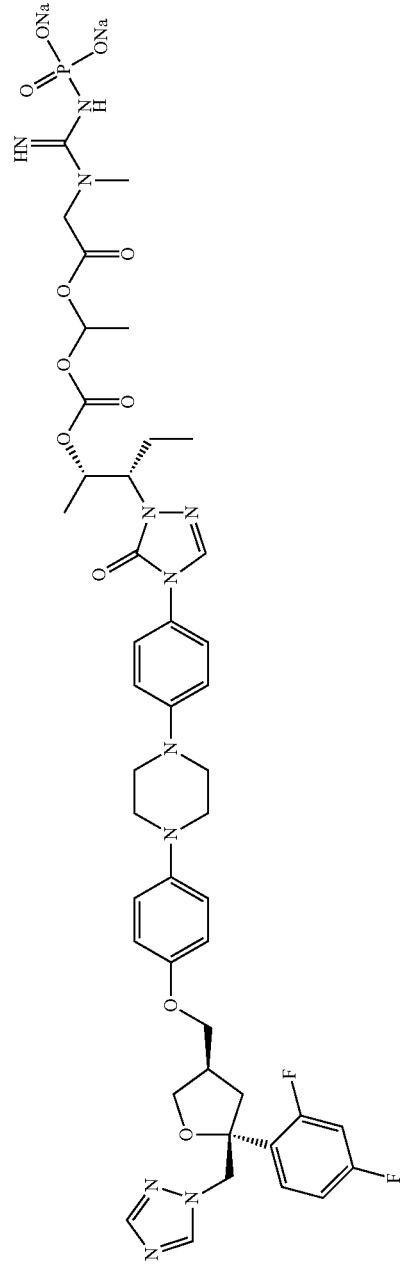

-continued
| No. | Structure formula |
|---|---|
| ST0086 | 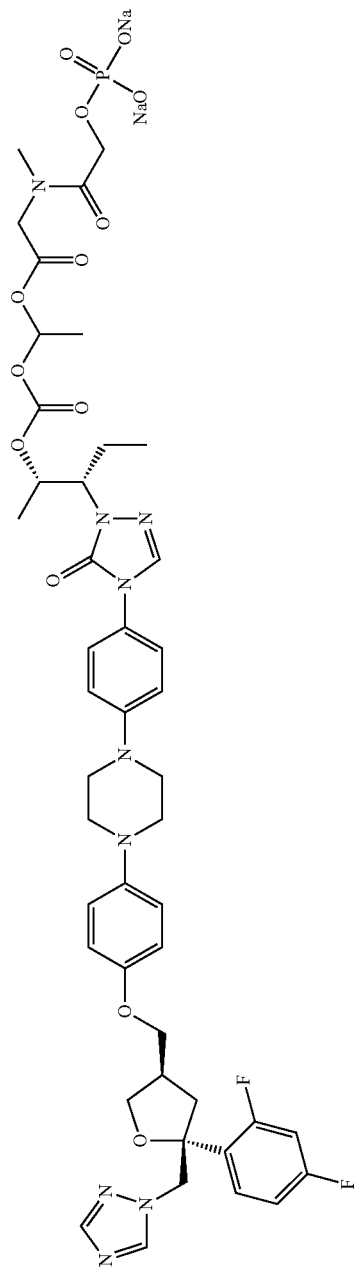 |
| ST0087 | |

-continued
| No. | Structure formula |
|---|---|
| ST0088 | 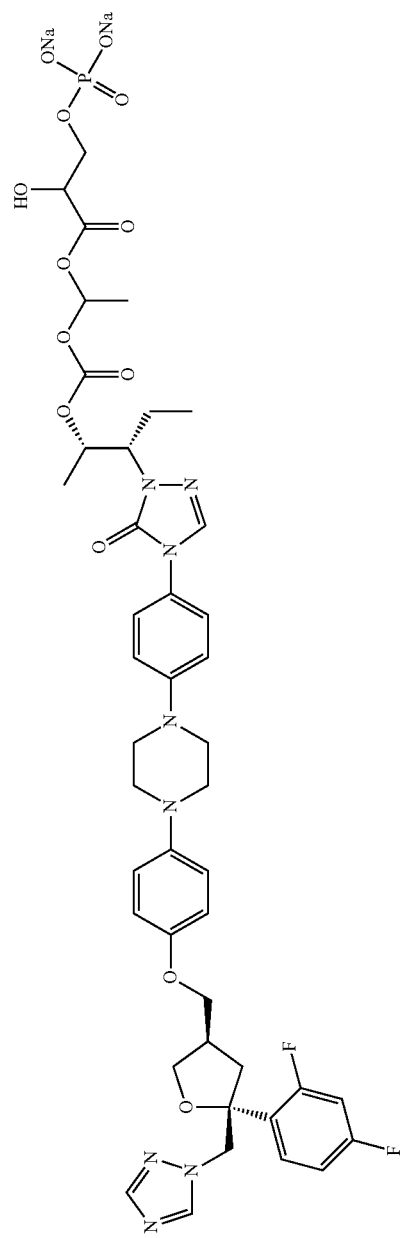 |
| ST0089 | |

-continued
| No. | Structure formula |
|---|---|
| ST0090 | 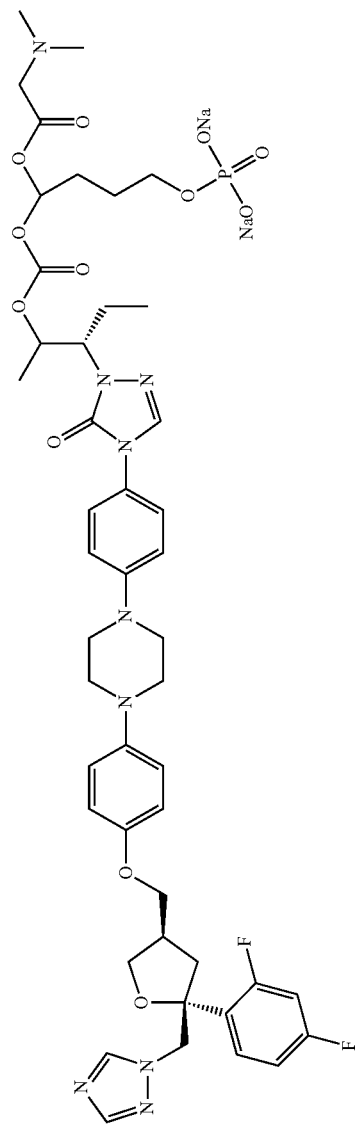 |
| ST0091 | |

-continued
| No. | Structure formula |
|---|---|
| ST0092 | 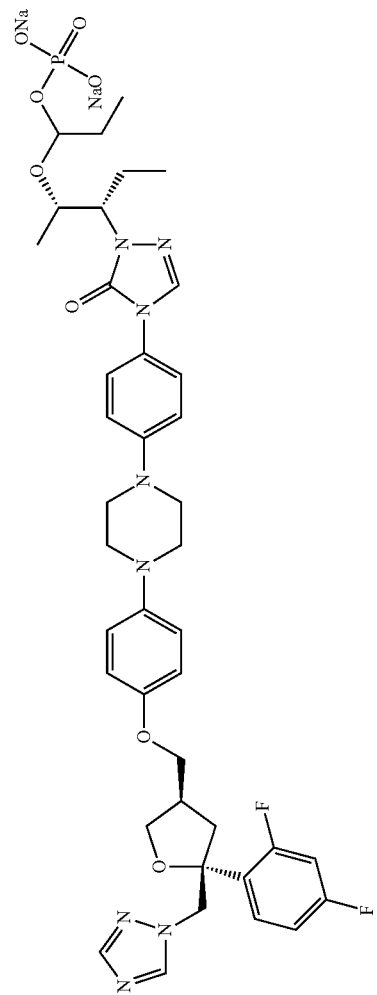 |
| ST0093 | |

-continued
| No. | Structure formula |
|---|---|
| ST0094 | 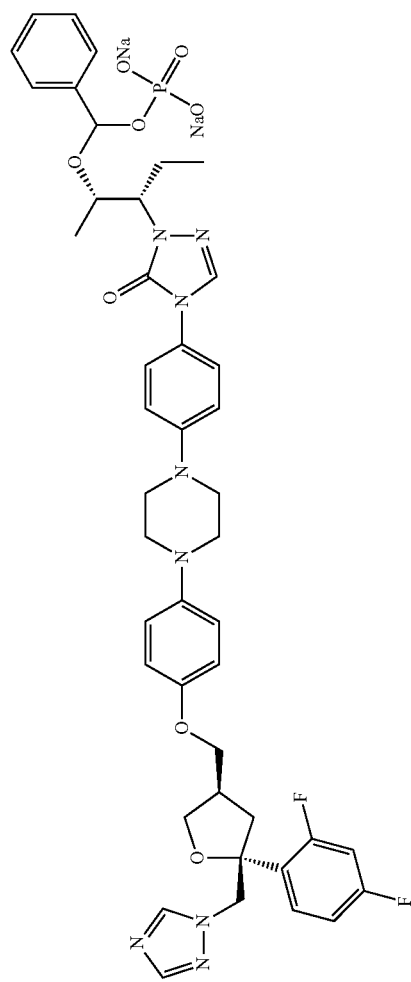 |
| ST0095 | |

| No. | Structure formula |
|---|---|
| ST0100 | 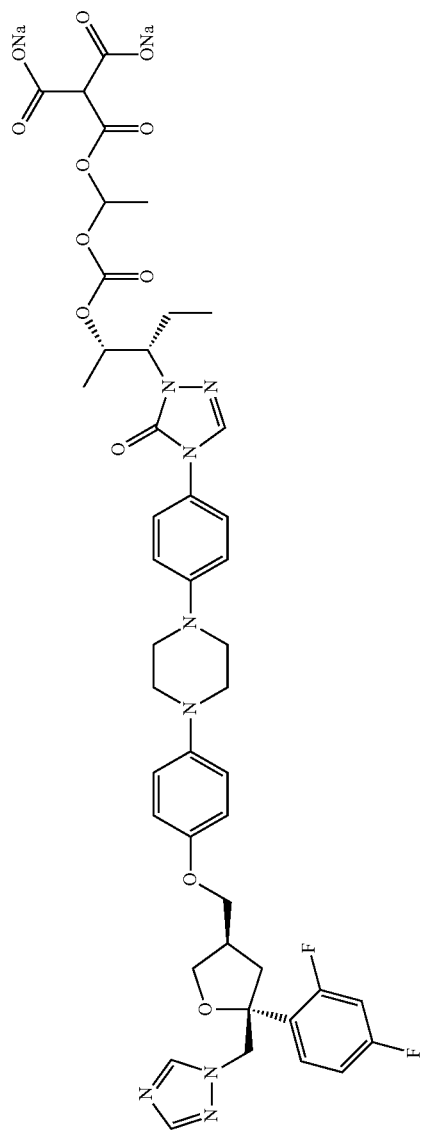 |
| ST0101 | 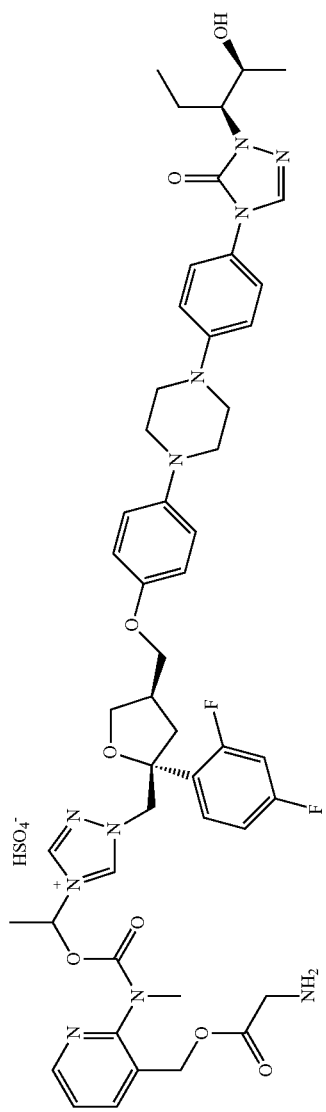 |

| No. | Structure formula |
|---|---|
| ST0102 | 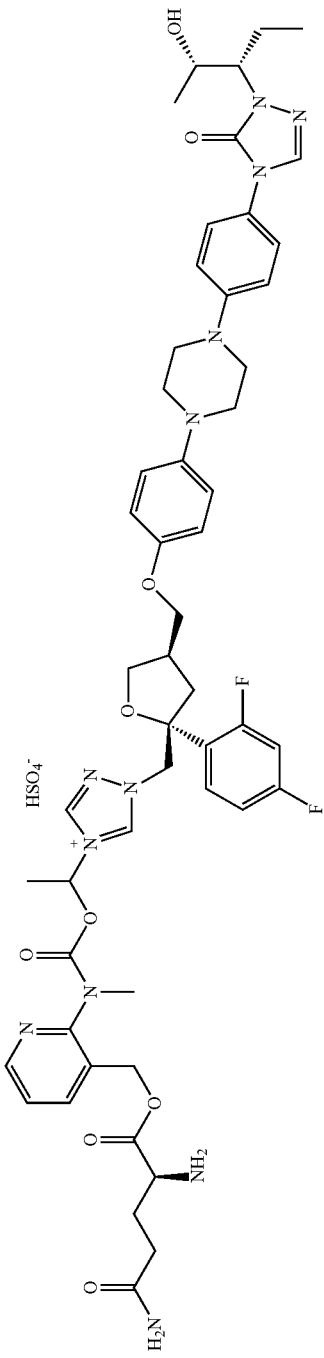 |
| ST0103 | 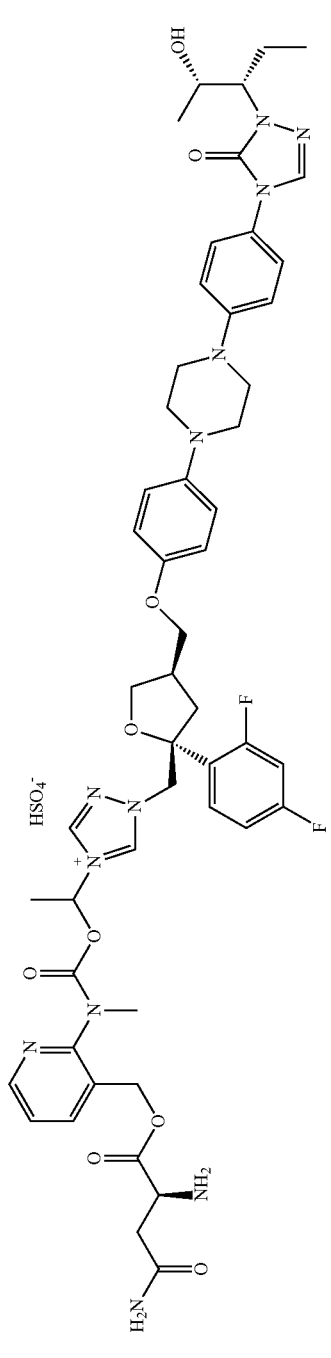 |
| ST0104 | 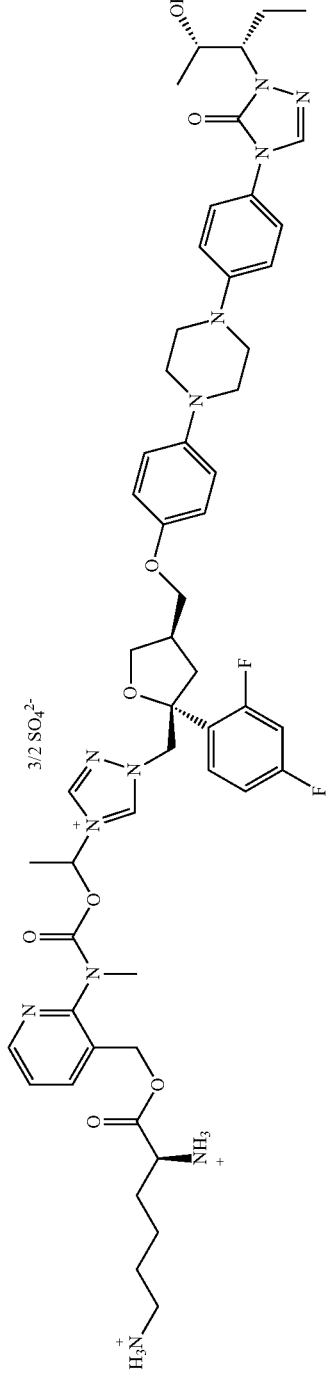 |

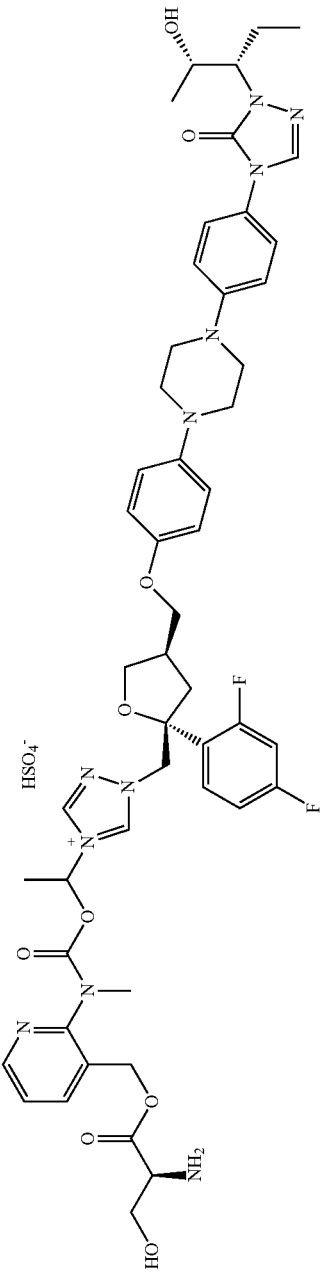

The present disclosure also provides a method for preparing the compound of the formula (I), which comprises preparing the compound of the formula (I) by using the compound represented by the following formula (II) as a raw material:

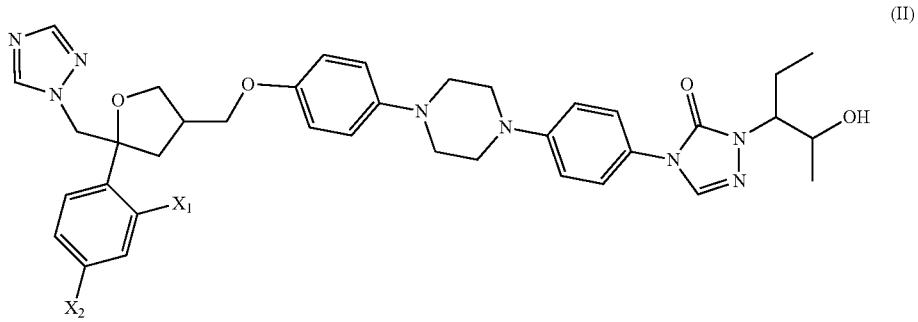

(II)

wherein, $X_1$ and $X_2$ have the definitions as described above.

According to an embodiment of the present disclosure, for example, the compound of the above formula (I') can be prepared by using the compound represented by the following formula (II') as a raw material:

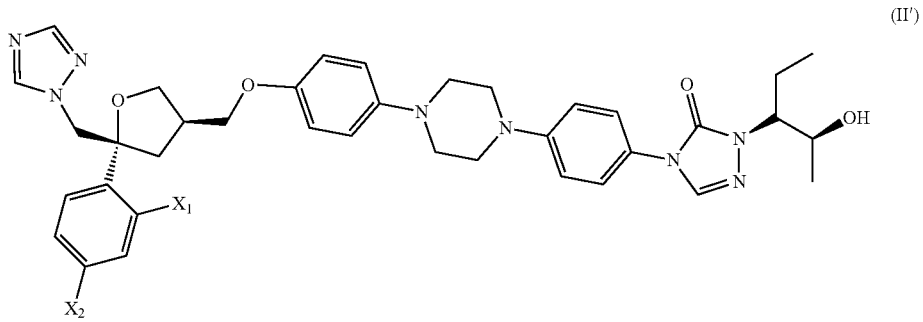

(II')

wherein, $X_1$ and $X_2$ have the definitions as described above.

According to the preparation method of the present disclosure, persons skilled in the art can select appropriate raw materials to react with the compound of formula (II) to obtain the compound of formula (I). For example, a suitable raw material can be selected to react with a compound of formula (II') to provide a compound of formula (I').

According to an embodiment of the present disclosure, the preparation method can include, for example, reacting a compound of formula (II) with a compound $R_z$-L, wherein $R_z$ is selected from $R_h$, $R_t$ or a group which can be derivatized as $R_h$ or $R_t$, wherein $R_h$ and $R_t$ have the definitions as described above, and L is a leaving group. For example, $R_z$-L can be selected from $R_h$-$L_1$ or $R_t$-$L_2$, wherein $R_h$ and $R_t$ have the definitions as described above, and $L_1$ and $L_2$ are selected from leaving groups.

According to an embodiment of the present disclosure, the preparation method can be carried out in the presence of a catalyst.

According to an embodiment of the present disclosure, the preparation method can be carried out in the absence of a solvent or in the presence of a solvent.

If desired, the compound of formula (II) can be first reacted with $R_h$-$L_1$ and the resulting compound can be further reacted with $R_t$-$L_2$;

Alternatively, the compound of formula (II) is first reacted with $R_t$-$L_2$ and the resulting compound can be further reacted with $R_h$-$L_1$.

If desired, one or more functional groups in the compound of formula (II) and/or compound $R_z$-L can be first protected with a protecting group (PG) and then subjected to the reaction. The functional group can be selected from, for example, one or more of amino group, amine group, hydroxyl group, mercapto group, carboxyl group, carbon-carbon double bond, and carbon-carbon triple bond. Each of the protecting groups (PG) can be selected from, for example, benzyloxycarbonyl (Cbz), tert-butoxycarbonyl (Boc), allyloxycarbonyl, trimethylsilyloxycarbonyl (Teoc), methoxycarbonyl, ethoxycarbonyl, phthaloyl (pht), p-toluenesulfonyl (Ts), trifluoroacetyl (Tfa), pivaloyl, benzoyl, trityl (Trt), 2,4-dimethoxybenzyl (Dmb), p-methoxybenzyl (PMB), benzyl (Bn), tert-butyldimethylsilyl (TBS), trimethylsilyl (TMS), triisopropylsilyl (TIPS—OR), tert-butyl (t-Bu).

If necessary, after the completion of the reaction, the protecting group can be removed for subsequent reactions or to obtain the target compound.

According to the present disclosure, when $R_z$ is selected from a group that can be derivatized as $R_h$ or $R_t$, $R_z$ represents a group that can be further reacted to give $R_h$ or $R_t$.

According to the present disclosure, preferably, the compound represented by the formula (II) or (II') as the substrate does not undergo a configuration conversion during the reaction.

As an illustrative example, the preparation method includes, but is not limited to, at least one of the following reactions:

1)

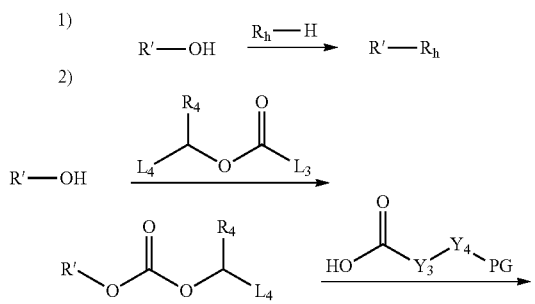

2)

3)

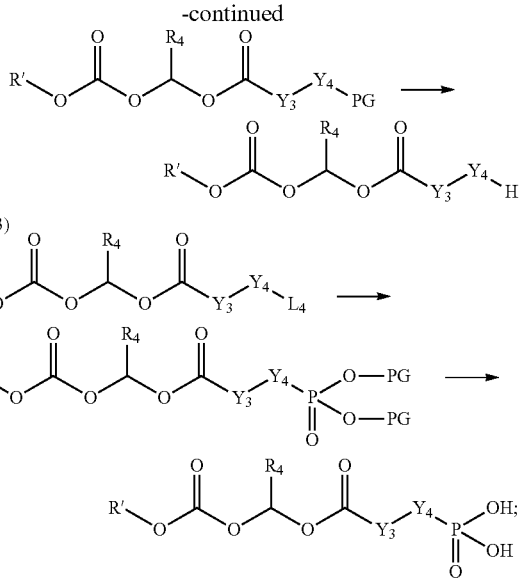

Preferably,

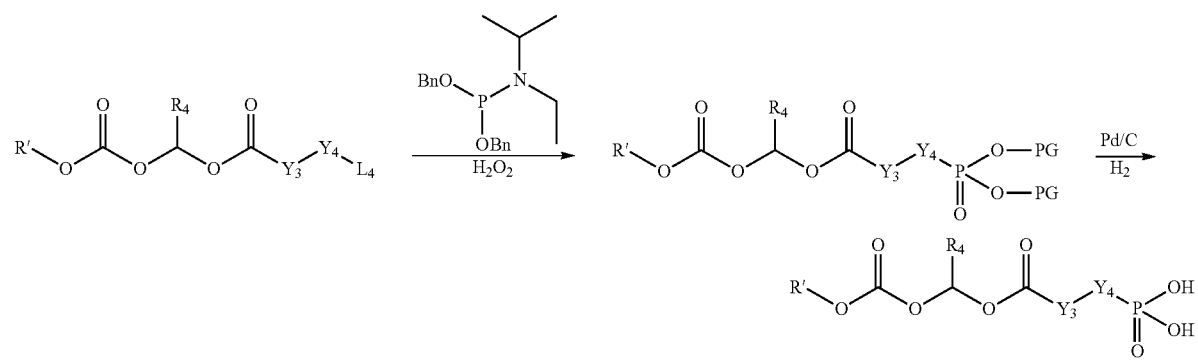

4)

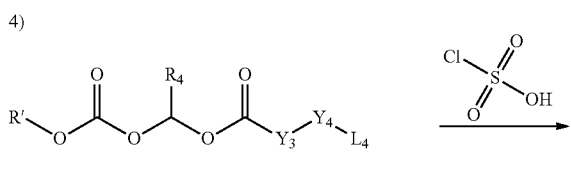

5)

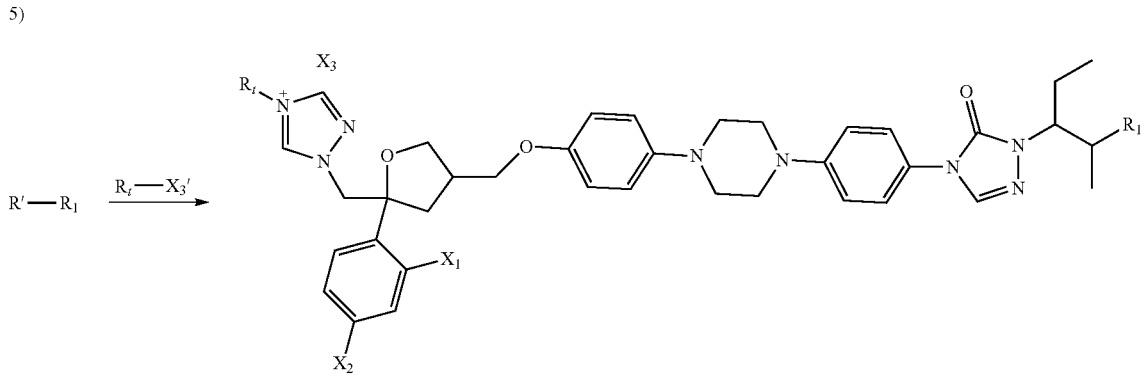

wherein, R' represents

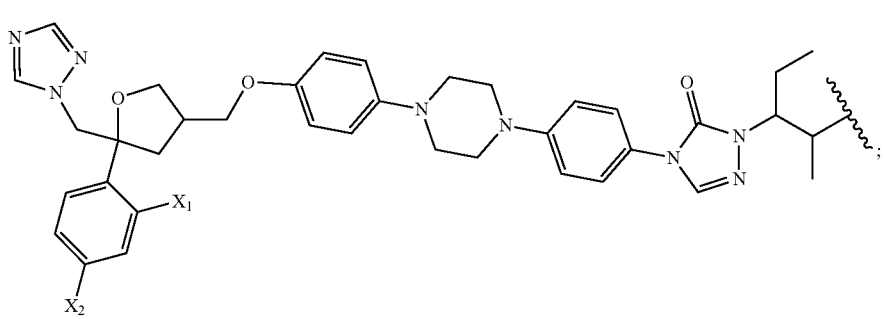

(II)

$R_4$, $R_h$, $X_1$, $X_2$, $X_3$, $Y_3$, $Y_4$, and PG have the definitions as described above.

$X_3'$ represents an organic substituent that can be converted to $X_3$;

$L_3$ and $L_4$ independently from each other are selected from leaving groups such as F, Cl, Br, or I;

Preferably, the reaction, for example the reaction 4) can be carried out in the presence of a catalyst such as NaBr, NaI or a mixture thereof.

The present disclosure also provides a method for preparing the compound $R_f$—$X_3'$, including but not limited to one or more of the following reactions:

a1)

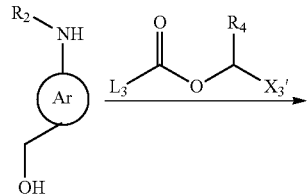

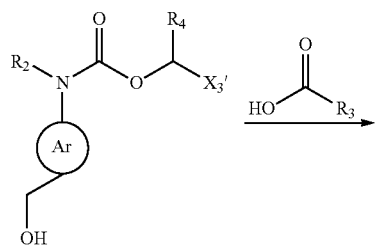

-continued a2)

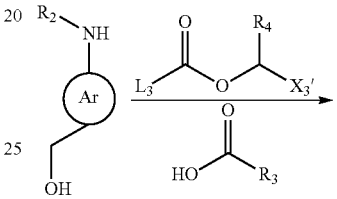

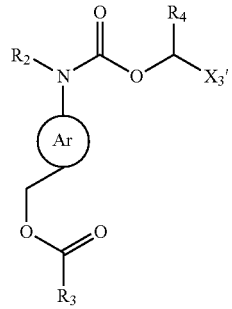

a3)

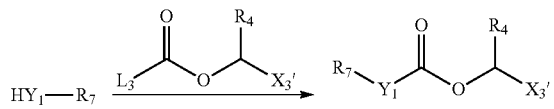

a4)

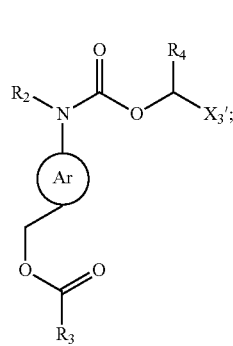

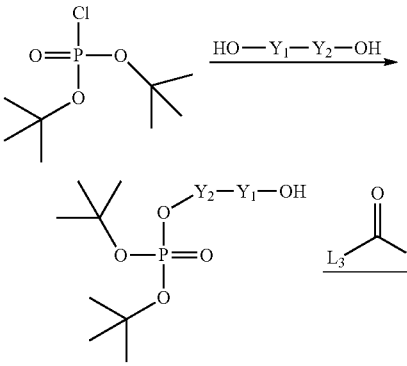

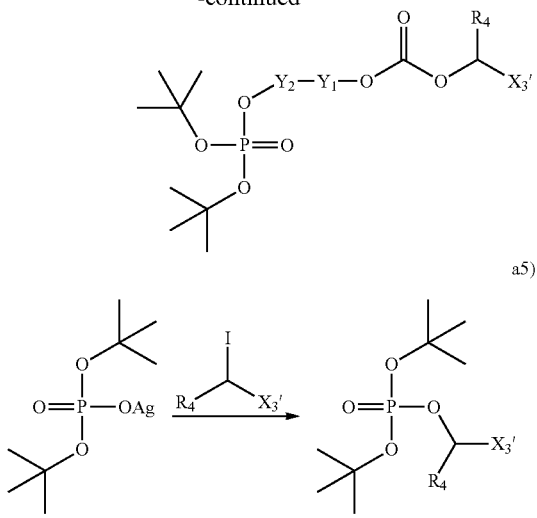

a5)

wherein, each substituent has the definition as described above;

Preferably, the method for preparing the compound $R_f$—$X_3$ is carried out in the presence of a base or a condensing agent.

The present disclosure also provides a compound represented by formula (VII):

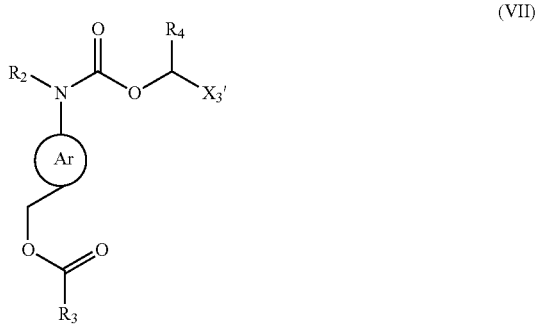

(VII)

wherein, $R_2$, $R_3$, $R_4$, $X_3$, and Ar have the definitions as described above.

The present disclosure also provides the use of the compound of formula (VII) in the preparation of a posaconazole derivative such as the compound of formula (I).

The present disclosure also provides a pharmaceutical composition comprising a therapeutically effective amount of the compound of the present disclosure (including the compound represented by formula (I), a racemate, stereoisomer, tautomer, oxynitride, or a pharmaceutically acceptable salt thereof). The pharmaceutical composition can also optionally contain a pharmaceutically acceptable adjuvant such as a carrier, an excipient. As an example, the adjuvant can be one or more selected from disintegrants, glidants, lubricants, diluents or fillers, binders, colorants.

The present disclosure also provide use of a compound of the present disclosure including a compound represented by formula (I), a racemate, stereoisomer, tautomer, oxynitride, or a pharmaceutically acceptable salt thereof in the preparation of an antibiotic drug, in particular an antifungal (including but not limited to Candida albicans, Aspergillus fumigatus) drug.

The present disclosure also provide use of a compound of the present disclosure including a compound represented by formula (I), a racemate, stereoisomer, tautomer, oxynitride, or a pharmaceutically acceptable salt thereof in the prevention or treatment of a disease. The disease is, for example, caused by a fungus (including but not limited to Candida albicans, Aspergillus fumigatus).

Definition and Explanation of Terms

Unless otherwise indicated, the definitions of groups and terms in the specification and claims of this application include definitions as examples, exemplary definitions, preferred definitions, definitions described in tables, definitions of specific compounds in examples, and the like which can be in any combination or association with each other. Such combined and associated group definitions and compound structures should fall within the scope of the description of the present application.

Whenever a numerical range recited in the specification and claims herein is defined as "an integer", it should be understood that both endpoints of the range and each integer within the range are recited. For example, "an integer of 0 to 10" or "an integer selected from 0 to 10" should be understood as describing each integer of 0, 1, 2, 3, 4, 5, 6, 7, 8, 9 and 10. When the numerical range is defined as "a number", it should be understood that both endpoints of the range, each integer within the range, and each decimal within the range are recited. For example, "a number from 0 to 10" should be understood to include not only each integer of 0, 1, 2, 3, 4, 5, 6, 7, 8, 9, and 10, but also at least the sum of each of the integers and 0.1, 0.2, 0.3, 0.4, 0.5, 0.6, 0.7, 0.8, and 0.9, respectively.

Unless otherwise indicated, when "a compound of the present disclosure" or "a compound according to the present disclosure" is used herein, it is intended to encompass a compound represented by Formula (I), a racemate, stereoisomer, tautomer, oxynitride, or a pharmaceutically acceptable salt thereof.

The term "halogen" refers to F, Cl, Br, and I. In other words, F, Cl, Br, and I can be described as "halogen" in this specification.

"Optionally substituted with" or "optionally substituted" means being substituted with a group selected from the substituents.

The term "$C_{1-40}$ alkyl" is understood to preferably denote a straight or branched saturated monovalent hydrocarbon group having 1 to 40 carbon atoms, preferably a $C_{1-10}$ alkyl group. "$C_{1-10}$ alkyl" is understood to preferably denote a straight or branched saturated monovalent hydrocarbon group having 1, 2, 3, 4, 5, 6, 7, 8, 9 or 10 carbon atoms. The alkyl group is, for example, methyl, ethyl, propyl, butyl, pentyl, hexyl, isopropyl, isobutyl, sec-butyl, tert-butyl, isoamyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl 2,3-dimethylbutyl, 1,3-dimethylbutyl or 1,2-dimethylbutyl, and the like or their isomers. In particular, the groups have 1, 2, 3, 4, 5, or 6 carbon atoms ("$C_{1-6}$ alkyl") such as methyl, ethyl, propyl, butyl, isopropyl, iso-butyl, sec-butyl, tert-butyl. More particularly, the groups have 1, 2 or 3 carbon atoms ("$C_{1-3}$ alkyl") such as methyl, ethyl, n-propyl or isopropyl.

The term "$C_{2-40}$ alkenyl" is understood to preferably denote a straight-chain or branched monovalent hydrocarbon group containing one or more double bonds and having 2 to 40 carbon atoms, preferably "$C_{2-10}$ alkenyl". "$C_{2-10}$ alkenyl" is understood to preferably denote a straight or branched monovalent hydrocarbon group containing one or more double bonds and having 2, 3, 4, 5, 6, 7, 8, 9 or 10 carbon atoms, particularly 2 or 3 carbon atoms ("$C_{2-3}$ alkenyl"). It is to be understood that where the alkenyl group contains more than one double bond, the double bonds can be separated from one another or conjugated. The alkenyl is, for example, vinyl, allyl, (E)-2-methylvinyl, (Z)-2-methylvinyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-ene, hex-5-enyl, (E)-hex-4-enyl, (Z)-hex-4-enyl, (E)-hex-3-enyl, (Z)-hex-3-enyl, (E)-hexa-2-alkenyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-ene (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, and 1-isopropylvinyl.

The term "$C_{2-40}$ alkynyl" is understood to denote a straight or branched monovalent hydrocarbon group containing one or more triple bonds and having 2 to 40 carbon atoms, preferably "$C_2$-$C_{10}$ alkynyl". The term "$C_2$-$C_{10}$ alkynyl" is understood to preferably denote a straight or branched monovalent hydrocarbon group containing one or more triple bonds and having 2, 3, 4, 5, 6, 7, 8, 9 or 10 carbon atoms, especially 2 or 3 carbon atoms ("$C_2$-$C_3$ alkynyl"). The alkynyl group is, for example, ethynyl, prop-1-ynyl, prop-2-ynyl, but-1-ynyl, but-2-ynyl, but-3-ynyl, penta-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbutane-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpentyl-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbutyl-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl. In particular, the alkynyl group is ethynyl, prop-1-ynyl or prop-2-ynyl.

The term "$C_{3-20}$ cycloalkyl" is understood to denote a saturated monovalent monocyclic or bicyclic hydrocarbon ring having 3 to 20 carbon atoms, preferably "$C_{3-10}$ cycloalkyl". The term "$C_{3-10}$ cycloalkyl" is understood to denote a saturated monovalent monocyclic or bicyclic hydrocarbon ring having 3, 4, 5, 6, 7, 8, 9 or 10 carbon atoms. The $C_{3-10}$ cycloalkyl group can be a monocyclic hydrocarbon group such as cyclopropyl, cyclobutyl, cyclopentyl, cyclohexyl, cycloheptyl, cyclooctyl, cyclodecyl or cyclodecyl, or a bicyclic hydrocarbon group such as decahydronaphthalene cyclyl.

The term "$C_{5-20}$ cycloalkenyl" is understood to denote a conjugated or non-conjugated monovalent monocyclic or bicyclic hydrocarbon ring having an unsaturation of 1, 2 or 3 and having 5 to 20 carbon atoms, preferably "$C_{5-10}$ cycloalkenyl". The term "$C_{5-10}$ cycloalkenyl" is understood to denote an unsaturated monovalent monocyclic or bicyclic hydrocarbon ring having 5, 6, 7, 8, 9 or 10 carbon atoms. The $C_{5-10}$ cycloalkenyl group can be a monocyclic hydrocarbon group such as 3-cyclopentenyl, 1-cyclohexenyl, 2-cyclohexenyl, 2,4-cyclopentadienyl, 2,5-cyclohexadienyl or 1,3,5-cycloheptatrienyl or 1,3,6-cycloheptatrienyl, or a bicyclic hydrocarbon such as hexahydronaphthalene cyclyl, and octahydronaphthalene cyclyl. Unless otherwise indicated, the term "$C_{5-20}$ cycloalkenyl" includes all possible isomeric forms thereof, such as positional isomers or configurational isomers thereof.

The term "3-20 membered heterocyclyl" denotes a saturated monovalent monocyclic or bicyclic hydrocarbon ring containing 1-5 heteroatoms independently selected from N, O and S, preferably "3-10 membered heterocyclyl". The term "3-10 membered heterocyclyl" denotes a saturated monovalent monocyclic or bicyclic hydrocarbon ring containing 1-5, preferably 1-3, heteroatoms selected from N, O and S. The heterocyclyl group can be attached to the rest of the molecule through any one of the carbon atoms, or if present, a nitrogen atom. In particular, the heterocyclyl can include, but is not limited to, 4-membered ring, such as azetidinyl, oxetanyl; 5-membered ring, such as tetrahydrofuranyl, dioxolyl, pyrrolidinyl, imidazolidinyl, pyrazolidinyl, pyrrolinyl; or 6-membered ring, such as tetrahydropyranyl, piperidinyl, morpholinyl, dithianyl, thiomorpholinyl, piperazinyl, or trithiyl; or 7-membered ring, such as diazepanyl. Optionally, the heterocyclyl can be benzo-fused. The heterocyclyl can be bicyclic, such as but not limited to a 5,5-membered ring, such as hexahydrocyclopenta[c]pyrrole-2(1H)-yl ring, or a 5,6-membered bicyclic ring, such as hexahydropyrrolo[1,2-a]pyrazin-2(1H)-yl ring. The nitrogen-containing ring can be partially unsaturated, i.e., it can contain one or more double bonds, such as but not limited to 2,5-dihydro-1H-pyrrolyl, 4H-[1,3,4]thiadiazinyl, 4,5-dihydrooxazolyl, or 4H-[1,4]thiazinyl, alternatively, it can be benzo-fused, such as but not limited to dihydroisoquinolyl. According to the present disclosure, the heterocyclyl is not aromatic.

The term "$C_{6-20}$ aryl" is understood to preferably denote a monovalent aromatic or partially aromatic monocyclic, bicyclic or tricyclic hydrocarbon ring having 6 to 20 carbon atoms, preferably "$C_{6-14}$ aryl". The term "$C_{6-14}$ aryl" is understood to preferably denote a monovalent aromatic or partially aromatic monocyclic, bicyclic or tricyclic hydrocarbon ring having 6, 7, 8, 9, 10, 11, 12, 13 or 14 carbon atoms ("$C_{6-14}$ aryl"), especially a ring having 6 carbon atoms ("$C_6$ aryl"), such as phenyl; or biphenyl, or a ring having 9 carbon atoms ("$C_9$ aryl"), such as indanyl or indenyl, or a ring having 10 carbon atoms ("$C_{10}$ aryl"), such as tetrahydronaphthyl, dihydronaphthyl or naphthyl, or a ring having 13 carbon atoms ("$C_{13}$ aryl"), such as fluorenyl, or a ring having 14 carbon atoms ("$C_{14}$ aryl"), such as fluorenyl.

The term "5-20 membered heteroaryl" is understood to include monovalent monocyclic, bicyclic or tricyclic aromatic ring systems having 5 to 20 ring atoms and containing 1 to 5 heteroatoms independently selected from N, O and S, such as "5-14 membered heteroaryl". The term "5-14 membered heteroaryl" is understood to include monovalent monocyclic, bicyclic or tricyclic aromatic ring systems having 5, 6, 7, 8, 9, 10, 11, 12, 13 or 14 ring atoms, especially 5 or 6 or 9 or 10 carbon atoms, and containing 1-5, preferably 1-3, heteroatoms independently selected from N, O and S, and in addition, can be benzo-fused in each case. In particular, the heteroaryl is selected from thienyl, furyl, pyrrolyl, oxazolyl, thiazolyl, imidazolyl, pyrazolyl, isoxazolyl, isothiazolyl, oxadiazolyl, triazolyl, thiadiazolyl, thio-4H-pyrazolyl, the like and their benzo derivatives, for example, benzofuranyl, benzothienyl, benzoxazolyl, benzisoxazolyl, benzimidazolyl, benzotriazolyl, indazolyl, indolyl, isoindolyl, and the like; or pyridyl, pyridazinyl, pyrimidinyl, pyrazinyl, triazinyl, and the like, and benzo derivatives thereof such as quinolyl, quinazolinyl, isoquinolinyl, and the like; or azocinyl, indolizinyl, purinyl, the like and their benzo derivatives; or cinnolinyl, phthalazinyl, quinazolinyl, quinoxalinyl, naphthyridinyl, pteridine, carbazolyl, acridinyl, phenazinyl, phenothiazinyl, phenoxazinyl, and the like.

Unless otherwise indicated, heterocyclyl, heteroaryl, or heteroarylene includes all possible isomeric forms thereof, such as its positional isomers. Thus, for some illustrative non-limiting examples, pyridyl or pyridylene group includes pyridin-2-yl, pyridylen-2-yl, pyridin-3-yl, pyridylen-3-yl, pyridin-4-yl, and pyridylen-4-yl; thienyl or thienylene group include thiophen-2-yl, thienylen-2-yl, thiophen-3-yl, and thienylen-3-yl.

The triazolyl in the present disclosure includes 1,2,3-triazolyl, 1,2,4-triazolyl or 1,3,5-triazolyl.

The above definition of the term "alkyl", such as "$C_{1-40}$ alkyl" applies equally to other terms containing "$C_{1-40}$ alkyl" such as the term "$C_{1-40}$ alkyloxy" or "$C_{1-40}$ alkoxy", "$C_{1-40}$ alkylsilyl" and "$C_{1-40}$ alkylsilyloxy" and the like. Similarly, the above definitions of the terms "$C_{2-40}$ alkenyl", "$C_{2-40}$ alkynyl", "$C_{3-20}$ cycloalkyl", "$C_{5-20}$ cycloalkenyl", "3-20 membered heterocyclyl", "$C_{6-20}$ aryl" and "5-20 membered heteroaryl" apply equally to other terms containing the same, such as the terms "$C_{2-40}$ alkenyloxy", "$C_{2-40}$ alkynyloxy", "$C_{3-20}$ cycloalkyloxy", "3-20 membered heterocyclyloxy", "$C_{6-20}$ aryloxy", "$C_{6-20}$ arylalkyl" and "5-20 membered heteroarylalkyl" and the like.

Unless otherwise indicated, the term "leaving group" as used herein denotes a charged or uncharged atom or group that disassociates during a substitution or displacement reaction. Suitable examples include, but are not limited to, H, F, Br, Cl, I, mesylate ester group, tosylate ester group, and the like.

In any method for preparing the compounds of the present disclosure, it can be necessary and/or desirable to protect sensitive or reactive groups on any of the molecules involved. This can be achieved by conventional protecting groups, such as those described in textbooks or reference books in the field. The protecting groups can be removed at a convenient subsequent stage using methods known in the art. Persons skilled in the art will recognize that depending on the particular protecting group, other reagents, including but not limited to Pd/C, Pd(OH)$_2$, PdCl$_2$, Pd(OAc)$_2$/Et$_3$SiH, Raney nickel, appropriately selected acids, appropriately selected bases, fluorides, and the like can be used for the step of removing the protecting groups.

The target compound can be isolated according to a known method, for example, by extraction, filtration or column chromatography.

According to its molecular structure, the compounds of the present disclosure can be chiral and thus can exist in various enantiomeric forms. Thus, these compounds can exist in the form of racemates or optically active forms. The compounds of the present disclosure or their intermediates can be separated into enantiomeric compounds by chemical or physical methods known to persons skilled in the art or used in this form for synthesis. In the case of racemic amines, diastereomers are prepared from the mixture by reaction with optically active resolving agents. Examples of suitable resolving agents are optically active acids such as tartaric acid, diacetyltartaric acid, dibenzoyltartaric acid, mandelic acid, malic acid, lactic acid, suitable N-protected amino acids (e.g., N-benzoylproline or N-phenylsulfonylproline) in R and S forms or various optically active camphorsulfonic acids. With the aid of optically active resolving agents (e.g., dinitrobenzoylphenylglycine immobilized on silica gel, cellulose triacetate or other carbohydrate derivatives or chiral derivatized methacrylate polymers). Suitable eluents for this purpose are aqueous-containing or alcohol-containing solvent mixtures, for example, hexane/isopropanol/acetonitrile.

Persons skilled in the art will understand that since nitrogen needs to have available lone pairs of electrons for oxidation to oxides, not all nitrogen-containing heterocycles can form N-oxides; persons skilled in the art will identify nitrogen-containing heterocycles capable of forming N-oxides. Persons skilled in the art will also recognize that tertiary amines can form N-oxides. Methods for synthesizing N-oxides of heterocyclic and tertiary amines are well known to persons skilled in the art and include the use of peroxyacids such as peracetic acid and m-chloroperoxybenzoic acid (MCPBA), hydrogen peroxide, alkyl hydroperoxides such as tert-butyl hydroperoxide, sodium perborate, and dioxirane such as dimethylbisoxirane oxidized heterocycle and tertiary amines. These methods for preparing N-oxides have been extensively described and reviewed in the prior art.

Pharmaceutically acceptable salts can be, for example, acid addition salts of the compounds of the present disclosure having a sufficiently basic nitrogen atom in the chain or ring, for example, acid addition salts formed with the following inorganic acids: such as hydrochloric acid, hydrofluoric acid, hydrobromic acid, hydroiodic acid, sulfuric acid, pyrosulfuric acid, phosphoric acid or nitric acid, or hydrosulfate; or acid addition salts formed with the following organic acids: formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxyl) benzoyl) benzoic acid, camphoric acid, cinnamic acid, cyclopentane propionic acid, digluconic acid, 3-hydroxy-2-naphthoic acid, nicotinic acid, embonic acid, pectinic acid, persulfuric acid, 3-phenyl propionic acid, picric acid, pivalic acid, 2-hydroxyethanesulfonic acid, itaconic acid, sulfamic acid, trifluoromethanesulfonic acid, dodecyl sulfate, ethanesulfonic acid, benzenesulfonic acid, p-toluenesulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, gluconic acid, glycerophosphoric acid, aspartic acid, sulfosalicylic acid, hemisulfuric acid or thiocyanate acid.

In addition, another suitable pharmaceutically acceptable salt of the compound of the present disclosure having sufficient acidity is alkali metal salt (e.g., sodium salt or potassium salt), alkaline earth metal salt (e.g., calcium salt or magnesium salt), ammonium salt, or a salt formed with an organic base that provides a physiologically acceptable cation, such as a salt formed with: sodium ion, potassium ion, N-methylglucosamine, dimethylglucosamine, ethylglucosamine, lysine, dicyclohexylamine, 1,6-hexamethylenediamine, ethanolamine, glycosamine, meglumine, sarcosine, serinol, trishydroxymethyl aminomethane, aminopropylene glycol, 1-amino-2,3,4-butanetriol. As an example, when 1, 2, or 3 of $M_1$, $M_2$, and $M_3$ is/are H, the pharmaceutically acceptable salt includes, for example, salts formed from —OP(O)(OM$_1$)(OM$_2$), —P(O)(OM$_1$)(OM$_2$), —OS(O)$_2$OM$_3$, and —S(O)$_2$OM$_3$, with, for example, above-mentioned sodium ion, potassium ion, ammonium ion, and the like;

In addition, basic nitrogen-containing groups can be quaternized with the following reagents: lower alkyl halides such as methyl, ethyl, propyl and butyl chlorides, bromides and iodides; dialkyl sulfates such as dimethyl sulfate, diethyl sulfate, dibutyl sulfate and diamyl sulfate; long-chain halides such as chloride, bromide and iodide of decyl, lauryl, myristyl and stearyl chloride, bromide and iodide; aralkyl halides such as benzyl and phenylethyl bromide, and the like. As an example, pharmaceutically acceptable salts include hydrochloride, sulfate, nitrate, bisulfate, hydrobromide, acetate, oxalate, citrate, mesylate, formate or meglumine salt and the like.

Since the compounds of the present disclosure can have a plurality of salt-forming sites, the "pharmaceutically acceptable salts" include not only the salts formed on one salt-forming site of the compound of the present disclosure but also the salts formed on 2, 3 or all salt formation sites. Therefore, the molar ratio of the compound of formula (I) and the acid ion (anion) or cation of the base required for forming the salt in the "pharmaceutically acceptable salt" can vary within a relatively large range, for example, 4:1-1:4, such as 3:1, 2:1, 1:1, 1:2, 1:3, and so on.

According to the present disclosure, pharmaceutically acceptable anions include acid ions selected from those ionized by inorganic or organic acids. The "inorganic acid" includes but is not limited to hydrochloric acid, hydrofluoric acid, hydrobromic acid, hydroiodic acid, sulfuric acid, pyrosulfuric acid, phosphoric acid, or nitric acid. The "organic acid" includes but is not limited to formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxyl)benzoyl) benzoic acid, camphoric acid, cinnamic acid, cyclopentane propionic acid, digluconic acid, 3-hydroxy-2-naphthoic acid, nicotinic acid, embonic acid, pectinic acid, persulfuric acid, 3-phenyl propionic acid, picric acid, pivalic acid, 2-hydroxyethanesulfonic acid, itaconic acid, sulfamic acid, trifluoromethanesulfonic acid, dodecyl sulfate, ethanesulfonic acid, benzenesulfonic acid, p-toluenesulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, gluconic acid, glycerophosphoric acid, aspartic acid, sulfosalicylic acid, hemisulfuric acid or thiocyanate.

The term "acid ion generated by ionization" encompasses all forms of acid ions that can be generated by ionization of the inorganic and organic acids, for example, different acid ions can be generated through primary ionization, secondary ionization, or tertiary ionization. As an example, phosphoric acid can generate dihydrogen phosphate by primary ionization, can generate hydrogen phosphate by secondary ionization, and can generate phosphate by tertiary ionization; sulfuric acid can generate hydrogen sulfate by primary ionization, and can generate sulfate by secondary ionization of sulfate. In the compound of the formula (I) of the present disclosure, a plurality of molecules can share one multivalent anion generated by multiple levels of ionization. All these possible generated acid ions are covered by the acid ions or anions described in the present disclosure.

The term "tautomer" refers to a functional isomer resulting from the rapid movement of an atom in a molecule at two positions. The compounds of the present disclosure can exhibit tautomerism. Tautomeric compounds can exist in two or more mutually convertible species. Prototropic tautomers result from the transfer of covalently bonded hydrogen atoms between two atoms. Tautomers generally exist in equilibrium and attempts to isolate a single tautomer often produce a mixture whose physicochemical properties are consistent with the mixture of compounds. The position of equilibrium depends on the chemical properties within the molecule. For example, in many aliphatic aldehydes and ketones such as acetaldehyde, the ketone type predominates; in phenols, the enol type predominates. The present disclosure includes all tautomeric forms of the compounds.

The term "effective amount" or "therapeutically effective amount" refers to an amount of a compound of the present disclosure that is sufficient to achieve the intended application (including but not limited to the treatment of diseases as defined below). The therapeutically effective amount can vary depending on such factors as the intended application (in vitro or in vivo), or the subject and disease condition being treated, such as the weight and age of the subject, the severity of the disease condition, and the manner of administration, etc., which can be easily determined by persons skilled in the art. The specific dose will vary depending on the particular compound selected, the dosing regimen upon which it is administered, whether it is to be administered in combination with other compounds, the timing of dosing, the tissue to be administered and the physical delivery system carried.

The term "adjuvant" refers to pharmaceutically acceptable inert ingredients. Examples of types of excipients include, but are not limited to, binders, disintegrants, lubricants, glidants, stabilizers, fillers, diluents, and the like. Excipients can enhance the handling characteristics of a pharmaceutical formulation, i.e., the formulation is more suitable for direct compression by increasing fluidity and/or tackiness. Examples of typical pharmaceutically acceptable carriers suitable for use in the above formulations are: saccharides such as lactose, sucrose, mannitol and sorbitol; starch types such as corn starch, tapioca starch and potato starch; cellulose and its derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil, and corn oil; nonionic, cationic and anionic surfactants; ethylene glycol polymers; fatty alcohols; and cereals hydrolyzed solids and other non-toxic compatible fillers, binders, disintegrants, buffers, preservatives, antioxidants, lubricants, colorants, etc. commonly used as excipients in pharmaceutical formulations.

Advantageous Effect

1. The present disclosure solved the problem of poor solubility of posaconazole and difficulty in improving its solubility by salt formation through the design of the prodrug, and developed a series of compounds having good salt forming properties or water solubility; the compounds or the pharmaceutically acceptable salts thereof have good stability and excellent solubility in vitro, and can rapidly transform and release active ingredients in vivo to exert its efficacy, thereby being suitable for the development of new antibiotic drugs;

2. The present disclosure solved the problem that posaconazole itself is insoluble in water and needs to be solubilized with a large amount of sulfobutyl ether-β-cyclodextrin (6.68 g/each injection) through the design of the prodrug, thereby reducing the toxicity risk caused by said adjuvant; it can be formulated into injections without the use of β-cyclodextrin having safety issues for solubilization, thus not only the use of drugs for patients who are inconvenient for oral administration can be achieved, but also the clinical safety can be greatly improved; patients with moderate to severe renal impairment can also be administrated, thereby expanding the applicable population of drugs;

3. The compounds of the present disclosure have good salt forming properties and water solubility, and can be quickly converted into posaconazole after oral administration into the gastrointestinal tract to exert its medicinal effect, thereby having strong antifungal effect and greatly improving the oral bioavailability of posaconazole;

4. The pharmaceutical compositions comprising the compounds of the present disclosure do not require the addition of special adjuvants, nor does it require the use of special processes, thereby simplifying the production process, reducing the production costs, reducing the safety concerns, and facilitating industrial production.

EXAMPLES

Hereinafter, the compound of the present disclosure and its preparation method and application will be further described in detail with reference to specific examples. The following examples merely illustrate and explain the present disclosure and should not be construed as limiting the scope of the present disclosure. The technologies implemented based on the above contents of the present disclosure all fall within the scope of the present disclosure.

The materials and reagents used in the examples are all commercially available unless otherwise specified.

Preparation Example

Example 1

Preparation of Compound ST0001 of the Present Disclosure 1.1 Preparation of Compound (ST0001-001)

10.3 g of dimethyl D-tartrate was weighed into a 250 ml three-necked flask, 100 ml of toluene, 17.7 g of benzaldehyde dimethyl acetal, and 600 mg of p-toluenesulfonic acid monohydrate were successively added, the temperature was raised to 80° C. to 90° C., and the reaction was incubated overnight. Under TLC monitoring, the raw materials were substantially reacted. The reaction solution was quenched with 40 ml of 2 wt % NaHCO₃ solution, extracted with MTBE, washed with H₂O and saturated brine respectively, dried over anhydrous MgSO₄, filtered, concentrated under reduced pressure, and separated by column chromatography to give 4.8 g of white solid (ST0001-001).

1.2 Preparation of Compound (ST0001-002)

4.8 g of ST0001-001 was dissolved in 90 ml of methanol, cooled to 0° C. to 5° C., 405 mg of NaBH₄ was added, and the reaction was incubated for 2 hours. Under TLC monitoring, most of the raw materials were completely reacted. 10 ml of H₂O was added to the reaction solution, and the solution was concentrated and extracted with DCM. The organic phase was dried, filtered, and concentrated to dryness under reduced pressure. Isolation by column chromatography yielded 1.2 g of the product (ST0001-002).

1.3 Preparation of Compound (ST0001-003)

808 mg of ST0001-002 was dissolved in 20 ml of DCM, 713 mg of tetrazol was added, and 3.5 g of dibenzyl N,N-diisopropylphosphoramidite was added dropwise at room temperature. Samples from the reaction were taken and monitored until raw materials were substantially reacted, and then 916 mg of peroxide was added, and reacted for 1 hr. Under TLC monitoring, the raw materials were substantially reacted, then the reaction was quenched by the addition of anhydrous sodium sulfite and the solution was separated. The organic phase was washed with saturated brine, filtered, and concentrated to dryness. Isolation by column chromatography yielded 600 mg of the product (ST0001-003).

1.4 Preparation of Compound (ST0001-004)

600 mg of ST0001-003 was dissolved in 10 ml of methanol, and 3.6 ml of KOH solution (1 mol/L) was added at room temperature, followed by stirring at room temperature for 2 hours. Under TLC monitoring, the raw materials were completely reacted, then pH was adjusted to 5 to 6 with 1 mol/L HCl. The solution was concentrated, added with 10 ml H₂O, extracted with EA, and the organic phase was washed with saturated brine, dried over anhydrous MgSO₄, filtered, and concentrated to dryness to give 589 mg of oil (ST0001-004).

1.5 Preparation of Compound (ST0001-005)

589 mg of ST0001-004 was dissolved in 10 ml of DCM, 937 mg of posaconazole (posa) and 223 mg of DMAP were added, and the temperature was lowered to 0° C. to 5° C., 376 mg of DCC was added, and the reaction was transferred to room temperature overnight. Under HPLC monitoring, the raw materials were completely reacted. After filtration and concentration to dryness, isolation by column chromatography yielded 480 mg of a white solid (ST0001-005).

1.6 Preparation of Compound (ST0001-006)

500 mg of ST0001-005 was dissolved in 3 ml of DCM, cooled to 0° C. to 5° C., 0.6 ml of trifluoroacetic acid was added, and the reaction was incubated for 5 to 6 hours. Under HPLC monitoring, the raw materials were reacted to less than 10%. The reaction was stopped and was concentrated to dryness at 20° C. to 25° C. 20 ml of DCM was added to the residue, and the mixture was adjusted to pH 8 to 9 with saturated NaHCO₃ solution, and separated. The organic phase was washed with saturated brine, dried over anhydrous MgSO₄, filtered, concentrated to dryness, and isolation by column chromatography to give 350 mg of an oil (ST0001-006).

1.7 Preparation of Compound (ST0001)

200 mg of ST0001-006 was dissolved in 6 ml of methanol, 100 mg of palladium-charcoal (5%) was added, the temperature was raised to 35° C. to 40° C., reacted overnight. Under HPLC monitoring, the raw materials were completely reacted. The reaction was filtered with celite, and concentrated to dryness to obtain 250 mg of solid. The solid was dissolved in 2 ml of purified water. 110 mg of N-methyl-D-glucosamine was added, and then the reaction was stirred at room temperature for 1 hr, filtered. The aqueous phase was concentrated to dryness, pulped three times with acetone (1 ml×3) and dried in vacuum to give 250 mg of the title compound (ST0001), ESI-MS (m/z): 899 [M+1].

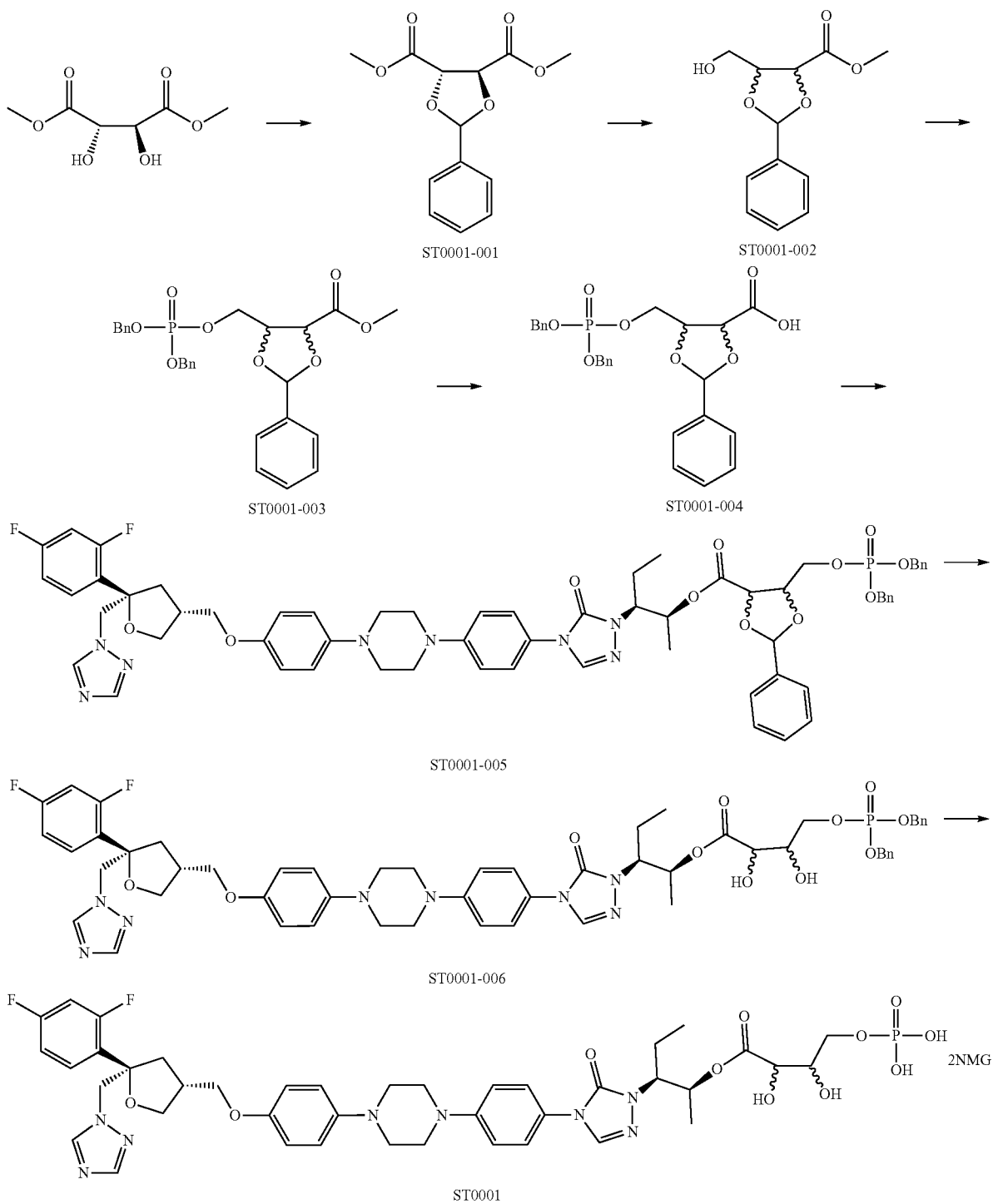

Wherein, NMG=Meglumine

Example 2

Preparation of Compound ST0002 of the Present Disclosure 2.1 Preparation of Compound (ST0002-002)

Under nitrogen atmosphere, 2.0 g of 2-methylamino-3-pyridinemethanol, 80 mL of dichloromethane, and N,N-diisopropylethylamine (1.87 g) were added to a 250 mL three-necked flask, stirred and cooled to −15 to −20° C., and a solution of 2.0 g of 1-chloroethyl chloroformate in dichloromethane (20 mL) was added dropwise and the addition was completed over 1 hr. The reaction temperature was kept at −15 to −20° C. to allow reacting for 16 hours to obtain a reaction solution. 2.8 g of BOC-glycine (CAS No.: 4530-20-5, wherein BOC represents tert-butyloxycarbonyl), 0.53 g of DMAP were added to the reaction solution, stirred, and 2.47 g of 1-ethyl-3-(3-dimethylaminopropyl)carbodiimide was added in batches over 10 minutes, and the reaction was kept at the temperature of −15 to −20° C. for 8 hours. It was determined by TLC that the reaction was complete, the reaction solution was concentrated, methyl tert-butyl ether was added for dissolution, and successively washed with 0.1 M hydrochloric acid, saturated sodium bicarbonate, and brine, dried, filtered, and concentrated to obtain a crude product, which was purified by silica gel column chromatography to give 3.0 g of a colorless oily compound (ST0002-002).

2.2 Preparation of Compound (ST0002-003)

In a 250 mL three-necked flask, 3.0 g of (ST0002-002) and 70 mL of acetonitrile were added and dissolved by stirring. 4.45 g of posaconazole (posa) and 0.11 g (0.1 eq) of sodium iodide were added, and the mixture was heated to 50 to 60° C. for 5 hours. It was determined by TLC that the reaction was complete. The reaction solution was concentrated to give a crude product as a pale yellow oil, which was purified by silica gel column chromatography to give 1.4 g of pure product (ST0002-003).

2.3 Preparation of Compound (ST0002)

1.4 g of ST0002-003 compound was dissolved in 14 mL of ethyl acetate at room temperature, and dissolved with stirring, and a solution of hydrogen chloride in ethyl acetate was added dropwise over 10 minutes, then the mixture was sequentially stirred at room temperature for 1 hr. It was determined by TLC that the reaction was complete. The solution was quickly filtered under nitrogen and the solid was washed with ethyl acetate and acetone respectively to give 1.0 g of pale yellow (ST0002) product, MS (ESI, ½*(M−Cl)): 483.

2.4 Preparation of Compound (0002) Sulfate

At room temperature, 0.5 g of the compound (ST0002) was dissolved in 30 mL of purified water, 30 g of an ion exchange resin (sulfate type) was added, stirred at 0° C. for 3 to 5 hours, filtered, and the filtrate was lyophilized to obtain 0.2 g of an amorphous sulphate compound (ST0101). It was determined by ion chromatography to be the target product; MS (ESI, (M−SO$_4$)): 966.4.

2.5 Preparation of Compound (0002)

At room temperature, 0.5 g of the onium salt compound (ST0002) was dissolved in 30 mL of purified water, 2.2 equivalents of NaOH was added, stirred for 1 hr, extracted with dichloromethane, and the organic phase was dried and concentrated to give compound (0002); MS (ESI, (M−Cl)): 966.4.

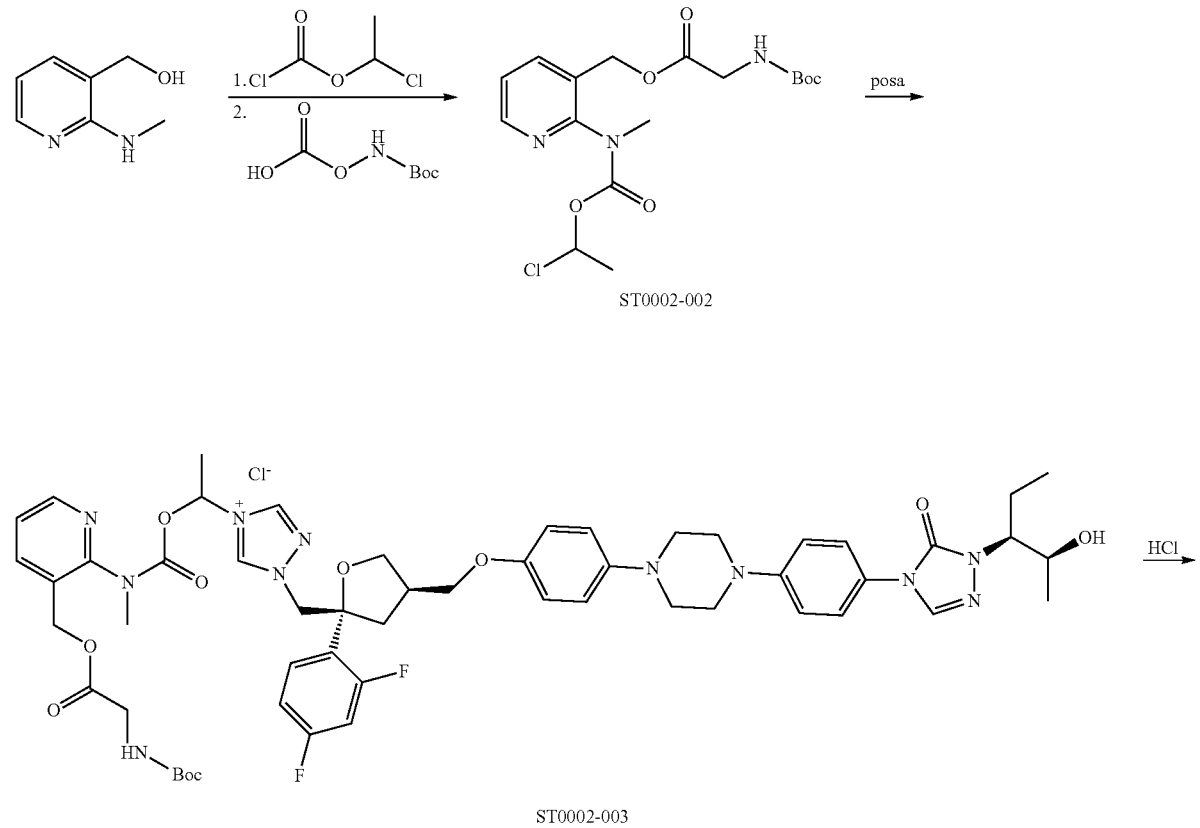

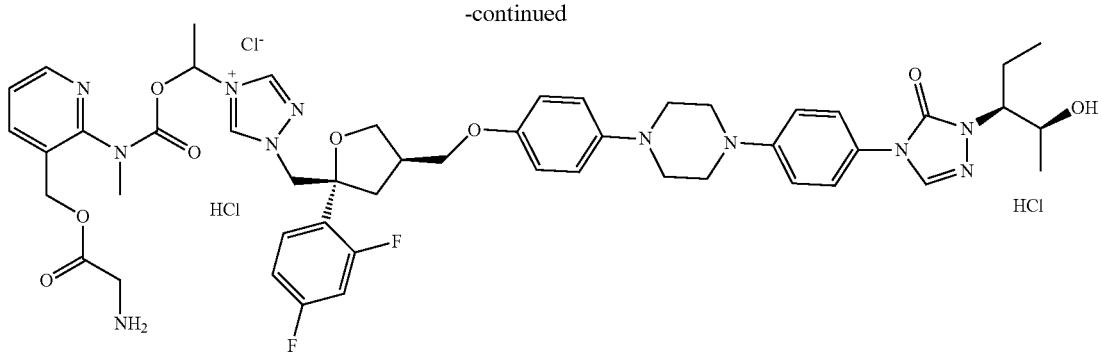

ST0002

As described above, the compound of the present disclosure can not only present in the form of onium chloride salt, but also can be obtained in the forms of corresponding onium iodide salt or onium bromide salt when the catalyst is NaBr or NaI or their amounts exceed a catalytic amount. Onium sulfate salts, onium phosphate salts and onium nitrate salts can be prepared by ion exchange resins. Each salt can be freed by an appropriate amount of base to give the corresponding free base of the compound.

Example 3

Preparation of Compound ST0003 of the Present Disclosure 3.1 Preparation of Compound (ST0003-002)
The preparation method referred to the example of the compound (ST0002-002).

3.2 Preparation of Compound (ST0003-003)
The preparation method referred to the example of the compound (ST0002-003).

3.3 Preparation of Compound (ST0003)
2.0 g of ST0003-003 compound was dissolved in 10 mL of methylene chloride at room temperature, and dissolved with stirring. A solution of hydrogen chloride in 1,4-dioxane was added dropwise over 10 minutes, and the mixture was stirred at room temperature for 1 hr. It was determined by TLC that the reaction was completed. The solution was decanted and concentrated to dryness and treated with acetone and methyl tert-butyl ether to give 1.41 g of solid product (ST0003), MS (ESI, ½*(M−Cl)): 512.5.

Referring to the preparation method of the compound (0002), onium salts with different anions or free products can be obtained.

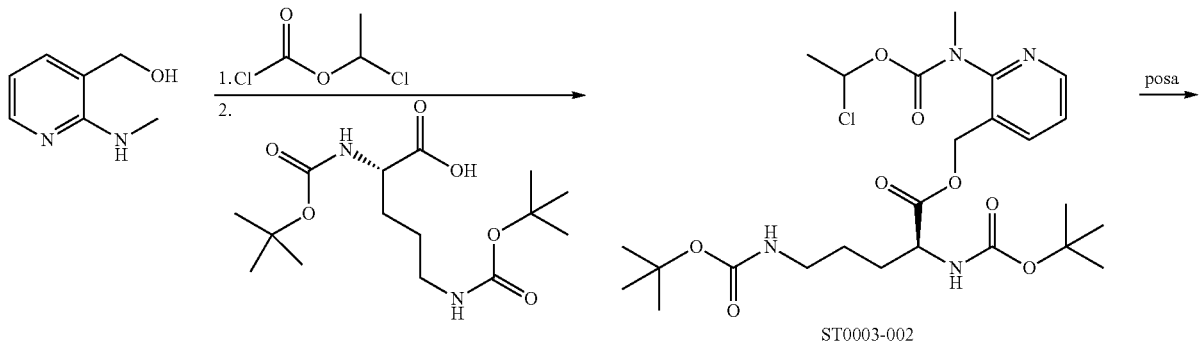

ST0003-002

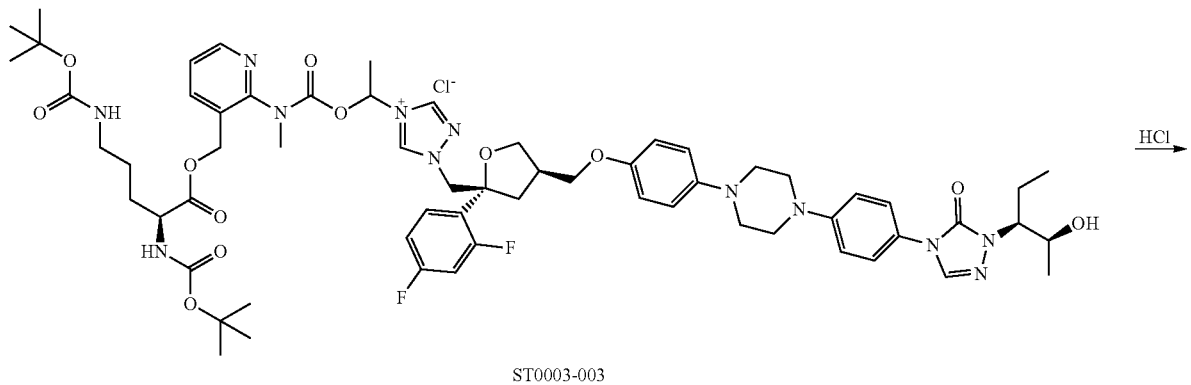

ST0003-003

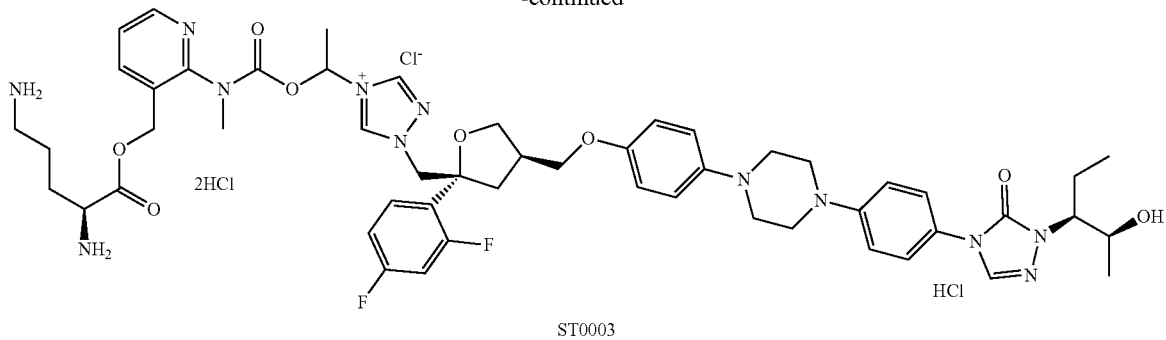

ST0003

Example 4

Preparation of Compound ST0004 of the Present Disclosure 4.1 Preparation of Compound (ST0004-002)

The preparation method referred to the example of the compound (ST0002-002).

4.2 Preparation of Compound (ST0004-003)

The preparation method referred to the example of the compound (ST0002-003).

4.3 Preparation of Compound (ST0004)

The preparation method referred to the example of the compound (ST0003). 2.2 g of (ST0004-003) was charged to give 1.92 g of a solid product (ST0004), MS (ESI, ½*(M−Cl)): 512.8.

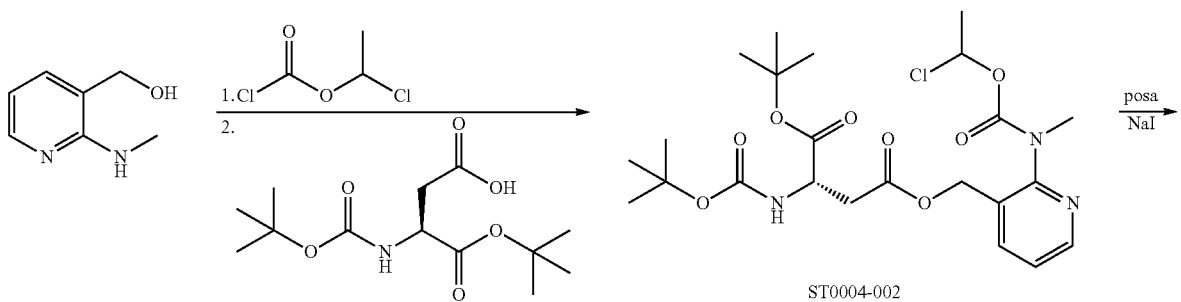

ST0004-002

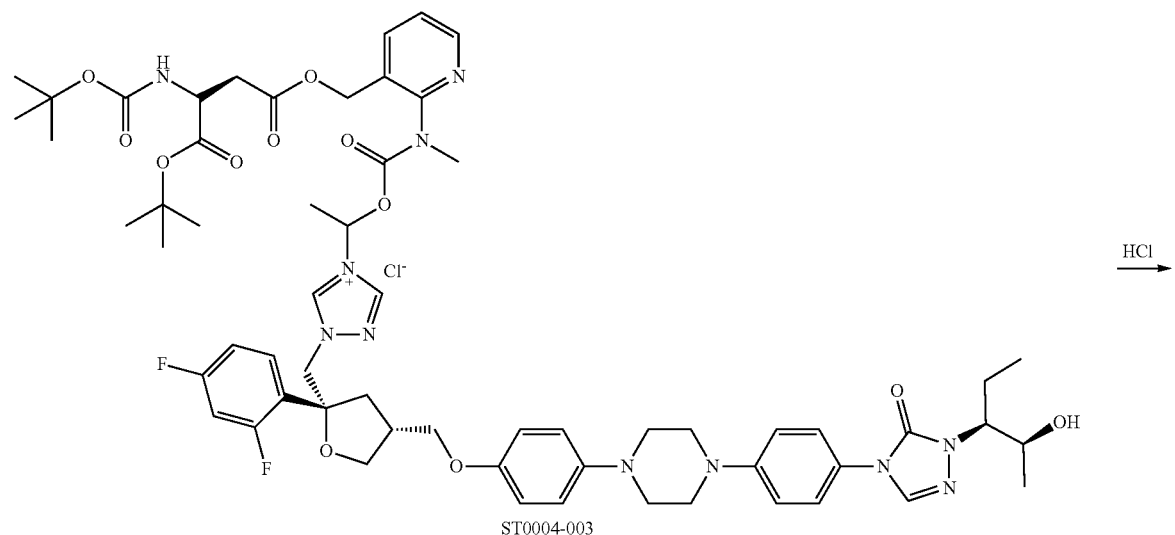

ST0004-003

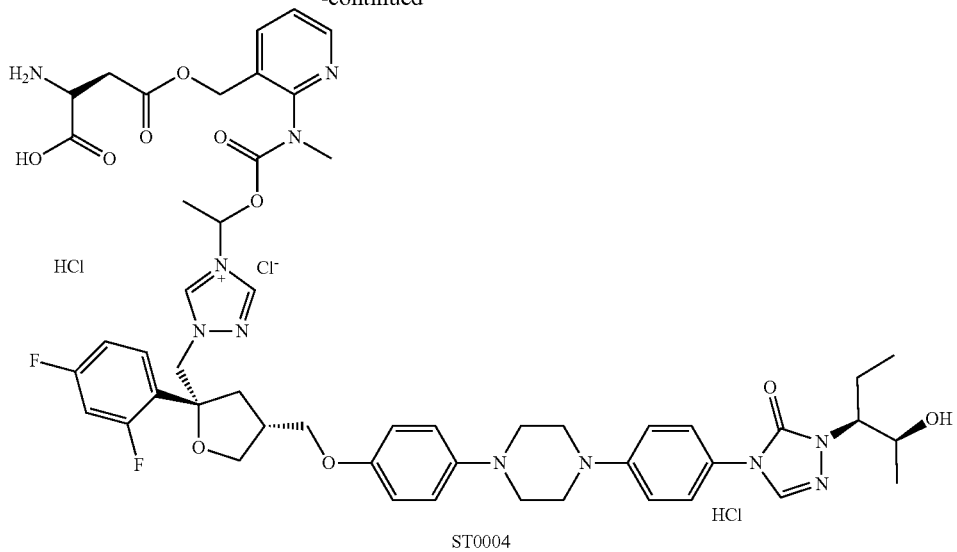

ST0004

Example 5

Preparation of Compound ST0005

5.1 Preparation of Compound (ST0005-002)

The preparation method referred to the example of the compound (ST0002-002).

5.2 Preparation of Compound (ST0005-003)

The preparation method referred to the example of the compound (ST0002-003).

5.3 Preparation of Compound (ST0005)

The preparation method referred to the example of the compound (ST0003). 2.0 g of (ST0005-003) was charged to give 1.0 g of a solid product (hydrochloride salt), which was purified by preparative HPLC to give 0.8 g of a white solid product (ST0005). MS (ESI, ½*(M−Cl)): 505.3.

5.4 Preparation of Free Products and Basic Salts of the Compound 5 mL of methanol was added to 0.16 g of the above hydrochloride salt, 2.5 equivalents of the solution of NaOH in methanol was added dropwise at 0° C., and the mixture was stirred for 30 minutes. 60 mL of methyl tert-butyl ether was added to the reaction solution, stirring was continued for 15 minutes, and the sodium salt of the compound was obtained by filtration.

Referring to the preparation method of the compound (0002), an appropriate amount of NaOH was used to give the corresponding free product.

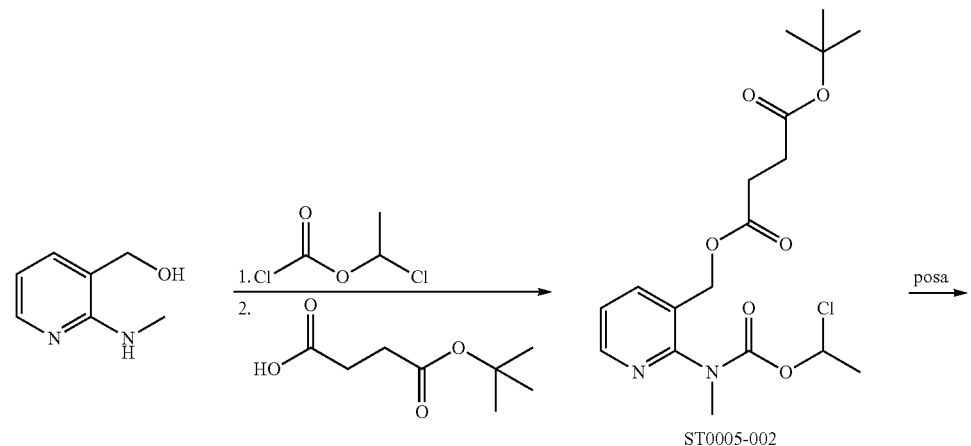

-continued

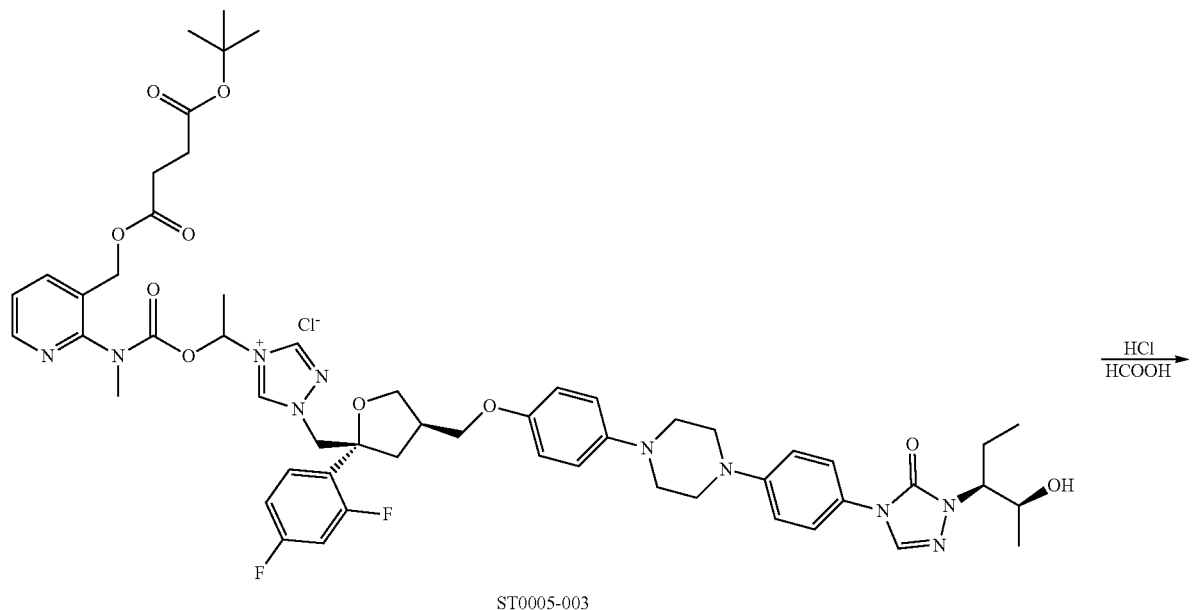

ST0005-003

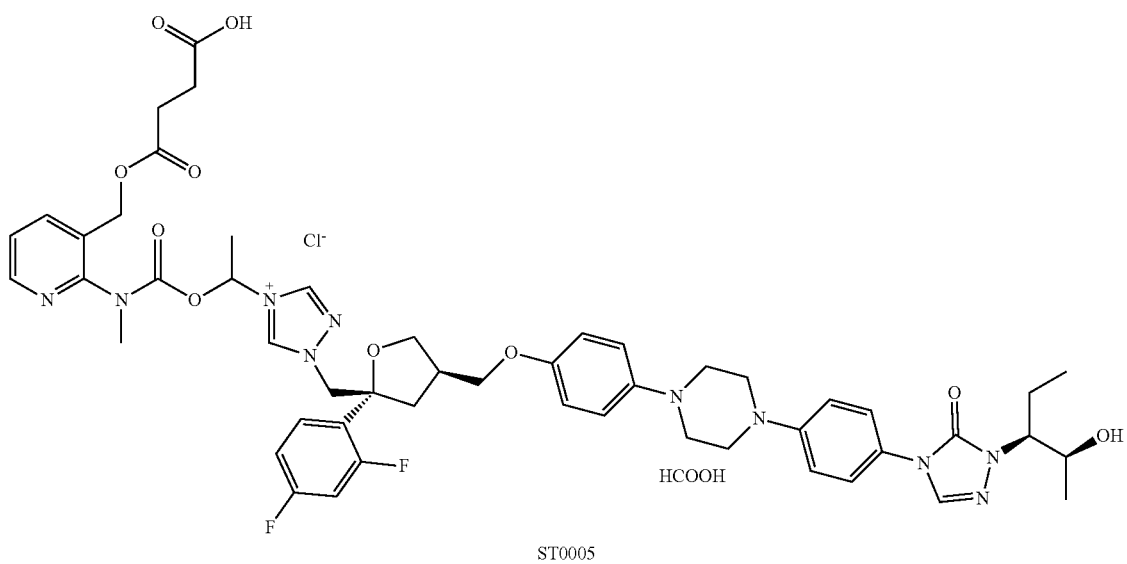

ST0005

Example 6

Preparation of Compound ST0006 of the Present Disclosure 6.1 Preparation of Compound (ST0006-002)

The preparation method of compound (ST0006-002) was referred to Journal of Inorganic Biochemistry 98 (2004), 1933-1946.

6.2 Preparation of Compound (ST0006-003)

The preparation method referred to the example of the compound (ST0002-002).

6.3 Preparation of Compound (ST0006-004)

The preparation method referred to the example of the compound (ST0002-003).

6.4 Preparation of Compound (ST0006)

The preparation method referred to the example of compound (ST0003). 1.0 g of (ST0006-004) was charged to give 0.5 g of a solid product (ST0006), MS (ESI, ½*(M−Cl)): 505.1.

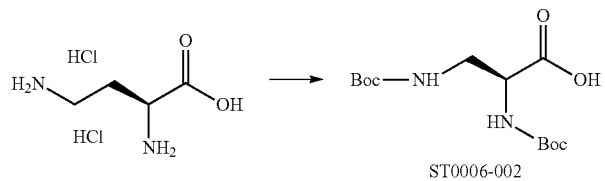
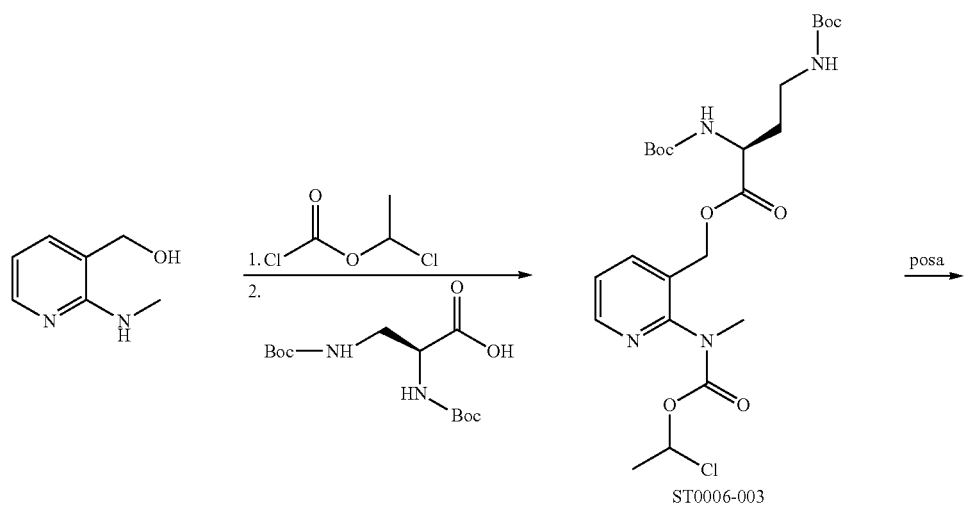
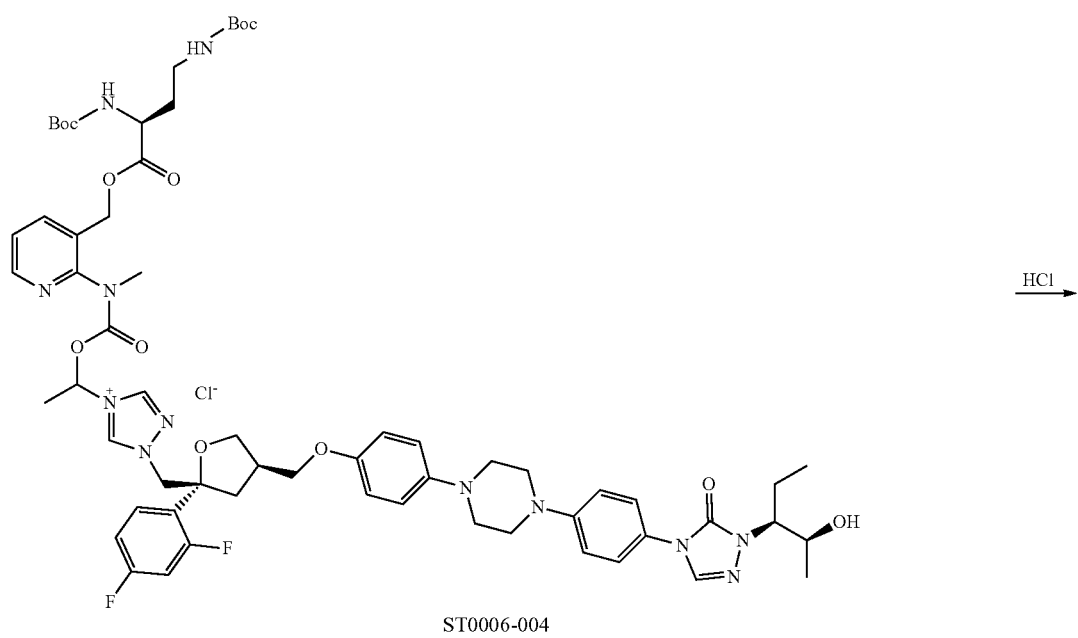

-continued

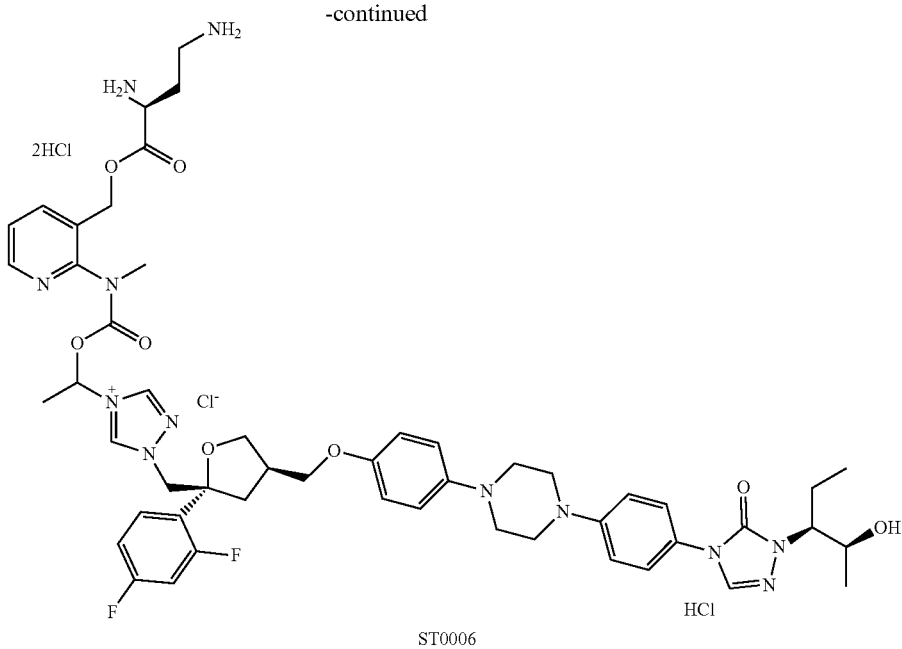

ST0006

Example 7

Preparation of Compound ST0007 of the Present Disclosure 7.1 Preparation of Compound (ST0007-003)

The preparation method referred to the example of the compound (ST0002-003). The amount of sodium iodide was 1.4 eq.

7.2 Preparation of Compound (ST0007)

The preparation method referred to the example of the compound (ST0003). 1.0 g of (ST0007-003) was charged to give 0.65 g of a solid product (ST0007), MS (ESI, ½*(M−I)): 512.5.

With reference to the preparation method of compound (0002), the free product of onium iodide salt could also be obtained.

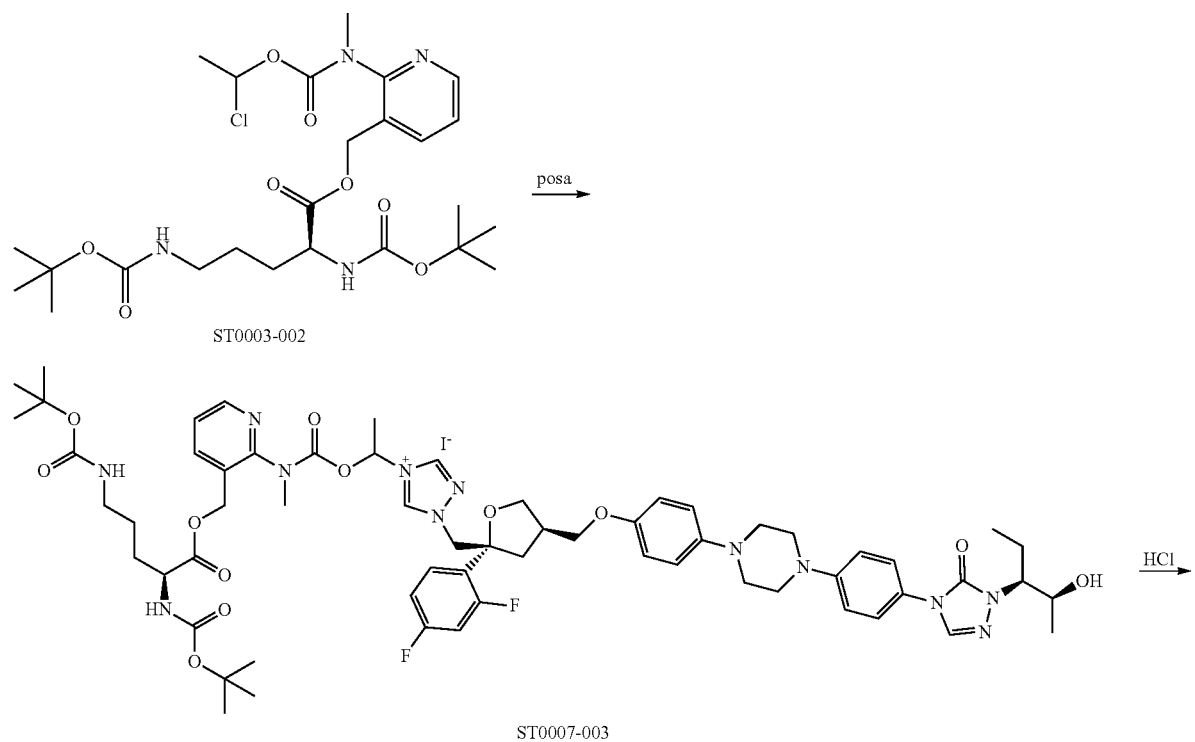

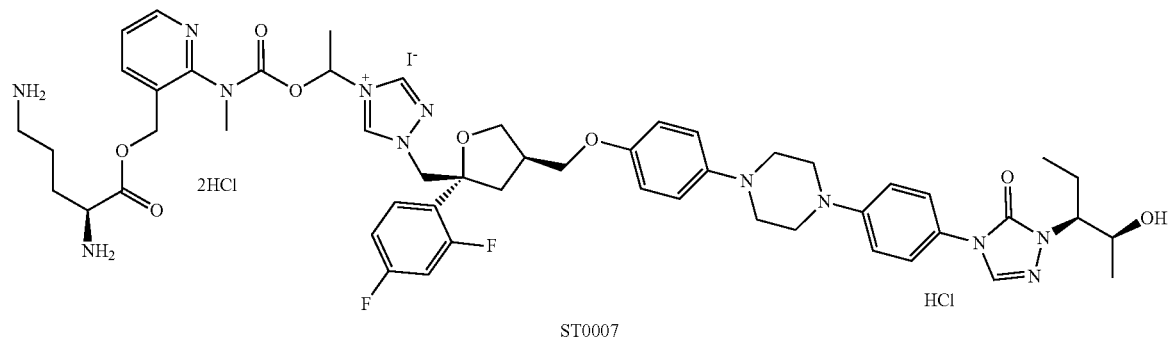

ST0007

Example 8

Preparation of Compound ST0008 of the Present Disclosure 8.1 Preparation of Compound (ST0008-002)
The preparation method referred to the example of the compound (ST0002-002).

8.2 Preparation of Compound (ST0008-003)
The preparation method referred to the example of the compound (ST0002-003).

8.3 Preparation of Compound (ST0008)
The preparation method referred to the example of the compound (ST0003). 1.0 g of (ST0008-003) was charged to give 0.63 g of solid product (ST0008), MS (ESI, ½*(M−Cl)): 511.6.

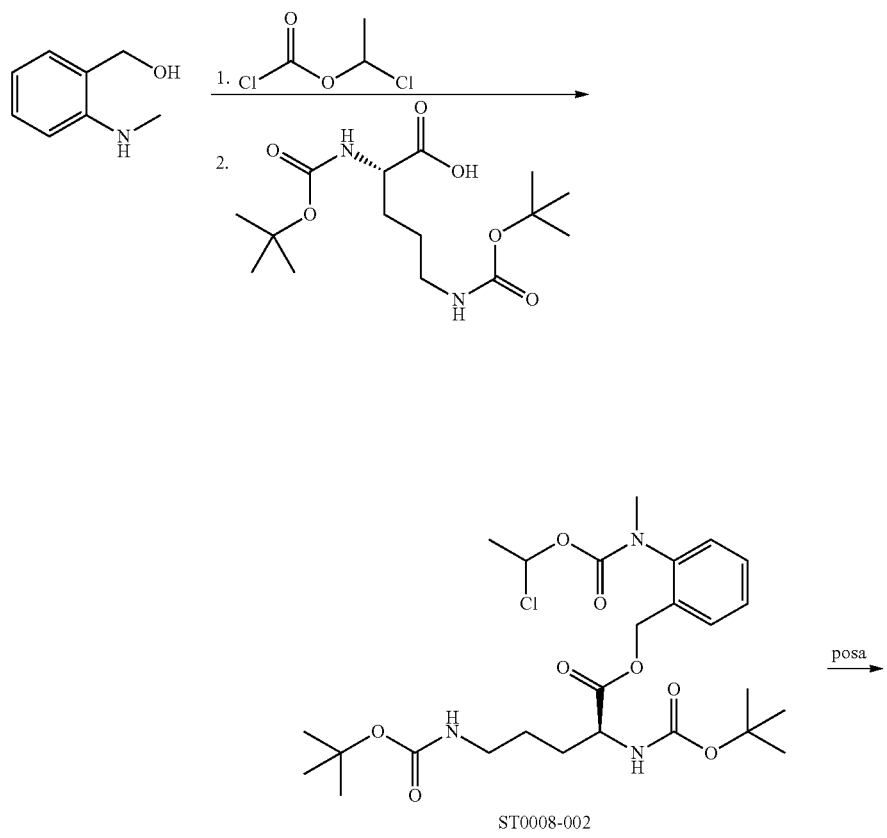

ST0008-002

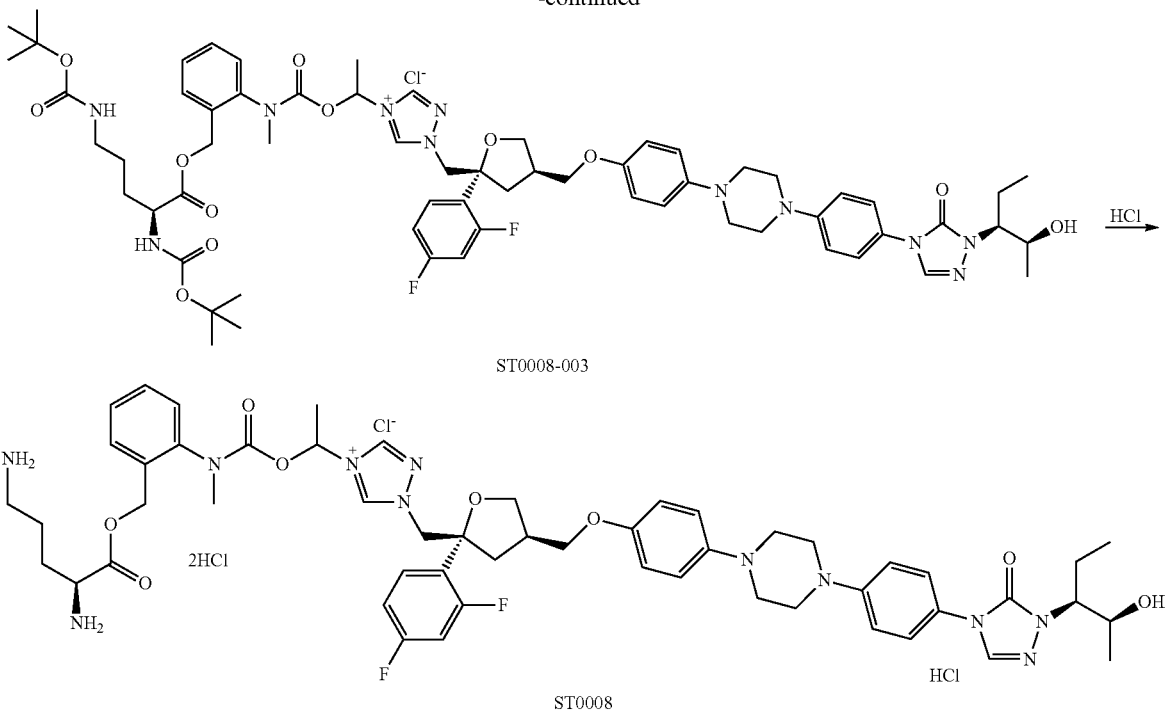

ST0008-003

ST0008

Example 9

Preparation of Compound ST0009 of the Present Disclosure

9.1 Preparation of Compound (ST0009-001)

1.0 g of posaconazole (posa) was weighted and dissolved in 10 ml DCM, 0.3 g of tetrazole was added, and 0.7 g of dibenzyl N,N-diisopropylphosphoramidite was added dropwise at room temperature. The mixture was reacted at room temperature for 3 hours. Under TLC monitoring, the raw materials were completely reacted. 0.4 g of t-butyl hydroperoxide was directly added dropwise to the above reaction solution at room temperature, and the mixture was reacted at room temperature for 1 hr. Under TLC monitoring, the raw materials were completely reacted. The reaction was quenched with 10% (w/v) sodium sulfite solution. After it was peroxide-free determined by starch-potassium iodide test paper, the solution was separated and the aqueous phase was further extracted once with DCM. The combined DCM layers were washed with saturated brine and dried over anhydrous MgSO$_4$, filtered, and concentrated to dryness. Purification by column chromatography gave the compound (ST0009-001).

9.2 Preparation of Compound (ST0009-002)

300 mg of the compound (ST0009-001) was dissolved in 12 ml absolute ethanol, 150 mg palladium-charcoal (5%) was added, heated to 40 to 45° C., and the reaction was incubated for 24 hours. Under TLC monitoring, the raw materials were completely reacted. The reaction was filtered through celite and concentrated to dryness. To the residue was added 4 ml of H$_2$O and 82 mg of N-methyl-D-glucosamine (NMG). The reaction was carried out at room temperature for 1 hr. The reaction mixture was concentrated to dryness under reduced pressure and pulped with acetone. The mixture was filtered and dried in vacuum to give 242 mg of the target compound (ST0009-002).

9.3 Preparation of Compound (ST0009-003)

The preparation method referred to the example of the compound (ST0002-003).

9.4 Preparation of Compound (ST0009)

The preparation method referred to the example of the compound (ST0003). 1.0 g of (ST0009-003) was charged to give 0.7 g of a solid product (ST0009), MS (ESI, ½*(M−Cl)): 552.1.

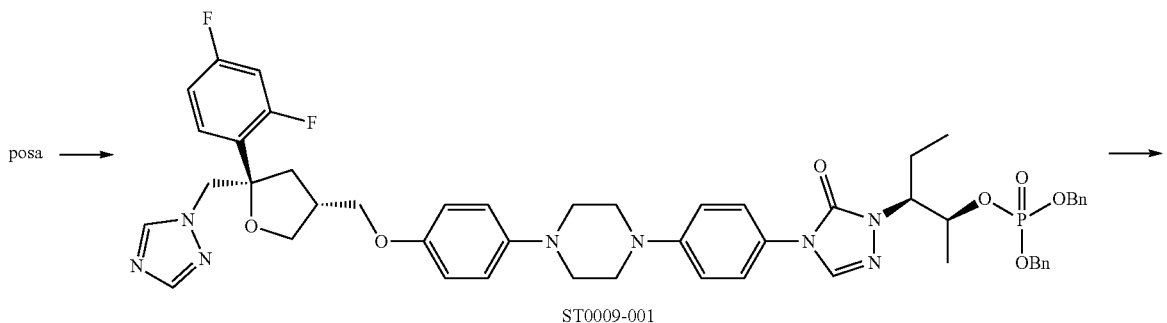

ST0009-001

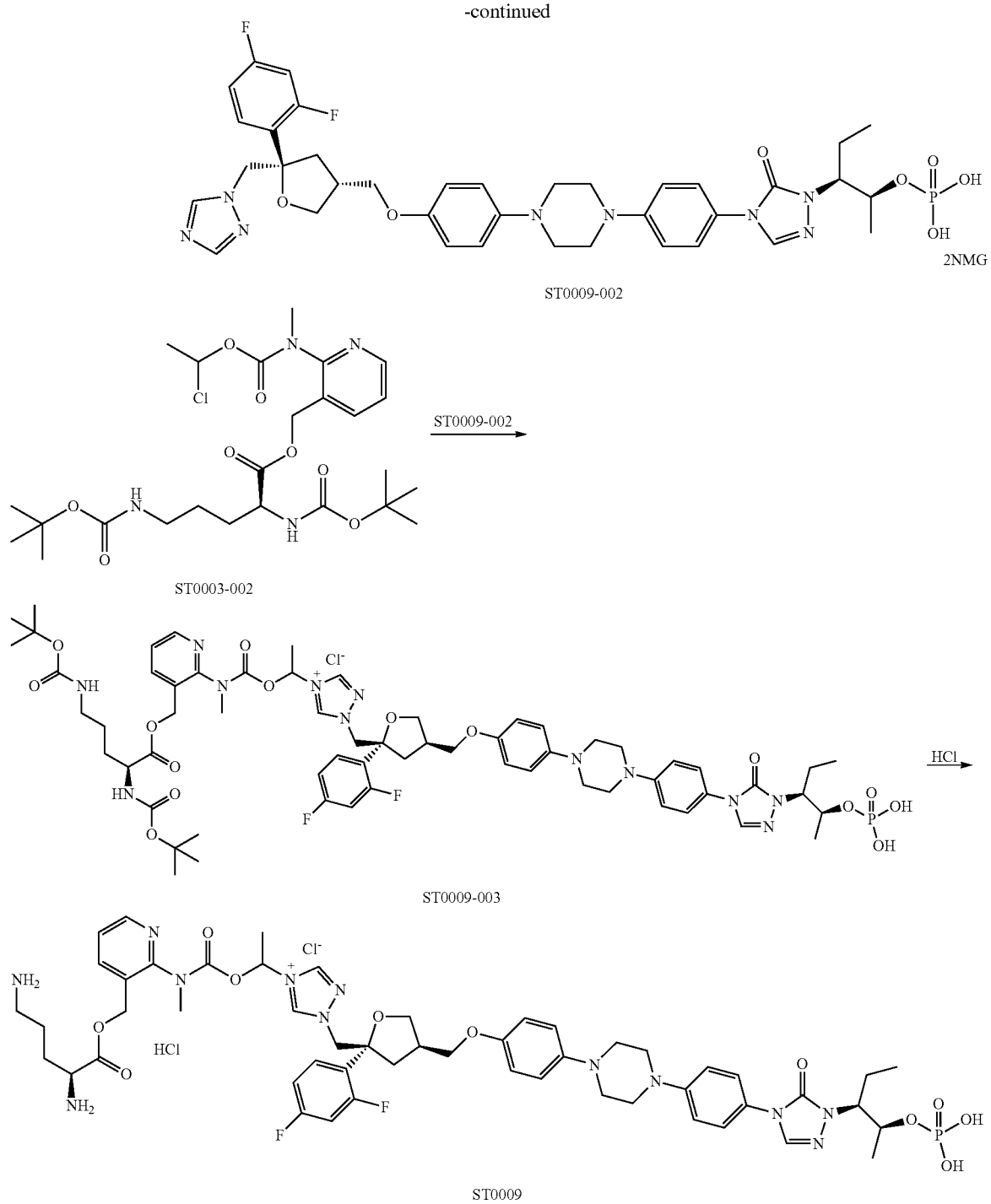

Example 10

Preparation of Compound ST0010 of the Present Disclosure 10.1 Preparation of Compound (ST0001-009)

5.01 g of L-serine was dissolved in 135 ml of methanol, 15 ml of 1 mol/L NaOH solution, 15 ml of triethylamine and 20.8 g of di-tert-butyl dicarbonate were added, and the mixture was stirred at room temperature overnight. Under TLC monitoring, the raw materials were completely reacted. After the reaction solution was concentrated to dryness, 75 ml of ethyl acetate was added, 3 mol/L hydrochloric acid was added dropwise to adjust the pH to 2. The mixture was separated, and the aqueous phase was extracted once with 75 ml of ethyl acetate, and the ethyl acetate layers were combined, washed with saturated brine, dried over MgSO$_4$, filtered, and concentrated to dryness to give 9.8 g of a compound (ST0001-008).

5.66 g of the compound (ST0001-008) was dissolved in 50 ml of N,N-dimethylformamide (DMF), cooled to 0 to 5° C. 5.83 g of imidazole and 5.80 g of TBSCl were added, and reacted at 0 to 5° C. for 1 hr. 1 mol/L hydrochloric acid was added to the reaction solution to adjust pH to 2. The mixture was extracted twice with MTBE (100 ml×2), washed three times with water (100 ml×3), dried over anhydrous MgSO₄, filtered, concentrated, and purified by column chromatography to give 5.3 g of the compound (ST0001-009).

10.2 Preparation of Compound (ST0010-002)

2.0 g of posaconazole (posa) was weighed and dissolved in 16 ml of DCM, 0.55 g of 4-dimethylaminopyridine (DMAP) and 1.43 g of compound (ST0001-009) were added. The temperature was lowered to 0 to 5° C., and 0.92 g of dicyclohexylcarbodiimide (DCC) was added, and the reaction was kept at 0 to 5° C. for 1 hr, moved to room temperature for reacting for 5 hours, then 0.92 g of DCC was supplemented, and reacted overnight. Under TLC monitoring, the raw materials were substantially reacted. Then the mixture was filtered, concentrated to dryness and purified by column chromatography to give 2.50 g of a white solid compound (ST0010-001).

1.48 g of the compound (ST0010-001) was dissolved in a 4 mol/L HCl solution and reacted for 3 hours at room temperature. Under TLC monitoring, the raw materials were substantially reacted. The reaction solution was concentrated to dryness under reduced pressure at 40 to 45° C., and 10 ml of acetone was added to the residue. The mixture was slurried at room temperature for 15 minutes and filtered. The filter cake was washed with 10 ml of methyl tert-butyl ether (MTBE) and dried in vacuum to give 0.8 g of the target compound (ST0010-002).

10.3 Preparation of Compound (ST0010-003)

The preparation method referred to the example of the compound (ST0002-003).

10.4 Preparation of Compound (ST0010)

The preparation method referred to the example of the compound (ST0003). 1.0 g of the compound (ST0010-003) was charged to obtain 0.67 g of a solid product (ST0010), MS (ESI, ½*(M−Cl)): 555.6.

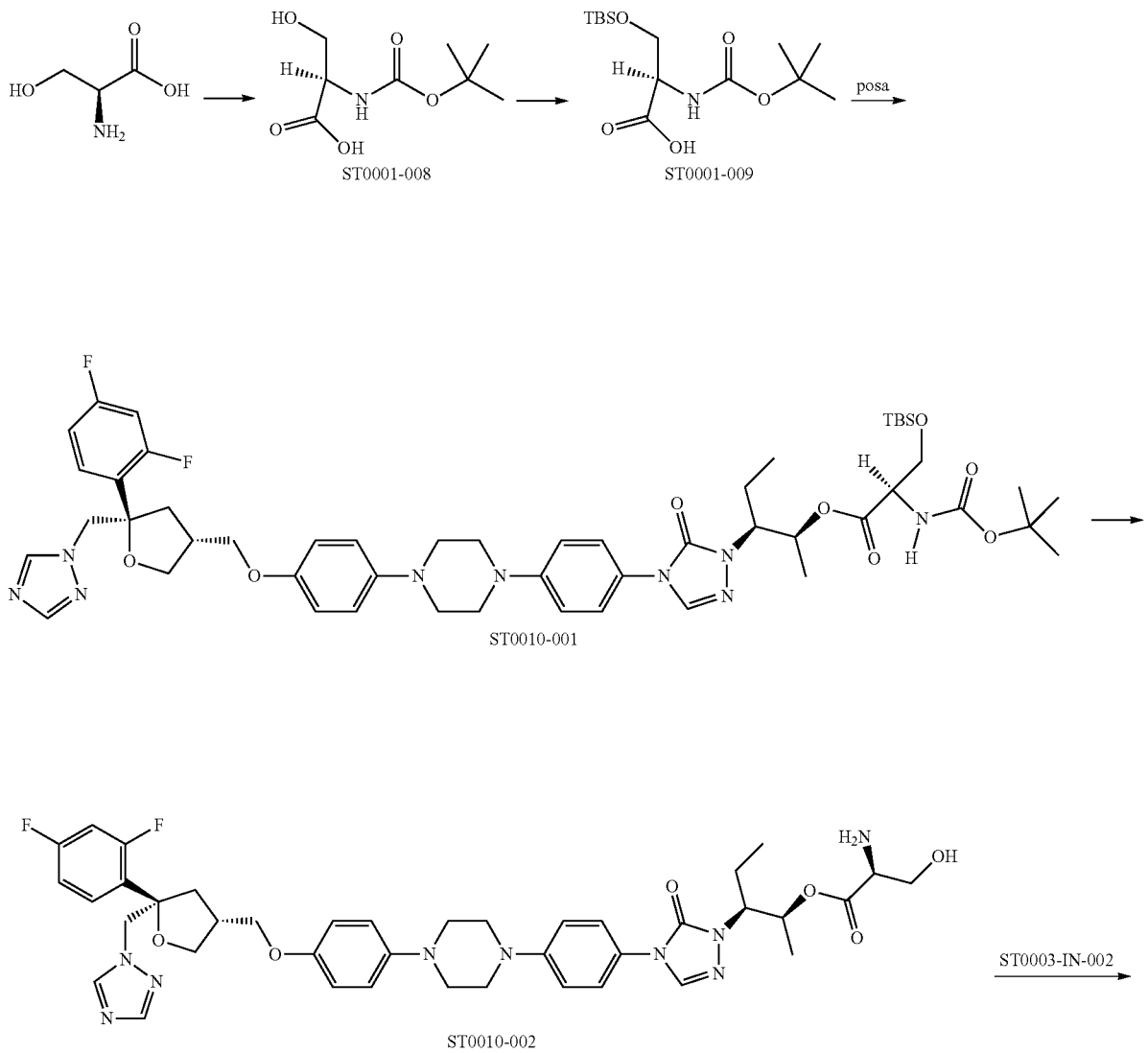

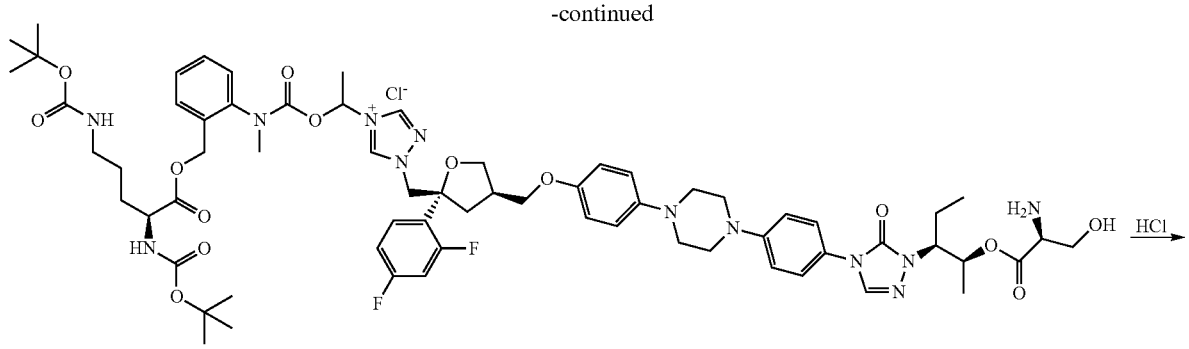
ST0010-003
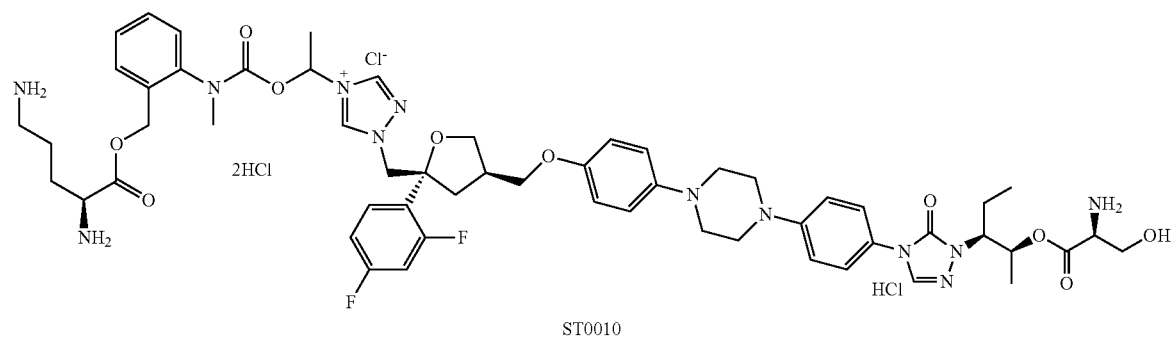
ST0010
Example 11
Preparation of Compound ST0011 of the Present Disclosure
11.1 Preparation of Compound (ST0011-003)
The preparation method referred to the example of the compound (ST0002-003), and the amount of sodium bromide was 1.4 eq.
11.2 Preparation of Compound (ST0011)
The preparation method referred to the example of the compound (ST0003). 1.0 g of (ST0011-003) was charged to obtain 0.66 g of a solid product (ST0011), MS (ESI, ½* (M-Br)): 512.5.
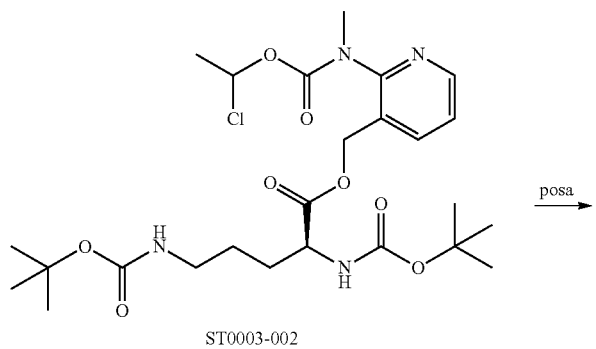
ST0003-002

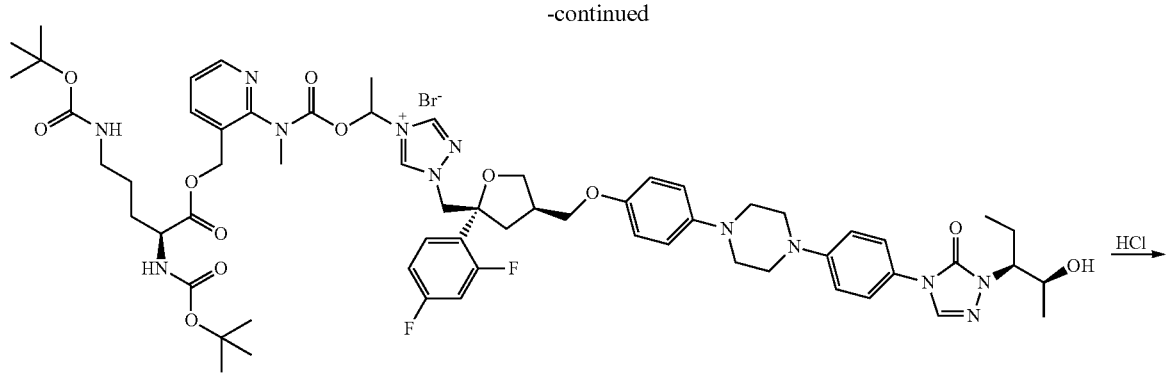

ST0010-003

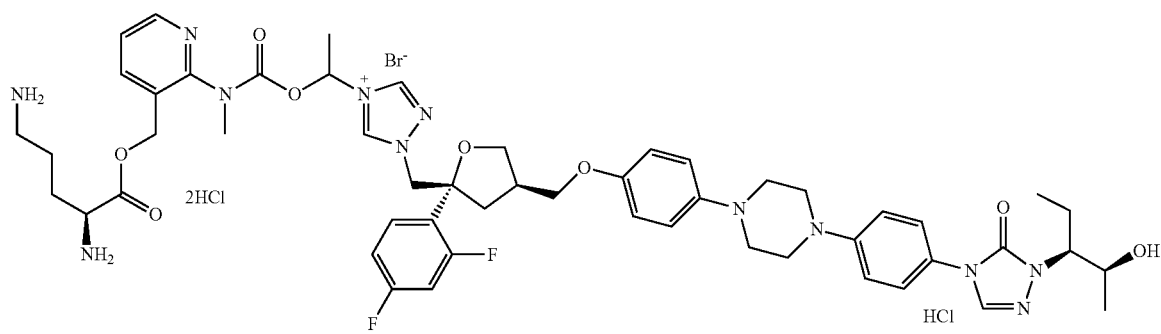

ST0011

Example 12

Preparation of Compound ST0012 of the Present Disclosure 12.1 Preparation of Compound (ST0012-002)

The preparation method referred to the example of the compound (ST0002-002).

12.2 Preparation of Compound (ST0012-003)

The preparation method referred to the example of the compound (ST0002-003).

12.3 Preparation of Compound (ST0012)

2.0 g of the ST0012-003 compound was dissolved in 10 mL of methylene chloride at room temperature and stirred to dissolve. A solution of hydrogen chloride in 1,4-dioxane was added dropwise over 10 minutes, then the mixture was stirred at room temperature for 1 hr. It was determined by TLC that the reaction was complete. The solution was decanted, concentrated to dryness and treated with acetone and methyl tert-butyl ether to give 1.51 g of a solid product (ST0012), MS (ESI, ½*(M−Cl)): 533.6.

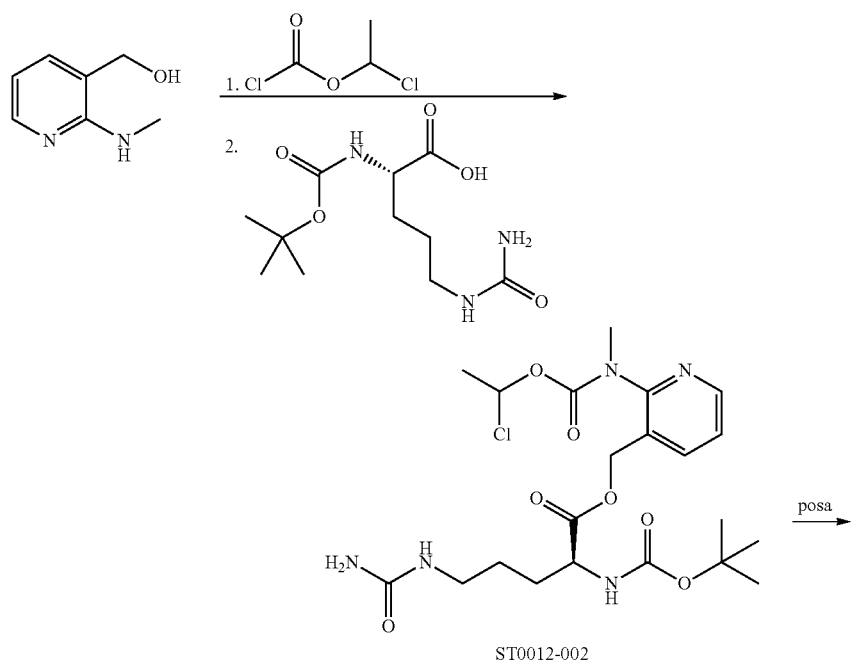

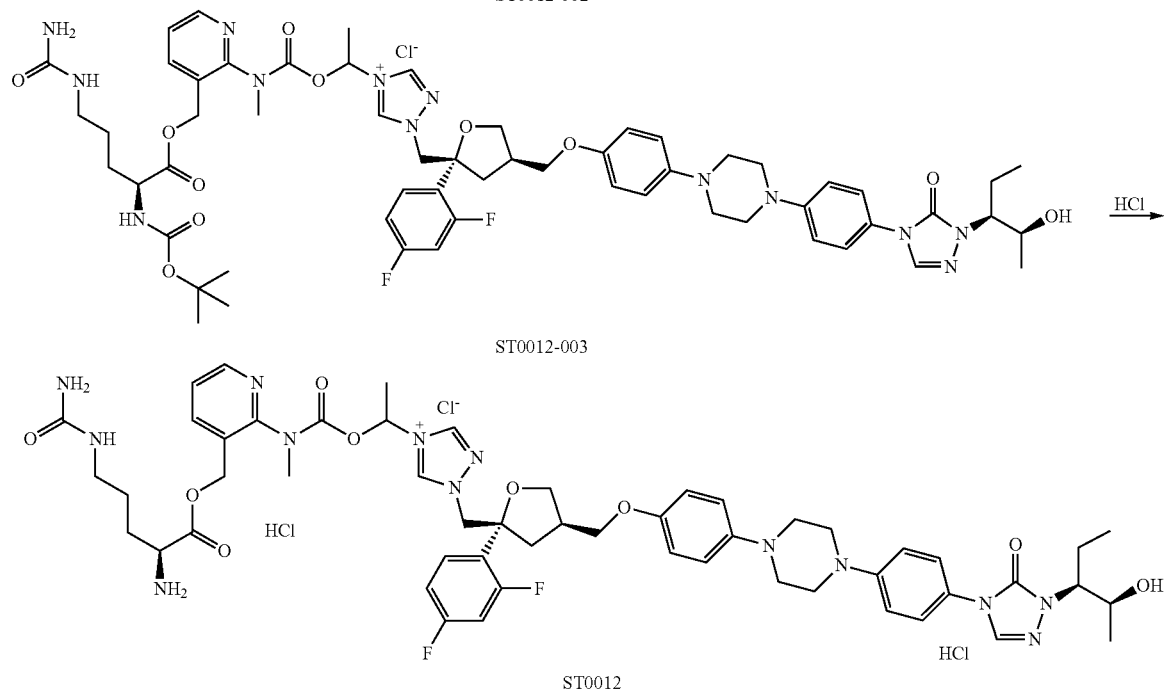

Example 13

Preparation of Compound ST0013 of the Present Disclosure 13.1 Preparation of Compound (ST0013-003)

At room temperature, 2.5 g of ST0003-003 was weighed and dissolved in 15 mL acetonitrile and 8 mL purified water, 8 g ion exchange resin (sulfate type) was added, stirred at 0° C. under nitrogen protection for 2 hours. The mixture was filtered, rinsed with acetonitrile. The filtrate was concentrated to remove acetonitrile. 50 mL of dichloromethane and 30 mL of brine were added and the mixture was stirred and separated. The organic phase was washed once more with brine; dried over anhydrous magnesium sulfate, filtered and concentrated to give 2.4 g of the compound ST0013-003.

13.2 Preparation of Compound (ST0013)

2.4 g of compound ST0003-003 was dissolved in 24 mL of methylene chloride under nitrogen protection, stirred to dissolve and cooled to 0° C. 12 mL of trifluoroacetic acid was added dropwise. Under TLC monitoring, the raw materials were completely reacted. The reaction was concentrated to dryness. 50 mL of water was added to dissolve. An equivalent of 6 M/L sulfuric acid was added and lyophillized to give 1.8 g product (ST0013), MS (ESI, ½*(M–SO$_4$)): 512.5.

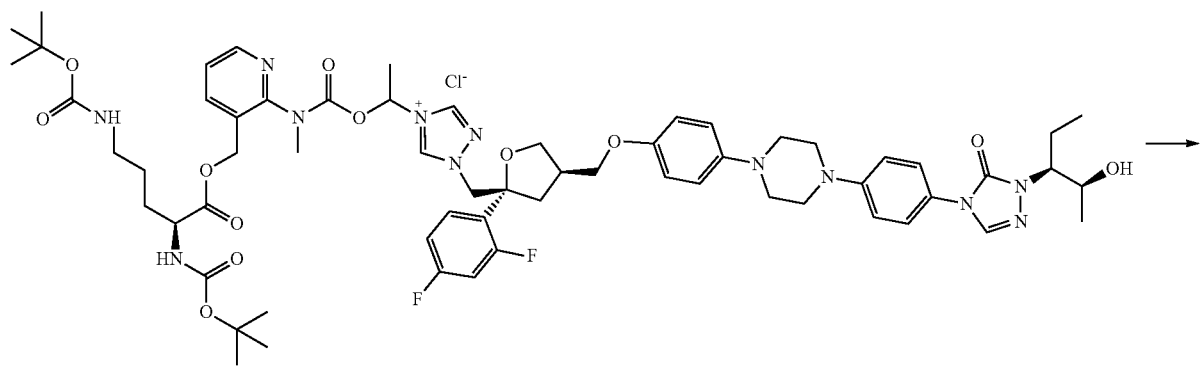

ST0003-003

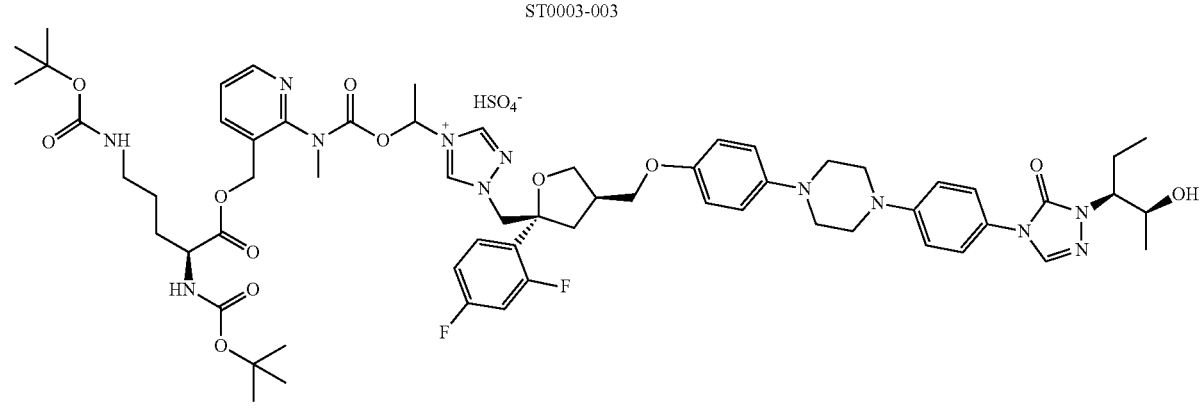

ST00013-003

Example 14

Preparation of Compound ST0014 of the Present Disclosure 14.1 Preparation of Compound (ST0014-003)

The preparation method referred to the example of the compound (ST0013-003) except the ion exchange resin was phosphate type.

14.2 Preparation of Compound (ST0014)

The preparation method referred to the example of the compound (ST0013). 1.0 g of (ST0014-003) was charged, and finally an equivalent phosphoric acid was added and lyophilized to give 0.7 g of a solid product (ST0014), MS (ESI, ½*(M−H2PO4)): 512.5.

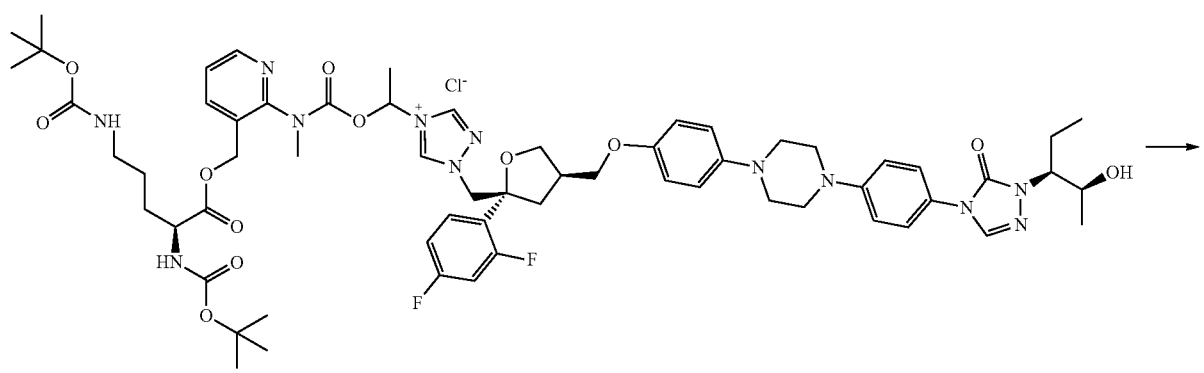

ST0003-003

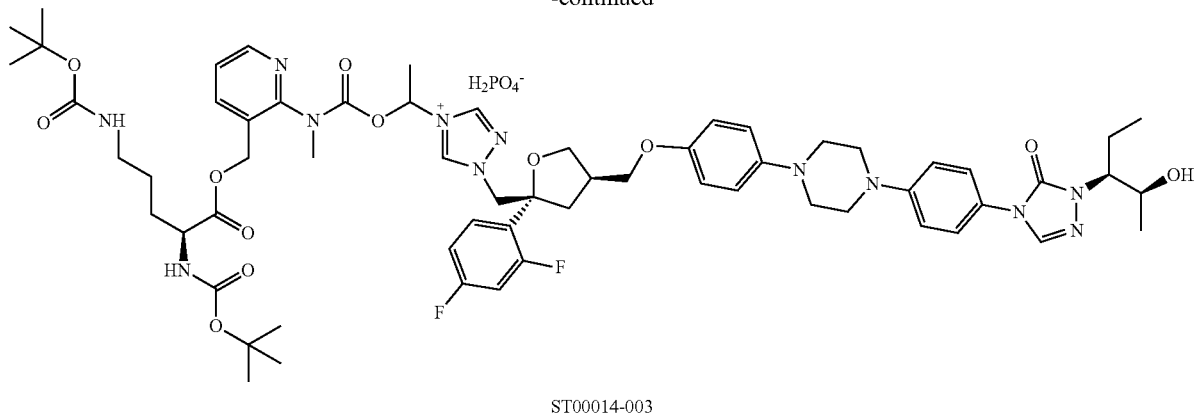

ST00014-003

Example 15

Preparation of Compound ST0015 of the Present Disclosure 15.1 Preparation of Compound (ST0015-003)

The preparation method referred to the example of the compound (ST0013-003), except the ion exchange resin was nitrate type.

15.2 Preparation of Compound (ST0015)

The preparation method referred to the example of the compound (ST0013). 1.0 g of (ST0015-003) was charged, and finally an equivalent of nitric acid was added and lyophilized to give 0.6 g of a solid product (ST0015), MS (ESI, ½*(M–NO₃)): 512.5.

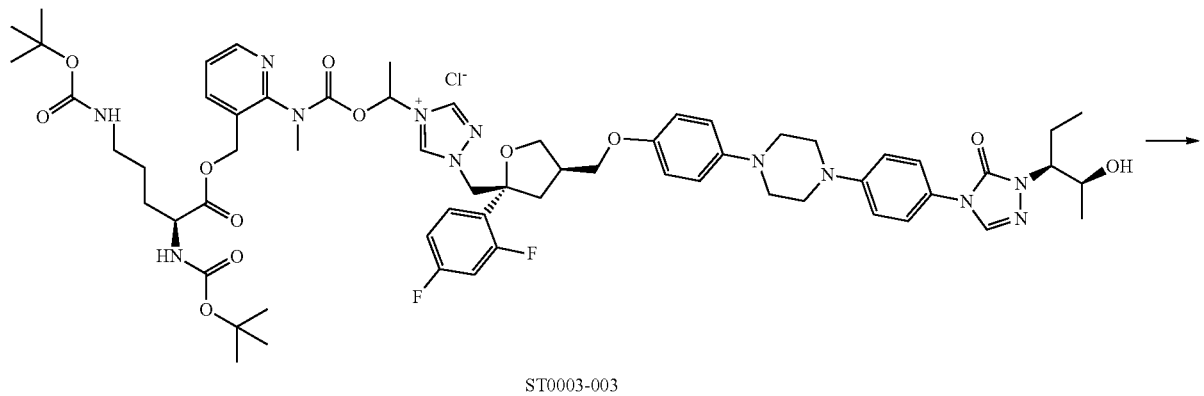

ST0003-003

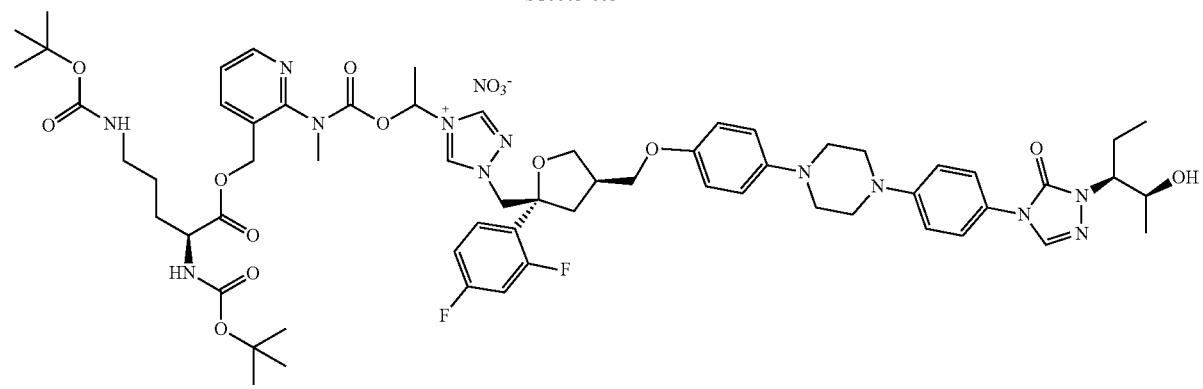

ST00015-003

Example 16

Preparation of Compound (ST0022) of the Present Disclosure

16.1 Preparation of Compound (ST0022-001)

Under nitrogen protection, 80 mL of methylene chloride, 1.40 g of 2-methylamino-3-pyridinemethanol, and 1.50 g of N,N-diisopropylethylamine were successively added, and the above reaction system was cooled to −15 to −20° C. A solution of 1.45 g of 1-chloroethyl chloroformate in dichloromethane (20 mL) was added dropwise. The reaction was carried out at −15 to −20° C. for 16 hours. To the above reaction solution, 2.50 g of N-Boc-L-glutamine (CAS No. 13726-85-7) and 0.24 g of DMAP were added at a temperature of −15 to −20° C. and stirred to dissolve. Then, 1.91 g of 1-ethyl-3-(3-dimethylaminopropyl)carbodiimide hydrochloride was added, and the reaction was continued at a temperature of −15 to −20° C. for 2 hours. It was determined by TLC that the reaction was complete. The reaction solution was concentrated, methyl tert-butyl ether was added for dissolution, washed successively with 0.1 M hydrochloric acid, saturated sodium bicarbonate solution, and brine, dried, filtered, and concentrated to give a crude product, which is purified by silica gel column chromatography to give 3.1 g of a colorless oily compound (ST0022-001).

16.2 Preparation of Compound (ST0022-002)

To a reaction flask, 70 mL of acetonitrile and 2.36 g of (ST0022-001) was added, stirred to dissolve, then 3.50 g of posaconazole, 0.01 g of sodium iodide were added, and the reaction system was heated to 50 to 60° C. for 5 hours. It was determined by TLC that the reaction was complete. The reaction solution was concentrated to give an oily product which was purified by silica gel column chromatography to give 4.2 g of the compound (ST0022-002).

16.3 Preparation of Compound (ST0022)

At room temperature, 1.15 g of compound ST0022-002 was dissolved in 10 mL of dioxane. After stirring and dissolving, the system was cooled to 0° C., and 4 mL of HCl/dioxane solution was added dropwise at 0° C. After the addition was completed, the reaction was continued to be stirred at room temperature for 1 hr. It was determined by TLC that the reaction was complete. The reaction mixture was filtered to give 0.68 g of a solid as the compound (ST0022). MS (ESI, (M−Cl)): 1037.5.

Referring to the method of the example of compound (0002), a sulfate type ion exchange resin was used to give the corresponding sulfate (ST0102); MS (ESI, (M−SO₄)): 1037.5.

Similarly, different salts such as onium bromides, onium iodides, onium nitrate salts, and onium phosphate salts or corresponding free bases thereof can be obtained using different catalysts or ion exchanges, and the product identification can be performed by ion chromatography and mass spectrometry.

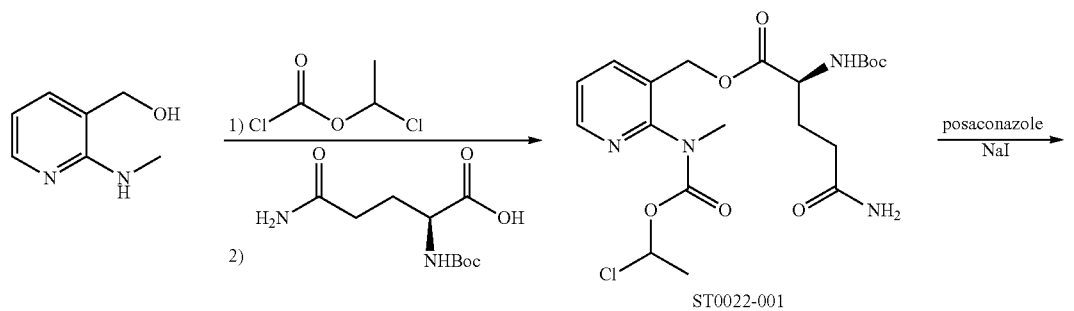

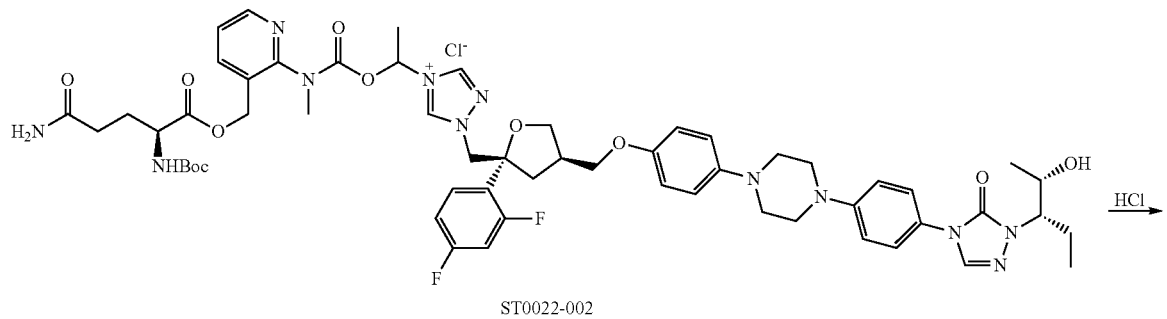

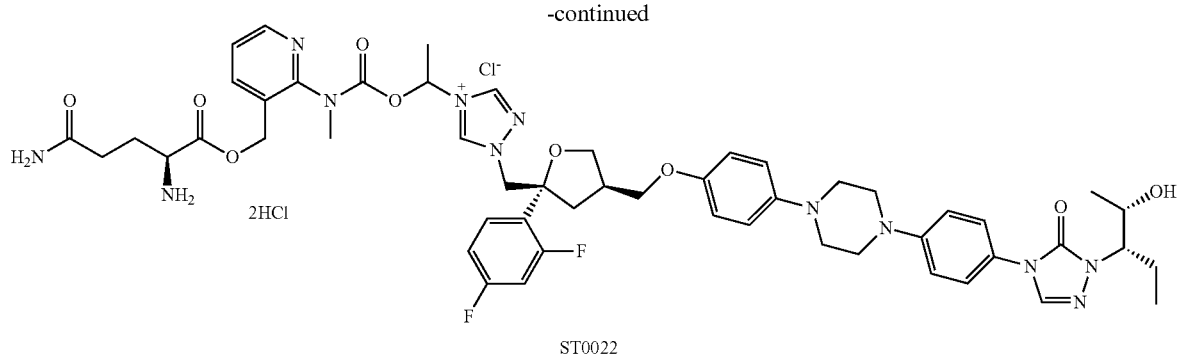

ST0022

Example 17

Preparation of Compound (ST0023) of the Present Disclosure

The preparation method referred to Example 16, wherein N-Boc-L-asparagine (CAS No. 7536-55-2) was used to replace N-Boc-L-glutamine in Example 16. MS (ESI, (M−Cl)): 1023.5.

Referring to the method of the compound (0002), a sulfate type ion exchange resin was used to give the corresponding sulfate (ST0103); MS (ESI, (M−SO₄)): 1023.5.

Similarly, different salts such as onium bromides, onium iodides, onium nitrate salts, and onium phosphate salts or corresponding free bases thereof can be obtained using different catalysts or ion exchanges, and the product identification can be performed by ion chromatography and mass spectrometry.

Example 18

Preparation of Compound (ST0024) of the Present Disclosure 18.1 Preparation of Compound (ST0024-001)

Under nitrogen protection and stirring, 80 mL of dichloromethane, 1.40 g of 2-methylamino-3-pyridinemethanol, and 1.50 g of N,N-diisopropylethylamine were successively added to a reaction flask. The above reaction system was cooled to −15 to −20° C., and a solution of 1.45 g of 1-chloroethyl chloroformate in dichloromethane (20 mL) was added dropwise. The reaction solution was kept at a temperature of −15 to −20° C. for 16 hours. To the above reaction solution were slowly added 3.50 g of (S)-2,6-di-tert-butoxycarbonylaminohexanoic acid (CAS No.: 2483-46-7) and 0.24 g of DMAP while keeping the temperature at −15 to −20° C. After stirring and dissolving, 1.91 g of 1-ethyl-3-(3-dimethylaminopropyl)carbodiimide hydrochloride was added in batches, and then the reaction was kept at a temperature of −15 to −20° C. for 8 hours. It was determined by TLC that the reaction was complete. The reaction solution was concentrated, methyl tert-butyl ether was added for dissolution, washed successively with 0.1 M hydrochloric acid, saturated sodium bicarbonate solution, and brine, dried, filtered, and concentrated to give a crude product which was purified by silica gel column chromatography to give 3.1 g of a colorless oily (ST0024-001) compound.

18.2 Preparation of Compound (ST0024-002)

To a 250 mL three-neck flask, 70 mL of acetonitrile and 3.0 g of the compound (ST0024-001) was added, stirred to dissolve, then 1.75 g of posaconazole and 0.11 g of sodium iodide were added, and the reaction system was heated to 50 to 60° C. for 5 hours. It was determined by TLC that the reaction was complete. The reaction solution was concentrated to give an oily product which was purified by silica gel column chromatography to give 2.9 g of the compound (ST0024-002).

18.3 Preparation of Compound (ST0024)

At room temperature, 0.80 g of the compound ST0024-002 was dissolved in 10 mL of dioxane. After stirring and dissolving, the system was cooled to 0° C., and 4 mL of HCl/dioxane solution was slowly added dropwise at 0° C. After the addition was completed, the reaction was continued to be stirred at room temperature for 1 hr. It was determined by TLC that the reaction was complete. The solution was quickly filtered under a nitrogen atmosphere and the solid was washed with ethyl acetate and acetone respectively to give 0.54 g of a white compound (ST0024). MS (ESI, (M−Cl)): 1037.5.

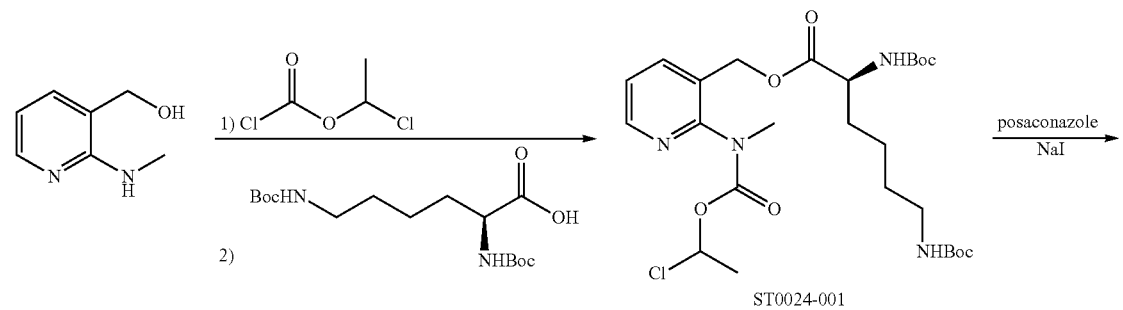

ST0024-001

-continued

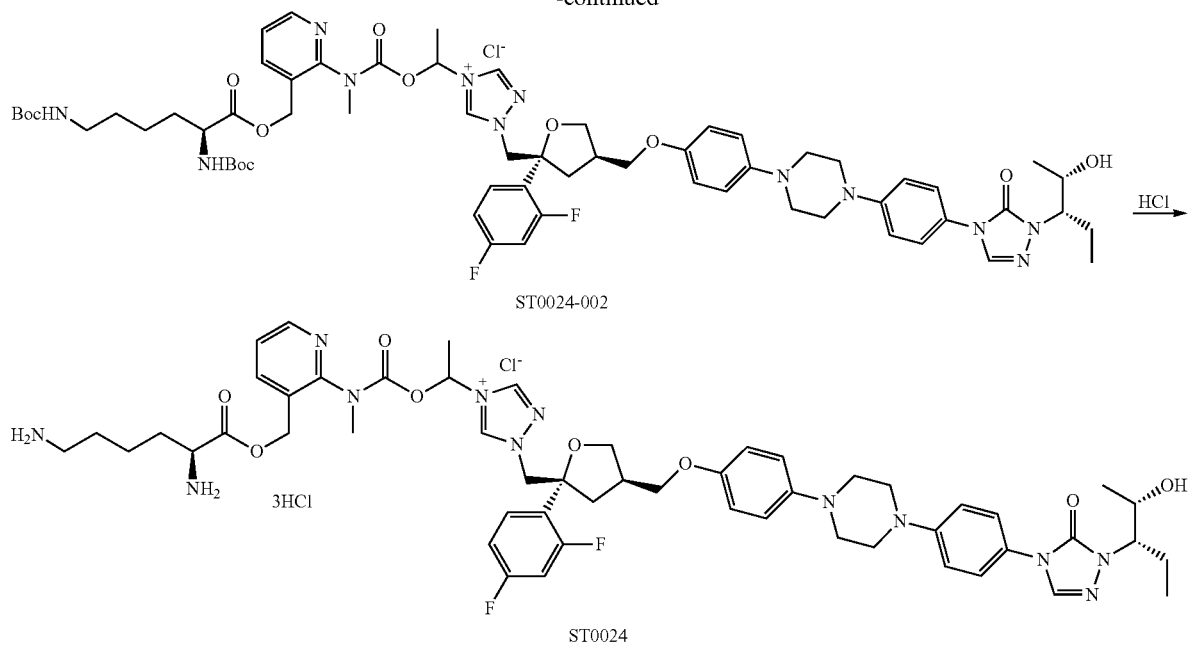

ST0024-002

ST0024

Referring to the method of the compound (0002), a sulfate type ion exchange resin was used to give a corresponding sulfate (ST0104); MS (ESI, (M−SO$_4$)): 1037.5.

Similarly, different salts such as onium bromides, onium iodides, onium nitrate salts, and onium phosphate salts or corresponding free bases thereof can be obtained using different catalysts or ion exchanges, and the product identification can be performed by ion chromatography and mass spectrometry.

Example 19

Preparation of Compound (ST0025) of the Present Disclosure

The preparation method referred to Example 16, wherein N-Boc-O-t-butyldimethylsilyl-L-serine (CAS No. 90181-25-2, its preparation method referred to Example 3 of a patent reference CN103626825A) was used to replace N-Boc-L-glutamine in Example 16. MS (ESI, (M−Cl)): 996.5.

Referring to the method of the compound (0002), a sulfate type ion exchange resin was used to give the corresponding sulfate (ST0105); MS (ESI, (M−SO$_4$)): 996.5.

Similarly, different salts such as onium bromides, onium iodides, onium nitrate salts, and onium phosphate salts or corresponding free bases thereof can be obtained using different catalysts or ion exchanges, and the product identification can be performed by ion chromatography and mass spectrometry.

Example 20

Preparation of Compound (ST0026) of the Present Disclosure

The preparation method referred to Example 16, wherein N-Boc-O-t-butyldimethylsilyl-L-threonine (CAS No. 90181-26-3, its preparation method referred to the prepara-tion of 614b on page 377 of a patent reference WO2013130660A) was used to replace N-Boc-L-glutamine in Example 16. MS (ESI, (M−Cl)): 1010.5.

Referring to the method of the compound (0002), a sulfate type ion exchange resin was used to give a corresponding sulfate (ST0106); MS (ESI, (M−SO$_4$)): 1010.5.

Similarly, different salts such as onium bromides, onium iodides, onium nitrate salts, and onium phosphate salts or corresponding free bases thereof can be obtained using different catalysts or ion exchanges, and the product identification can be performed by ion chromatography and mass spectrometry.

Example 21

Preparation of Compound (ST0027) of the Present Disclosure

The preparation method referred to Example 16, wherein N-Boc-O-t-butyldimethylsilyl-L-tyrosine (CAS No. 94732-15-7, its preparation method referred to WO2008106860A1, page 21, preparation of compound 14) was used to replace N-Boc-L-glutamine in Example 16. MS (ESI, (M−Cl)): 1072.5.

Example 22

Preparation of Compound (ST0038) of the Present Disclosure (S)-2-tert-butoxycarbonylamino-5-tert-butoxycarbonyl-carbaminovaleric acid was used as a raw material (its preparation method referred to *Bioorg. Med. Chem. Lett.* 15(2005) 3934-3941, and also referred to the preparation of the compound (ST0001-008) in Example 10 to protect the amino group), by referring to the process in Example 16, to obtain the compound ST0038; MS (ESI, (M−Cl)): 1037.5.

Example 23

Preparation of Compound (ST0040) of the Present Disclosure (S)-2-tert-butoxycarbonylamino-4-tert-butoxycarbomethylaminobutyric acid was used as a raw material (its preparation method referred to Example 22), by referring to the preparation method of compound ST0038, to obtain the compound ST0040; MS (ESI, (M−Cl)): 1023.5.

Example 24

Preparation of Compound (0045) of the Present Disclosure

Compound (0045) was obtained with reference to the preparations of 16.1 and 16.2 in Example 16, wherein dimethyl glycine (CAS No. 1118-68-9) was used to replace N-Boc-L-glutamine in Example 16; MS (ESI, (M−Cl)): 976.5. Hydrochloric acid was added to the resulting product to give a corresponding salt ST0045.

Example 25

Preparation of Compound 0017 of the Present Disclosure 25.1 Preparation of Compound (0017-001)

Under nitrogen protection, 0.01 mol of tert-butyl 2-glycolate (0017-SM, CAS No.: 50595-15-8), 80 mL of dichloromethane, and 0.01 mol of N,N-diisopropyl ethylamine were added to a reaction flask, stirred and cooled to −15 to −20° C., and a 0.01 mol solution of 1-chloroethyl chloroformate in dichloromethane (20 mL) was added dropwise. The reaction solution was maintained at a temperature of −15 to −20° C. for 16 hours. To the reaction solution was added water, stirred, and separated. The organic phase was washed with brine, dried, filtered, and concentrated to obtain a crude product, which was purified by silica gel column chromatography to give 1.90 g of the compound (0017-001).

25.2 Preparation of Compound (0017-002)

To a reaction flask, 0.005 mol of the above-prepared compound (0017-001) and 70 mL of acetonitrile were added, stirred to dissolve. 0.005 mol of posaconazole and 0.1 g of sodium iodide were added, and heated to 50 to 60° C. for 5 hours. It was determined by TLC that the reaction was complete. The reaction solution was concentrated to give an oily product which was purified by silica gel column chromatography to give 2.95 g of the compound (0017-002).

25.3 Preparation of Compound 0017

0.001 mol of the compound (0017-002) was dissolved in 20 mL of ethyl acetate at room temperature, and stirred to dissolve. A solution of hydrogen chloride in ethyl acetate (5 mL, 4 mol/L) was added dropwise at 0° C. After the addition was completed, the temperature was raised to room temperature with continuously stirring for 1 hr. It was determined by TLC that the reaction was complete. The reaction solution was filtered to give 0.62 g of compound 0017. MS (ESI, M−Cl): 847.4.

Referring to the preparation method of the compound (0005) sodium salt, the above compound was reacted with a solution of sodium hydroxide in alcohol to obtain its sodium salt ST0017.

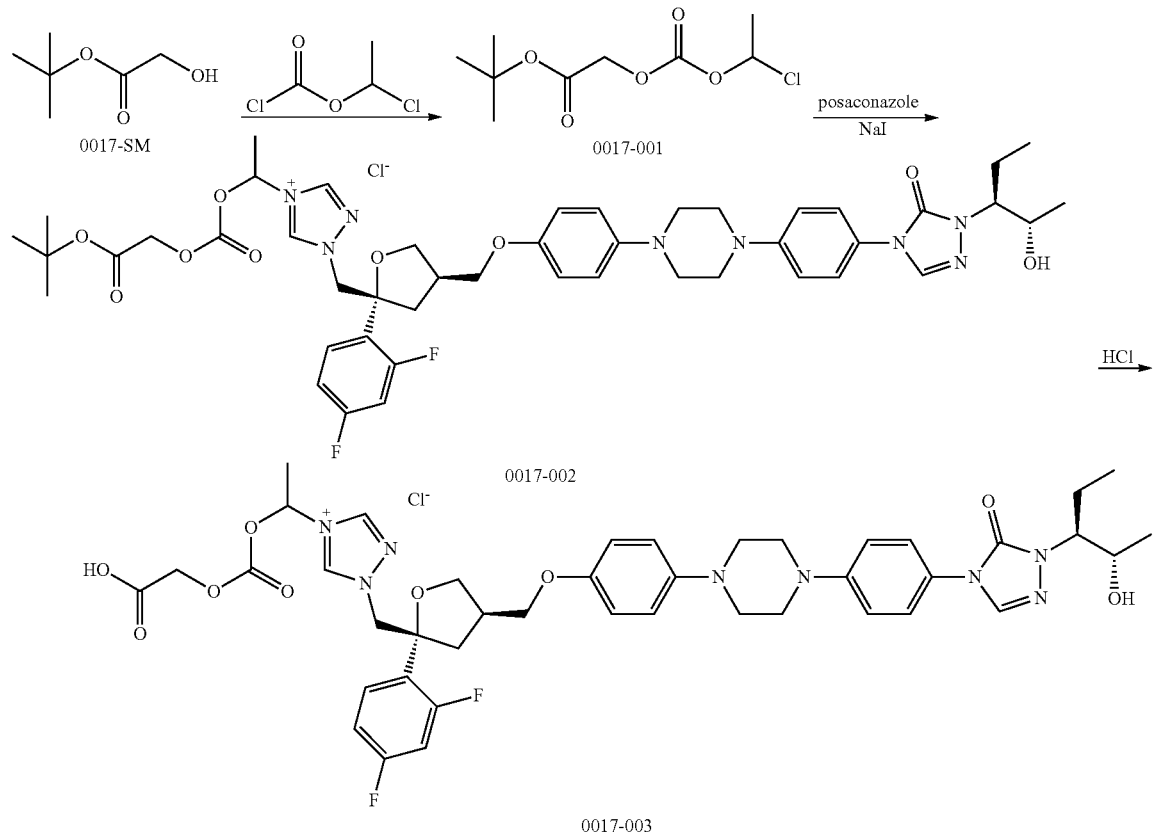

Example 26

Preparation of Compound ST0018 of the Present Disclosure

26.1 Preparation of Compound 0018-SM 0.01 mol of 0018-SM-001 was dissolved in tetrahydrofuran, 0.012 mol of triethylamine was added, cooled down to −5 to 5° C., 0.012 mol of isopropyl chloroformate was added dropwise, and reacted at room temperature for 3 hours. After filtration, the filtrate was added dropwise into a 0.02 mol aqueous solution of $NaBH_4$ (5 mL), the temperature was controlled within a range of −5 to 5° C. The reaction was warmed to room temperature and carried out overnight. To the reaction solution, 50 mL of water and 50 mL of ethyl acetate were added, and the mixture was stirred and separated. The organic phase was washed successively with dilute hydrochloric acid with pH=2, 1 M sodium bicarbonate and saturated brine, dried, filtered and concentrated to give a crude product, which is purified by silica gel column chromatography to give 1.56 g of compound (0018-SM).

The preparation route of the compound (0018-SM) was showed as follows:

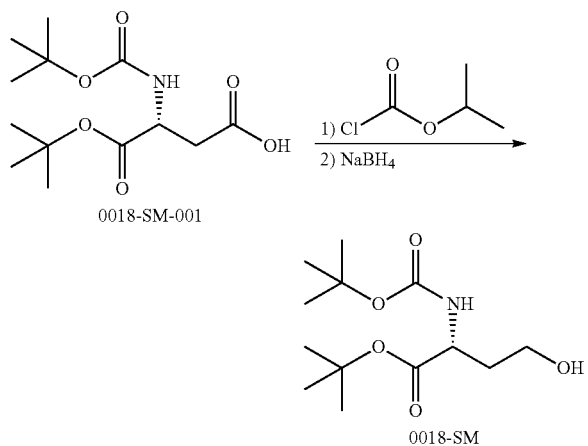

26.2 Preparation of Compound ST0018

The preparation method referred to Example 25, wherein the compound 0018-SM was used instead of the raw material 2-tert-butyl glycolate (CAS No. 50595-15-8) in Example 25 to obtain the target compound; MS (ESI, M−Cl): 890.4.

Example 27

Preparation of Compound ST0019 of the Present Disclosure

The preparation method referred to Example 25, wherein t-butyl glycinate (CAS No. 6456-74-2) was used instead of the raw material 2-tert-butyl 2-glycolate in Example 25 to obtain the target compound 0019, which was reacted with an alcoholic solution of sodium hydroxide to give the corresponding sodium salt ST0019; MS (ESI, M−Na+H−Cl): 846.4.

Example 28

Preparation of Compound ST0020 of the Present Disclosure

The preparation method referred to Example 25, wherein tert-butyl (S)-2-tert-butoxycarbonylamino-4-aminobutyrate (CAS No. 190447-69-9) was used instead of the raw material 2-tert-butyl glycolate (CAS No. For 50595-15-8) in Example 25 to obtain the target compound. MS (ESI, M−Cl): 889.4.

Example 29

Preparation of Compound ST0029 of the Present Disclosure

The preparation method referred to Example 25, wherein tert-butyl N-Boc-L-serine (CAS No. 7738-22-9) was used instead of the raw material 2-tert-butyl glycolate (CAS No. 50595-15-8) in Example 10 to obtain the target compound. MS (ESI, M−Cl): 876.4.

Example 30

Preparation of Compound ST0030 of the Present Disclosure

30.1 Preparation of Compound (0030-SM-002)

To the three-necked flask, 7.68 g of L-cysteine di-tert-butyl ester dihydrochloride (0030-SM-001), 180 mL of DMF, and 3.84 g of triethylamine were successively added, stirred at room temperature for 5 minutes, and two equivalents of Boc anhydride was slowly added thereto over 20 minutes, and the reaction was carried out at room temperature for 2 hours, and the endpoint of the reaction was determined by TLC. The reaction solution was poured into 600 mL of water and extracted twice with MTBE. The organic phase was washed twice with 1N HCl, brine, dried, filtered, and concentrated to give 8.10 g of an oily product, which solidified after being placed to give a white solid product compound (0030-SM-002).

30.2 Preparation of tert-butyl N-(tert-butoxycarbonyl)-L-cysteine (0030-SM)

1 g of the compound (0030-SM-002) was weighed and added into 26 mL of diethyl ether under the protection of nitrogen, stirred to dissolve and cooled to 0° C. 1.4 mL of acetic acid was added, and 7.34 g of activated zinc powder was added in batches over 20 minutes, and the reaction was incubated for 20 hours. The endpoint of the reaction was determined by TLC plate. The mixture was filtered, and the filter cake was washed with acetic acid. The filtrate was concentrated to dryness, 1N HCl was added, and the mixture was extracted twice with ethyl acetate. The organic phase was washed with brine, dried, and concentrated to give 1.02 g of oily tert-butyl N-(tert-butoxycarbonyl)-L-cysteine (0030-SM).

30.3. 
The preparation method referred to Example 25, wherein tert-butyl N-(tert-butoxycarbonyl)-L-cysteine (0030-SM, CAS No. 98330-15-5) was used instead of the raw material 2-tert-butyl glycolate (CAS No. 50595-15-8) in Example 25 to obtain the target compound. MS (ESI, M−Cl): 892.4.

The preparation route of the compound ST0030 was showed as follows:
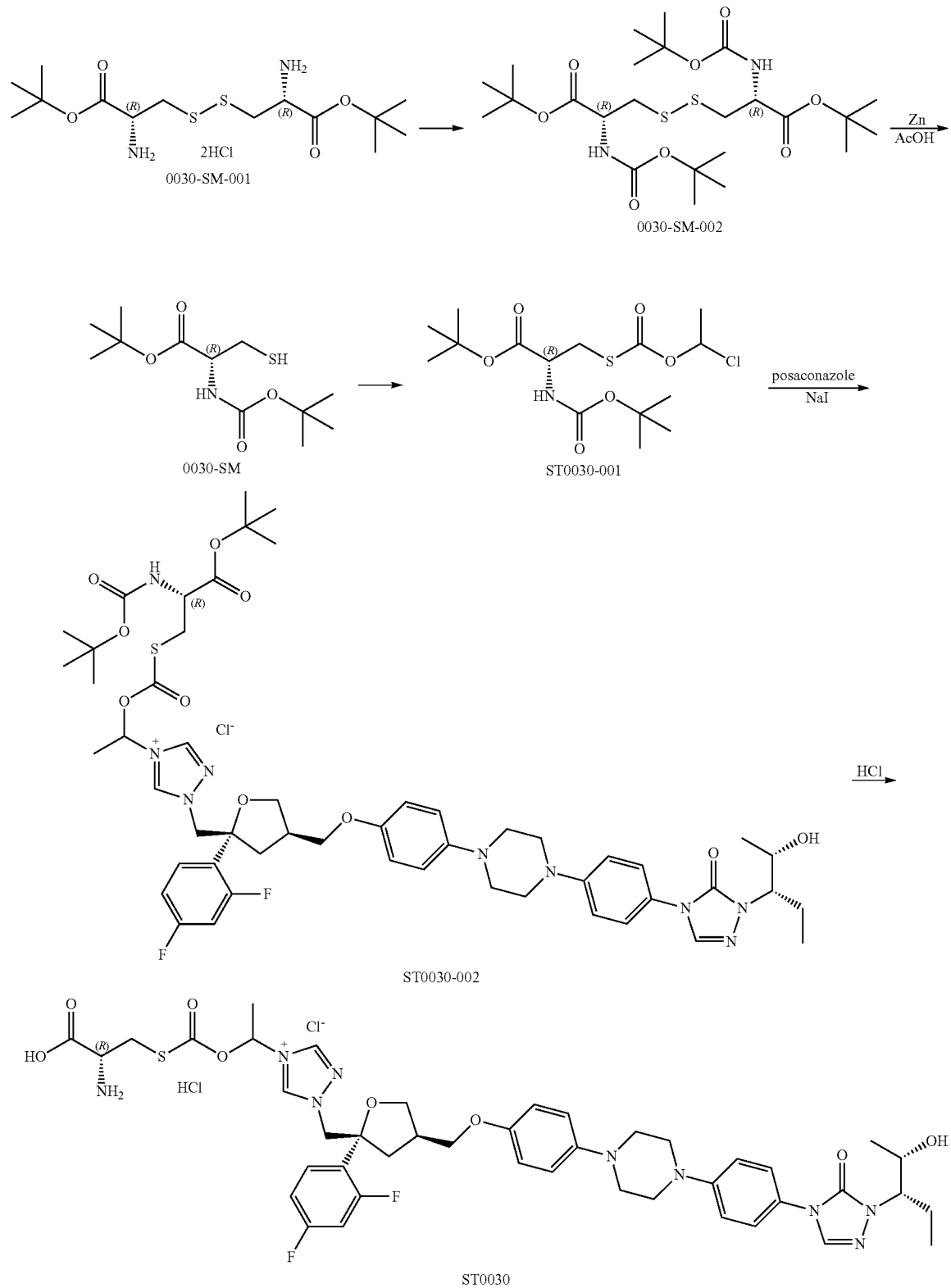

Example 31

Preparation of Compound ST0031 of the Present Disclosure

The preparation method referred to Example 25, wherein t-butyl N-(3-aminopropyl)carbamate (CAS No. 75178-96-0) was used instead of the raw material 2-tert-butyl glycolate (CAS No. 50595-15-8) in Example 25 to obtain the target compound. MS (ESI, M−Cl): 845.4.

Example 32

Preparation of Compound ST0032 of the Present Disclosure 32.1 Preparation of Compound (ST0032-SM-002)

5 g of ST0032-SM-001 was dissolved in DMF (50 mL) under nitrogen protection, 2 molar equivalents of potassium carbonate was added, stirred at room temperature for 5 to 10 minutes. 0.1 molar equivalents of CuI and 1.2 molar equivalents of methylamine hydrochloride were added, and the mixture was heated to 100° C. for 20 hours. The endpoint of the reaction was determined by TLC. The mixture was filtered, concentrated, and purified by column chromatography to give 1.71 g of the compound (ST0032-SM-002).

32.2 Preparation of Compound (ST0032-SM)

0.5 g of the compound (ST0032-SM-002) and 1.5 molar equivalents of boc anhydride were dissolved in 8 mL of ethanol, about 50 mg of Raney Ni was added, and the reaction was carried out in a hydrogen atmosphere for 18 hours. The endpoint of the reaction was determined by TLC. The mixture was filtered, concentrated, and purified by column chromatography to give 308 mg of the product compound (ST0032-SM).

32.3 The preparation method referred to Example 25, wherein the compound (ST0032-SM) was used instead of the raw material 2-tert-butyl glycolate (CAS No. 50595-15-8) in Example 10 to obtain the target compound; MS (ESI, M−Cl): 908.4.

The preparation route of the compound (ST0032-SM) was showed as follows:

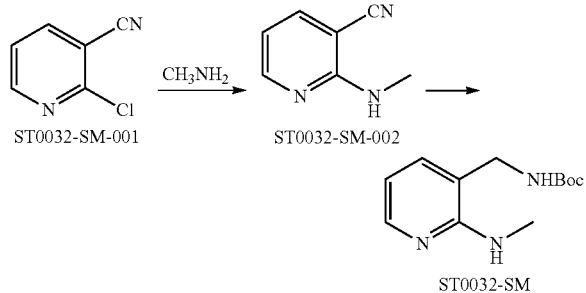

Example 33

Preparation of Compound ST0033 of the Present Disclosure 33.1 Preparation of Compound (0033-SM-002)

Reference: transformation of aminoacyl tRNAs for the In Vitro Selection of "Drug-like" Molecules, by Merryman, Chuck and Green Rachel From chemistry & Biology, 11(4), 575-582; 2004.

33.2 Preparation of Compound (0033-SM-003)

The preparation method was referred to the preparation of compound (0030-SM-002) in Example 30.1

33.3 Preparation of tert-Butyl N-methyl-N-Boc-cysteine (0033-SM)

The preparation method was referred to the preparation of compound (0030-SM) of Example 30.2.

33.4. The preparation method referred to Example 25, wherein tert-Butyl N-methyl-N-Boc-cysteine (0033-SM) was used instead of the raw material 2-tert-butyl glycolate (CAS No. 50595-15-8) in Example 25 to obtain the target compound; MS (ESI, M−Cl): 906.4.

The preparation route of the compound tert-Butyl N-methyl-N-Boc-cysteine (0033-SM) was showed as follows:

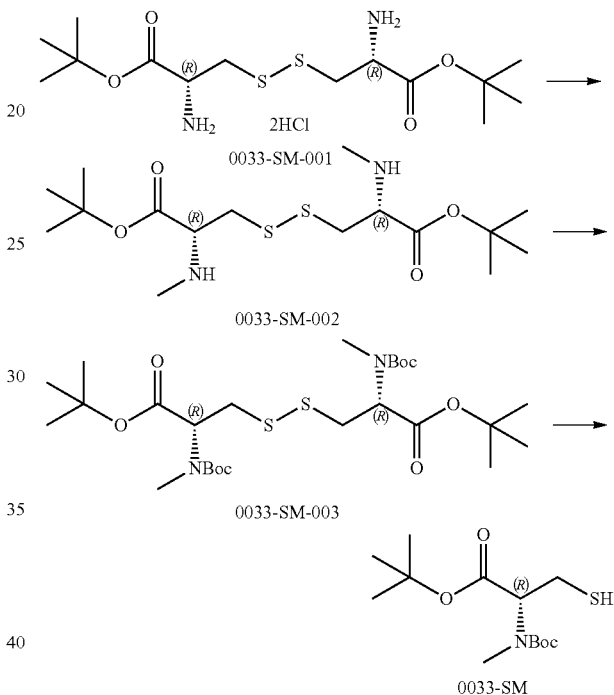

Example 34

Preparation of Compound 0034 of the Present Disclosure 34.1 Preparation of Compound (0034-001)

The preparation method referred to the preparation of compound (0017-001) of Example 25, wherein benzyl thioglycolate (0034-SM, CAS No. 7383-63-3) was used instead of the raw material 2-tert-butyl glycolate (CAS No. 50595-15-8).

34.2 Preparation of Compound (0034-002)

The preparation method referred to the preparation of compound (0017-002) of Example 25 to obtain compound (0034-002).

34.3 Preparation of Compound (0034)

To a reaction flask, 15 mL of methanol and 0.001 mol of compound (0034-002) were added, stirred and dissolved, 0.1 g of Pd/C catalyst was added, and the reaction was carried out at 25° C. under hydrogen atmosphere overnight. The reaction solution was filtered under reduced pressure, and the filtrate was concentrated under reduced pressure to give 0.45 g of compound (0034); MS (ESI, M−Cl): 863.4.

Referring to the preparation method of compound (0002), the above product was reacted with sodium hydroxide to obtain its salt (ST0034).

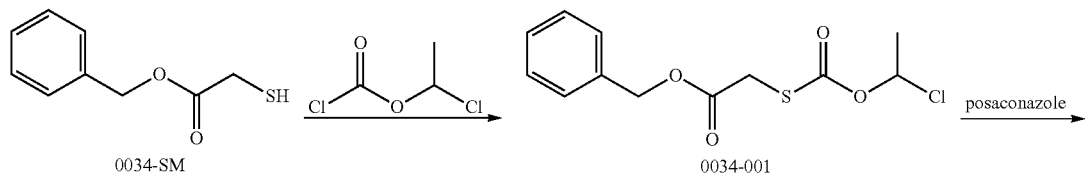

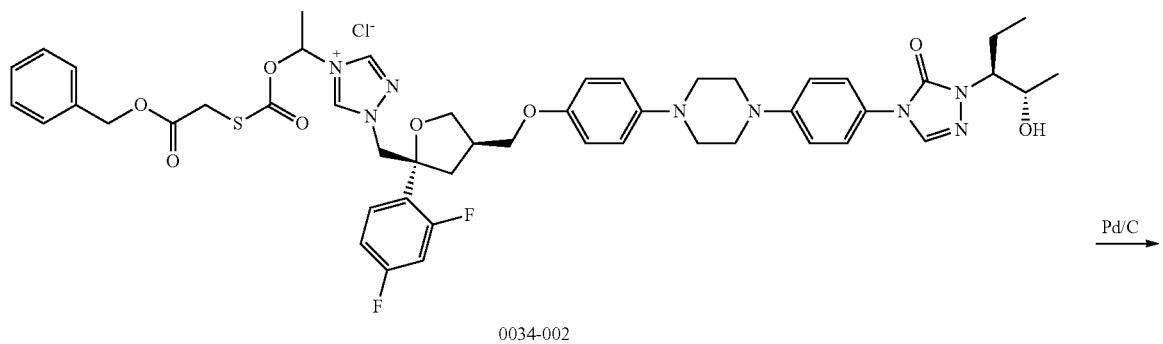

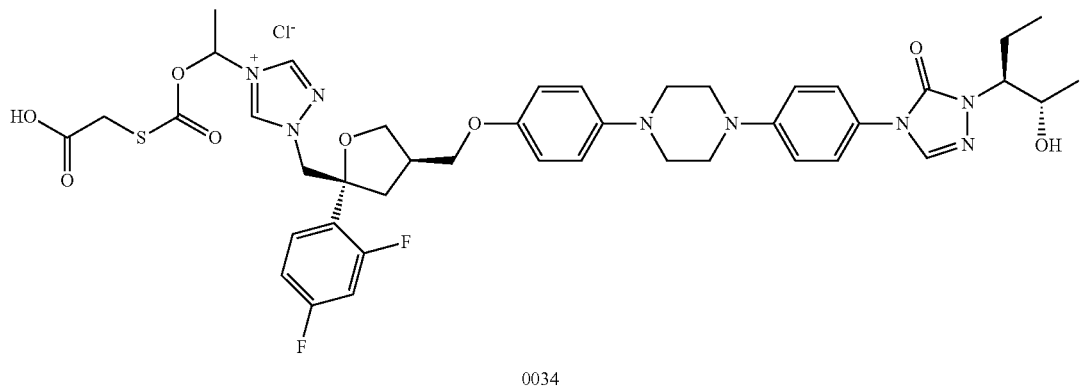

Example 35

Preparation of Compound 0035 of the Present Disclosure

The preparation method referred to the preparation of the compound (0034) of Example 34, wherein 2-benzyloxy-ethanethiol (0035-SM, CAS No. 127084-56-4) was used instead of the raw material benzyl thioglycolate to prepare the compound (0035); MS (ESI, M–Cl): 849.4.

Example 36: Preparation of Compound 0036 of the Present Disclosure 36.1 Preparation of Compound (0036-001)

The preparation method referred to the preparation of the compound (0017-001) of Example 25, wherein 2-triphenyl-methyl mercaptoethanol (0036-SM, CAS No. 29167-28-0) was used instead of the raw material 2-tert-butyl glycolate.

36.2 Preparation of Compound (0036-002)

The preparation method referred to the preparation of the compound (0017-002) of Example 25.

36.3 Preparation of Compound (0036)

To a reaction flask, 15 mL of methylene chloride and 0.001 mol of compound (0017-002) were added, stirred to dissolve, 3 mL of trifluoroacetic acid was added dropwise, and reacted overnight at 0° C. The reaction mixture was concentrated under reduced pressure to give 0.48 g of the compound (0036); MS (ESI, M−Cl): 849.4.

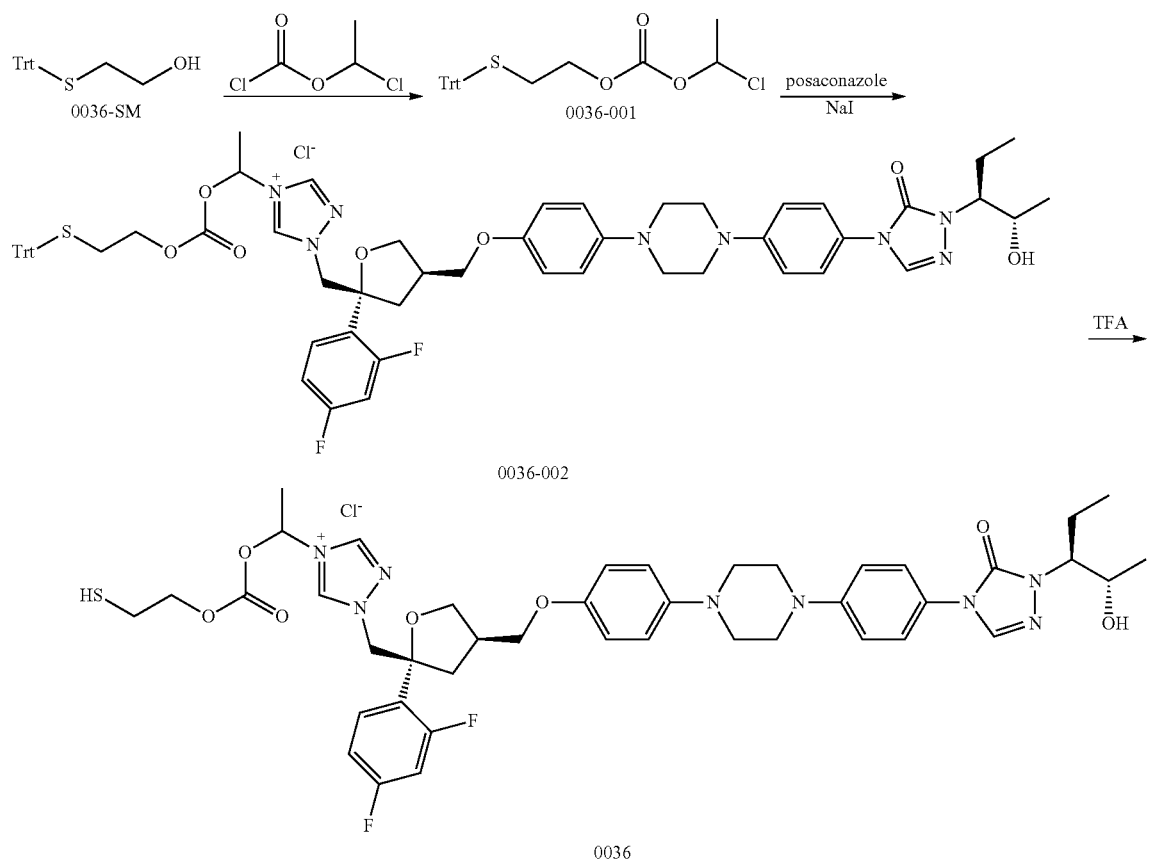

Example 37

Preparation of Compound ST0037 of the Present Disclosure 37.1 Preparation of Compound (ST0037-SM-002)

The preparation method referred to the reference *chem. Asian J*, 2014, 9, 739-743.

37.2 Preparation of Compound (ST0037-SM)

The preparation method referred to the preparation of compound 27 on page 73 of the patent reference WO 2015/112801.

37.3 Preparation of Compound ST0037

The preparation method referred to Example 25, wherein ST0037-SM was used instead of the raw material 2-tert-butyl glycolate (CAS No. 50595-15-8) in Example 25 to obtain the target compound. MS (ESI, M−Cl): 922.4.

The compound (ST0037-SM) was prepared as follows:

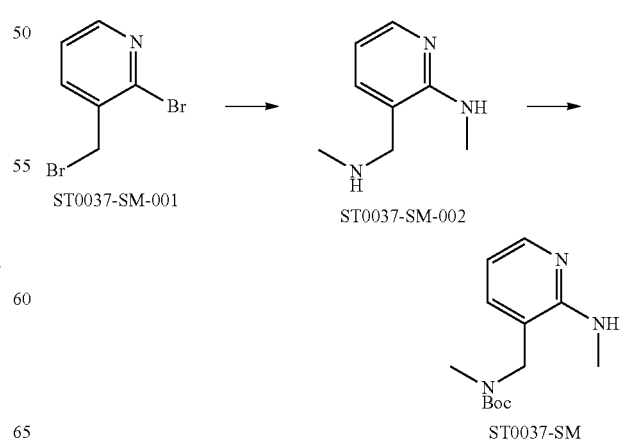

Example 38

Preparation of Compound 0039 of the Present Disclosure

The preparation method referred to Example 25, wherein bis-tert-butylphosphonic acid (CAS No. 33494-81-4) was used instead of the raw material 2-tert-butyl glycolate (CAS No. 50595-15-8) in Example 25 to obtain the target compound. MS (ESI, M−Cl): 869.4.

It reacted with sodium hydroxide to give the corresponding salt (ST0039).

Example 39

Preparation of Compound ST0042 of the Present Disclosure

39.1 Preparation of Compound (ST0042-001)

Under nitrogen protection, 0.01 mol of ethylene glycol was dissolved in dichloromethane (45 mL), stirred and cooled to −5 to 5° C., pyridine (0.012 mol) was added, and 0.01 mol of di-tert-butylphosphoryl chloride (CAS No. 56119-60-9) was added dropwise, and the reaction was incubated after completion of the dropwise addition. The endpoint of the reaction was determined by TLC. 0.1 M hydrochloric acid (30 mL) was added and the mixture was stirred and separated. The organic phase was washed sequentially with saturated sodium bicarbonate and brine, dried, filtered, concentrated, and purified by silica gel column chromatography to give 2.10 g of compound ST0042-001 as an oil.

39.2 Preparation of Compound (ST0042-002)

Under nitrogen protection, 0.005 mol of compound ST0042-001 was dissolved in acetonitrile (60 mL), pyridine (0.012 mol) was added, 1-chloroethyl chloroformate (0.006 mol) was added dropwise, and the reaction was incubated after completion of the dropwise addition. The endpoint of the reaction was determined by TLC. 0.1 M hydrochloric acid (30 mL) was added and the mixture was stirred and separated. The organic phase was washed sequentially with saturated sodium bicarbonate and brine, dried, filtered, concentrated, and purified by silica gel column chromatography to give 1.20 g of compound ST0042-002.

39.3 Preparation of Compound (ST0042-003)

Under nitrogen protection, 0.0025 mol of compound ST0042-002 was dissolved in acetonitrile (60 mL), 0.0025 mol of posaconazole and a catalytic amount of sodium iodide were added, and the reaction mixture was stirred and heated to 65 to 70° C. for 16 hours. It was determined by TLC that the reaction was complete. The mixture was cooled to room temperature, mixed with silica gel, and purified by column chromatography to give 1.4 g of a foamy solid ST0042-003.

39.4 Preparation of Compound (0042)

0.0015 mol of the compound (ST0042-003) was dissolved in 10 mL of ethyl acetate at room temperature, stirred to dissolve, and HCl/dioxane (4 mol/L, 5 mL) was added dropwise at 0° C. After the addition was completed, the mixture was heated to room temperature to continue stirring. It was determined by TLC that the reaction was complete. Filtration gave 0.76 g of the compound (0042); MS (ESI, (M−Cl)): 913.3.

39.5 Preparation of Compound (ST0042)

Under nitrogen protection, 0.001 mol of the compound (0042) was dissolved in 5 mL of methanol, stirred and cooled to −5 to 5° C., and 0.002 mol of sodium hydroxide aqueous solution (1 mL) was added dropwise, and the reaction was incubated for 10-20 minutes after completion of the dropwise addition. The mixture was concentrated at room temperature until a small amount of methanol remained, and MTBE was added to precipitate a solid, which was the compound (ST0042). MS (ESI, (M−Cl−2Na+2H)): 913.3.

The compound (ST0042) was prepared as follows:

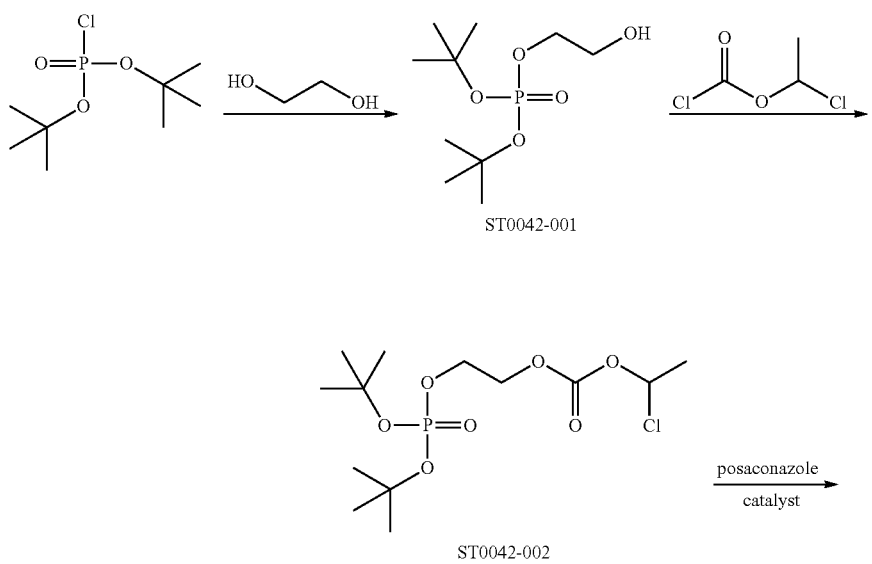

-continued

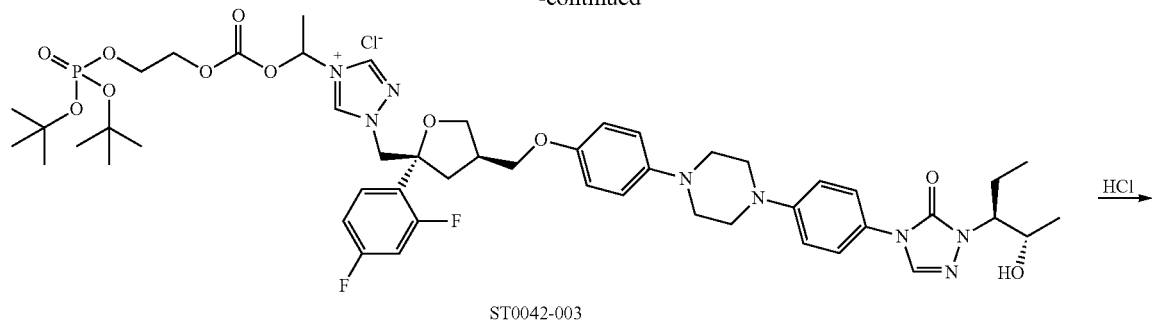

ST0042-003

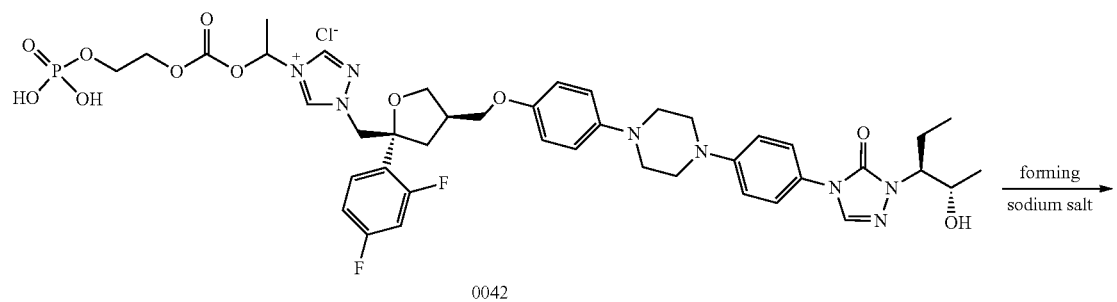

0042

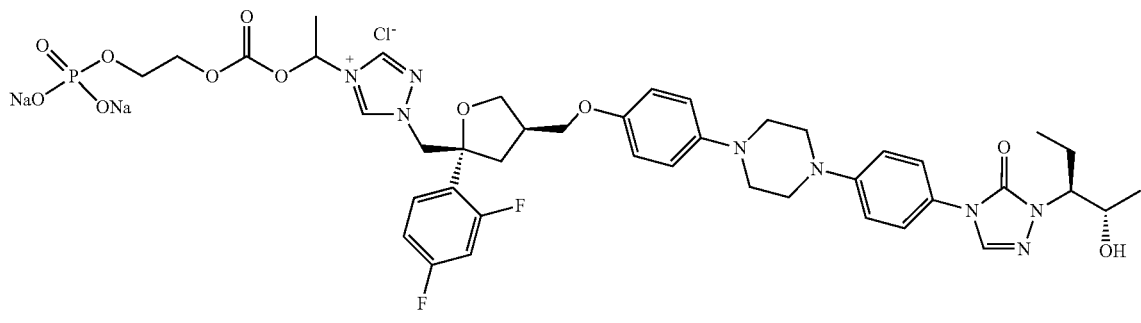

ST0042

Example 40

Preparation of Compound ST0043 of the Present Disclosure

Starting from triethylene glycol as a raw material, reference was made to the preparation method of compound ST0042 to obtain the target compound. MS (ESI, (M−Cl−2Na+2H)): 1001.4.

Example 41

Preparation of Compound ST0044 of the Present Disclosure

Starting from diethylene glycol as a raw material, reference was made to the preparation method of compound ST0042 to obtain the target compound. MS (ESI, (M−Cl−2Na+2H)): 957.3.

Example 42

Preparation of Compound 0041 of the Present Disclosure 42.1 Preparation of Compound (0041-001)

To a reaction flask, 15 ml of acetonitrile, 15 ml of water, and 3.96 g of silver carbonate were added, stirred for 5 minutes, 3 g of di-tert-butyl phosphate was added, and stirred for 1 hr at room temperature. The reaction solution was concentrated to dryness under reduced pressure, and dried in vacuum to obtain di-tert-butyl phosphate silver salt.

To a reaction flask, toluene, 0.01 mol of di-tert-butyl phosphate silver salt, and 0.01 mol of 1-chloro-1-iodomethane were added, and the mixture was heated to 100° C. overnight. The reaction solution was cooled to room temperature, filtered, and the filtrate was concentrated to a crude product, which was purified by silica gel column chromatography to give 1.8 g of compound (0041-001).

42.2 Preparation of Compound (0041-002)

Under nitrogen protection, 0.005 mol of 0041-001 was dissolved in acetonitrile (100 mL), 0.01 mol of posaconazole and 0.1 g of sodium iodide were added, and the mixture was stirred and heated to 70° C. for 16 hours. It was determined by TLC that the reaction was complete. The mixture was cooled to room temperature, and purified by column chromatography to give 2.8 g of solid 0041-002.

42.3 Preparation of Compound (0041)

0.5 g of the 0041-002 compound was dissolved in 5 mL of methylene chloride, stirred to dissolve, and a solution of hydrogen chloride in dioxane was added dropwise. After the completion of the dropwise addition, the solution was allowed to stir at room temperature for 30 to 40 minutes. It was determined by TLC that the reaction was complete. After standing, the supernatant was decanted and concentrated to give 0.260 g of the product (0041). MS (ESI, M−Cl): 811.3.

It reacted with an alcohol solution of sodium hydroxide to give the corresponding sodium salt ST0041; MS (ESI, M−2Na+2H−Cl): 811.3.

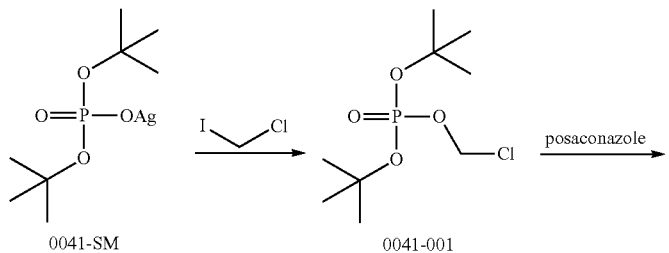

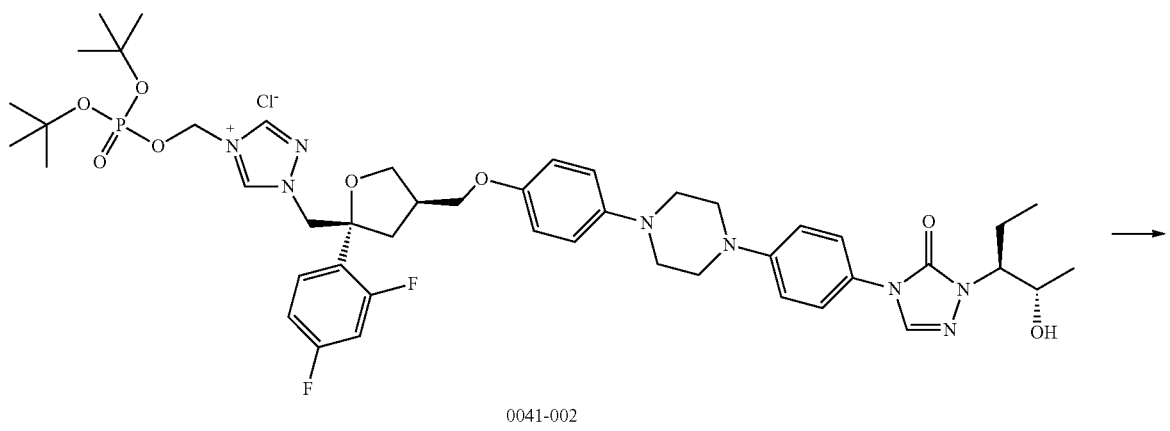

0041-002

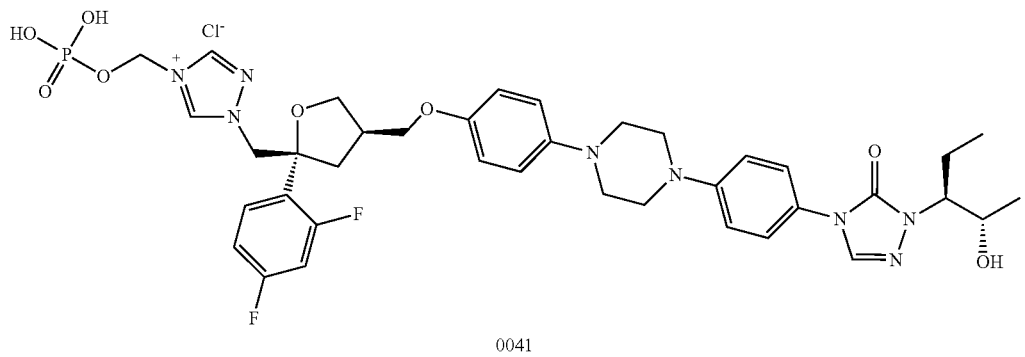

0041

Example 43

Preparation of Compound ST0016 of the Present Disclosure

Starting from 1-chloro-1-iodoethane as a raw material, reference was made to Example 42 and Example 39 to obtain the target compound. MS (ESI, M−Cl−2Na+2H): 825.3.

Example 44

Preparation of Compound 0021 of the Present Disclosure

Under nitrogen protection, 0.001 mol of posaconazole and 0.01 g of sodium iodide were dissolved in acetonitrile (100 mL), and 0.0012 mol of tert-butyl chloroacetate was added at room temperature, and the reaction mixture was stirred and heated to 70° C. for 16 hours. It was determined by TLC that the reaction was complete. The mixture was cooled to room temperature, and purified by column chromatography to give 0.5 g of solid compound 0021-001.

0.5 g of the above solid was dissolved in 5 mL of methylene chloride, stirred to dissolve, and a solution of hydrogen chloride in dioxane was added dropwise. After the completion of the dropwise addition, the solution was allowed to stir at room temperature for 30 to 40 minutes. It was determined by TLC that the reaction was complete. After standing, the supernatant was decanted and concentrated to give 270 mg of the product (0021); MS (ESI, (M−Cl)): 759.4.

Referring to the preparation method of the compound ST0005, the corresponding sodium salt ST0021 can also be obtained.

Example 45

Preparation of Compound ST0028 of the Present Disclosure 45.1 Preparation of Compound (ST0028-001)

10 g of D-xylose (0028-SM) was taken and added in 20 mL of anhydrous methanol, 0.01 eq of ammonium chloride was added, stirred (suspension) and cooled to 0° C. Ammonia gas was introduced into the reaction system to gradually clarify, and continued to introduce about 1 hr. The reaction solution was cooled to precipitate crystals. Filtration gave 2.5 g of a solid product ST0028-001.

45.2 Preparation of Compound (ST0028-002)

To a three-necked flask protected with nitrogen, 15 g of 2,2-dimethoxypropane, 40 mL of anhydrous acetone were added and stirred, 1.6 eq of p-toluenesulfonic acid was added, stirred at room temperature for about 15 minutes. 2.5 g of compound ST0028-001 was added, and the reaction was stirred until a solid precipitated, which was filtered to give 2 g of the compound (ST0028-002).

45.3 Preparation of Compound (ST0028-003)

0.01 mol of compound (ST0028-002) was dissolved in 50 mL of methylene chloride, stirred and cooled down to −15 to −20° C. under the protection with nitrogen. 0.024 mol of N,N-diisopropylethylamine was added, stirred and cooled to −15 to −20° C., and 0.011 mol of a solution of 1-chloroethyl chloroformate in dichloromethane (20 mL) was added dropwise. The reaction solution was kept at a temperature of −15 to −20° C. for 16 hours, and the reaction solution was directly used in the next step reaction.

45.4 Preparation of Compound (ST0028-004)

While keeping a temperature of −15 to −20° C., 0.012 mol of Boc-sarcosine and 0.003 mol of DMAP were added to the above reaction mixture, and 0.012 mol of 1-ethyl-3-(3-

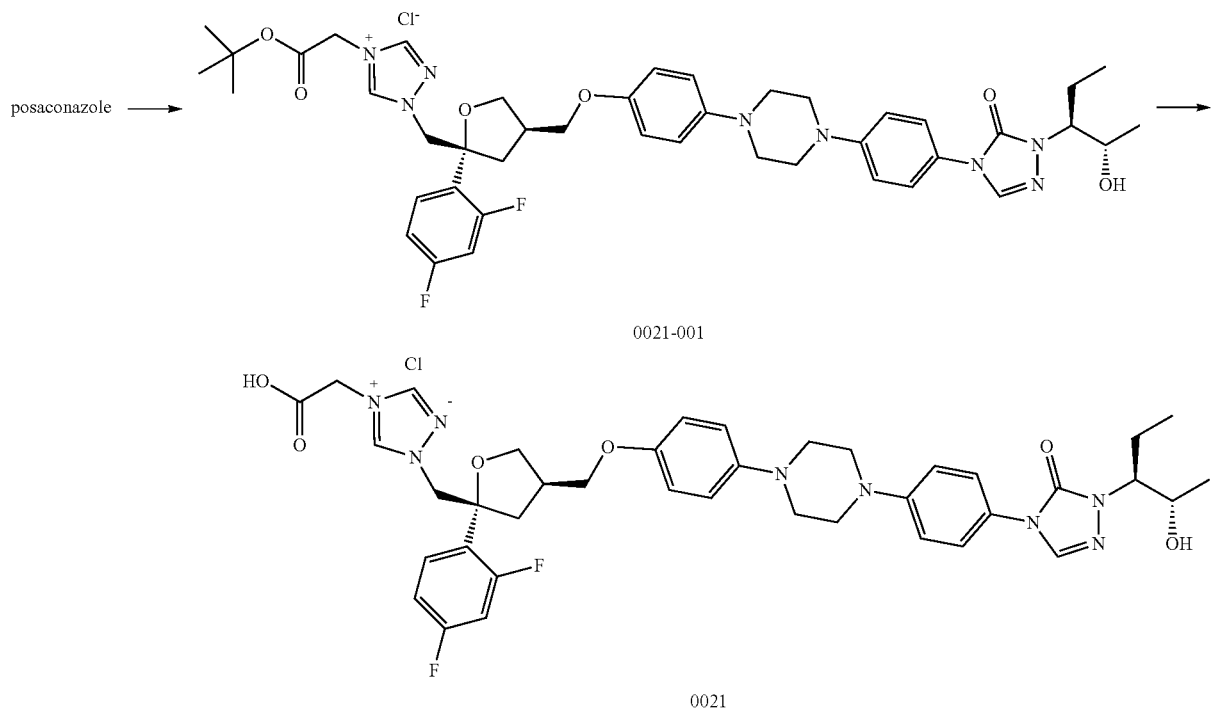

dimethylaminopropyl)carbodiimide hydrochloride (EDCI-.HCl) was added in batches, and reacted at the temperature of −15 to −20° C. for 2 to 3 hours. 50 mL of 0.1N HCl was added to the reaction solution, stirred, and transferred to room temperature and separated. The organic phase was washed with 0.1N HCl, saturated sodium bicarbonate solution and brine, respectively, dried, filtered, and concentrated to give the compound (ST0028-004).

45.5 Preparation of Compound (ST0028-005)

Reference was made to the 16.2 preparation method for the preparation of the compound (ST0022-002).

45.6 Preparation of Compound ST0028

Reference was made to the 16.3 preparation method of compound ST0022 to prepare the target compound. MS (ESI, (M−Cl)): 991.4.

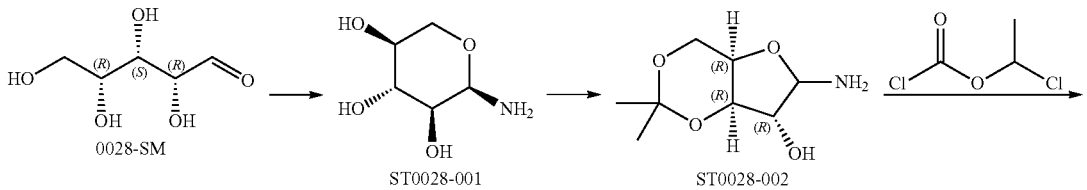

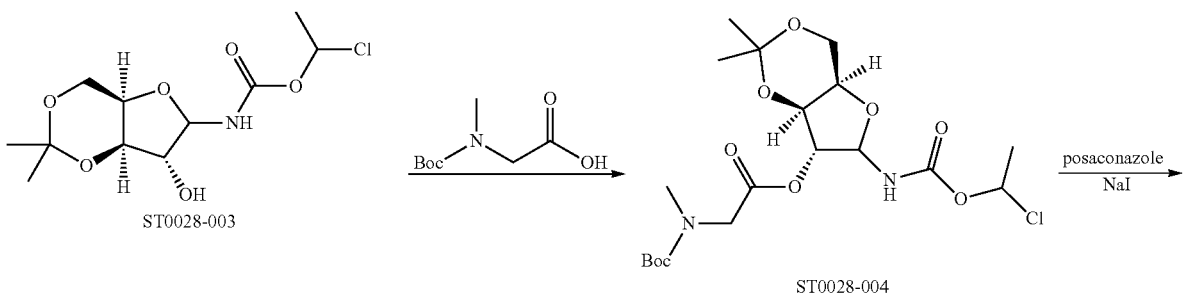

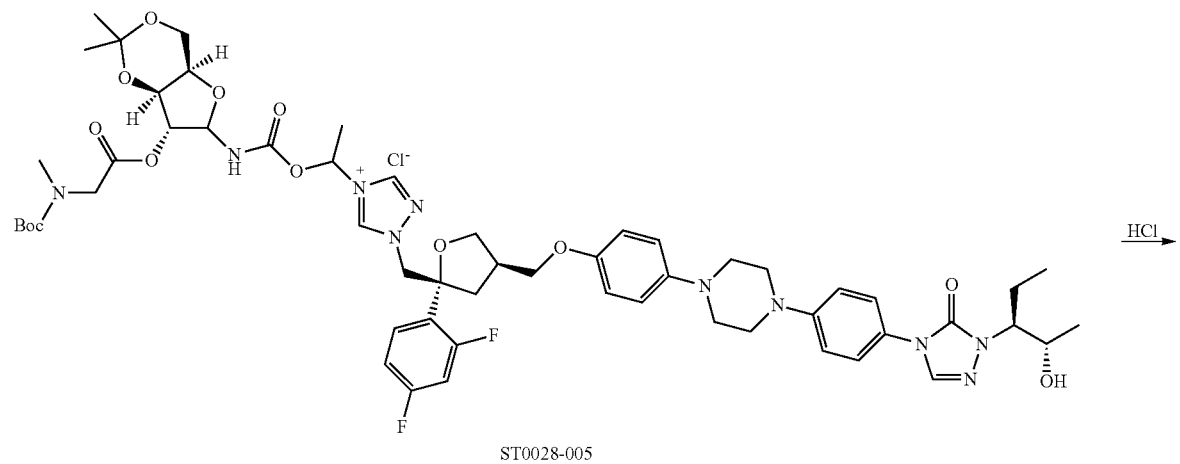

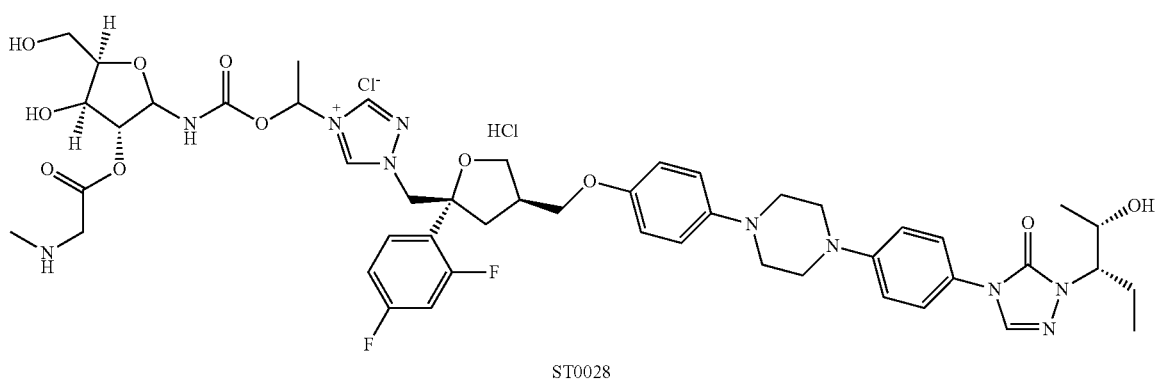

Example 46

Preparation of Compound ST0062 of the Present Disclosure 46.1 Preparation of Compound (ST0062-001)

Under nitrogen protection, 2.0 g of butylene glycol and 20 mL of dichloromethane were added to a three-necked flask, stirred and cooled to −3 to 3° C., imidazole (2.0 eq) was added, and a TBSCl solution in dichloromethane (1.2 eq) was added dropwise. After the addition dropwise was completed, the reaction was moved to room temperature for 16 hours. It was determined by TLC that the reaction was complete. Water (40 mL) and methylene chloride (20 mL) were added and the mixture was stirred and separated. The organic phase was collected, washed with saturated brine, dried, filtered, concentrated, and purified by silica gel column chromatography to give the compound (ST0062-001).

46.2 Preparation of Compound (ST0062-002)

150 mL of methylene chloride and 2.2 g of the compound (ST0062-001) were added to a reaction flask, cooled to 0° C., 50 mg of 2,2,6,6-tetramethyl piperidine oxide, 120 mg of sodium bromide, 125 mg of tetrabutyl ammonium bromide, 25 mL of water, 50 mL of saturated sodium bicarbonate were sequentially added, stirred for 0.5 hours. While keeping the temperature of the reaction flask at 0 to 5° C., 13 mL of a 1.83 mol/L sodium hypochlorite aqueous solution was added dropwise, and stirred for 2.5 hours. 20 mL of methanol was added to the reaction solution, stirred for 0.5 hours, adjusted to about pH 2 with 2 mol/L hydrochloric acid, and separated. The organic phase was dried over anhydrous magnesium sulfate, filtered and concentrated under reduced pressure to give a crude product, which is purified by silica gel column chromatography to give the compound (ST0062-002).

46.3 Preparation of Compound (ST0062-003)

To a reaction flask, 10 mL of dichloromethane, 2.8 g of posaconazole, and 0.23 g of pyridine were added, stirred, cooled to −5 to 5° C., and 1-chloroethyl chloroformate in dichloromethane (0.41 g, 10 mL) was added dropwise. After the addition dropwise was completed, the reaction temperature was maintained at −5 to 5° C. for 2 to 3 hours. The reaction solution was washed with 20 mL of 0.1 M hydrochloric acid, and separated. The organic phase was washed with saturated brine, dried over anhydrous magnesium sulfate, filtered and concentrated under reduced pressure to give a crude product, which was purified by silica gel column chromatography to give the compound (ST0062-003).

46.4 Preparation of Compound (ST0062-004)

To a reaction flask, 30 mL of DMF, 0.87 g of the compound (ST0062-002) and 1.30 g of cesium carbonate were sequentially added, stirred for 30 minutes, 1.65 g of the compound (ST0062-003) was added, stirred at 50° C. overnight. 50 mL of water and 50 mL of ethyl acetate were added to the reaction solution, and separated. The organic phase was washed sequentially with water and saturated aqueous sodium chloride solution, and the organic phase was dried over anhydrous sodium sulfate, filtered, and the filtrate was concentrated under reduced pressure to give a crude product, which was purified by silica gel column chromatography to give the compound (ST0062-004).

46.5 Preparation of Compound (ST0062-005)

To a reaction flask, 15 mL of tetrahydrofuran and 1.0 g of the compound (ST0062-004) were added, stirred to dissolve, cooled to 0° C., then 1 mL of acetic acid was added, and 4 mL 1 mol/L tetrabutylammonium fluoride tetrahydrofuran solution was added dropwise, then reacted at 0° C. overnight. Water and ethyl acetate were added to the reaction solution and separated. The organic phase was washed sequentially with water and saturated aqueous sodium chloride solution, dried over anhydrous sodium sulfate, filtered, and the filtrate was concentrated under reduced pressure to give a crude product, which was purified by silica gel column chromatography to give the compound (ST0062-005).

46.6 Preparation of Compound (ST0062-006)

To a reaction flask, 15 mL of dichloromethane, 0.75 g of the compound (ST0062-005) and 0.18 g of tetrazolium were added, stirred, and cooled to 0° C. 1.19 g of dibenzyl diisopropyl phosphoramidite was added dropwise. After the addition dropwise was completed, the reaction was carried on at room temperature overnight. 2 mL of 30% hydrogen peroxide was added and stirred for 30 minutes. 25 mL of a 10% sodium sulfite aqueous solution was added to the reaction system, and the mixture was stirred for 15 minutes, and separated. The organic phase was washed with saturated aqueous sodium chloride solution, dried over anhydrous sodium sulfate, filtered, and the filtrate was concentrated under reduced pressure to give a crude product, which was purified by silica gel column chromatography to give the compound (ST0062-006).

46.7 Preparation of Compound (ST0062-007)

To a reaction flask, 15 mL of methanol and 0.5 g of the compound (ST0062-006) were added, stirred to dissolve, 0.1 g of Pd/C catalyst was added, and the reaction was carried on overnight at 0° C. under hydrogen atmosphere. The reaction solution was filtered under reduced pressure, and the filtrate was concentrated to obtain the compound (ST0062-007).

46.8 Preparation of Compound (ST0062)

To a reaction flask, 3 mL of methanol and 0.16 g of compound (ST0062-007) were added, stirred to dissolve, cooled to 0° C. A solution of sodium hydroxide in methanol (13 mg, 4 mL) was added dropwise, and stirred for 30 minutes. 70 mL of methyl tert-butyl ether was added to the reaction solution, stirred for 15 minutes, and filtered under reduced pressure to give the compound (ST0062); LCMS (ESI, (M−2Na+3H)): 955.3.

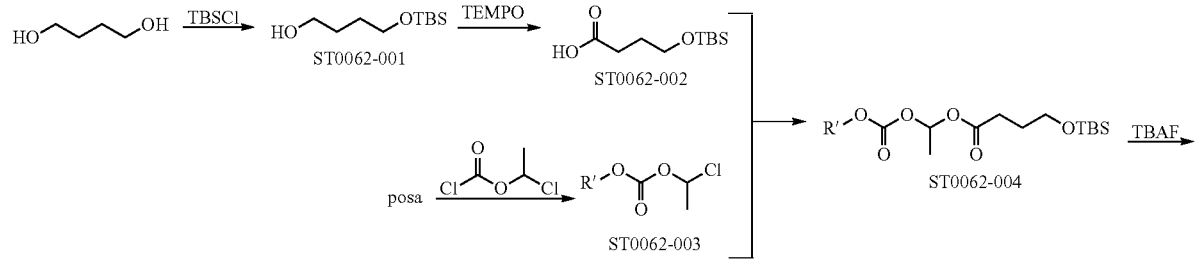

-continued

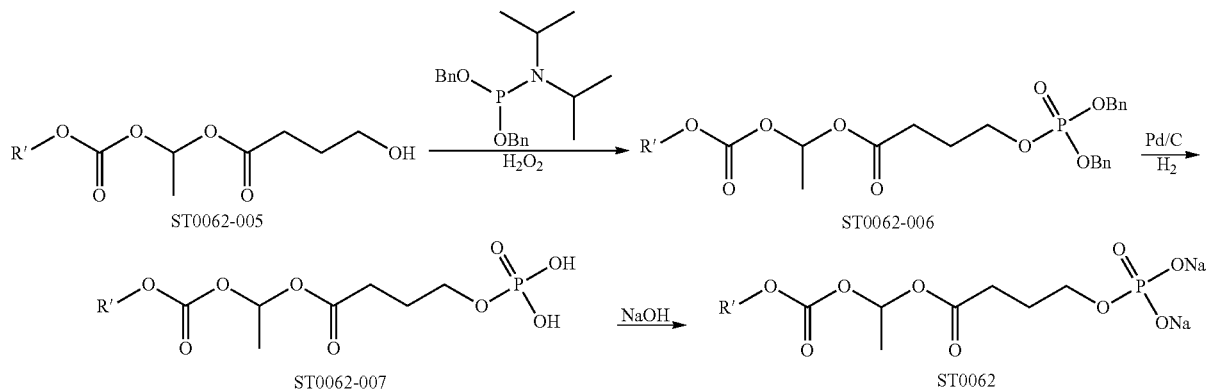

Wherein, R' is

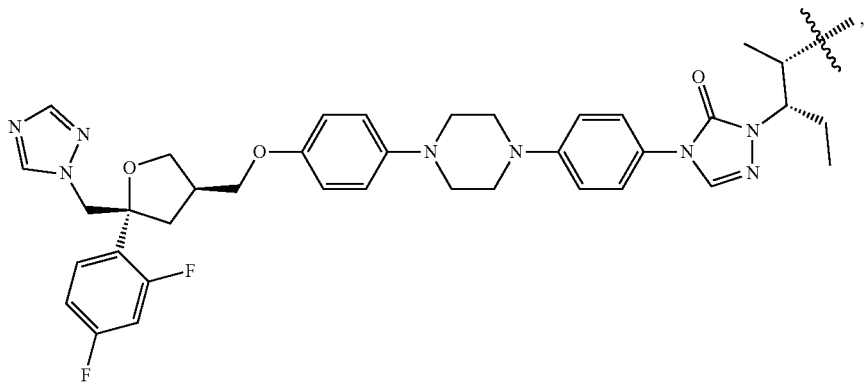

and the group also has the definition in the following examples.

Example 47

Following a Similar Procedure to Example 46, the Following Compounds of the Present Disclosure were Prepared, Wherein ST0073 and ST0074 were Prepared by Reacting Chloromethyl Chloroformate as a Raw Material with Posaconazole:

| No. | LC-MS: M-2Na + 3H |
|---|---|
| ST0063 | 983.3 |
| ST0064 | 989.3 |
| ST0065 | 927.3 |
| ST0066 | 941.3 |
| ST0067 | 1003.3 |
| ST0068 | 969.3 |
| ST0069 | 1011.4 |
| ST0070 | 997.4 |
| ST0071 | 1025.4 |
| ST0072 | 1039.4 |
| ST0073 | 969.3 |
| ST0074 | 983.3 |

Example 48

Preparation of Compound ST0077 of the Present Disclosure 48.1 Preparation of Compound (0077)

Under nitrogen protection, 0.5 g of (ST0062-005) was dissolved in 15 mL of dichloromethane, stirred and cooled to −5 to 5° C., triethylamine (2.0 eq) was added, and a solution of chlorosulfonic acid in dichloromethane (2.0 eq) was added dropwise. After the addition dropwise was completed, the reaction was incubated for 10 to 30 minutes. It was determined by TCL that the reaction was completed. A solution of triethylamine in dichloromethane was added dropwise, and the pH was adjusted to 6 to 7. Water was added and the organic phase was separated and collected, washed with saturated aqueous sodium chloride solution, dried, filtered, concentrated, and purified by column chromatography to give the compound (0077). MS (ESI, M+H): 955.35.

48.2 Preparation of Compound (ST0077)

Under nitrogen protection, 280 mg of compound (0077) was dissolved in 5 mL of methanol, stirred and cooled to −5 to 5° C., and a solution of sodium hydroxide in methanol (0.9 eq) was added dropwise, and the reaction was incubated for 10-30 minutes after completion of the addition dropwise. The mixture was concentrated at room temperature until a small amount of methanol remained, and MTBE was added to precipitate solid product (ST0077).

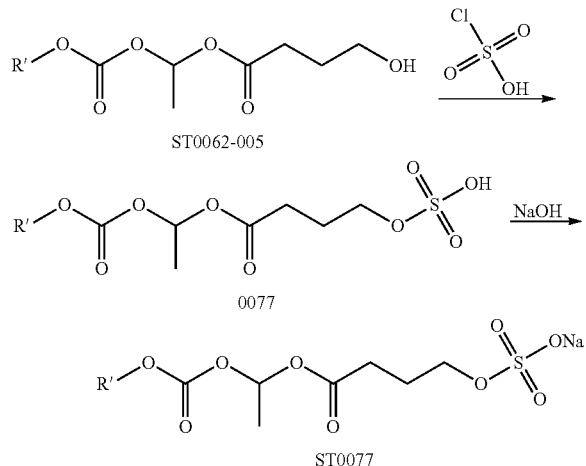

ST0062-005

0077

ST0077

Example 49

Following a Similar Procedure to Example 48, the Following Compounds were Prepared, Wherein ST0083 was Prepared by Reacting Chloromethyl Chloroformate as a Raw Material with Posaconazole:

| No. | LC-MS: M-Na + 2H |
|---|---|
| ST0075 | 927.3 |
| ST0076 | 941.3 |
| ST0078 | 969.3 |
| ST0079 | 983.3 |
| ST0080 | 1003.3 |
| ST0081 | 997.3 |
| ST0082 | 1011.4 |
| ST0083 | 941.3 |

Example 50

Preparation of Compound ST0059

50.1 Preparation of Compound (ST0059-001)

The present compound can be directly purchased. Also, using ethylene glycol as a raw material and referring to the preparation method of compound (ST0062-006), the compound (ST0059-001) can be obtained by controlling the equivalent ratio of ethylene glycol and dibenzyl diisopropylphosphoramidite to 1:1.1.

50.2 Preparation of Compound (ST0059-002)

To a reaction flask, 15 mL of toluene, 2.8 g of posaconazole, 1.3 g of carbonyl diimidazole and 20 mg potassium hydroxide were successively added, heated to 60° C., and stirred for 3 to 4 hours. 50 mL of dichloromethane was added to the reaction solution, which was then washed successively with water, 10% aqueous citric acid solution and saturated aqueous sodium chloride solution. The organic phase was dried, filtered and concentrated under reduced pressure to give the compound (ST0059-002).

50.3 Preparation of Compound (ST0059-003)

To a reaction flask, 15 mL of toluene, 1.2 g of the compound (ST0059-002), 0.52 g of the compound (ST0059-001) and 20 mg of potassium hydroxide were successively added, heated to 60° C., stirred for 3 to 4 hours. 50 mL of dichloromethane was added to the reaction solution, which was then washed successively with water, 10% aqueous citric acid solution and saturated aqueous sodium chloride solution. The organic phase was dried, filtered and concentrated under reduced pressure to give a crude product, which was purified by silica gel column chromatography to give compound (ST0059-003).

50.4 Preparation of Compound (ST0059)

The compound (ST0059-003) was used as a raw material to give the product (ST0059) according to the method for preparing the compound (ST0062-007) and the compound (ST0062); LC-MS (ESI, (M−2Na+3H)): 869.3.

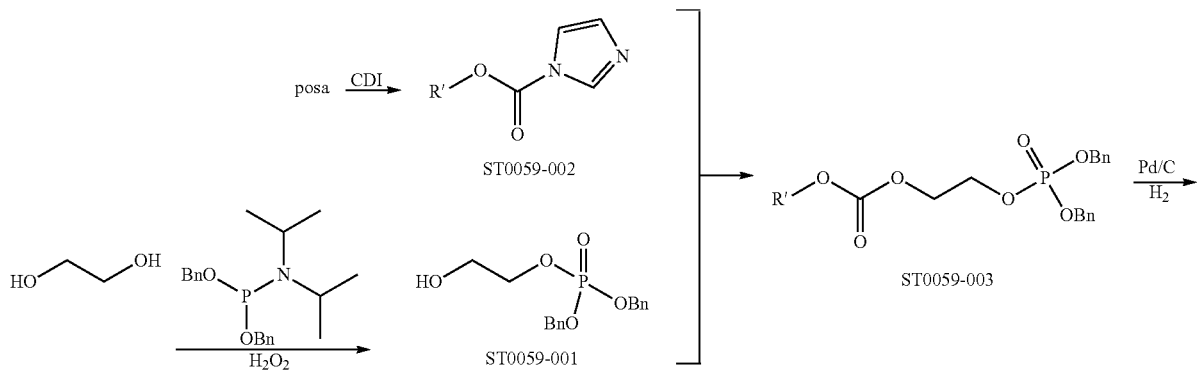

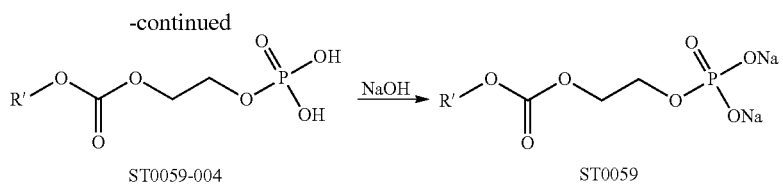

ST0059-004 → ST0059

Example 51

Following a Similar Procedure to Example 50, the Following Compounds were Prepared

| No. | LC-MS: M-2Na + 3H |
|---|---|
| ST0060 | 913.3 |
| ST0061 | 957.3 |

Example 52

Preparation of Compound ST0046

52.1 Preparation of Compound (ST0046-002)

To a reaction flask, 30 ml of DMF, 0.47 g of monobenzyl succinate and 0.65 g of cesium carbonate were successively added, stirred for 30 minutes, 1.6 g of compound (ST0062-003) was added, and the mixture was stirred at room temperature overnight. 60 ml of water and 60 ml of ethyl acetate were added to the reaction solution, which was then separated. The organic phase was washed successively with 1N hydrochloric acid and saturated aqueous sodium chloride solution, dried over anhydrous sodium sulfate, filtered, and the filtrate was concentrated under reduced pressure to give a crude product, which was purified by silica gel column chromatography to give the compound (ST0046-002).

52.2 Preparation of Compound (0046)

The compound (ST0046-002) was used as a raw material to give the compound (0046) with reference to the method for preparing the compound (ST0062-007); LCMS (ESI, (M+H)): 889.3.

52.3 Preparation of Compound (ST0046)

The compound (0046) was used as a raw material to give the compound (ST0046) with reference to the method for preparing the compound (ST0062); LCMS (ESI, (M−Na+2H)): 889.3.

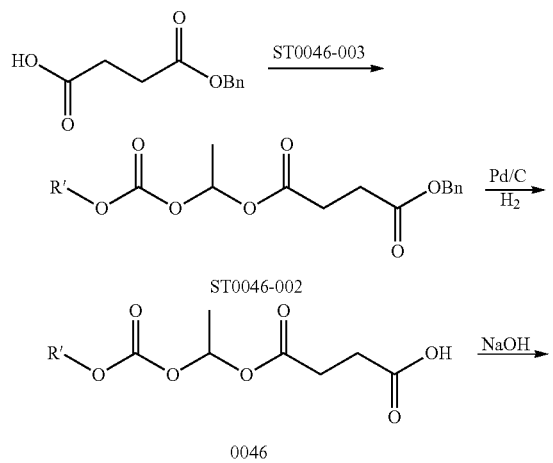

-continued

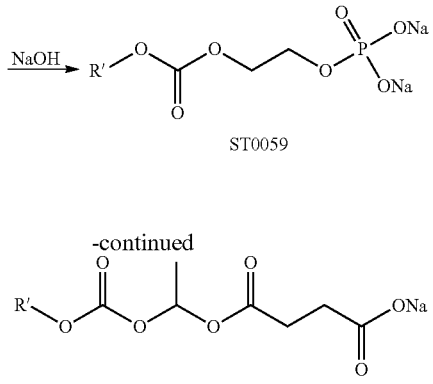

ST0046

When the raw material was butyric acid, its was reacted with the compound (ST0062-003) to obtain a compound ST0051. When the raw material was methyl tricarboxylic acid, a compound ST0100 was prepared. Following the above procedure, the following compounds were also prepared:

| No. | LC-MS |
|---|---|
| ST0047 | (M-Na + 2H): 861.3 |
| ST0048 | (M-Na + 2H): 875.3 |
| ST0049 | (M-Na + 2H): 937.3 |
| ST0050 | (M-2Na + 3H): 953.3 |
| ST0100 | (M-2Na + 3H): 919.3 |
| ST0051 | (M + H): 859.4 |

Example 53

Preparation of Compound (ST0053) and Compound (ST0054)

53.1 Preparation of Compound (ST0053-002)

To a reaction flask, 20 mL of DMF and 0.38 g of N-tert-butoxycarbonylsarcosine were successively added, 0.65 g of cesium carbonate was added, stirred for 30 minutes, 1.6 g of the compound (ST0062-003) was added, and the mixture was stirred at room temperature overnight. 50 ml of water and 50 ml of ethyl acetate were added to the reaction solution, which was then separated. The organic phase was washed successively with water and saturated aqueous sodium chloride solution, dried over anhydrous sodium sulfate, filtered, and the filtrate was concentrated under reduced pressure to give a crude product, which was purified by silica gel column chromatography to give the compound (ST0053-002).

53.2 Preparation of Compound (ST0053)

To a reaction flask, 5 mL of dichloromethane and 0.6 g of compound (ST0053-002) were added, stirred, cooled to −5 to 5° C. 10 mL of a solution of hydrogen chloride in dioxane was added, stirred for 2 hours. The reaction was filtered under reduced pressure and dried to give the compound (ST0053); LCMS (ESI, (M−Cl)): 860.39.

53.3 Preparation of Compound (ST0054-006)

The compound (ST0053) was used as a raw material to give the compound (ST0054-006) according to the method for preparing the compound (ST0062-006).

53.4 Preparation of Compound (0054)

The compound (ST0054-006) was used as a raw material to give the compound (0054) with reference to the method for preparing the compound (ST0062-007); LCMS (ESI, (M+H)): 940.3.

53.5 Preparation of Compound (ST0054)

The compound (0054) was used as a raw material to give the compound (ST0054) with reference to the method for preparing the compound (ST0062); LCMS (ESI, (M−2Na+3H)): 940.3.

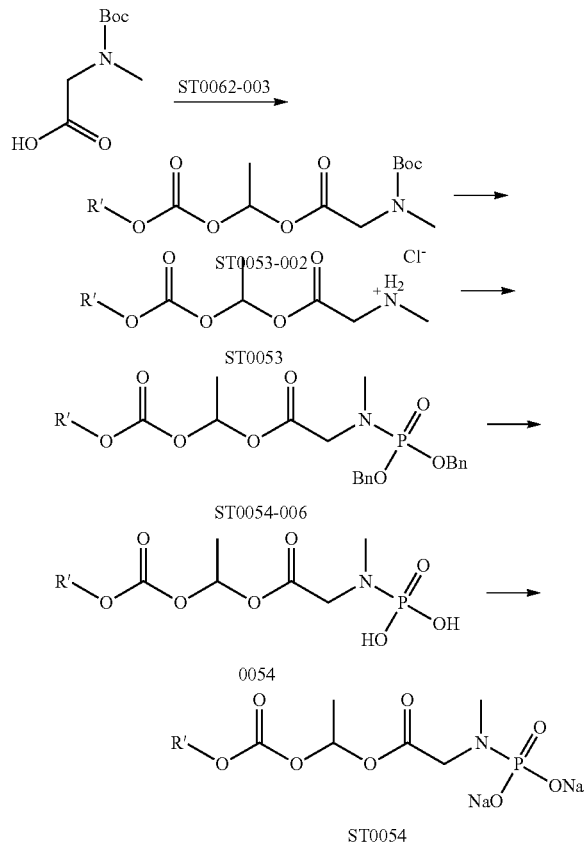

Example 54

Following a Similar Procedure to Example 52 or its Intermediate Procedures, the Following Compounds were Prepared:

| No. | LC-MS |
| --- | --- |
| ST0052 | (M−Cl)): 846.3 |
| ST0055 | (M−2Na + 3H)): 926.3 |
| 0058 | (M + H)): 874.4 |

Example 55

Preparation of Compound ST0056

55.1 Preparation of Compound (0056)

The compound (ST0053) was used as a raw material to give the compound (0056) according to the method for preparing the compound (0077), MS (ESI, M+H): 940.3.

55.2 Preparation of Compound (ST0056)

The compound (0056) was used as a raw material to give the compound (ST0056) according to the method for preparing the compound (ST0077), MS (ESI, M−Na+2H): 940.3.

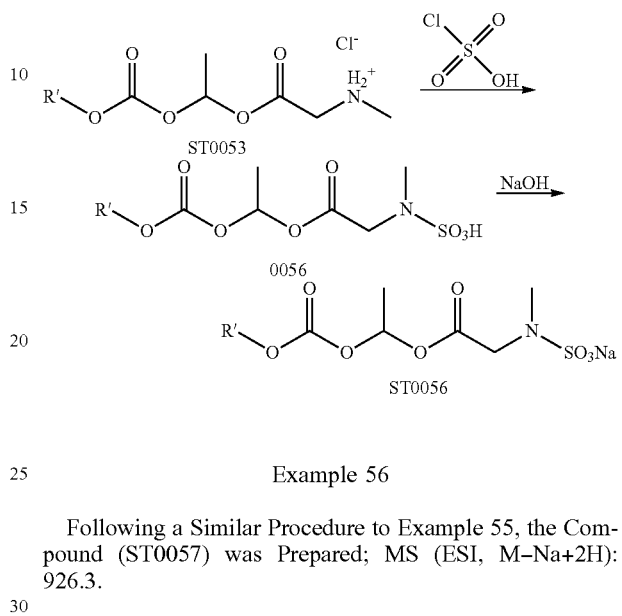

Example 56

Following a Similar Procedure to Example 55, the Compound (ST0057) was Prepared; MS (ESI, M−Na+2H): 926.3.

Example 57

Preparation of Compound ST0084

57.1 Preparation of Compound (ST0084-002)

To a reaction flask, 100 mL of dichloromethane, 2 g of creatinine, and 1.2 eq of diisopropylethylamine were added, stirred, cooled to −5 to 5° C., and 1.1 eq of benzyl chloroformate was added dropwise. After the addition dropwise was completed, the reaction was carried on at room temperature overnight. The reaction solution was washed with saturated brine, dried, filtered, and concentrated under reduced pressure to give a crude product, which was purified by silica gel column chromatography to give the compound (ST0084-002).

57.2 Preparation of Compound (ST0084-004)

To a reaction flask, 30 mL of methanol and 2.2 g of the compound (ST0084-002) were added, stirred and heated to 45 to 50° C. for 2 to 3 hours to obtain a solution of the compound (ST0084-003) in methanol.

20 mL of 1 mol/L sodium hydroxide solution was added to the reaction system, and reacted at room temperature for 3.5 to 4 hours. The reaction solution was concentrated under reduced pressure to about 5 mL, added with 30 mL of water, extracted with methyl tert-butyl ether, the aqueous phase was adjusted to pH 1-2 with 6 mol/L hydrochloric acid, extracted with ethyl acetate, and the organic phases were combined and washed with saturated brine, dried over anhydrous magnesium sulfate, filtered and concentrated under reduced pressure to give compound (ST0084-004).

57.3 Preparation of Compound (ST0084-005)

To a reaction flask, 25 mL of DMF, 1.5 g of compound (ST0084-004), and 0.76 g of cesium carbonate were added, stirred for 0.5 hours, and 1.60 g of compound ST0062-003 was added, stirred and heated to 45-50° C. overnight. The reaction mixture was added with 100 mL of water and 100 mL of ethyl acetate, and separated. The organic phase was washed with saturated aqueous sodium chloride, dried over anhydrous magnesium sulfate, filtered and concentrated under reduced pressure to give a crude product, which is purified by silica gel column chromatography to give the compound (ST0084-005).

57.4 Preparation of Compound (ST0084-006)

To a reaction flask, 15 mL of methanol, 0.1 mL of acetic acid, and 1.0 g of compound (ST0084-005) were added and stirred to dissolve, 0.35 g of a Pd/C catalyst was added and the reaction was carried on at 0° C. under hydrogen atmosphere overnight. The reaction solution was filtered under reduced pressure, and the filtrate was concentrated under reduced pressure to give the compound (ST0084-006).

57.5 Preparation of Compound (ST0084-007)

To a reaction flask, 5 mL of methanol and 0.5 g of compound (ST0084-006) were added, stirred and cooled to −5 to 5° C. A solution of dibenzylphosphite in carbon tetrachloride (0.31 g, 5 mL) was added dropwise. The reaction system was added with 0.31 g of triethylamine, kept at the temperature of −5 to 5° C. for 3 hours. The reaction system was concentrated under reduced pressure to give a crude product, which is purified by silica gel column chromatography to give the compound (ST0084-007).

57.6 Preparation of Compound (0084)

The compound (ST0084-007) was used as a raw material to give the compound (0084) with reference to the method for preparing the compound (ST0062-007), MS (ESI, M+H): 982.3.

57.7 Preparation of Compound (ST0084)

The compound (0084) was used as a raw material to give the compound (ST0084) with reference to the method for preparing the compound (ST0062), MS (ESI, M−2Na+3H): 982.3.

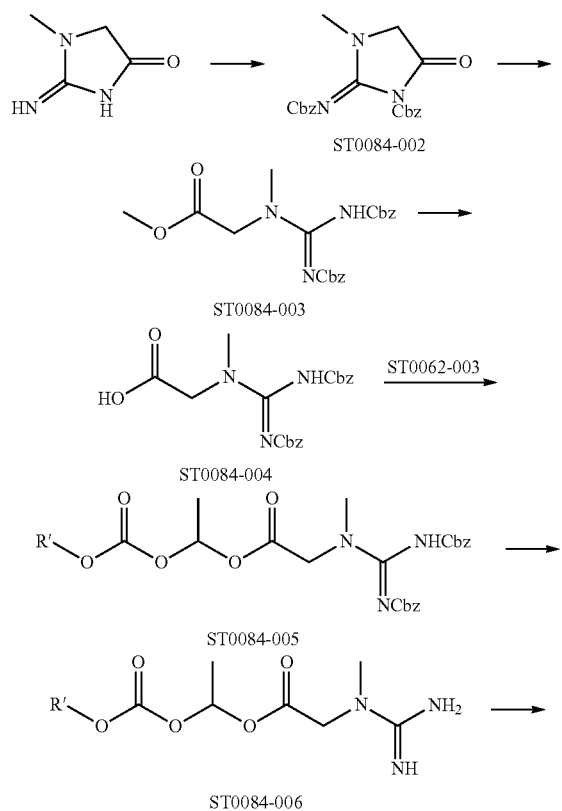

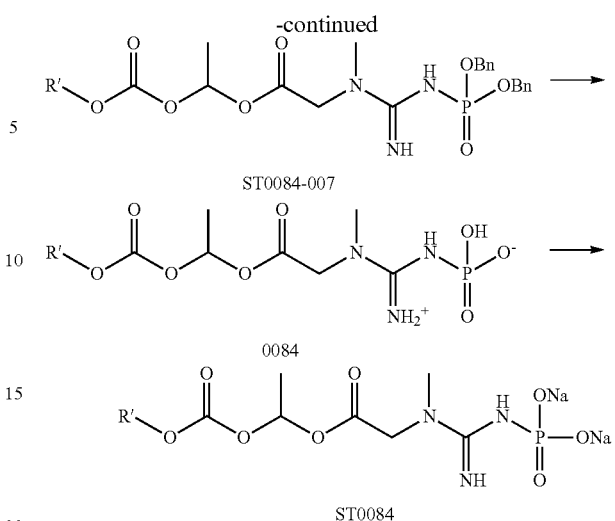

Example 58

Preparation of Compound ST0085

58.1 Preparation of Compound (ST0085-002)

To a reaction flask, 50 mL of DMF, 1.3 g of glycine benzyl ester hydrochloride, 2 g of compound ST0084-004, 1.7 g of EDCI, 170 mg of DMAP, and 0.7 g of triethylamine were added, and stirred overnight. The reaction solution was added with 80 mL of water and 150 mL of ethyl acetate, stirred and separated. The organic phase was washed successively with 1 M hydrochloric acid and saturated saline, dried over anhydrous magnesium sulfate, filtered, and concentrated under reduced pressure to give a crude product, which was purified by silica gel column chromatography to give the compound ST0085-002.

58.2 Preparation of Compound (ST0085-003)

To a reaction flask, 20 mL of methanol and 1.5 g of ST0085-002 were added and stirred, cooled to 0 to 5° C., and an aqueous solution of lithium hydroxide monohydrate (0.25 g, 1 mL) was added dropwise to react for 2 hours. The reaction solution was added with 50 mL of water, washed with terephthalic ether, and the aqueous phase was adjusted to pH 3-4 with 0.1 M hydrochloric acid and extracted with dichloromethane. The organic phase was dried over anhydrous magnesium sulfate, filtered, and the filtrate was concentrated under reduced pressure to give the compound ST0085-003.

58.3 Preparation of Compound (ST0085-004)

To a reaction flask, 40 mL of DMF, 1.08 g of the compound ST0085-003, and 0.76 g of cesium carbonate were added and stirred for 0.5 hours, 2.8 g of compound ST0062-003 was added, stirred, heated to 45-50° C., and reacted overnight. The reaction solution was added with 100 mL of water and 100 mL of ethyl acetate, and separated. The organic phase was washed with saturated aqueous sodium chloride, dried over anhydrous magnesium sulfate, filtered and concentrated under reduced pressure to give a crude product, which is purified by silica gel column chromatography to give the compound ST0085-004.

58.4 Preparation of Compound (ST0085-005)

To a reaction flask, 15 mL of methanol, 0.1 mL of acetic acid, and 1.0 g of the compound ST0085-004 were added, stirred to dissolve, 0.35 g of a Pd/C catalyst was added, and the reaction was carried on at 0° C. under hydrogen atmosphere overnight. The reaction solution was filtered and the filtrate was concentrated to give 0.5 g of the compound ST0085-005.

58.5 Preparation of Compound (ST0085-006)

To a reaction flask, 5 mL of methanol and 0.5 g of the compound ST0085-005 were added, stirred, cooled to −5 to 5° C., and a solution of dibenzyl phosphite in carbon tetrachloride (0.30 g, 5 mL) was added dropwise. The reaction system was added with 0.30 g of triethylamine, kept at the temperature of −5 to 5° C. for 3 hours. The reaction system was concentrated under reduced pressure to obtain a crude product, which is purified by silica gel column chromatography to give the compound ST0085-006.

58.6 Preparation of Compound (0085)

ST0085-006 was used as a raw material to give the compound 0085 with reference to the method for preparing the compound ST0062-007.

58.7 Preparation of Compound (ST0085)

The compound (0085) was used as a raw material to give the compound ST0085 with reference to the method for preparing the compound ST0062; MS (ESI, M−2Na+3H): 1039.4.

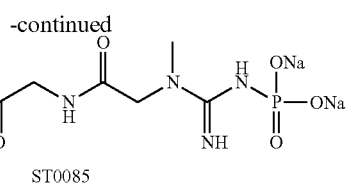

ST0085

Example 59

Preparation of Compound ST0086

59.1 Preparation of Compound ST0086-002

To a reaction flask, 50 mL of DMF, 3.9 g of cesium carbonate, and 2.58 g of methylglycine benzyl ester hydrochloride were added and stirred for 15 minutes. 3.26 g of dibenzyl chloromethyl phosphate was added and reacted at room temperature overnight. The reaction solution was added with 100 mL of water and 100 mL of ethyl acetate, and separated. The organic phase was washed with saturated brine, dried over anhydrous magnesium sulfate, filtered, and concentrated under reduced pressure to give a crude product, which was purified by silica gel column chromatography to give the compound ST0086-002.

59.2 Preparation of Compound ST0086-003

The compound ST0086-002 was used as a raw material to give the compound ST0086-003 with reference to the preparation of the compound (ST0085-003).

59.3 Preparation of Compound (ST0086-004)

The compounds ST0086-003 and ST0062-003 were used as raw materials to give the compound ST0086-004 with reference to the preparation of the compound (ST0085-004).

59.4 Preparation of Compound (0086)

ST0086-004 was used as a raw material to give the compound 0086 with reference to the method for preparing the compound ST0062-007; MS (ESI, M+H): 970.3.

59.5 Preparation of Compound (ST0086)

The compound 0086 was used as a raw material to give the compound ST0086 with reference to the method for preparing the compound ST06065; MS (ESI, M−2Na+3H): 970.3.

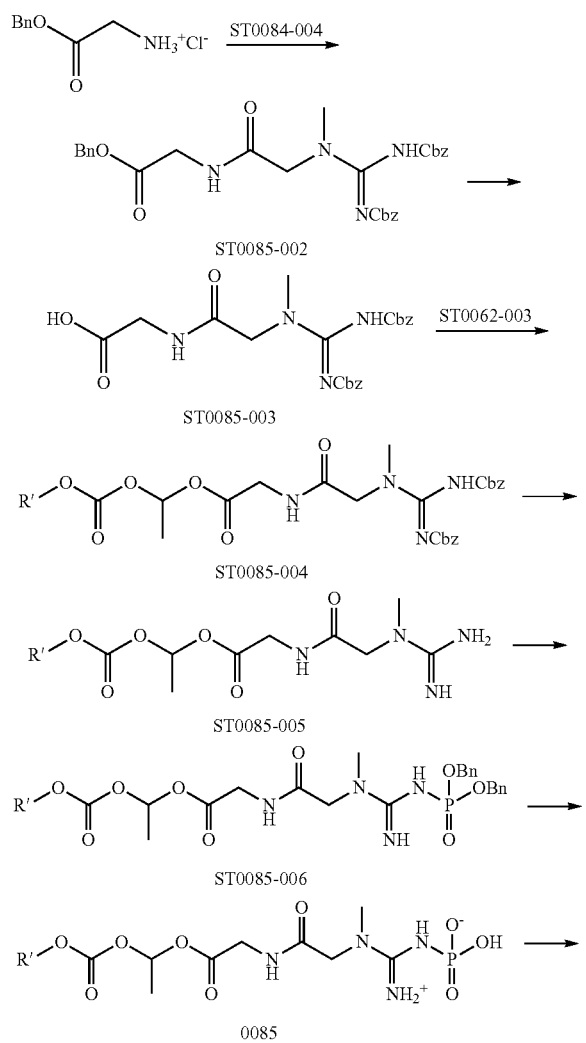

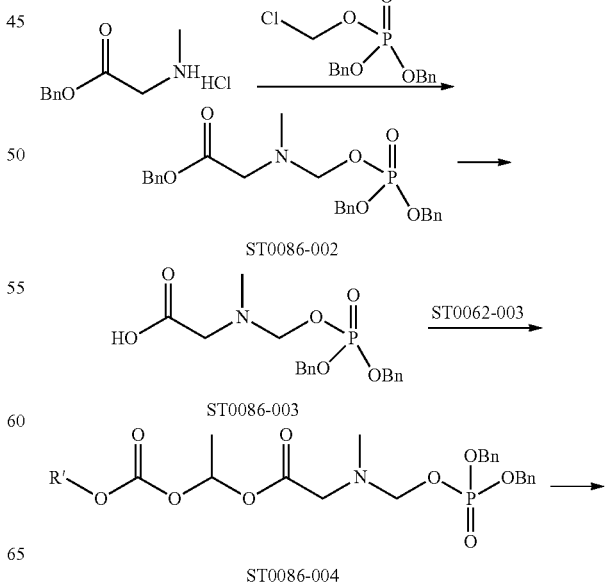

-continued

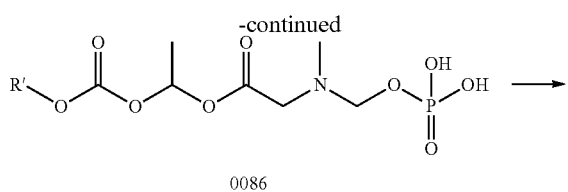
0086

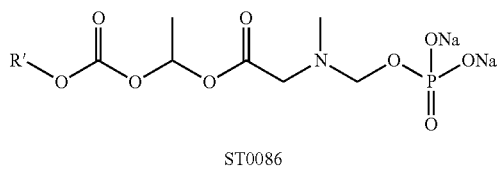
ST0086

Example 60

Preparation of Compound (ST0087)

60.1 Preparation of dibenzyl phosphate silver salt

To a reaction flask, 15 ml of acetonitrile, 15 ml of water, and 3.96 g of silver carbonate were added, stirred for 5 minutes, 4 g of dibenzyl phosphate was added, and stirred at room temperature for 1 hr. The reaction solution was concentrated to dryness under reduced pressure and dried in vacuum to give silver dibenzyl phosphate salt.

60.2 Preparation of Compound (ST0087-002)

To a reaction flask, 5 ml of toluene, 0.50 g of silver dibenzyl phosphate salt, and 0.30 g of benzyl bromoacetate were added, and heated to 115° C. to react overnight. The reaction solution was filtered under reduced pressure, the filter cake was rinsed with toluene, and the filtrate was concentrated under reduced pressure to give the compound (ST0087-002).

60.3 Preparation of Compound (ST0087-003)

To a reaction flask, 15 mL of methanol and 0.5 g of compound (ST0087-002) were added, and 3.7 mL of 1 mol/L of sodium hydroxide was added dropwise. After the addition dropwise was completed, the reaction was carried on at room temperature for 3 hours. The reaction solution was concentrated under reduced pressure to 10 ml, added with 25 ml of water, and washed with methyl tert-butyl ether. The aqueous phase was adjusted to pH 1-2 with dilute hydrochloric acid, and extracted with ethyl acetate. The organic phase was washed with saturated sodium chloride and dried over anhydrous sodium sulfate to give the compound (ST0087-003).

60.4 Preparation of Compound (ST0087-004)

Methyl glycine benzyl ester hydrochloride and the compound (ST0087-003) were used as raw materials to give the compound ST0087-004 with reference to the method for preparing the compound ST0085-002.

60.5 Preparation of Compound (ST0087)

Compound ST0087-004 was used as a raw material to give the compounds 0087 and ST0087 with reference to the method for preparing the compound ST0086-002; MS (ESI, M−2Na+3H): 998.3.

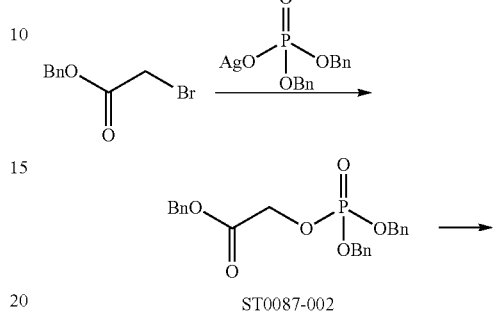

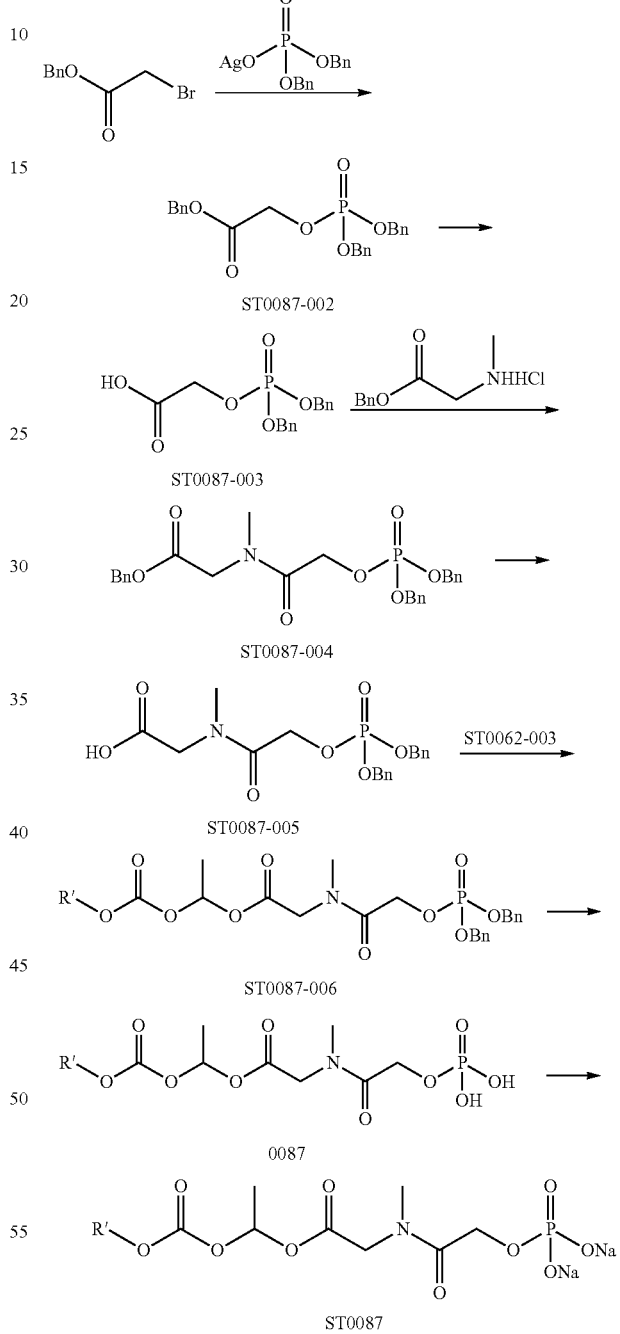

Example 61

Following a Similar Procedure to Example 60, Compound ST0088 was Prepared from Benzyl Glycine Ester as a Raw Material; MS (ESI, M−2Na+3H): 984.3.

Example 62

Preparation of Compound ST0089

62.1 Preparation of Compound (ST0089-001)

Benzyl phosphono carboxylic acid ester was prepared according to the route on page 1464 of the literature, Tetrahedron 61 (2005)1459-1480, Synthetic studies of the cyclic depsipeptides bearing the 3-amino-6-hydroxy-2-piperidone(Ahp) unit. Total synthesis of the proposed structure of micropeptin T-20, and was hydrolyzed to give compound ST0089-001. The specific operation procedure referred to the preparation method of ST0084-004.

62.2 Preparation of Compound (ST0089-002)

The compounds ST0089-001 and ST0062-003 were used as raw materials to give the compound ST0089-002 with reference to the method for preparing the compound (ST0085-004).

62.3 Preparation of Compound (0089)

ST0089-002 was used as a raw material to give the compound ST0089 with reference to the method for preparing the compound ST0062-007; MS (ESI, M+H): 957.3.

62.4 Preparation of Compound (ST0089)

The compound ST0089-003 was used as a raw material to give the compound ST0089 with reference to the method for preparing the compound ST06065; MS (ESI, M−2Na+3H): 957.3.

Example 63

Preparation of Compound ST0090

63.1 Preparation of Compound (ST0090-001)

To a reaction flask, 50 mL of dichloromethane and 3 g of the compound (ST0062-001) were added, stirred and cooled to −5 to 5° C. 8.1 g of Dess-Matin oxidant was added in batches, and the mixture was reacted overnight at −5 to 5° C. The reaction solution was added with 100 mL of saturated aqueous sodium bicarbonate solution, stirred and separated. The organic phase was washed sequentially with 10% aqueous sodium thiosulfate and saturated brine, dried over anhydrous magnesium sulfate, filtered, and concentrated under reduced pressure to give a crude product, which was purified by silica gel column chromatography to give 1.5 g of the compound (ST0090-001).

63.2 Preparation of Compound (ST0090-002)

To a reaction flask, 15 mL of diethyl ether and 2.0 g of compound (ST0090-001) were added, stirred, and cooled to −5 to 5° C., 3.6 g triphosgene was added, pyridine was added dropwise, and the reaction was carried on at −5 to 5° C. for 3 hours. The reaction solution was filtered under reduced pressure, and the filtrate was concentrated to give the compound (ST0090-002).

63.3 Preparation of Compound (ST0090-003) to Compound (ST0090-005)

The compound (ST0090-002) was used as a raw material to give the compound ST0090-005 with reference to the method for preparing the compounds ST0062-003 to ST0062-005 using posaconazole.

63.4 Preparation of Compounds (0090) and (ST0090)

The compound (ST0090-005) was used as a raw material to give the compound (0090) and its sodium salt (ST0090) with reference to the method for preparing the compounds (0077) and (ST0077), MS (ESI, M−Na+2H): 998.3.

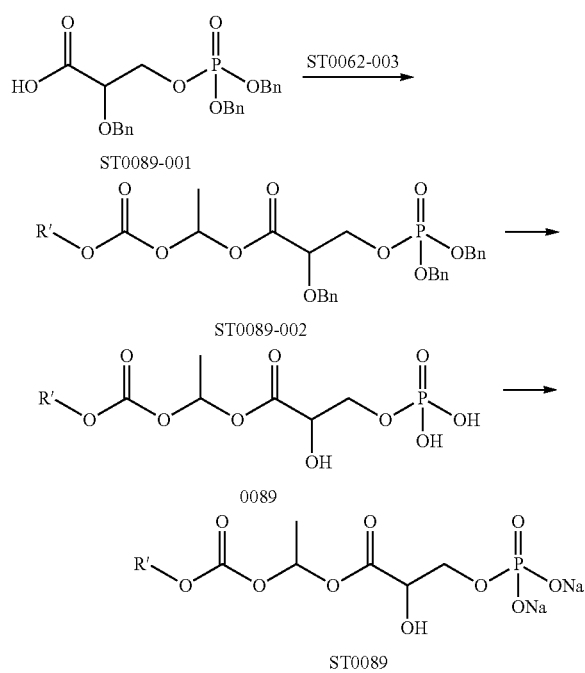

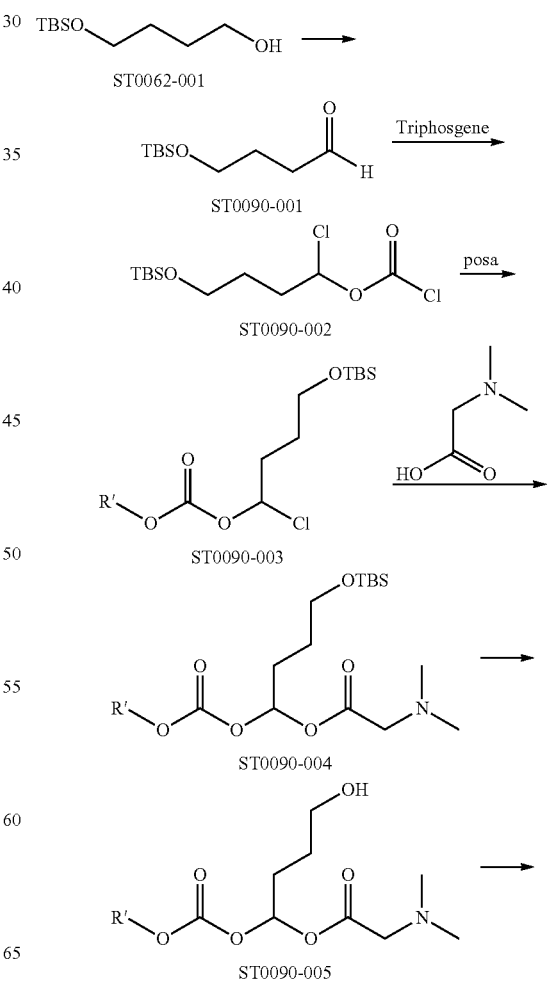

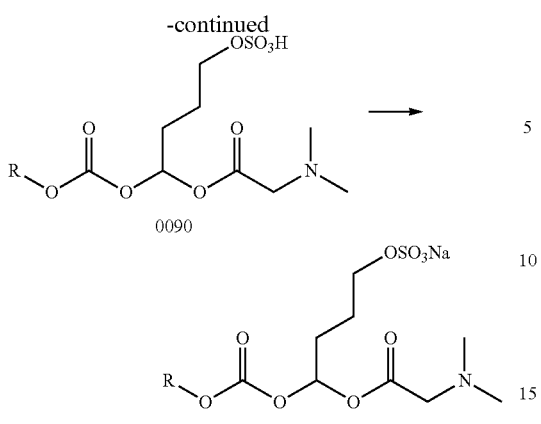

0090

ST0090

Example 64

Following a Similar Procedure to Example 63, the Compound (ST0090-003) and Boc-Sarcosine were Used as Raw Materials to Prepare the Compound (ST0092-006). The Compound (ST0092-007) was Obtained by Deprotection with Reference to Preparation Method of Compounds (ST0053-002) and (ST0053). With Reference to the Preparation Method of (ST005), the Free Compound (0092) and its Salt Compound (ST0092) were Obtained by Reacting the Compound (ST0092-007) with NaOH and Controlling the Amount of Alkali; MS (ESI, M−Na+2H): 984.3.

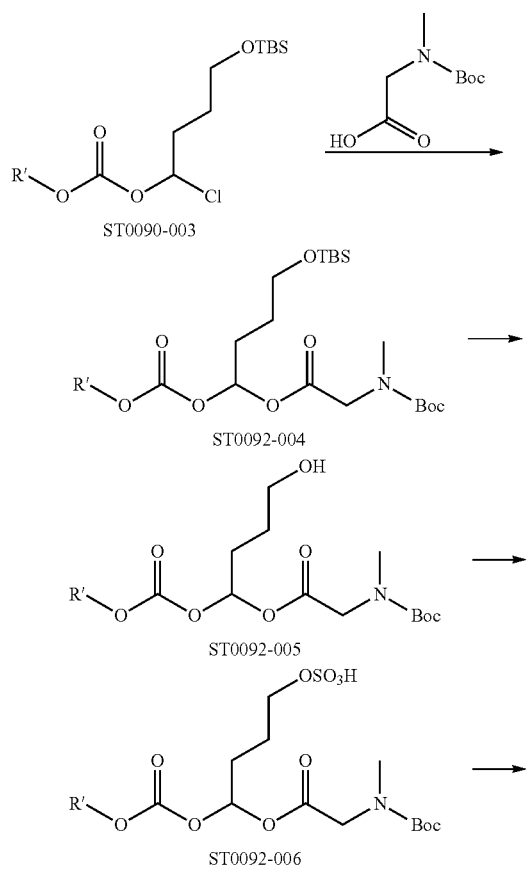

ST0090-003

ST0092-004

ST0092-005

ST0092-006

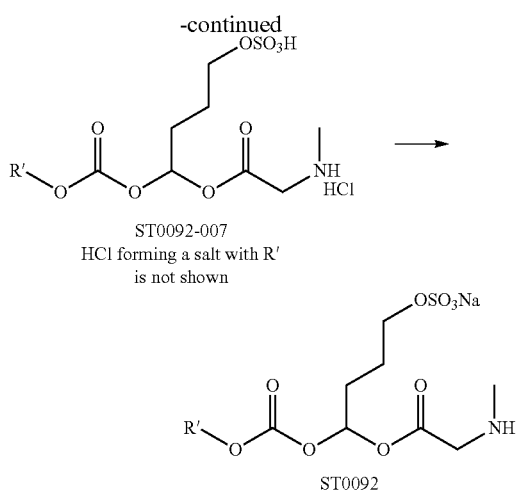

ST0092-007
HCl forming a salt with R'
is not shown

ST0092

Example 65

Preparation of Compound ST0091

The compound (ST0090-005) was used as a raw material to give the compound ST0091 with reference to the method for preparing the compounds ST0062; MS (ESI, M−2Na+ 3H): 998.4.

Example 66

Preparation of Compound ST0093

66.1 Preparation of Compound ST0093-002

To a reaction flask, 50 mL of toluene, 3.9 g of dibenzyl phosphate tert-butyl silver salt, and 4.1 g of 1-chloro-1-iodopropane were added, heated to 100° C. to react overnight. The reaction solution was cooled to room temperature, filtered, and the filtrate was concentrated to a crude product, which is purified by column chromatography to give the compound ST0093-002.

66.2 Preparation of Compound ST0093-003

To a reaction flask, 20 mL of tetrahydrofuran, 2.4 g of posaconazole, and 0.15 g of sodium hydride were added, and stirred at room temperature for 0.5 hours, 1.2 g of compound ST0093-002 was added and reacted at 50° C. for 14 hours. The reaction solution was concentrated, added with 25 mL of ethyl acetate and 250 mL of water, and separated. The organic phase was dried over anhydrous magnesium sulfate, filtered and concentrated to give a crude product, which is purified by silica gel column chromatography to give the compound ST0093-003.

66.3 Preparation of Compound (0093)

To a reaction flask, 5 mL of dichloromethane and 0.5 g of ST0093-003 were added, stirred, cooled to 0 to 5° C., and 1 mL of trifluoroacetic acid was added dropwise. The reaction was stirred for 1 hr, added with 50 mL of methyl tert-butyl ether, stirred for 15 minutes and filtered under reduced pressure to give the compound (0093); LCMS (ESI, (M+H)): 839.3.

The compound (0093) was used as a raw material to give the compound (ST0093) with reference to the method for preparing the compounds (ST0062); LCMS (ESI, (M−2Na+ 3H)): 839.3.

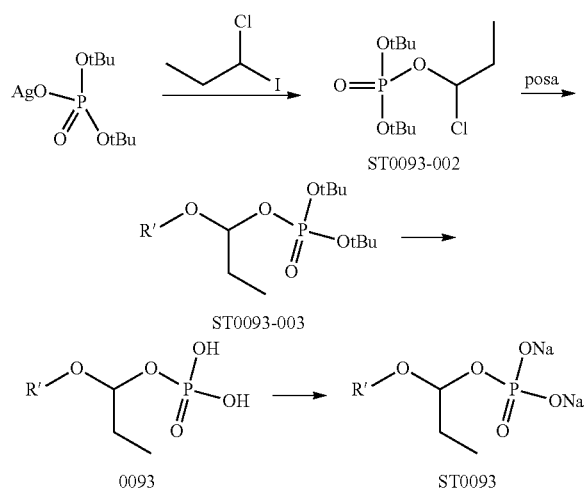

Example 67

Following a Similar Procedure to Example 66, Bromo-Iodo-Methylbenzene was Used as a Raw Material to Give Compound ST0094; MS (ESI, M −2Na+3H): 887.3.

Example 68

Preparation of Compound ST0095

To a reaction flask, 5 mL of methylene chloride and 0.19 g of posaconazole were added, stirred, cooled to −5 to 5° C., 55 mg of triethylamine was added, and a solution of chlorosulfonic acid in dichloromethane (63 mg, 1 mL) was added dropwise, and reacted at −5 to 5° C. for 0.5 hours. The reaction solution was added with 15 mL of water and 15 mL of dichloromethane, stirred and separated. The organic phase was washed with saturated brine, dried over anhydrous magnesium sulfate, filtered, and concentrated under reduced pressure to give a crude product, which is purified by silica gel column chromatography to give the compound 0095; MS (ESI, M+H): 781.2.

The compound (0095) was used as a raw material to give the compound (ST0095) by reacting with sodium hydroxide with reference to the method for preparation (ST0062).

Biological Activity and Related Properties Test

Example I:

Determination of the Solubility of the Compound of the Present Disclosure

Experimental Conditions: 25±2° C.

Experimental Instrument: Agilent 1260 HPLC

Dissolving Medium: deionized water

Experimental Protocol: 1 mg of posaconazole and appropriate amounts of each other compound were weighed, placed in 1 ml of deionized water, and shaked vigorously for 30 s every 5 minutes. After 30 min, The dissolved state was observed, and the solubility of each compound was determined by external standard calibration method using HPLC. It was found in the experiment that different salts of the same compound differ slightly in their solubility which were exemplarily shown in the following table:

TABLE 1

Results of solubility test

| Compound No. | Solubility (mg/mL) | Compound No. | Solubility (mg/mL) |
|---|---|---|---|
| Posaconazole | <1 | ST0062 | >50 |
| ST0001 | 47.7 | ST0063 | >50 |
| ST0002 | 30.8 | ST0064 | >50 |
| ST0003 | >50 | ST0065 | >50 |
| ST0004 | >50 | ST0054 | 40.9 |
| ST0005 | >50 | ST0055 | 35.4 |
| ST0006 | >50 | ST0084 | 45.8 |
| ST0007 | >50 | ST0089 | 25.2 |
| ST0008 | >50 | ST0088 | 23.8 |
| ST0009 | >50 | ST0096 | 23.2 |
| ST0010 | >50 | ST0097 | 26.6 |
| ST0011 | >50 | ST0098 | 38.4 |
| ST0012 | >50 | ST0099 | 32.2 |
| ST0016 | >50 | ST0066 | >50 |
| ST0022 | >50 | ST0056 | >50 |
| ST0023 | >50 | ST0057 | >50 |
| ST0024 | >50 | ST0075 | >50 |
| ST0025 | >50 | ST0076 | >50 |
| ST0026 | >50 | ST0077 | >50 |
| ST0027 | >50 | ST0078 | >50 |
| ST0028 | 35.7 | ST0079 | >50 |
| ST0030 | 21.8 | ST0085 | >50 |
| ST0032 | 30.5 | ST0068 | >50 |
| ST0037 | >50 | ST0081 | >50 |
| ST0038 | >50 | ST0069 | 43.7 |
| ST0039 | >50 | ST0070 | >50 |
| ST0040 | >50 | ST0082 | >50 |
| ST00041 | >50 | ST0045 | >50 |
| ST0059 | >50 | ST0083 | >50 |
| ST0060 | >50 | ST0071 | 23.4 |
| ST0061 | >50 | ST0095 | >50 |
| ST0093 | 27.9 | ST0073 | >50 |
| ST0042 | >50 | ST0074 | >50 |
| ST0043 | >50 | | |
| ST0044 | >50 | | |

From the above data, it can be seen that the solubility of the compound of the present disclosure in pure water is significantly higher than that of posaconazole. This advantage makes it possible to avoid the safety risks caused by the use of β-cyclodextrin-type solubilizers.

Example II

In Vitro Stability Test of Compounds of the Present Disclosure

This example detects the metabolic stability of the compounds of the present disclosure in human (rat) plasma and intestinal S9 in vitro. In a human (rat) plasma reaction system, 990 μl of human (rat) plasma was taken and incubated at 37° C. for 5 minutes, and 10 μl of the compound mother liquor was used to initiate the reaction. In the human (rat) intestinal S9 stability experiment, in the order shown in Table 2 below, the samples were added and incubated in a 37° C. water bath to initiate the reaction, each sample performed in triplicates. Respectively, at 1 minute, 2 minutes, 5 minutes, 15 minutes, 30 minutes after the reaction began, 100 μL of each was taken and added to a centrifuge tube containing 400 μL of 0° C. precooled internal standard working solution. The reaction was terminated, vortexed and mixed for 1 minute, centrifuged at 10000×g for 10 minutes in a 4° C. precooled high-speed centrifuge, and the supernatant was detected with HPLC. The test results were used to calculate metabolic half-life using WinNonlin (version 6.2 Pharsight, Mountain View, Calif.) with a non-compartmental model.

Compound stock solution concentration: 1 mM

Reaction matrix: human (rat) plasma, intestinal S9 purchased from Research Institute for Liver Diseases (Shanghai) Co., Ltd.

TABLE 2

Composition of reaction systems of each compound in human (rat) intestine S9

| | Component | Volume (μL) | Initial concentration | Final concentration |
|---|---|---|---|---|
| 1 mL Human (rat) intestine S9 incubation system | PBS buffer (pH 7.4) | 740 | 0.1M | 0.1M |
| | Intestine S9 | 50 | 20 mg/mL | 1 mg/mL |
| | Pre-incubation for 5 minutes at 37° C. | | | |
| | Aqueous compound solution | 10 | 1 mM | 10 μM |
| | NADPH regeneration system | | | |
| | MgCl$_2$ | | 100 mM | 5 mM |
| | NADP | 200 | 20 mM | 1 mM |
| | Glucose-6-sodium phosphate | | 200 mM | 10 mM |
| | Sodium glucose-6-phosphate dehydrogenase | | 20 unit/mL | 1 unit/mL |

This example detected the metabolic half-lives of the compounds of the present disclosure in human (rat) plasma and intestinal S9 in vitro. It was found in the experiment that the in vitro stability test data for different salts of the same compound were similar. Said data were exemplarily shown in the following table.

TABLE 3

Metabolic half-life of each compound in human (rat) plasma and intestine S9

| Compound | Human plasma $T_{1/2}$ (min) | Human intestine S9 $T_{1/2}$ (min) | Rat plasma $T_{1/2}$ (min) | Rat intestine S9 $T_{1/2}$ (min) |
|---|---|---|---|---|
| ST0002 | 0.78 ± 0.15 | 14.89 ± 3.56 | 1.12 ± 0.35 | 18.52 ± 4.56 |
| ST0018 | 18.65 ± 5.63 | 50.13 ± 5.98 | 11.52 ± 1.23 | 45.21 ± 6.95 |
| ST0022 | 1.39 ± 0.52 | 17.72 ± 4.52 | 1.12 ± 0.45 | 18.96 ± 5.36 |
| ST0023 | 0.94 ± 0.15 | 15.02 ± 3.78 | 0.55 ± 0.78 | 16.69 ± 2.96 |
| ST0024 | 1.57 ± 0.34 | 12.21 ± 5.90 | 2.51 ± 0.69 | 15.63 ± 5.96 |
| ST0025 | 0.92 ± 0.03 | 25.03 ± 4.76 | 1.22 ± 0.85 | 22.525 ± 5.96 |
| ST0026 | 1.03 ± 0.09 | 16.35 ± 7.54 | 2.69 ± 1.21 | 18.96 ± 5.96 |
| ST0027 | 20.35 ± 3.65 | 45.92 ± 8.12 | 15.93 ± 7.85 | 39.52 ± 6.69 |
| ST0035 | 21.08 ± 1.07 | 35.76 ± 7.97 | 25.96 ± 8.65 | 42.63 ± 5.96 |
| ST0044 | 17.34 ± 4.12 | 32.94 ± 6.66 | 12.69 ± 5.63 | 27.69 ± 6.96 |
| ST0045 | 15.21 ± 3.99 | 33.21 ± 4.23 | 11.95 ± 2.96 | 25.98 ± 5.69 |
| ST0053 | 19.86 ± 3.01 | 50.22 ± 5.15 | 21.25 ± 4.52 | 48.25 ± 6.85 |
| ST0093 | 18.95 ± 2.76 | 61.98 ± 14.26 | 15.69 ± 4.88 | 57.25 ± 12.56 |
| ST0063 | 0.85 ± 0.45 | 16.27 ± 2.12 | 1.21 ± 0.75 | 19.36 ± 5.69 |
| ST0066 | 11.35 ± 2.27 | 40.35 ± 5.21 | 12.58 ± 4.54 | 36.65 ± 8.66 |
| ST0077 | 1.97 ± 1.29 | 21.29 ± 5.09 | 1.55 ± 0.56 | 19.26 ± 5.65 |
| ST0078 | 2.22 ± 0.58 | 24.22 ± 8.75 | 2.57 ± 0.74 | 28.24 ± 5.65 |
| ST0079 | 2.56 ± 0.42 | 28.71 ± 8.90 | 2.06 ± 0.77 | 27.88 ± 11.25 |
| ST0080 | 12.79 ± 3.57 | 40.32 ± 12.74 | 13.28 ± 4.78 | 45.39 ± 11.34 |
| ST0070 | 0.95 ± 0.31 | 20.21 ± 8.02 | 1.12 ± 0.56 | 17.58 ± 5.85 |
| ST0082 | 8.99 ± 2.52 | 42.13 ± 13.69 | 9.36 ± 1.56 | 52.56 ± 8.69 |
| ST0083 | 3.72 ± 0.45 | 26.19 ± 8.41 | 4.36 ± 0.95 | 29.28 ± 7.16 |
| ST0072 | 18.27 ± 1.97 | 46.75 ± 12.78 | 25.56 ± 12.97 | 39.89 ± 10.85 |
| ST0073 | 0.92 ± 0.11 | 16.25 ± 6.08 | 0.75 ± 0.23 | 15.96 ± 8.96 |
| ST0074 | 0.86 ± 0.07 | 20.01 ± 4.66 | 1.26 ± 0.54 | 18.265 ± 5.66 |

It can be seen from the data in the table that the compounds of the present disclosure have very close half-lives in human and rat genus plasma and two genera of intestine S9. The above examples have reference significance for the action of the drug in human body.

Example III

Solid Stability Test of the Compound of the Present Disclosure

Experimental conditions: 25° C.±2° C., relative humidity 60%±2%

Experimental instruments: Agilent 1260 HPLC; stability test chamber

Experimental method: each compound of the present disclosure was packaged (the inner packaging material was a penicillin bottle; the outer packaging material was a double-layered aluminum foil bag with an internal and external desiccants), and placed in the stability test chamber with temperature of 25° C.±2° C. and relative humidity of 60%±2%. The changes of the total impurity content of the test compounds for 30 days were examined. The results are shown as follows:

TABLE 4

Solid stability test results

| Compound No. | Total impurity increment in 30 days | Compound No. | Total impurity increment in 30 days |
|---|---|---|---|
| ST0002 | 0.63% | ST0103 | 0.29% |
| ST0101 | 0.47% | ST0026 | 0.46% |
| ST0022 | 0.48% | ST0106 | 0.32% |
| ST0102 | 0.36% | ST0063 | 0.38% |
| ST0025 | 0.55% | ST0065 | 0.89% |
| ST0105 | 0.34% | ST0055 | 0.85% |
| ST0024 | 0.62% | ST0084 | 1.31% |
| ST0104 | 0.27% | ST0089 | 2.05% |
| ST0021 | 0.97% | ST0056 | 2.33% |
| ST0027 | 0.75% | ST0057 | 1.96% |
| ST0028 | 1.62% | ST0075 | 0.87% |
| ST0034 | 1.85% | ST0076 | 2.31% |
| ST0035 | 2.58% | ST0077 | 0.25% |
| ST0036 | 0.87% | ST0078 | 0.40% |
| ST0038 | 1.06% | ST0079 | 0.42% |
| ST0040 | 1.34% | ST0085 | 0.86% |
| ST0046 | 0.92% | 0058 | 0.47% |
| ST0053 | 0.85% | ST0051 | 1.23% |
| ST0041 | 1.45% | ST0080 | 1.15% |
| ST0047 | 1.67% | ST0067 | 0.97% |
| ST0048 | 0.95% | ST0091 | 1.07% |
| ST0049 | 1.82% | ST0068 | 1.62% |
| ST0059 | 0.76% | ST0081 | 1.52% |
| ST0060 | 0.83% | ST0069 | 0.88% |
| ST0061 | 1.24% | ST0070 | 0.30% |
| ST0100 | 2.57% | ST0082 | 0.83% |
| ST0093 | 0.91% | ST0092 | 0.52% |
| ST0042 | 1.05% | ST0045 | 1.68% |
| ST0043 | 2.14% | ST0083 | 0.45% |
| ST0044 | 0.64% | ST0071 | 0.50% |
| ST0062 | 0.43% | ST0072 | 1.50% |
| ST0041 | 1.45% | ST0095 | 0.41% |
| ST0003 | 0.68% | ST0073 | 0.28% |
| ST0013 | 0.45% | ST0074 | 0.33% |
| ST0023 | 0.42% | | |

From the analysis of above data, after the compounds or salts thereof according to the present disclosure being allowed to stand for 30 days under the conditions of a temperature of 25° C.±2° C. and a humidity of 60%±2%, All these compounds exhibit good stability, and the different salts of the compounds also exhibit better stability.

Example IV

Pharmacokinetics (PK) Studies of Intravenous Administration of Compounds of the Present Disclosure Administration amount: 2.5 mg/kg (calculated as posaconazole)
Administration volume: 2.5 ml/kg
Drug concentration: 1 mg/mL
Administration vehicle: normal saline
Administration route: tail vein injection Experimental animals: SD rats, SPF grade, weighing 180-220 g, equal amount of male and female. Rats were randomly divided into groups of 6 with 3 males and 3 females.

Experimental protocol: blood samples were collected at different time points after tail vein administration and plasma posaconazole concentrations were measured.

The PK parameters of plasma posaconazole are shown in the following table.

TABLE 5

Main pharmacokinetic parameters of each compound for single intravenous administration to rats

| Compounds | $T_{1/2}$ (h) | $AUC_{last}$ (ng/mL * h) |
|---|---|---|
| posaconazole | — | — |
| posaconazole (cyclodextrin) | 10.88 ± 3.21 | 13209 ± 5092 |
| ST0001 | 12.75 ± 3.27 | 8298 ± 2542 |
| ST0002 | 13.12 ± 4.13 | 9568 ± 2250 |
| ST0003 | 12.95 ± 4.08 | 11714 ± 2113 |
| ST0006 | 11.17 ± 3.41 | 10562 ± 1590 |
| ST0007 | 12.27 ± 4.35 | 10568 ± 1787 |
| ST0008 | 11.21 ± 3.38 | 8952 ± 2584 |
| ST0009 | 12.35 ± 3.54 | 8985 ± 2255 |
| ST0010 | 10.35 ± 4.38 | 7485 ± 2257 |
| ST0011 | 11.45 ± 2.85 | 10958 ± 1458 |
| ST0012 | 13.03 ± 4.12 | 11256 ± 2036 |
| ST0018 | 12.43 ± 2.65 | 7952 ± 2130 |
| ST0022 | 11.85 ± 3.54 | 11562 ± 2565 |
| ST0023 | 11.41 ± 2.95 | 12899 ± 3652 |
| ST0024 | 11.17 ± 3.41 | 11354 ± 1562 |
| ST0025 | 10.95 ± 4.35 | 12985 ± 3251 |
| ST0026 | 12.04 ± 3.65 | 11652 ± 2584 |
| ST0027 | 12.55 ± 4.11 | 7452 ± 1955 |
| ST0035 | 10.35 ± 4.38 | 7485 ± 2257 |
| ST0044 | 12.65 ± 4.21 | 8152 ± 2358 |
| ST0045 | 12.55 ± 2.95 | 9221 ± 3256 |
| ST0052 | 11.85 ± 3.14 | 7565 ± 5625 |
| ST0050 | 13.52 ± 4.56 | 8563 ± 3125 |
| ST0062 | 12.32 ± 1.55 | 8152 ± 3511 |
| ST0063 | 12.95 ± 2.85 | 12420 ± 1058 |
| ST0098 | 12.35 ± 4.15 | 7595 ± 1566 |
| ST0077 | 13.58 ± 4.25 | 12657 ± 3584 |
| ST0078 | 13.58 ± 2.58 | 11965 ± 2548 |
| ST0079 | 12.89 ± 3.65 | 11885 ± 3658 |
| ST0090 | 12.75 ± 3.68 | 7956 ± 3598 |
| ST0070 | 11.58 ± 4.58 | 12777 ± 4585 |
| ST0083 | 11.28 ± 3.58 | 11589 ± 2598 |
| ST0072 | 10.58 ± 4.65 | 6859 ± 2985 |
| ST0073 | 12.78 ± 3.55 | 12795 ± 3688 |
| ST0074 | 11.52 ± 3.87 | 12856 ± 4862 |

$T_{1/2}$: half-life,
$AUC_{last}$: area under the time curve,
"—": posaconazole was not detected so that the parameters could not be calculated.

As can be seen from the data in the above table, posaconazole was dissolved in saline solution as a control and was not detected in the sample. However, after intravenous administration of the compound of the present disclosure, its exposure to posaconazole in rats is much greater than that of the posaconazole control group, which is close to that of posaconazole (cyclodextrin), indicating that most of the compounds of the present disclosure have been converted to posaconazole after intravenous administration and do not require the use of the excipient β-cyclodextrin which is a safety issue for solubilization, thereby avoiding the safety risks resulting therefrom.

Example V

Pharmacokinetic (PK) Study of Intragastric Administration of Compounds of the Present Disclosure Administration amount: 2.5 mg/kg (calculated as posaconazole)

Administration volume: 10 ml/kg

Drug concentration: 0.25 mg/mL

Administration vehicle: the positive drug posaconazole group used CMC—Na, while other groups used normal saline (physiological saline)

Administration route: intragastric administration

Experimental animals: SD rats, SPF grade, weighing 180-220 g, equal amount of male and female. Rats were randomly divided into groups of 6 with 3 males and 3 females.

Experimental protocol: after oral intragastric administration, blood samples were collected at different time points to determine the concentration of posaconazole in the plasma and the pharmacokinetic parameters of posaconazole were obtained.

TABLE 6

Main pharmacokinetic parameters of each compound for single intragastric administration to rats

| Compound | $C_{max}$ (ng/mL) | $T_{1/2}$ (h) | $AUC_{last}$ (ng/mL * h) |
|---|---|---|---|
| Posaconazole (CMC-Na) | 60 ± 12 | 12.38 ± 2.91 | 1229 ± 272 |
| ST0002 | 224 ± 48 | 10.81 ± 4.09 | 3834 ± 851 |
| ST0003 | 410 ± 96 | 10.49 ± 2.49 | 6309 ± 1412 |
| ST0006 | 297 ± 75 | 9.17 ± 2.69 | 5562 ± 1690 |
| ST0007 | 89 ± 30 | 10.12 ± 3.55 | 1562 ± 158 |
| ST0008 | 101 ± 25 | 14.62 ± 3.82 | 2413 ± 613 |
| ST0009 | 64 ± 17 | 12.66 ± 2.91 | 1618 ± 209 |
| ST0010 | 98 ± 39 | 12.78 ± 2.75 | 2582 ± 509 |
| ST0011 | 82 ± 23 | 13.18 ± 3.47 | 2502 ± 785 |
| ST0012 | 487 ± 105 | 10.73 ± 2.33 | 6574 ± 1516 |
| ST0019 | 102 ± 26 | 11.41 ± 3.25 | 1985 ± 358 |
| ST0022 | 305 ± 99 | 12.25 ± 4.11 | 6854 ± 1256 |
| ST0023 | 325 ± 101 | 11.56 ± 3.65 | 7152 ± 985 |
| ST0024 | 415 ± 125 | 12.88 ± 2.88 | 7258 ± 1158 |
| ST0025 | 389 ± 158 | 13.55 ± 4.87 | 6589 ± 1854 |
| ST0026 | 452 ± 201 | 12.47 ± 3.24 | 7325 ± 2231 |
| ST0040 | 254 ± 58 | 12.74 ± 4.58 | 4562 ± 1254 |
| ST0041 | 278 ± 102 | 13.56 ± 3.85 | 3854 ± 1455 |
| ST0043 | 225 ± 85 | 12.54 ± 4.56 | 5045 ± 2105 |
| ST0053 | 105 ± 65 | 11.85 ± 3.14 | 3285 ± 1452 |
| ST0093 | 125 ± 58 | 12.44 ± 2.14 | 3056 ± 1265 |
| ST0063 | 325 ± 180 | 13.45 ± 2.85 | 7856 ± 2132 |
| ST0066 | 95 ± 45 | 14.21 ± 3.25 | 3562 ± 524 |
| ST0077 | 425 ± 152 | 11.32 ± 3.78 | 6975 ± 2156 |
| ST0078 | 325 ± 102 | 12.65 ± 3.21 | 5652 ± 1124 |
| ST0079 | 298 ± 74 | 11.25 ± 2.95 | 5598 ± 2145 |
| ST0080 | 98 ± 58 | 13.24 ± 4.52 | 4152 ± 2320 |
| ST0070 | 352 ± 125 | 12.65 ± 5.25 | 7262 ± 1586 |
| ST0082 | 145 ± 29 | 11.54 ± 4.21 | 3789 ± 1056 |
| ST0083 | 258 ± 88 | 12.52 ± 3.85 | 5985 ± 1252 |
| ST0073 | 324 ± 101 | 11.85 ± 4.35 | 7522 ± 3251 |
| ST0074 | 354 ± 89 | 12.87 ± 3.22 | 7647 ± 1855 |

$C_{max}$: peak plasma concentration,
$T_{1/2}$: half-life
$AUC_{last}$: area under the time curve As can be seen from the data in the table, after intragastric administration of the compounds of the present disclosure, the exposure dose of posaconazole in rats were significantly higher than that of posaconazole (CMC—Na) group, indicating that the bioavailability of the compounds of the present disclosure was better than that of posaconazole (CMC—Na).

Example VI

Experiment of Intravenous Administration of the Compound of the Present Disclosure Against *Candida Albicans* Vaginitis 1. Experimental Material
1.1 Experimental Instruments Blood cell count plate, paraffin microtome, SPX-250B biochemical incubator, ultra-clean bench, micro adding sample appliance, pressure steam sterilizer, light microscope, and electronic analytical balance.

1.2 Experimental Reagents

Estradiol benzoate injection, polyethylene glycol, Sabourand's dextrose agar solid medium.

1.3 Experimental Animals

KM mice, weighing 18-22 g, female, provided by Hubei Experimental Animal Center.

1.4 Experimental Strains

The standard strain of *Candida albicans* was purchased from the American Type Culture Collection, strain number ATCC10231.

2. Experimental Method

The above mice were weighed and randomly divided into groups: a posaconazole group, a test compound group, and a vehicle group, 20 in each group. Since posaconazole was insoluble in the vehicle (physiological saline), the posaconazole group was a commercially available posaconazole injection (MSD/Schering-Plough, 3PAR80701, the same below), i.e., solubilized formulation using sulfobutyl ether-β cyclodextrin. Prior to being infected with *Candida albicans*, animals in each group were given subcutaneous injections of 0.5 ml of estradiol benzoate (2 mg/ml) for 6 consecutive days to allow them to enter the estrus phase. Injections were continued once every 2 days until the completion of the experiment. After 6 days, 20 μl of *Candida albicans* solution in a concentration of $3.5 \times 10^6$ CFU/ml was injected vaginally into each mouse, causing a vaginal infection model. From the first day after infection, each group of animals was given 20 mg/kg of the corresponding drug (calculated as posaconazole) in the tail vein at an administration volume of 0.1 ml/10 g once a day for 5 consecutive days. The model group was given an equal volume of solvent (physiological saline). On the 3rd and 5th days after infection, the vagina of mice were wiped with sterile cotton swabs. The cotton swabs were soaked in 0.9 ml physiological saline. The fungal solutions were diluted to 10-fold increments to give a series of concentrations, and then 100 μl of each concentration of the bacteria solutions was taken and inoculated on Sabourand's dextrose agar solid medium containing 0.5% (W/V) chloramphenicol to observe the fungal load of *Candida albicans* on the vagina.

3. Experimental Results

TABLE 7

*Candida albicans* vaginitis (intravenous administration): vaginal fungal load of mice in each group

| Group | Dose (mg/kg) | Time (days) 3 | 5 |
|---|---|---|---|
| Vehicle | — | 4.08 ± 0.36 | 4.48 ± 0.52 |
| Posaconazole (cyclodextrin) | 20 | 4.08 ± 0.25 | 3.90 ± 0.22 |
| ST0003 | 20 | 4.11 ± 0.30 | 3.85 ± 0.28 |
| ST0007 | 20 | 4.08 ± 0.52 | 3.87 ± 0.31 |
| ST0008 | 20 | 4.05 ± 0.25 | 3.86 ± 0.21 |
| ST0009 | 20 | 4.05 ± 0.23 | 3.89 ± 0.54 |
| ST0011 | 20 | 4.09 ± 0.39 | 3.75 ± 0.47 |
| ST0012 | 20 | 4.01 ± 0.28 | 3.75 ± 0.26 |

Note:
the data was expressed as the mean ± standard deviation of the logarithm of the CFU values of 20 mice.

From the experimental results, it can be seen that after 5 days of intravenous administration, the fungal loads of the compounds of the present disclosure group were significantly lower than that of the vehicle group, and were consistent with the posaconazole (cyclodextrin) group, thereby achieving significant therapeutic effects and avoiding the safety risks caused by the solubilization using β-cyclodextrin-type excipients.

Example VII

Experiment of Intragastric Administration of the Compound of the Present Disclosure Against *Candida Albicans* Vaginitis 1. Experimental Material
1.1 Experimental Instruments Blood cell count plate, paraffin microtome, SPX-250B biochemical incubator, ultra-clean bench, micro adding sample appliance, pressure steam sterilizer, light microscope, and electronic analytical balance.

1.2 Experimental Reagents

Estradiol benzoate injection, polyethylene glycol, Sabourand's dextrose agar solid medium.

1.3 Experimental Animals

KM mice, weighing 18-22 g, female, provided by Hubei Experimental Animal Center.

1.4 Experimental Strains

The standard strain of *Candida albicans* was purchased from the American Type Culture Collection, strain number ATCC10231.

2. Experimental Method

The mice were weighed and randomized into groups: a posaconazole (CMC—Na) group, a test compound group, and a vehicle group, 20 in each group. Posaconazole (Wuhan Zhongyou Pharmaceutical Co., Ltd., C010-1000401, the same below) was used to prepare a suspension with CMC—Na. The other test drugs were dissolved with physiological saline and sonicated until they were cleared for administration. Prior to being infected with *Candida albicans*, animals in each group were given subcutaneous injections of 0.5 ml of estradiol benzoate (2 mg/ml) for 6 consecutive days to allow them to enter the estrus phase. Injections were continued once every 2 days until the completion of the experiment. After 6 days, 20 μl of *Candida albicans* solution in a concentration of $3.5 \times 10^6$ CFU/ml was injected vaginally into each mouse, causing a vaginal infection model. From the first day after infection, each group of animals was given intragastric administration of the corresponding drug 20 mg/kg (calculated as posaconazole) at an administration volume of 0.1 ml/10 g once a day for 15 consecutive days. The model group was given an equal volume of solvent (physiological Saline). On the 3rd, 5th, 7th, 11th, and 15th day after infection, the vagina of mice were wiped with sterile cotton swabs. The cotton swabs were soaked in 0.9 ml physiological saline. The fungal solutions were diluted to 10-fold increments to give a series of concentrations, and then 100 μl of each concentration of the bacteria solutions was taken and inoculated on Sabourand's dextrose agar solid medium containing 0.5% (W/V) chloramphenicol to observe the fungal load of *Candida albicans* on the vagina.

3. Experimental Results

TABLE 8

*Candida albicans* vaginitis (intragastric administration): vaginal fungal load of mice in each group

| Group | Dose (mg/kg) | Time (days) 3 | 5 | 7 | 11 | 15 |
|---|---|---|---|---|---|---|
| Vehicle | — | 4.24 ± 0.31 | 4.39 ± 0.48 | 5.23 ± 0.47 | 5.48 ± 0.45 | 5.87 ± 0.65 |
| Posaconazole (CMC-Na) | 20 | 4.21 ± 0.34 | 4.29 ± 0.58 | 4.15 ± 0.38 | 3.78 ± 0.31 | 2.95 ± 0.22 |
| ST0002 | 20 | 4.18 ± 0.22 | 4.35 ± 0.41 | 3.97 ± 0.47 | 3.05 ± 0.27 | 2.29 ± 0.19 |
| ST0003 | 20 | 4.23 ± 0.41 | 4.05 ± 0.37 | 3.28 ± 0.36 | 2.47 ± 0.18 | 1.42 ± 0.20 |
| ST0006 | 20 | 4.32 ± 0.29 | 4.18 ± 0.20 | 3.49 ± 0.54 | 2.84 ± 0.37 | 1.75 ± 0.17 |
| ST0007 | 20 | 4.35 ± 0.54 | 4.47 ± 0.65 | 4.23 ± 0.41 | 3.81 ± 0.27 | 2.87 ± 0.24 |
| ST0008 | 20 | 4.21 ± 0.32 | 4.34 ± 0.47 | 3.85 ± 0.35 | 3.31 ± 0.29 | 2.68 ± 0.18 |
| ST0010 | 20 | 4.21 ± 0.32 | 4.38 ± 0.41 | 3.97 ± 0.55 | 3.37 ± 0.28 | 2.75 ± 0.41 |
| ST0011 | 20 | 4.18 ± 0.27 | 4.35 ± 0.47 | 3.85 ± 0.67 | 3.29 ± 0.20 | 2.81 ± 0.27 |
| ST0012 | 20 | 4.17 ± 0.43 | 4.12 ± 0.35 | 3.10 ± 0.34 | 2.42 ± 0.19 | 1.47 ± 0.22 |

Note:
the data was expressed as the mean ± standard deviation of the logarithm of the CFU values of 20 mice.

From the experimental results, it can be seen that after 15 days of administration, the fungi loads of the compounds of the present disclosure dissolved with physiological saline were significantly lower than that of the vehicle group and were consistent with the posaconazole (CMC—Na) group. Particularly, the compound ST0002, ST0003, ST0006 and ST0012 had lower fungal loads than the posaconazole group and achieved significant therapeutic effects.

Example VIII

Experiment of Intravenous Administration of Compounds of the Present Disclosure Against Systemic Fungal Infection in Mice 1. Experimental Material 1.1 Experimental Instruments Multiskan MK3 enzyme-labeled detector, watertight electric constant temperature incubator, ZQ-F160 full-temperature oscillation incubator, MJX intelligent mold incubator, SW-CT-IF ultra-clean bench, UV spectrophotometer.

1.2 Experimental Reagents dimethyl sulfoxide, Sabourand's dextrose agar solid medium (SDA).

1.3 Experimental Animals

ICR mice, weighing 18-22 g, male, provided by Hubei Experimental Animal Center.

1.4 Experimental Strains

The standard strain of *Candida albicans* was purchased from the American Type Culture Collection, strain number ATCC10231.

2. Experimental Method

Prior to the experiment, a small amount of *Candida albicans* was picked from an SDA (sacharomyces agar, the same below) medium kept at 4° C. with an inoculation loop and inoculated into 1 ml YPD (Yeast Extract Peptone Dextrose Medium) culture medium, cultured at 30° C. with 200 rpm shaking and activated for 16 hours, so that the fungus was in the late stage of exponential growth. Counted with a hemocytometer and the fungal solution concentration was adjusted to $1 \times 10^3$-$5 \times 10^3$ CFU/ml with RPMI1640 medium (Roswell Park Memorial Institute 1640, the same below). Monoclonal *Candida albicans* on SDA plate was picked up, inoculated into 1 ml YPD (Yeast Extract Peptone Dextrose Medium, the same below) culture medium, cultured at 35° C., 200 rpm for 16 hours until late exponential growth phase. *Candida albicans* was inoculated into fresh medium for culturing for 6 hours at 1%, centrifuged at 1000×g for 5 minutes, washed with physiological saline three times until the supernatant was colorless, counted with a hemocytometer, and the cell concentration was adjusted to $5 \times 10^6$ cells/ml. A tail vein injection of 0.1 ml/10 g caused a systemic fungal infection in mice. The mice were randomly divided into groups of 10 in each group to give a posaconazole group, a test compound group, and a vehicle group. Since posaconazole was insoluble in the vehicle (physiological saline), the posaconazole group was a commercially available posaconazole injection, i.e., solubilized using sulfobutyl ether-βcyclodextrin. Two hours after the establishment of a mouse systemic fungal infection model, each administration group was administered by tail vein injection of 20 mg/kg (calculated as posaconazole), and the administration volume was 0.1 ml/10 g, and the model group was given 0.1 ml/10 g of 0.9% sodium chloride solution, once daily for 5 continuos days. The death of the mice was observed and the survival time was recorded. A total of 7 days of observations were performed. All dead mice were burned with ethanol.

3. Experimental Results

TABLE 9

Systemic fungal infection (intravenous administration): survival rate of mice in each group after administration (%)

| Group | Dose (mg/kg) | Time (days) | | | | | | |
|---|---|---|---|---|---|---|---|---|
| | | 1 | 2 | 3 | 4 | 5 | 6 | 7 |
| Vehicle | — | 90% | 70% | 50% | 40% | 20% | 0% | 0% |
| Posaconazole (cyclodextrin) | 20 | 100% | 100% | 100% | 100% | 100% | 100% | 90% |
| ST0003 | 20 | 100% | 100% | 100% | 100% | 100% | 100% | 90% |
| ST0012 | 20 | 100% | 100% | 100% | 100% | 100% | 100% | 90% |
| ST0002 | 20 | 100% | 100% | 100% | 100% | 100% | 90% | 90% |
| ST0023 | 20 | 100% | 100% | 100% | 100% | 100% | 90% | 90% |
| ST0025 | 20 | 100% | 100% | 100% | 100% | 100% | 90% | 90% |
| ST0063 | 20 | 100% | 100% | 90% | 90% | 90% | 90% | 90% |
| ST0077 | 20 | 100% | 100% | 100% | 100% | 90% | 90% | 90% |
| ST0070 | 20 | 100% | 90% | 90% | 90% | 90% | 90% | 90% |
| ST0073 | 20 | 100% | 100% | 100% | 100% | 90% | 90% | 90% |
| ST0074 | 20 | 100% | 100% | 90% | 90% | 90% | 90% | 90% |

It can be seen from the experimental data that the survival rates of mice of the compounds of the present disclosure group were significantly higher than that of the vehicle group; the survival rates of mice on the 7th day of the listed compounds were the same as that of the posaconazole (cyclodextrin) group, thus good effects were obtained.

Example IX

Experiment of Intragastric Administration of Compounds of the Present Disclosure Against Systemic Fungal Infection in Mice 1. Experimental Material 1.1 Experimental Instruments Multiskan MK3 enzyme-labeled detector, watertight electric constant temperature incubator, ZQ-F160 full-temperature oscillation incubator, MJX intelligent mold incubator, SW-CT-IF ultra-clean bench, UV spectrophotometer.

1.2 Experimental Reagents dimethyl sulfoxide, Sabourand's dextrose agar solid medium (SDA).

1.3 Experimental Animals

ICR mice, weighing 18-22 g, male, provided by Hubei Experimental Animal Center.

1.4 Experimental Strains

The standard strain of *Candida albicans* was purchased from the American Type Culture Collection, strain number ATCC10231.

2. Experimental Method

Prior to the experiment, a small amount of *Candida albicans* was picked from an SDA medium kept at 4° C. with an inoculation loop and inoculated into 1 ml YPD culture medium, cultured at 30° C. with 200 rpm shaking and activated for 16 hours, so that the fungus was in the late stage of exponential growth. Counted with a hemocytometer and the fungal solution concentration was adjusted to $1\times10^3$ to $5\times10^3$ CFU/ml with RPMI1640 medium. Monoclonal *Candida albicans* on SDA plate was picked up, inoculated into 1 ml YPD (Yeast Extract Peptone Dextrose Medium, the same below) culture medium, cultured at 35° C., 200 rpm for 16 hours until late exponential growth phase. *Candida albicans* was inoculated into fresh medium for culturing for 6 hours at 1%, centrifuged at 1000×g for 5 minutes, washed with physiological saline three times until the supernatant was colorless, counted with a hemocytometer, and the cell concentration was adjusted to $5\times10^6$ cells/ml. A tail vein injection of 0.1 ml/10 g caused a systemic fungal infection in mice. The mice were randomly divided into groups of 10 in each group to give a posaconazole (CMC—Na) group, a test compound group, and a vehicle group, and the posaconazole was formulated into a suspension using CMC—Na, and the other test drugs were dissolved with physiological saline and sonicated until clear for administration. Two hours after the establishment of a mouse systemic fungal infection model, each administration group was administered by intragastric administration of 20 mg/kg (calculated as posaconazole), and the administration volume was 0.1 ml/10 g, and the model group was given 0.1 ml/10 g of 0.9% sodium chloride solution, once daily for 5 continuous days. The death of the mice was observed and the survival time was recorded. A total of 7 days of observations were performed. All dead mice were burned with ethanol.

3. Experimental Results

TABLE 10

Systemic fungal infection (intragastric administration): survival rate of mice in each group after administration (%)

| Group | Dose (mg/kg) | 1 | 2 | 3 | 4 | 5 | 6 | 7 |
|---|---|---|---|---|---|---|---|---|
| | | | | Time (days) | | | | |
| Vehicle | — | 90% | 70% | 50% | 40% | 20% | 0% | 0% |
| Posaconazole (CMC-Na) | 20 | 100% | 100% | 90% | 70% | 60% | 50% | 50% |
| ST0002 | 20 | 100% | 100% | 90% | 80% | 80% | 70% | 70% |
| ST0003 | 20 | 100% | 100% | 100% | 90% | 80% | 80% | 80% |
| ST0006 | 20 | 100% | 100% | 90% | 80% | 70% | 70% | 70% |
| ST0008 | 20 | 100% | 90% | 90% | 80% | 80% | 60% | 60% |
| ST0010 | 20 | 100% | 100% | 90% | 70% | 70% | 60% | 60% |
| ST0011 | 20 | 100% | 100% | 90% | 80% | 70% | 60% | 60% |
| ST0012 | 20 | 100% | 100% | 100% | 80% | 80% | 80% | 80% |
| ST0022 | 20 | 100% | 100% | 100% | 90% | 80% | 80% | 70% |
| ST0023 | 20 | 100% | 100% | 90% | 90% | 90% | 80% | 80% |
| ST0024 | 20 | 100% | 90% | 90% | 80% | 80% | 70% | 70% |
| ST0025 | 20 | 100% | 100% | 90% | 90% | 80% | 80% | 80% |
| ST0026 | 20 | 100% | 100% | 90% | 80% | 70% | 70% | 70% |
| ST0043 | 20 | 90% | 90% | 80% | 60% | 60% | 60% | 60% |
| ST0053 | 20 | 90% | 80% | 70% | 60% | 60% | 60% | 60% |
| ST0093 | 20 | 70% | 70% | 60% | 60% | 60% | 60% | 60% |
| ST0063 | 20 | 90% | 90% | 80% | 80% | 80% | 80% | 80% |
| ST0066 | 20 | 80% | 80% | 70% | 70% | 70% | 60% | 60% |
| ST0077 | 20 | 100% | 90% | 80% | 80% | 80% | 70% | 70% |
| ST0078 | 20 | 90% | 90% | 80% | 70% | 70% | 70% | 70% |
| ST0079 | 20 | 90% | 90% | 90% | 80% | 80% | 70% | 70% |
| ST0080 | 20 | 90% | 90% | 90% | 90% | 70% | 70% | 60% |
| ST0070 | 20 | 100% | 90% | 90% | 90% | 80% | 70% | 70% |
| ST0082 | 20 | 90% | 70% | 70% | 70% | 70% | 70% | 60% |
| ST0083 | 20 | 90% | 90% | 80% | 70% | 70% | 70% | 70% |
| ST0073 | 20 | 100% | 90% | 80% | 80% | 80% | 70% | 70% |
| ST0074 | 20 | 100% | 100% | 90% | 80% | 80% | 80% | 70% |

It can be seen from the experimental data that the survival rates of mice of the compounds of the present disclosure group were significantly higher than that of the vehicle group; the survival rates of mice on the 7th day of the listed compounds were better than that of the posaconazole group (CMC—Na), indicating higher bioavailabilities.

Example X

Experiment of Intravenous Administration of the Compound of the Present Disclosure Against Lung *Aspergillus Fumigatus* Infection in Immunosuppressed Mice

1. Experimental Material

1.1 Experimental Instruments

Multiskan MK3 enzyme-labeled detector, watertight electric constant temperature incubator, ZQ-F160 full-temperature oscillation incubator, MJX intelligent mold incubator, SW-CT-IF ultra-clean bench, UV spectrophotometer.

1.2 Experimental Reagents

Cyclophosphamide, dexamethasone, sodium pentobarbital, Sabourand's dextrose agar solid medium.

1.3 Experimental Animals

ICR mice, weighing 20-25 g, male, provided by Beijing Vital River Laboratory Animal Technology Co., Ltd.

1.4 Experimental Strains

*Aspergillus fumigatus* AF293, from the Guangdong Provincial Microbial Culture Collection Center.

2. Experimental Method

ICR male mice were injected intraperitoneally with cyclophosphamide 150 mg/kg and injected subcutaneously with dexamethasone 150 mg/kg for 10 consecutive days. At the same time, the blood was taken to measure the changes of peripheral white blood cells and neutrophils, and mice with neutrophils consistently lower than 100/µl were selected as successfully immunosuppressed mice. Immediately after the last injection, the mice were anesthetized with ethyl ether, and mice were transferred from the initial state of excitement to inhibition. After their bodies were relaxed, the mice were immediately taken. Left hand was used to grasp the mouse to make it stand upright, the middle finger pressed the mouth so that it could breath only with the nose, and the ring finger gently pressed the abdomen to move the diaphragm muscle upward. 30 µl of conidia suspension (*Aspergillus fumigatus* AF293, $3\times10^6$ conidia) was sent to the nostrils of the anesthetized mice by a micropipette to allow spontaneous inhalation. After the mouse returned to normal breathing, it was returned to the cage. One day after the inoculation, the mice were randomly divided into groups of 10 mice, to respectively give a test compound group and a vehicle group. Since posaconazole was insoluble in the vehicle (physiological saline), only the vehicle group was used as a control group. Each administration group was administered by tail vein injection of 20 mg/kg (calculated as posaconazole), and the administration volume was 0.1 ml/10 g, and the model group was given 0.1 ml/10 g of 0.9% sodium chloride solution, once daily for 5 continuous days. The death of the mice was observed and the survival time was recorded. Seven days later, the mice were sacrificed and their lung tissues were taken to observe the fungal loads of *Aspergillus fumigatus* in the lungs of the mice.

3. Experimental Results

TABLE 11

Lung *Aspergillus fumigatus* infection (intravenous administration): survival rate of mice in each group after administration (%)

| Group | Dose (mg/kg) | Time (days) | | | | | | |
|---|---|---|---|---|---|---|---|---|
| | | 1 | 2 | 3 | 4 | 5 | 6 | 7 |
| Vehicle | — | 90% | 80% | 80% | 70% | 50% | 50% | 40% |
| ST0001 | 20 | 100% | 100% | 90% | 90% | 80% | 70% | 70% |
| ST0002 | 20 | 100% | 100% | 100% | 100% | 90% | 90% | 80% |
| ST0003 | 20 | 100% | 100% | 100% | 100% | 100% | 90% | 90% |
| ST0004 | 20 | 100% | 90% | 80% | 80% | 70% | 60% | 50% |
| ST0005 | 20 | 100% | 90% | 80% | 80% | 70% | 60% | 50% |
| ST0006 | 20 | 100% | 100% | 100% | 100% | 90% | 90% | 80% |
| ST0007 | 20 | 100% | 100% | 100% | 100% | 90% | 90% | 80% |
| ST0008 | 20 | 100% | 100% | 100% | 90% | 80% | 80% | 70% |
| ST0009 | 20 | 100% | 100% | 100% | 90% | 80% | 80% | 70% |
| ST0010 | 20 | 100% | 100% | 90% | 80% | 80% | 70% | 60% |
| ST0011 | 20 | 100% | 100% | 100% | 100% | 90% | 90% | 90% |
| ST0012 | 20 | 100% | 100% | 100% | 100% | 100% | 90% | 90% |

TABLE 12

Lung *Aspergillus fumigatus* infection (intravenous administration): lung fungal load in each group of mice

| Group | Dose (mg/kg) | $10^4$ CFU/ml |
|---|---|---|
| Vehicle | — | 6.58 ± 1.23 |
| ST0001 | 20 | 2.28 ± 0.77 |
| ST0002 | 20 | 1.89 ± 0.22 |
| ST0003 | 20 | 1.39 ± 0.32 |
| ST0004 | 20 | 3.51 ± 1.38 |
| ST0005 | 20 | 3.40 ± 1.26 |
| ST0006 | 20 | 1.73 ± 0.34 |
| ST0007 | 20 | 1.68 ± 0.31 |
| ST0008 | 20 | 2.07 ± 0.42 |
| ST0009 | 20 | 2.03 ± 0.46 |
| ST0010 | 20 | 2.75 ± 0.37 |
| ST0011 | 20 | 1.46 ± 0.27 |
| ST0012 | 20 | 1.42 ± 0.30 |

Note:
the data was expressed as the mean ± standard deviation of CFU values in mouse lung tissue.

From the experimental results, it can be seen that after 7 days of intravenous administration, the survival rates of mice of the compounds of the present disclosure groups were significantly higher than that of the vehicle group, and the lung fungal loads of the mice were significantly lower than that of the vehicle group, and a good therapeutic effects were obtained. Especially, in the tests of the compounds ST0002, ST0003, ST0006, ST0007, ST0011 and ST0012, not only the survival rates of the mice were high, but also the therapeutic effects were obvious and the safety were high.

Example XI

Experiment of Intragastric Administration of the Compound of the Present Disclosure Against Lung *Aspergillus Fumigatus* Infection in Immunosuppressed Mice 1. Experimental Material 1.1 Experimental Instruments Multiskan MK3 enzyme-labeled detector, watertight electric constant temperature incubator, ZQ-F160 full-temperature oscillation incubator, MJX intelligent mold incubator, SW-CT-IF ultra-clean bench, UV spectrophotometer.

1.2 Experimental Reagents

Cyclophosphamide, dexamethasone, sodium pentobarbital, Sabourand's dextrose agar solid medium.

1.3 Experimental Animals

ICR mice, weighing 20-25 g, male, provided by Beijing Vital River Laboratory Animal Technology Co., Ltd.

1.4 Experimental Strains

*Aspergillus fumigatus* AF293, from the Guangdong Provincial Microbial Culture Collection Center.

2. Experimental Method

ICR male mice were injected intraperitoneally with cyclophosphamide 150 mg/kg and injected subcutaneously with dexamethasone 150 mg/kg for 10 consecutive days. At the same time, the blood was taken to measure the changes of peripheral white blood cells and neutrophils, and mice with neutrophils consistently lower than 100/µl were selected as successfully immunosuppressed mice. Immediately after the last injection, the mice were anesthetized with ethyl ether, and mice were transferred from the initial state of excitement to inhibition. After their bodies were relaxed, the mice were immediately taken. Left hand was used to grasp the mouse to make it stand upright, the middle finger pressed the mouth so that it could breath only with the nose, and the ring finger gently pressed the abdomen to move the diaphragm muscle upward. 30 µl of conidia suspension (*Aspergillus fumigatus* AF293, $3\times10^6$ conidia) was sent to the nostrils of the anesthetized mice by a micropipette to allow spontaneous inhalation. After the mouse returned to normal breathing, it was returned to the cage. One day after the inoculation, mice were randomly divided into groups of 10 mice, to respectively give a posaconazole (CMC—Na) group, a test compound group, and a vehicle group, and posaconazole was formulated into a suspension using CMC—Na, and the other test drugs were dissolved with physiological saline and sonicated until clear for administration. Each administration group was administered by intragastric administration of 20 mg/kg (calculated as posaconazole), and the administration volume was 0.1 ml/10 g, and the model group was given 0.1 ml/10 g of 0.9% sodium chloride solution, once daily for 5 continuous days. Seven days later, the mice were sacrificed and their lung tissues were taken to observe the fungal loads of *Aspergillus fumigatus* in the lungs of the mice.

3. Experimental Results

TABLE 13

Lung *Aspergillus fumigatus* infection (intragastric administration): lung fungal load in each group

| Group | Dose (mg/kg) | $10^4$ CFU/ml |
|---|---|---|
| Vehicle | — | 6.18 ± 1.41 |
| Posaconazole (CMC-Na) | 20 | 4.48 ± 1.37 |
| ST0002 | 20 | 3.05 ± 0.51 |
| ST0003 | 20 | 2.83 ± 0.48 |
| ST0006 | 20 | 2.97 ± 0.47 |
| ST0007 | 20 | 4.12 ± 0.87 |
| ST0008 | 20 | 3.49 ± 0.64 |
| ST0009 | 20 | 3.91 ± 0.85 |
| ST0010 | 20 | 3.40 ± 0.63 |
| ST0011 | 20 | 3.47 ± 0.71 |
| ST0012 | 20 | 2.95 ± 0.46 |

Note:
the data was expressed as the mean ± standard deviation of CFU values in mouse lung tissue.

From the experimental results, it can be seen that after 7 days of administration, the mice fungal loads of the compounds of the present disclosure (dissolved with physiological saline) groups were significantly lower than that of the vehicle group, and were not inferior to the posaconazole (CMC—Na) group. In particular, the fungal loads of ST0002, ST0003, ST0006 and ST0012 were significantly lower than that of the posaconazole (CMC—Na) group, and good results were obtained.

Example XII

Experiment of Intravenous Administration of the Compound of the Present Disclosure Against *Aspergillus fumigatus* Keratitis in Rats 1. Experimental Material 1.1 Experimental Instruments Ophthalmic surgery microscope, ophthalmic surgical instruments, blood cell count plate, slit lamp microscope with camera system, Mettler AE240 electronic balance, autoclave, electric thermostatic blast drying oven, water purifier, RMZ135 paraffin slicer, DK-524 thermostat water bath, TGL-16B tabletop centrifuge, E600 microscopic imaging system.

1.2 Experimental Reagents

Glucose, peptone, agar, gentamycin, chloramphenicol eye drops, sodium pentobarbital, paraformaldehyde, gram stain, HE stain, xylene, neutral gum, paraffin, APES.

1.3 Experimental Animals

SD rats, weighing 180-210 g, male, provided by Beijing Vital River Laboratory Animal Technology Co., Ltd.

1.4 Experimental Strains

*Aspergillus Fumigutus* (AF) strains: purchased from Institute of Microbiology, Chinese Academy of Medical Sciences 2. Experimental Method Before the experiment, the standard strain was inoculated on the slant containing a freshly prepared Sabourand's weak dextrose agar medium, cultured at 25° C. for 6-9 days and then taken out for later use. 1 ml of sterile saline was taken to repeatedly blow the incline, and aspirated. Spores were counted using a hemocytometer, and the concentration was expressed in Colony-Forming Units (CFU)/ml, and the fungal suspension having a spore concentration of $1\times10^8$ CFU/ml was prepared by adjustion, and oscillated to homogenous.

The test rats were randomly divided into groups of 10 rats, to respectively give a test compound group and a vehicle group. Since posaconazole was insoluble in the vehicle (physiological saline), only the vehicle group was used as a control group. Three days before the experiment, chloramphenicol eye drops were given to both eyes, 4 times/day, 3% sodium pentobarbital (1.5 ml/kg) was used for intraperitoneal anesthesia, and 1% tetracaine was dropped into the eyes. Routine disinfection and drape were performed. Under the microscope of eye surgery, 4 mm trephine was used to locate the central part of the cornea. an epithelial layer with a diameter of 4 mm on the center of the cornea was completely removed with a sterile scalpel. The colonies with a diameter of 3 to 4 mm in diameter were scraped with an inoculation loop and applied directly to surface of the cornea of which the epithelial layer had been removed, and then the cornea contact lens was placed on the cornea. The subconjunctival injection of 0.5 million units of gentamycin was performed and then canthorrhaphy (tarsorrhaphy) was performed. After 3 days, each administration group was administered by tail vein injection of 10 mg/kg (calculated as posaconazole), and the administration volume was 0.1 ml/10 g, and the vehicle group was given 0.1 ml/10 g of 0.9% sodium chloride solution, once daily for 5 continuous days. On the 7th day of administration, the palpebral fissure was opened, the corneal lesions were observed under an ophthalmic slit lamp, and the ulcer margin and the bottom tissue was scraped to smears and then subjected to Gram stain and 10% KOH smear, and the scrapes were inoculated on SDA medium at 25° C. and the numbers of fungi were determined.

3. Experimental Results

TABLE 14

*Aspergillus fumigatus* keratitis (intravenous administration): cornea fungal load in each group

| Group | Dose (mg/kg) | Amount of active fungi in cornea at day 7 ($10^3$ CFU/ml) |
|---|---|---|
| Vehicle | — | 28.89 ± 8.85 |
| ST0001 | 10 | 3.73 ± 0.63 |
| ST0002 | 10 | 2.37 ± 0.49 |
| ST0003 | 10 | 1.48 ± 0.38 |
| ST0004 | 10 | 5.58 ± 1.12 |
| ST0005 | 10 | 5.90 ± 1.06 |
| ST0006 | 10 | 1.92 ± 0.41 |
| ST0007 | 10 | 1.87 ± 0.35 |
| ST0008 | 10 | 2.59 ± 0.37 |
| ST0009 | 10 | 2.76 ± 0.45 |
| ST0010 | 10 | 3.93 ± 0.73 |
| ST0011 | 10 | 1.79 ± 0.44 |
| ST0012 | 10 | 1.45 ± 0.37 |

Note:
The data was expressed as the mean ± standard deviation of the CFU values of active fungi in the cornea of 10 rats.

From the experimental results, it can be seen that after 7 days of intravenous administration, the rat cornea fungal loads of the compounds of the present disclosure groups were significantly lower than that of the vehicle group, and the therapeutic effects were very significant.

The invention claimed is:

1. A compound represented by formula (I), a racemate, stereoisomer, tautomer, or a pharmaceutically acceptable salt thereof:

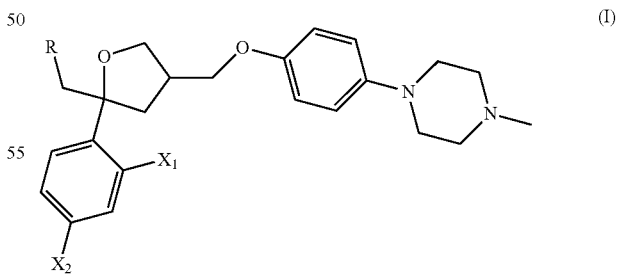

(I)

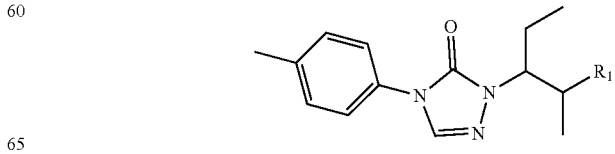

wherein, R is

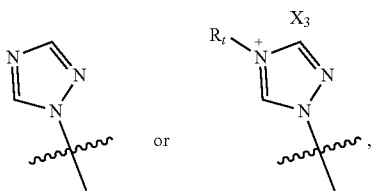

or, which are unsubstituted or substituted with one or more $R_a$ or $R_b$;

$R_t$ is

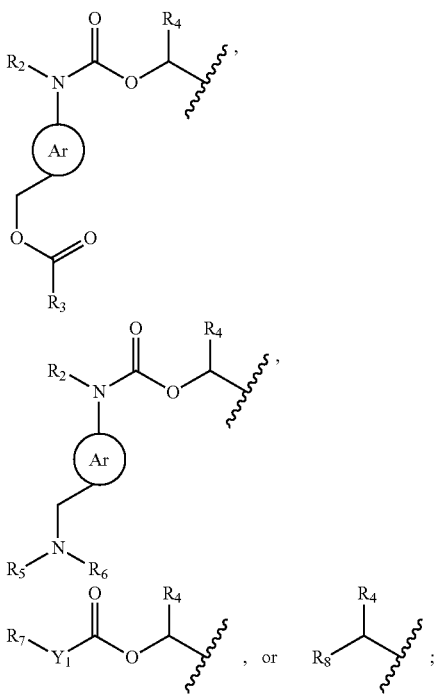

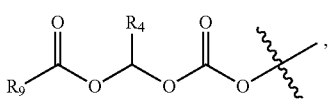

$O(O)C(NH_2)CH_2OH$, or $-OS(O)_2OM_3$;

$R_2$ and $R_4$ are independently H or $C_{1-40}$ alkyl that is unsubstituted or substituted with one or more $R_a$;

$R_3$ is a $C_{1-40}$ alkyl that is unsubstituted or substituted with one or more $R_b$;

$R_5$ and $R_6$ are independently H, or independent chosen from the following groups that are unsubstituted or optionally substituted with one or more $R_m$: $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, or $-C(O)R_f$;

Ar is chosen from the following groups that are unsubstituted or substituted with one or more $R_c$: $C_{6-20}$ aryl, 5-20 membered heteroaryl, wherein the heteroaryl has 1-5 heteroatoms independently chosen from N, O, or S;

$R_7$ is chosen from the following groups that are unsubstituted or substituted with one or more $R_c$: $C_{1-40}$ alkyl, $C_{3-20}$ cycloalkyl, 3-20 membered heterocyclyl, $C_{6-20}$ aryl, 5-20 membered heteroaryl, $-Y_2P(O)(OM_1)(OM_2)$, $-C(O)R_f$, or $-(CH_2CH_2O)_z-R_b$, wherein z is an integer of 1 to 10;

$R_8$ is H, or chosen from the following groups that are unsubstituted or substituted with one or more $R_b$: $C_{1-40}$ alkyl, $C_{3-20}$ cycloalkyl, 3-20 membered heterocyclyl, $C_{6-20}$ aryl, 5-20 membered heteroaryl, $NR_dR_e$, $-CONR_dR_e$, $-C(O)Y_2R_f$, $-Y_2(O)CR_f$, $-Y_2P(O)(OM_1)(OM_2)$, or $-Y_2S(O)_2OM_3$;

$R_9$ is chosen from the following groups that are unsubstituted or substituted with one or more $R_b$: $R_{10}-Y_3-Y_4-$, $R_{11}-C(O)-Y_5-Y_6-$, $C_{1-40}$ alkyl, $C_{1-40}$ alkoxy, $C_{3-20}$ cycloalkyl, 3-20 membered heterocyclyl, $C_{6-20}$ aryl, 5-20 membered heteroaryl, $-Y_2-N(R_4)-C(=NH)-NH_2$, $-Y_3-N(R_2)-C(O)-Y_2-N(R_4)-C(=NH)-NH_2$, or $-(CH_2CH_2O)_z-H$, wherein z is an integer of 1 to 10;

$R_{10}$ and $R_{11}$ are independently H, or are chosen from the following groups that are unsubstituted or substituted with one or more $R_b$: $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, $-Y_2P(O)(OM_1)(OM_2)$, or $-Y_2S(O)_2OM_3$;

$Y_1, Y_2, Y_3, Y_4, Y_5$ and $Y_6$ are independently chosen from a chemical bond, $-O-$, $-S-$ or the following groups that are unsubstituted or substituted with one or more $R_a$: $-NH-$, $C_{1-40}$ alkyl, $C_{1-40}$ alkoxy, $C_{3-20}$ cycloalkyl, 3-20 membered heterocyclyl, $C_{6-20}$ aryl, 5-20 membered heteroaryl, or $-(CH_2CH_2O)_m$, wherein m is an integer of 0 to 10;

provided that, when two or more of $Y_1, Y_2, Y_3, Y_4, Y_5$ and $Y_6$ are adjacent, the adjacent groups are not chemical bonds at the same time;

each $R_a$ is independently chosen from H, $C_{1-40}$ alkyl, $C_{1-40}$ alkoxy, $C_{2-40}$ alkenyl, $C_{2-40}$ alkynyl, $C_{3-20}$ cycloalkyl, F, Cl, Br, I, OH, SH, CN, =O, $NR_dR_e$, $-C(O)Y_2R_f$, $-Y_2(O)CR_f$, $-CONR_dR_e$, $-Y_2P(O)(OM_1)(OM_2)$, or $-Y_2S(O)_2OM_3$;

each $R_b$ is independently chosen from H, F, Cl, Br, I, OH, SH, CN, or the following groups that are unsubstituted or substituted with one or more $R_a$: $C_{1-40}$ alkyl, $C_{1-40}$ alkoxy, $C_{2-40}$ alkenyl, $C_{2-40}$ alkynyl, $C_{3-20}$ cycloalkyl, $C_{3-20}$ cycloalkyloxy, 3-20 membered heterocyclyl, 3-20 membered heterocyclyloxy, $C_{6-20}$ aryl, $C_{6-20}$ aryloxy, 5-20 membered heteroaryl, 5-20 membered heteroaryloxy, $NR_dR_e$, $-CONR_dR_e$, $-C(O)Y_2R_f$, $-Y_2(O)CR_f$, $-Y_2P(O)(OM_1)(OM_2)$, or $-Y_2S(O)_2OM_3$;

each $R_c$ is independently chosen from F, Cl, Br, I, OH, SH, CN, or the following groups that are unsubstituted or substituted with one or more $R_a$: $C_{1-40}$ alkyl, $C_{1-40}$ alkoxy, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, $NR_dR_e$, $-CONR_dR_e$, $-C(O)Y_2R_f$, $-Y_2(O)CR_f$, $-Y_2P(O)(OM_1)(OM_2)$, or $-Y_2S(O)_2OM_3$;

$X_1$ and $X_2$ are independently chosen from F, Cl, Br, or I;
$X_3$ is a pharmaceutically acceptable anion;
$R_1$ is $R_h$;
$R_h$ is each $R_d$ and $R_e$ are independently H, or chosen from the following groups that are unsubstituted or substituted with one or more $R_m$: $C_{1-40}$ alkyl, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, —$CONR_fR_g$, —$C(O)Y_2R_f$, —$Y_2(O)CR_f$, —$Y_2P(O)(OM_1)(OM_2)$, or —$Y_2S(O)_2OM_3$;

each $R_f$ and $R_g$ are independently H, or chosen from the following groups that are unsubstituted or substituted with one or more $R_m$: $C_{1-40}$ alkyl, $C_{2-40}$ alkenyl, $C_{2-40}$ alkynyl, $C_{3-20}$ cycloalkyl, COOH, 3-20 membered heterocyclyl, $C_{6-20}$ aryl, or 5-20 membered heteroaryl;

each $R_m$ is independently chosen from H, F, Cl, Br, I, OH, SH, CN, or the following groups that are unsubstituted or substituted with one or more $R_a$: $C_{1-40}$ alkyl, $C_{1-40}$ alkoxy, $C_{2-40}$ alkenyl, $C_{2-40}$ alkynyl, $C_{3-20}$ cycloalkyl, 3-20 membered heterocyclyl, $C_{6-20}$ aryl, 5-20 membered heteroaryl, $NR_dR_e$, —$CONR_dR_e$, —$C(O)Y_2R_f$, $Y_2(O)CR_f$, —$Y_2P(O)(OM_1)(OM_2)$, or —$Y_2S(O)_2OM_3$;

$M_1$, $M_2$, and $M_3$ are independently selected from H or $C_{1-40}$ alkyl that is unsubstituted or substituted with one or more $R_b$;

provided that when R is

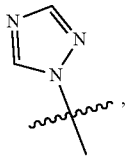

$R_1$ is not hydroxyl; and when $R_t$ is

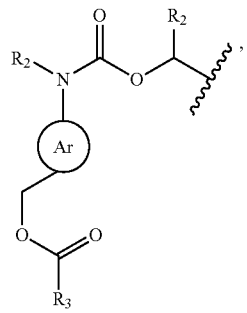

$R_3$ is not —$CH_2NHCH_3$;

wherein the heterocyclyl and heteroaryl are independent from each other and each has 1-5 heteroatoms independently chosen from N, O or S.

2. The compound, racemate, stereoisomer, tautomer, or pharmaceutically acceptable salt thereof according to claim 1, wherein:
$X_1$ and $X_2$ are independently chosen from F, $C_1$ or Br;
$X_3$ represents an acid ion generated by ionization of an inorganic acid or an organic acid;
$R_2$ is chosen from H, or $C_{1-40}$ alkyl that is unsubstituted or substituted with one or more $R_a$;
$R_3$ is selected from $C_{1-40}$ alkyl which is unsubstituted or optionally substituted with one or more $R_b$;
Ar is chosen from the following groups that are unsubstituted or substituted with one or more $R_c$: $C_{6-10}$ aryl, 5-10 membered heteroaryl.

3. The compound, racemate, stereoisomer, tautomer, or pharmaceutically acceptable salt thereof according to claim 1, wherein the pharmaceutically acceptable salt of the compounds of formula (I) is chosen from to:
alkali metal salts, alkaline earth metal salts, ammonium salts, salts of compounds of formula (I) with organic bases providing physiologically acceptable cations, or acid addition salts of compounds of formula (I) with an inorganic acid or an organic acid.

4. The compound, racemate, stereoisomer, tautomer, or pharmaceutically acceptable salt thereof according to claim 1, wherein the compound of formula (I) is a compound of formula (I'):

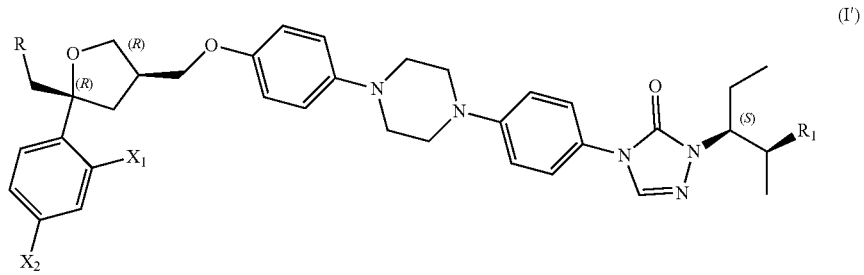

(I')

5. A method for preparing the compound, racemate, stereoisomer, tautomer, or pharmaceutically acceptable salt thereof according to claim 1, comprising reacting a compound of the formula (II)

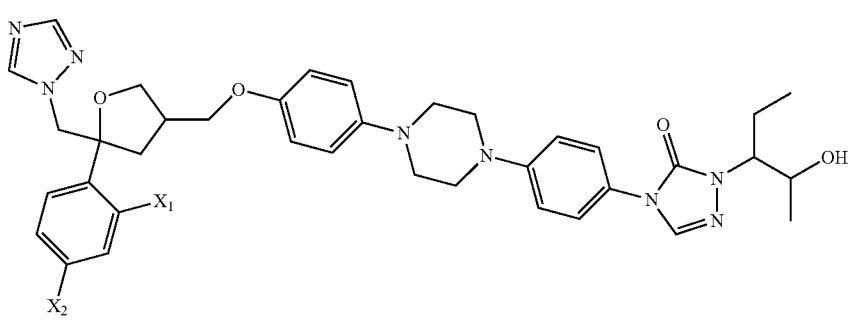

(II)

with a compound of $R_z$-L, wherein $R_z$ is $R_h$ or $R_t$, wherein L is a leaving group representing a charged or uncharged atom or group that is detached during the reaction.

6. The method according to claim 5, wherein the reacting step comprises one or more of the following reactions:

1)

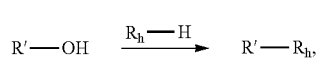

2)

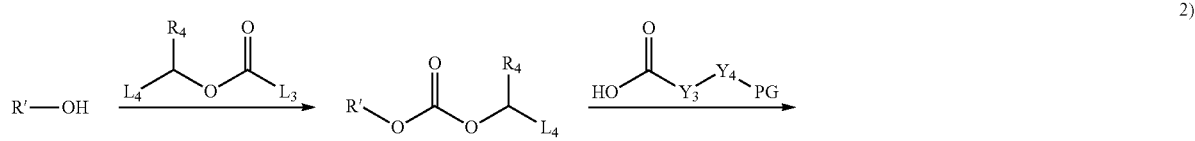

3)

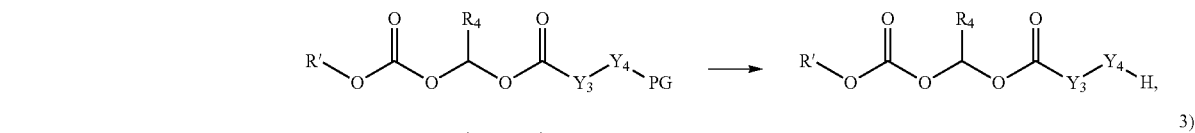

4)

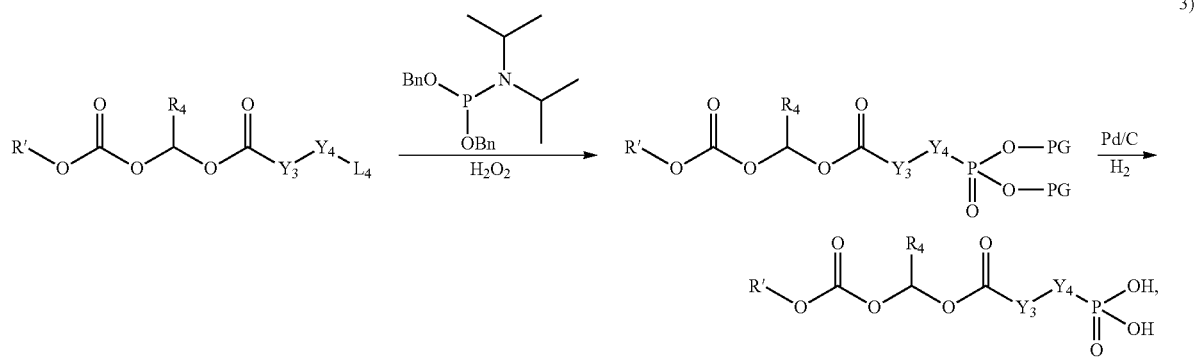

and

-continued

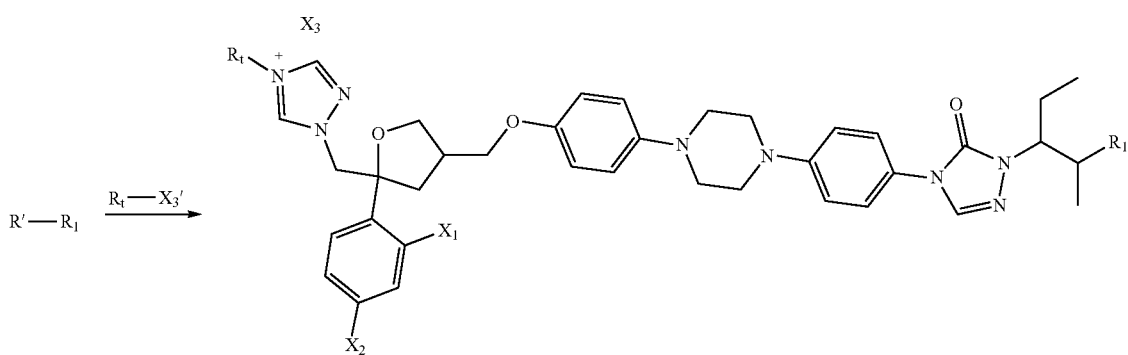

wherein, R' represents

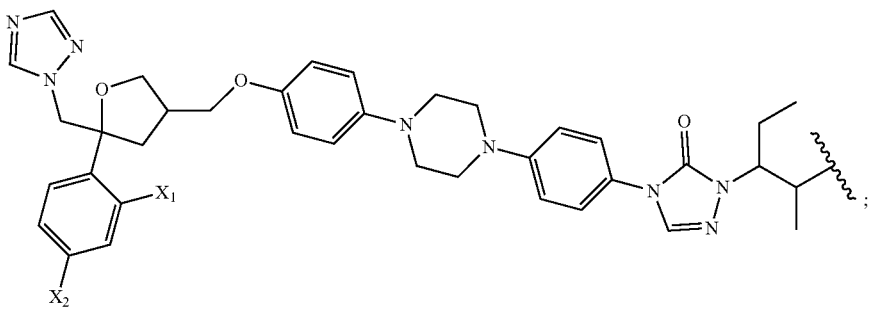

PG is a protecting group;

$X_3'$ is an organic substituent that is converted to $X_3$ in the reaction;

$L_3$ and $L_4$ are independently chosen from F, Cl, Br, or I.

7. A pharmaceutical composition, comprising a therapeutically effective amount of the compound, racemate, stereoisomer, tautomer, or pharmaceutically acceptable salt thereof according to claim 1.

8. A method of preventing or treating a disease caused by a fungus in a subject in need thereof, comprising administering to the subject an effective amount of the compound, racemate, stereoisomer, tautomer, or pharmaceutically acceptable salt thereof according to claim 1.

9. The compound, racemate, stereoisomer, tautomer or pharmaceutically acceptable salt thereof according to claim 1, wherein:

$X_1$ and $X_2$ are independently chosen from F, Cl or Br;

$X_3$ represents a monovalent acid ion generated by ionization of an inorganic or organic acid;

alternatively, when a plurality of cations are present in the structure of the compound of formula (I), $X_3$ represents a plurality of monovalent acid ions generated by ionization of an inorganic acid or an organic acid;

alternatively, when a plurality of cations in the structure of the compound of formula (I) share one polyvalent acid ion, $X_3$ represents a part of the polyvalent acid ion;

alternatively, $X_3$ represents a mixture of the monovalent acid ions as mentioned above, a mixture of the polyvalent acid ions as mentioned above, or a mixture of the monovalent acid ions and the polyvalent acid ions as mentioned above;

$R_2$ is H, or chosen from the following groups unsubstituted or substituted with one or more $R_a$: methyl, ethyl, propyl, isopropyl, or tert-butyl;

$R_3$ is chosen from $C_{1-40}$ alkyl substituted with one, two, or three substituents independently chosen from $C_{1-6}$ alkyl, —NH$_2$, —COOH, —OH, —CONH$_2$, N(CH$_3$)$_2$, NH(CH$_3$), NHCONH$_2$, (C$_6$H$_4$)—OH, or NH(CH$_2$)$_k$CH$_3$; and Ar is chosen from pyridyl or phenyl.

10. The compound, racemate, stereoisomer, tautomer or pharmaceutically acceptable salt thereof according to claim 9, wherein:

$X_3$ represents Cl$^-$, Br$^-$, I$^-$, HSO$_4^-$, NO$_3^-$, ½SO$_4^{2-}$, SO$_4^{2-}$, 3/2SO$_4^{2-}$, H$_2$PO$_4^-$, ½HPO$_4^{2-}$, 3/2HPO$_4^{2-}$, ⅓PO$_4^{3-}$, ⅔PO$_4^{3-}$, or PO$_4^{3-}$;

$R_3$ is chosen from —(CH$_2$)$_k$—NH$_2$, —CH(NH$_2$)—(CH$_2$)$_k$—COOH,

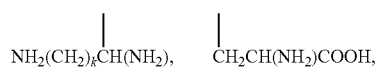

—(CH$_2$)$_k$—COOH, —CH(NH$_2$)—(CH$_2$)$_k$—NH—CONH$_2$, CH(NH$_2$)—(CH$_2$)$_k$—CONH$_2$, —CH(NH$_2$)—(CH$_2$)$_k$—OH, —CH(NH$_2$)—(CH$_2$)$_k$—CH(OH)—CH$_3$, —CH(NH$_2$)—(CH$_2$)$_k$—(C$_6$H$_4$)—OH, —CH(NH$_2$)—(CH$_2$)$_k$—NH—(CH$_2$)$_k$—CH$_3$, —(CH$_2$)$_k$—NH—(CH$_2$)$_k$—CH$_3$, or —(CH$_2$)$_k$—N(CH$_3$)$_2$, wherein k is independently chosen from 0, 1, 2, 3, 4, 5, 6, 7, 8, 9, or 10;

Ar is

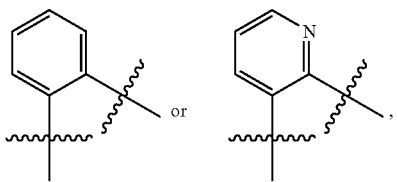 [SMILES: *c1ccccc1* ; *c1cccnc1*]

wherein the C atom at 2-position of the pyridyl is connected to N atom, and the C atom at 3-position is connected to methylene group.

11. The compound, racemate, stereoisomer, tautomer, or pharmaceutically acceptable salt thereof according to claim 10, wherein:
R is

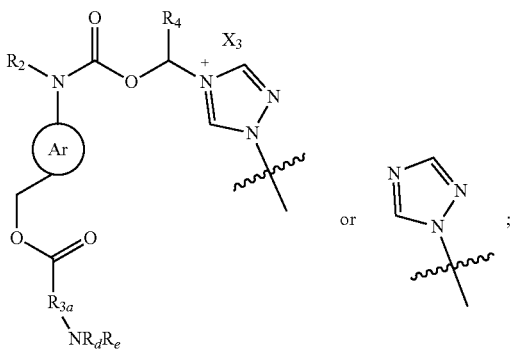

$R_{3a}$ is a $C_{1-40}$ alkyl that is unsubstituted or substituted with one or more substituents chosen from OH or $NR_dR_e$;
$R_h$ is chosen from

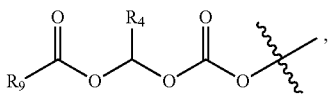

—O(O)C(NH2)CH2OH, or , —OS(O)$_2$OM$_3$,
$R_9$ is chosen from the following groups that are unsubstituted or substituted with one or more $R_b$: $R_{10}$—Y$_4$—, $R_{11}$—C(O)—Y$_5$—Y$_6$—, $C_{1-40}$ alkyl, $C_{1-40}$ alkoxy, —Y$_2$—N(R$_4$)—C(=NH)—NH$_2$, —Y$_3$—N(R$_2$)—C(O)—Y$_2$—N(R$_4$)—C(=NH)—NH$_2$, or —(CH$_2$CH$_2$O)$_z$—H, wherein z is 1, 2, 3, 4, 5, 6, 7, 8, 9, or 10;
$R_f$ is chosen from the following groups that are unsubstituted or substituted with one or more $R_m$: $C_{1-40}$ alkyl, COOH, 3-20 membered heterocyclyl, $C_{6-20}$ aryl, and 5-20 membered heteroaryl;
each $R_m$ is independently chosen from H, F, Cl, Br, I, OH, SH, CN, or the following groups that are unsubstituted or substituted with one or more $R_a$: $C_{1-40}$ alkyl, $C_{1-40}$ alkoxy, $C_{3-20}$ cycloalkyl, 3-20 membered heterocyclyl, $C_{6-20}$ aryl, 5-20 membered heteroaryl, NR$_d$R$_e$, —CONR$_d$R$_e$, C(O)Y$_2$R$_f$, Y$_2$(O)CR$_f$ —Y$_2$P(O)(OM$_1$)(OM$_2$), or —Y$_2$S(O)$_2$OM$_3$; and
$M_1$, $M_2$, and $M_3$ are independently chosen from H, methyl, ethyl, or isopropyl.

12. The compound, racemate, stereoisomer, tautomer, or pharmaceutically acceptable salt thereof according to claim 11, wherein:
$R_h$ is

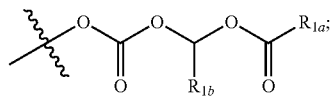

$R_{1a}$ is chosen from $C_{1-40}$ alkyl, $C_{6-20}$ aryl, $C_{6-20}$ arylalkyl, 5-20 membered heteroarylalkyl, 5-20 membered heteroaryl, which are unsubstituted or substituted with one or more C(O)OR$_f$, —OP(O)(OM$_1$)(OM$_2$), or —OS(O)$_2$OM$_3$; and
$R_{1b}$ is H or $C_{1-40}$ alkyl.

13. The compound, racemate, stereoisomer, tautomer, or pharmaceutically acceptable salt thereof according to claim 12, wherein:
R is

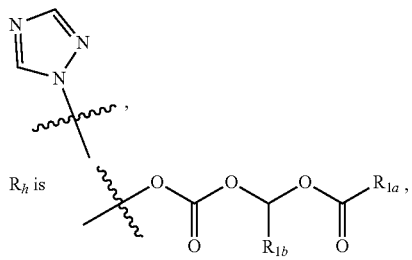

$R_{1a}$ is chosen from —(CH$_2$)$_k$—C(O)OR$_f$, —(CH$_2$)$_k$—(C$_6$H$_4$)—C(O)OR$_f$, —(CH$_2$)$_z$—OP(O)(OM$_1$)(OM$_2$), —(CH$_2$)$_k$—(C$_6$H$_4$)—OP(O)(OM$_1$)(OM$_2$), —(CH$_2$)$_k$—(C$_6$H$_4$)—OS(O)$_2$OM$_3$, or —(CH$_2$)$_z$—OS(O)$_2$OM$_3$,
wherein k is an integer of 0 to10; and
$R_{1b}$ is H, methyl, ethyl, or isopropyl.

14. The compound, racemate, stereoisomer, tautomer or pharmaceutically acceptable salt thereof according to claim 3, wherein the pharmaceutically acceptable salt of the compounds of formula (I) is selected from the group consisting of:
salts of compounds of formula (I) formed with sodium ion, potassium ion, calcium ion, magnesium ion, N-methylglucosamine, dimethylglucosamine, ethylglucosamine, lysine, dicyclohexylamine, 1,6-hexamethylenediamine, ethanolamine, glycosamine, meglumine, sarcosine, serinol, trishydroxymethyl aminomethane, aminopropylene glycol, 1-amino-2,3,4-butanetriol;
wherein the inorganic acid is selected from the group consisting of hydrochloric acid, hydrofluoric acid, hydrobromic acid, hydroiodic acid, sulfuric acid, pyrosulfuric acid, phosphoric acid, and nitric acid, and
wherein the organic acid is selected from the group consisting of formic acid, acetic acid, acetoacetic acid, pyruvic acid, trifluoroacetic acid, propionic acid, butyric acid, caproic acid, heptanoic acid, undecanoic acid, lauric acid, benzoic acid, salicylic acid, 2-(4-hydroxyl) benzoyl) benzoic acid, camphoric acid, cinnamic acid, cyclopentane propionic acid, digluconic acid, 3-hydroxy-2-naphthoic acid, nicotinic acid, embonic acid, pectinic acid, persulfuric acid, 3-phenyl propionic acid, picric acid, pivalic acid, 2-hydroxyethanesulfonic acid, itaconic acid, sulfamic acid, trifluoromethanesulfonic acid, dodecyl sulfate, ethanesulfonic acid, benzenesulfonic acid, p-toluenesulfonic acid, methanesulfonic acid, 2-naphthalenesulfonic acid, naphthalene disulfonic acid, camphorsulfonic acid, citric acid, tartaric acid, stearic acid, lactic acid, oxalic acid, malonic acid, succinic acid, malic acid, adipic acid, alginic acid, maleic acid, fumaric acid, D-gluconic acid, mandelic acid, ascorbic acid, gluconic acid, glycerophosphoric acid, aspartic acid, sulfosalicylic acid, hemisulfuric acid, and thiocyanic acid.

15. The compound, racemate, stereoisomer, tautomer or pharmaceutically acceptable salt thereof according to claim 3, wherein, when 1, 2 or 3 of $M_1$, $M_2$, and $M_3$ is/are H, the pharmaceutically acceptable salt of the compounds of formula (I) is selected a salt formed independently between —OP(O)(OM$_1$)(OM$_2$), —P(O)(OM$_1$)(OM$_2$), —OS(O)$_2$OM$_3$, or —S(O)$_2$OM$_3$ with an ion that is sodium ion, potassium ion, or ammonium ion.

16. The compound, racemate, stereoisomer, tautomer, or pharmaceutically acceptable salt thereof according to claim 1, wherein the compound of formula (I) is one of the following compounds and pharmaceutically acceptable salts thereof:

| No. | Structure |
|---|---|
| 0002 | 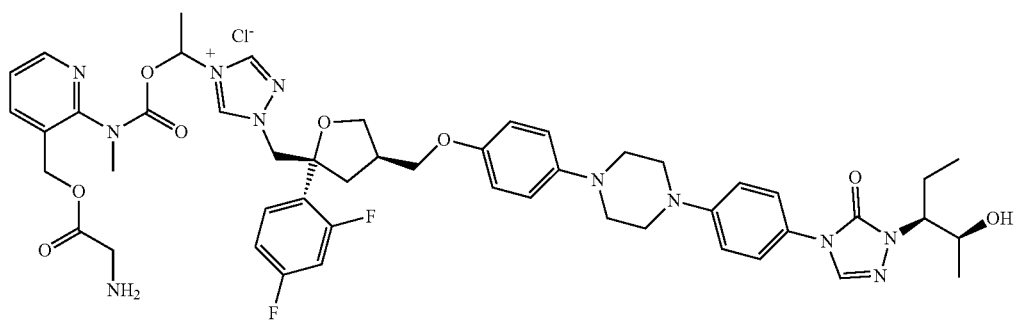 |
| 0003 | 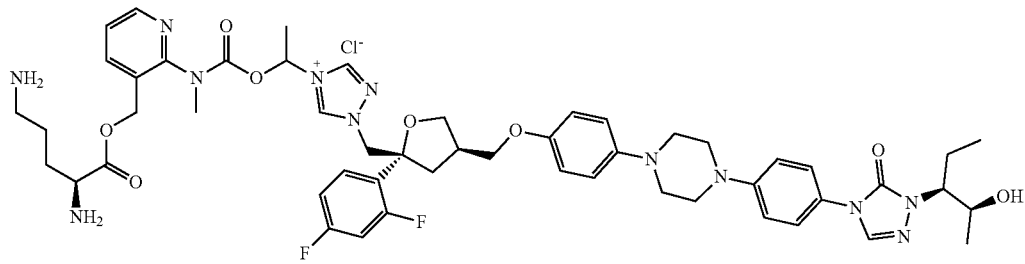 |
| 0004 | 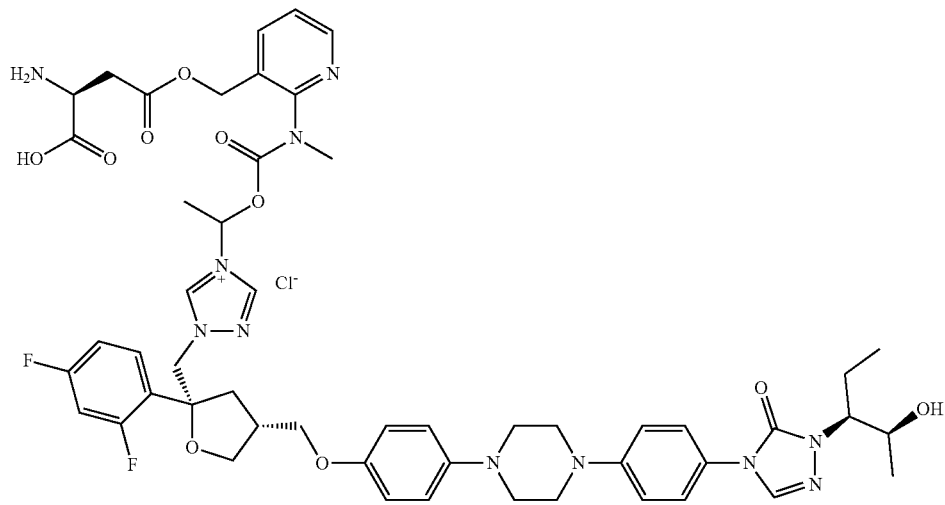 |

-continued
| No. | Structure |
|---|---|
| 0005 | 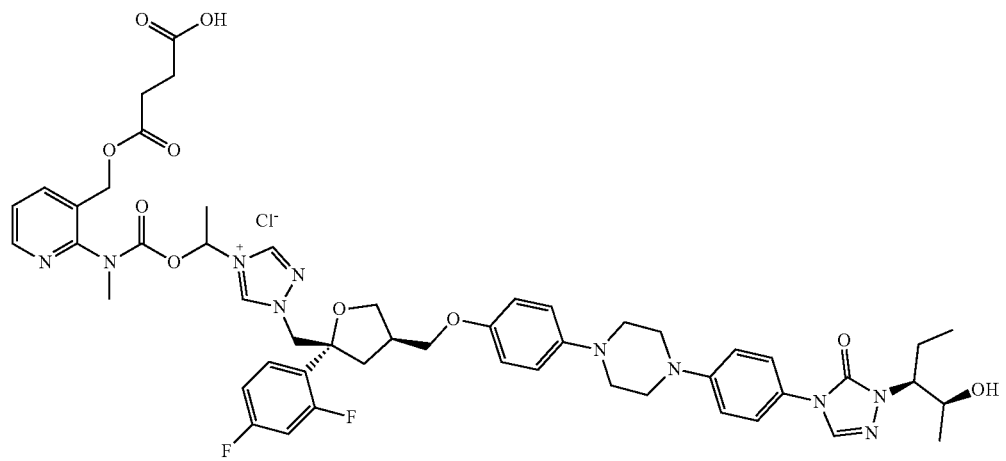 |
| 0006 | 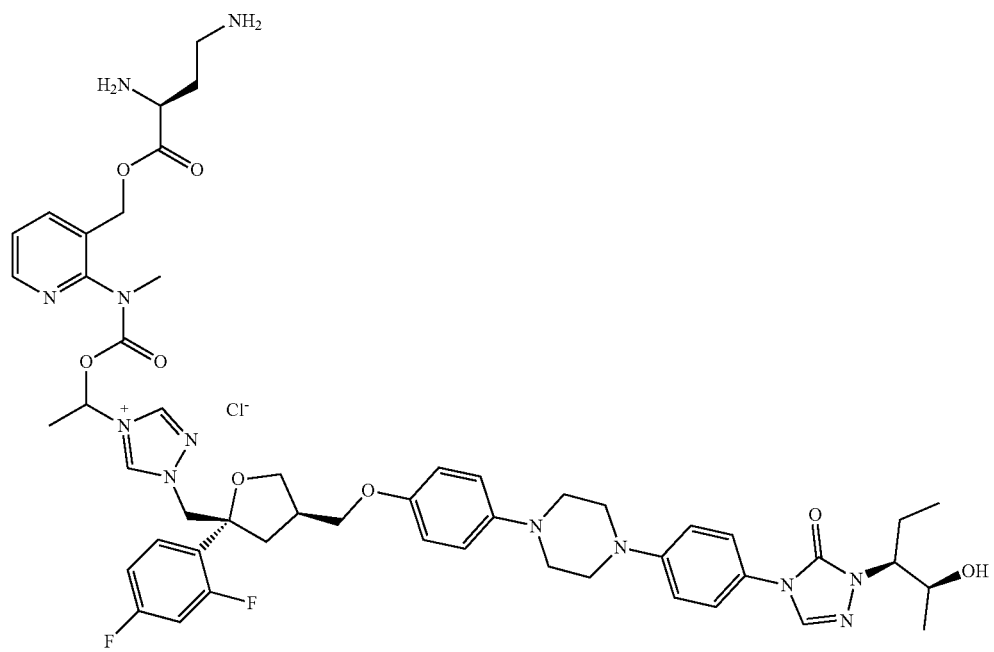 |
| 0007 | 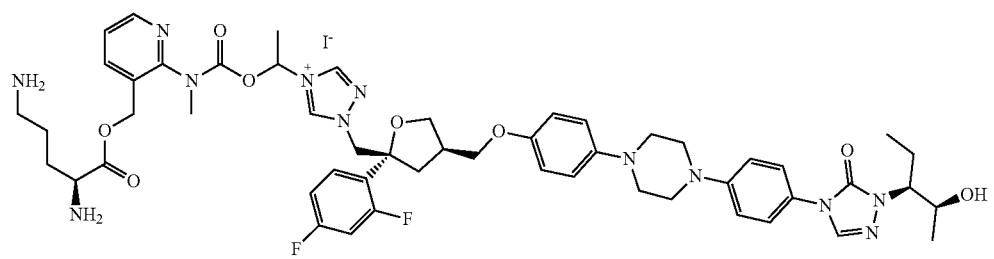 |

-continued

| No. | Structure |
| --- | --- |
| 0008 | 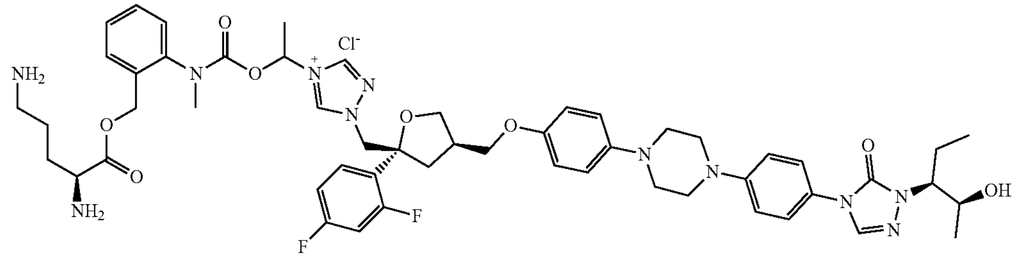 |
| 0010 | 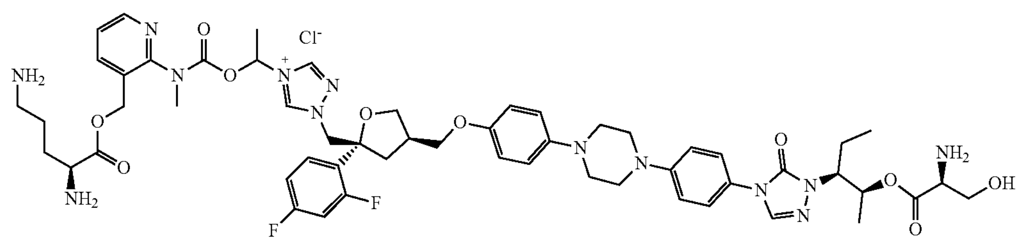 |
| 0011 | 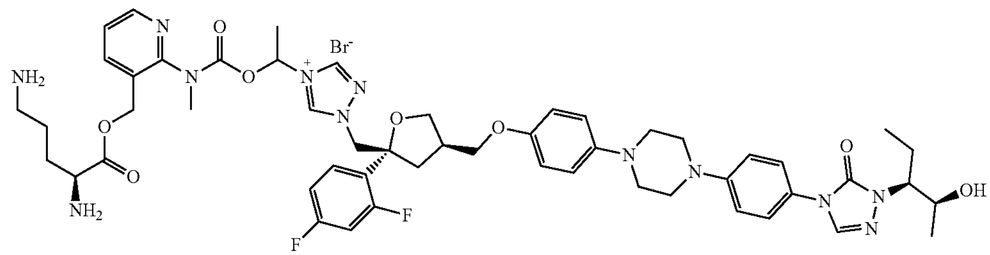 |
| 0012 | 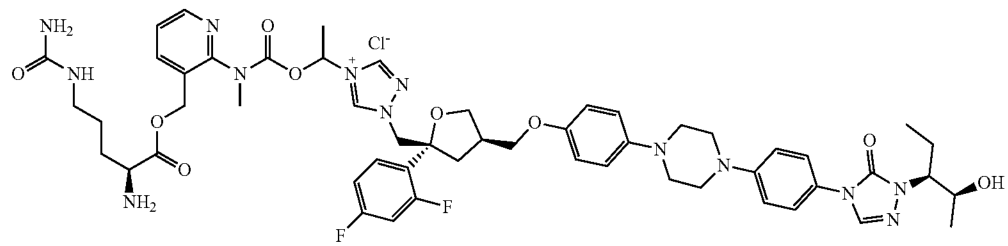 |
| 0013 | 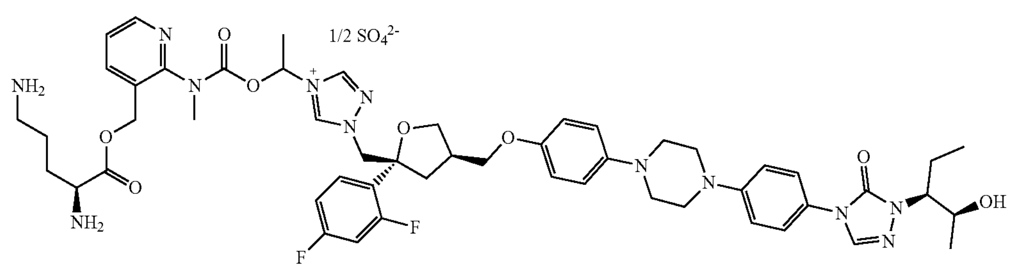 |
| 0014 | 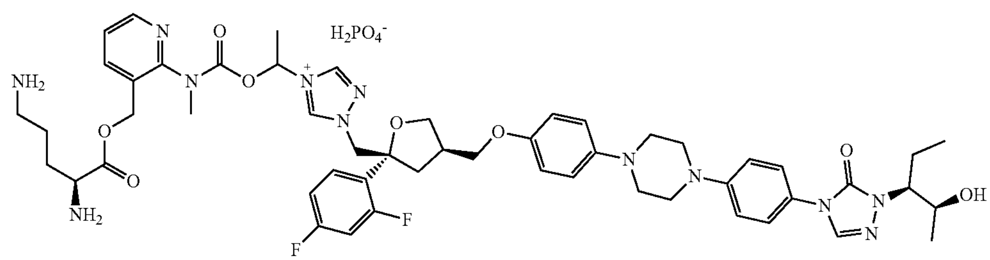 |

| No. | Structure |
|---|---|
| 0015 | 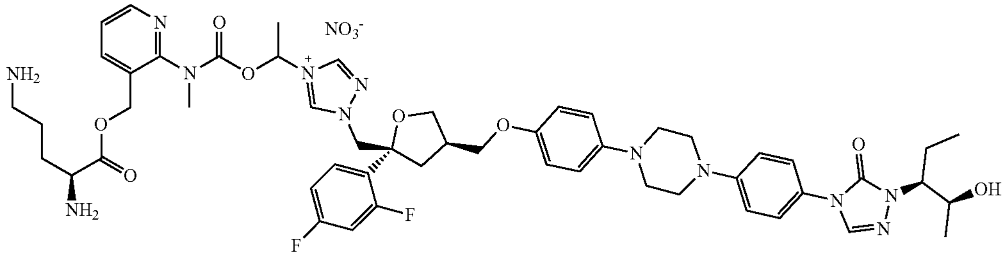 |
| 0016 | 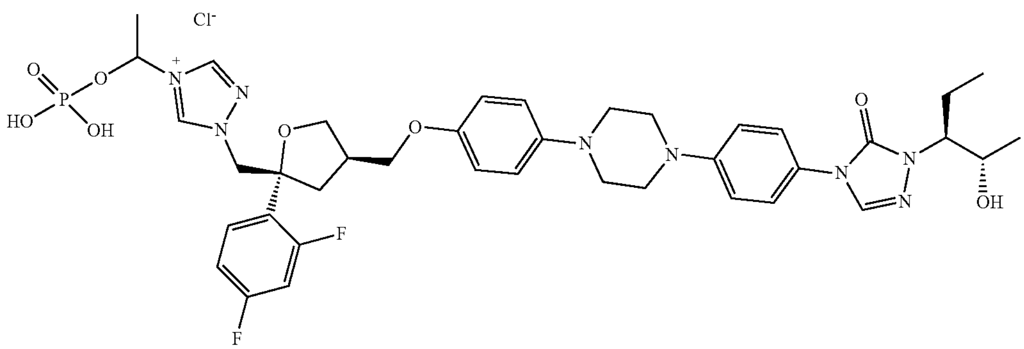 |
| 0017 | 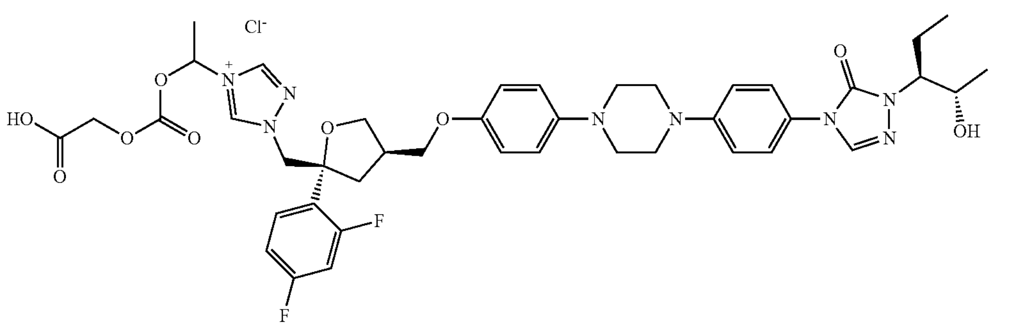 |
| 0018 | 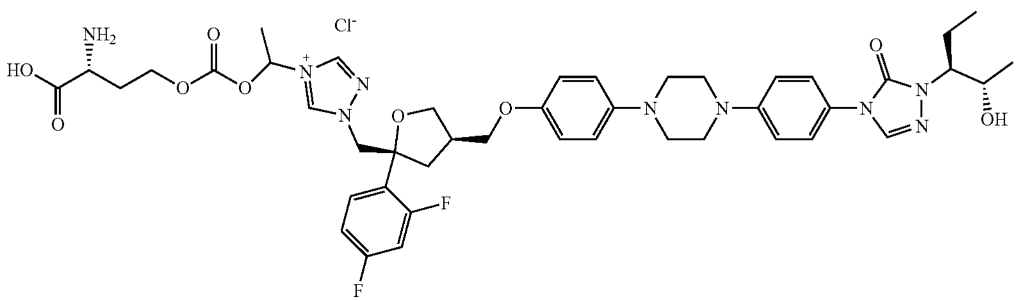 |
| 0019 | 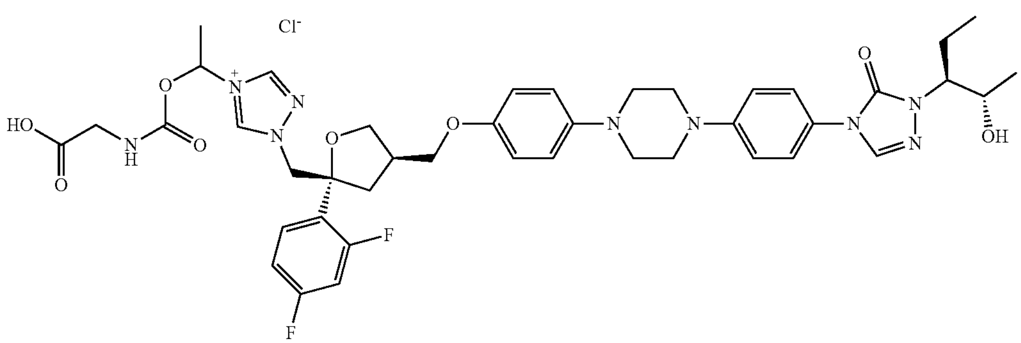 |

-continued
| No. | Structure |
|---|---|
| 0020 | 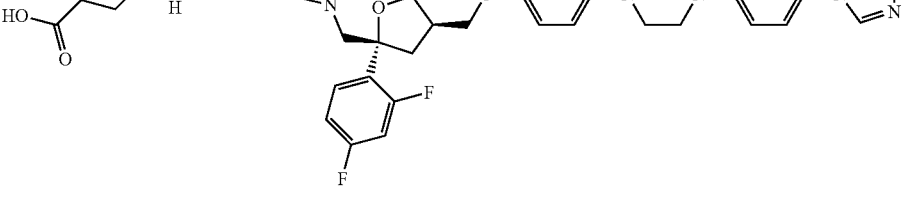 |
| 0021 | 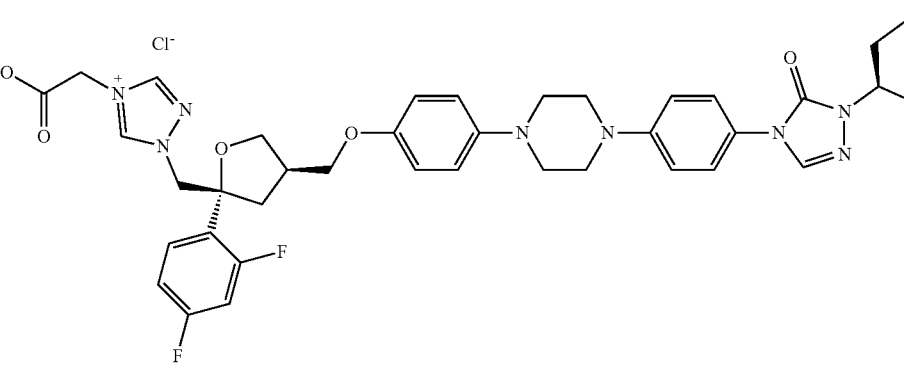 |
| 0022 | 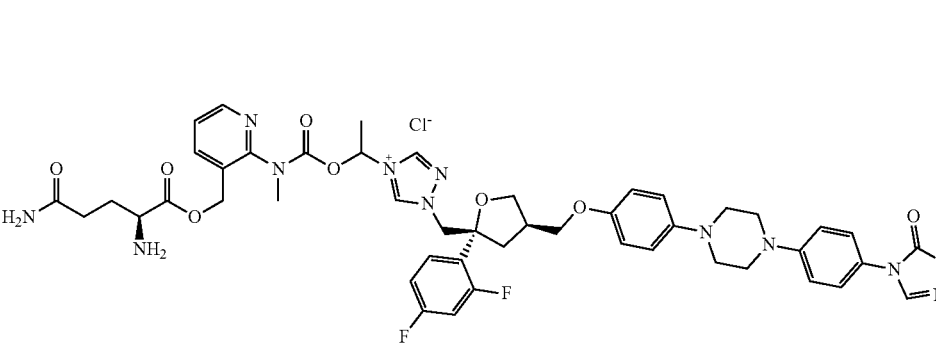 |
| 0023 | 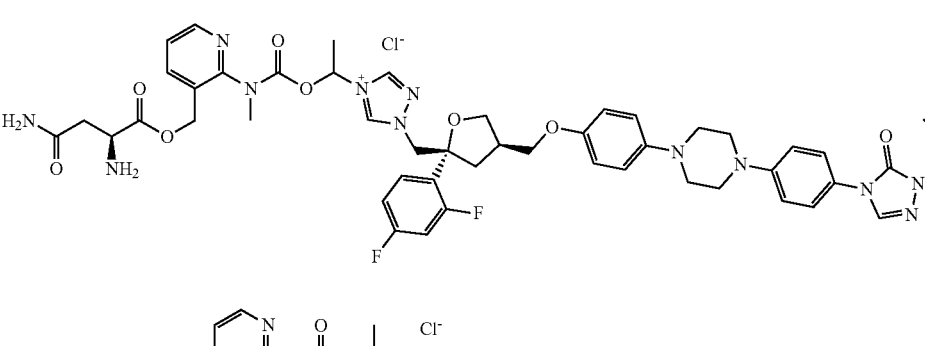 |
| 0024 | 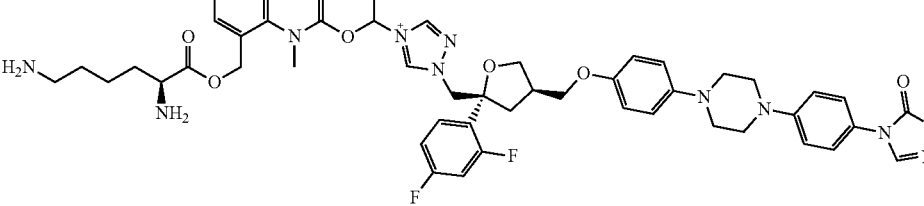 |

| No. | Structure |
|---|---|
| 0025 | 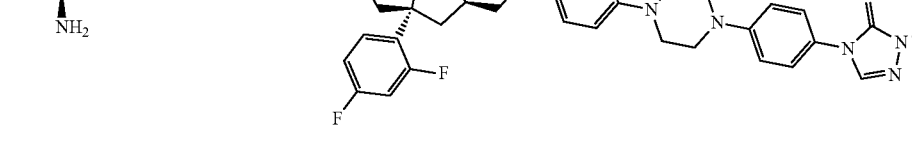 |
| 0026 | 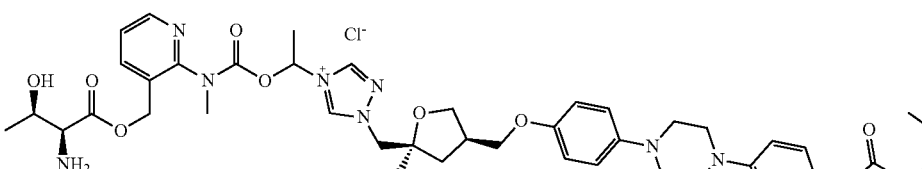 |
| 0027 | 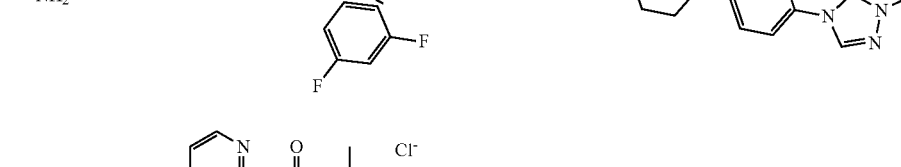 |
| 0028 | 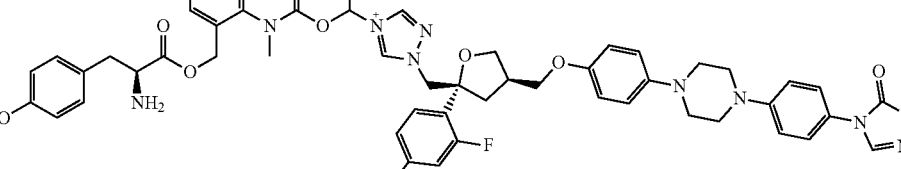 |
| 0029 | 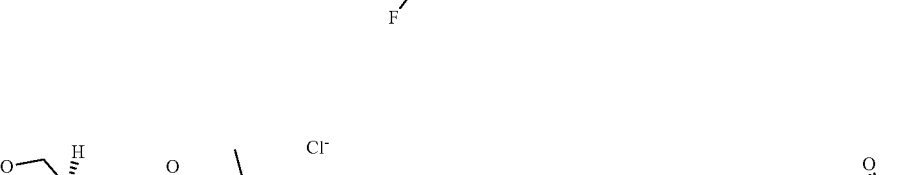 |

| No. | Structure |
|-----|-----------|
| 0030 | 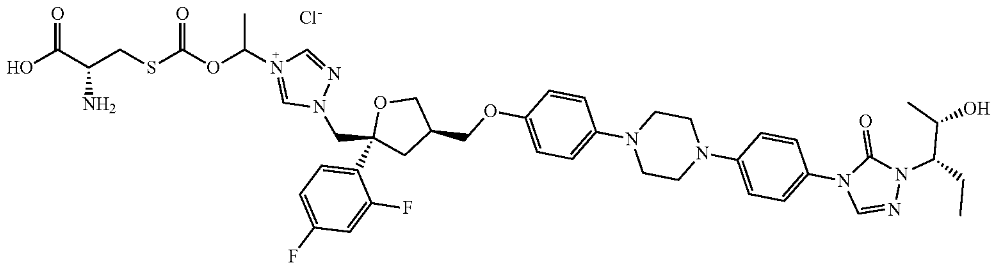 |
| 0031 | 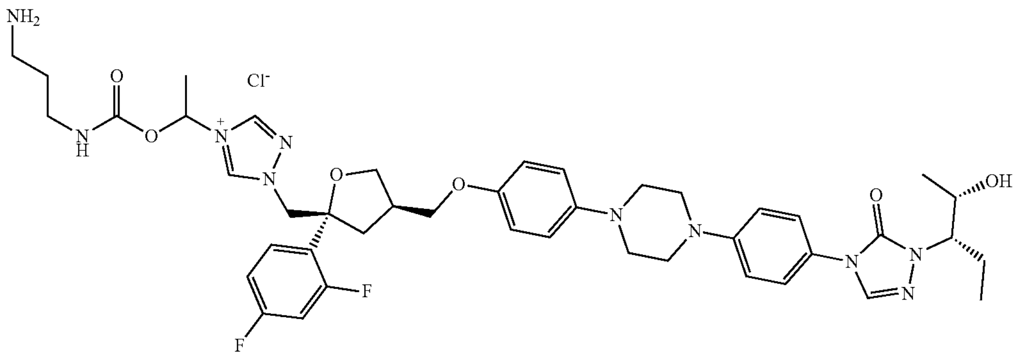 |
| 0032 | 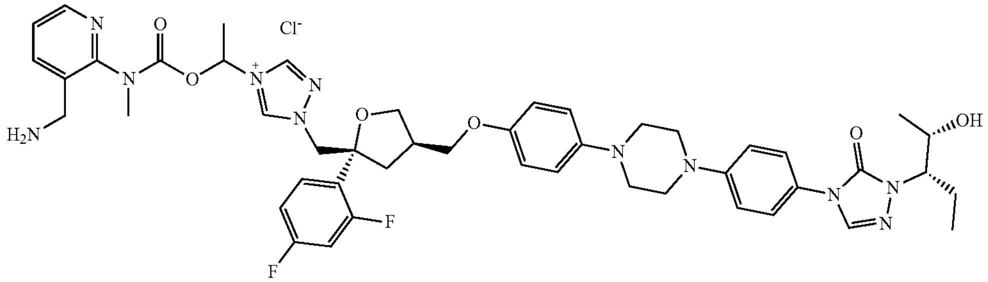 |
| 0033 | 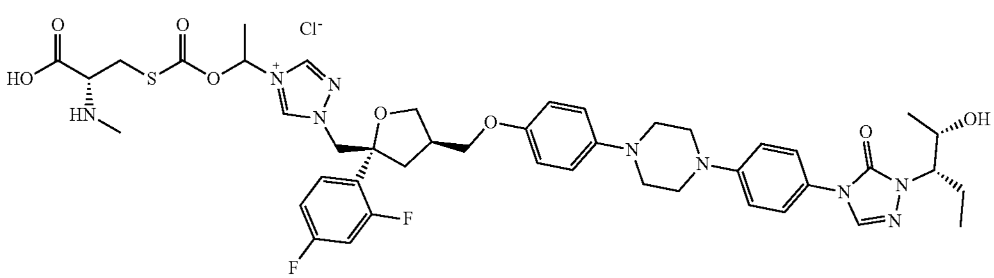 |
| 0034 | 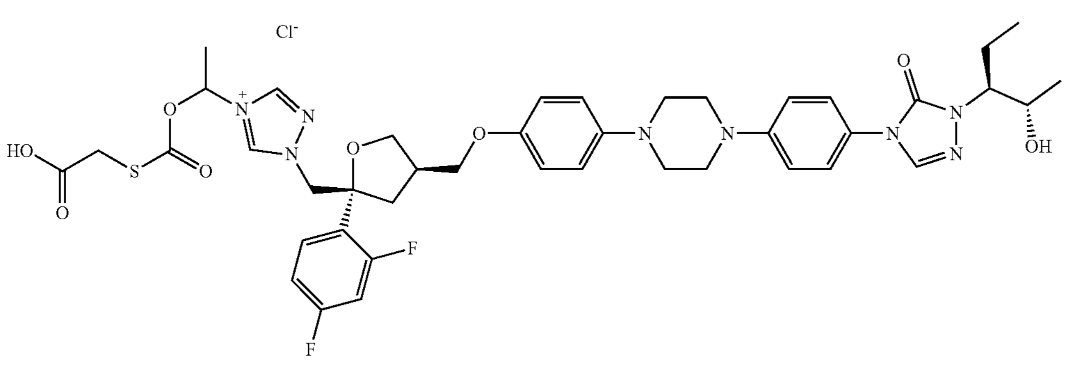 |

-continued
| No. | Structure |
|---|---|
| 0035 | 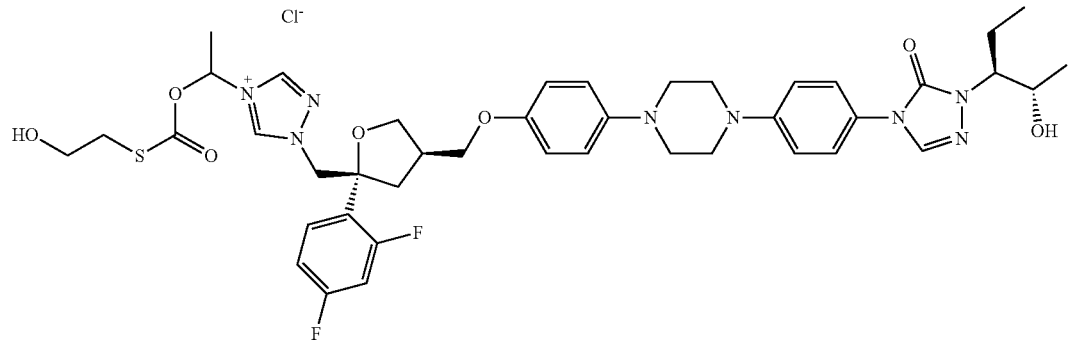 |
| 0036 | 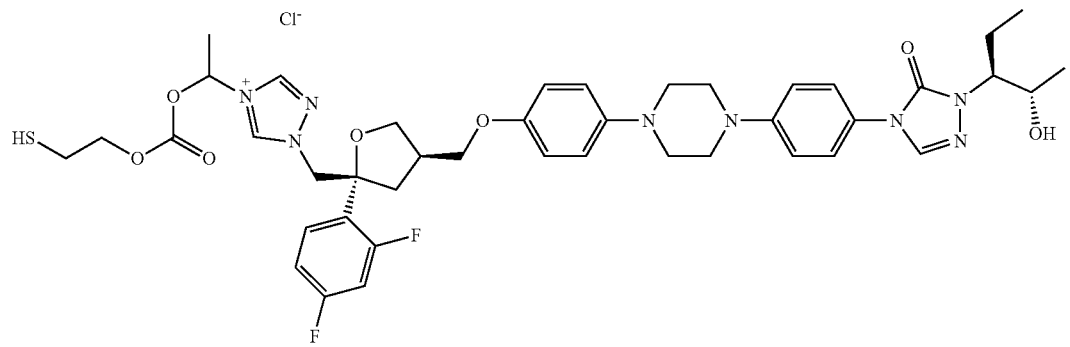 |
| 0037 | 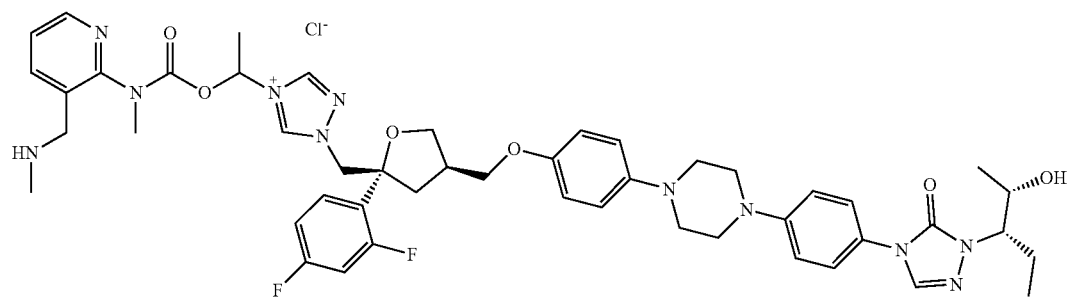 |
| 0038 | 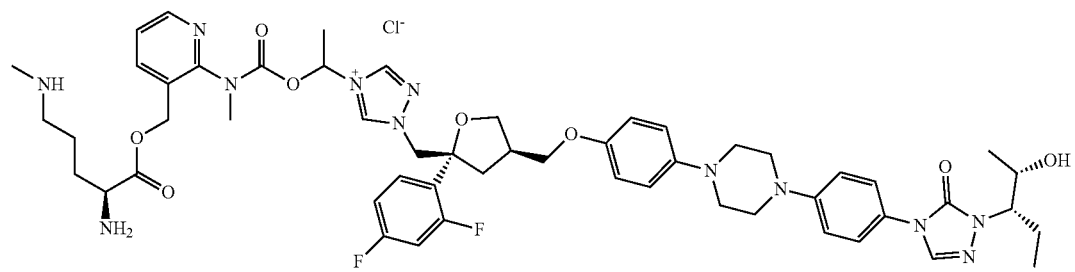 |
| 0039 | 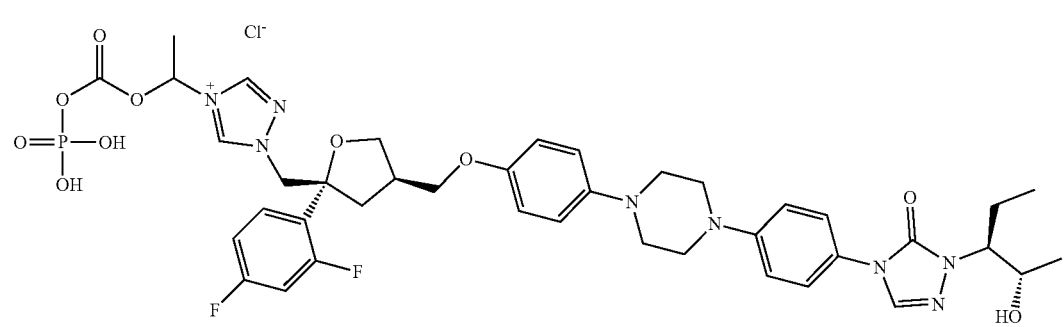 |

| No. | Structure |
|---|---|
| 0040 | 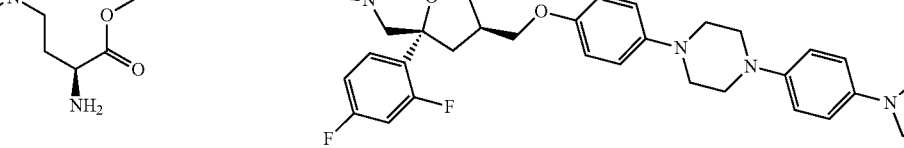 |
| 0041 | 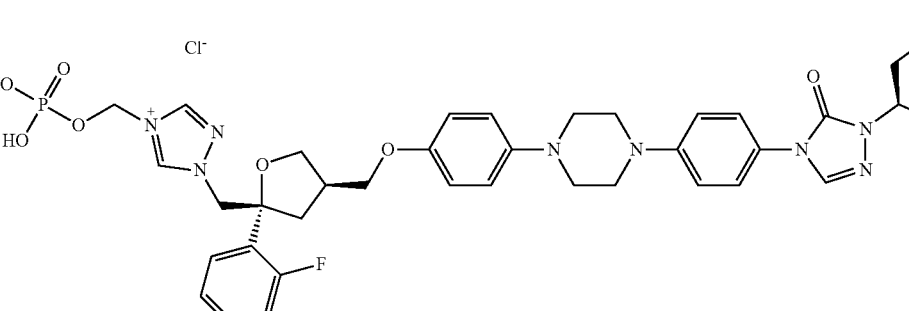 |
| 0042 | 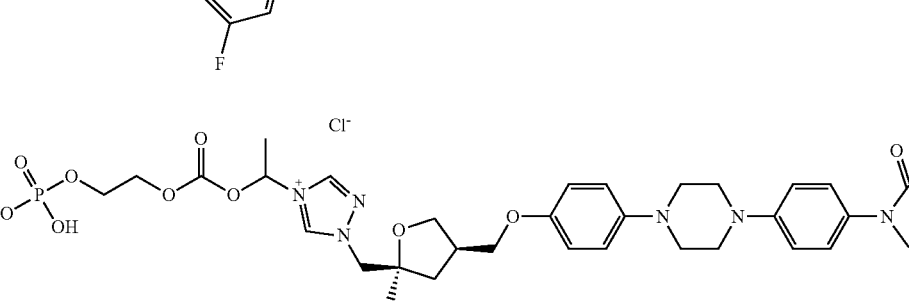 |
| 0043 | 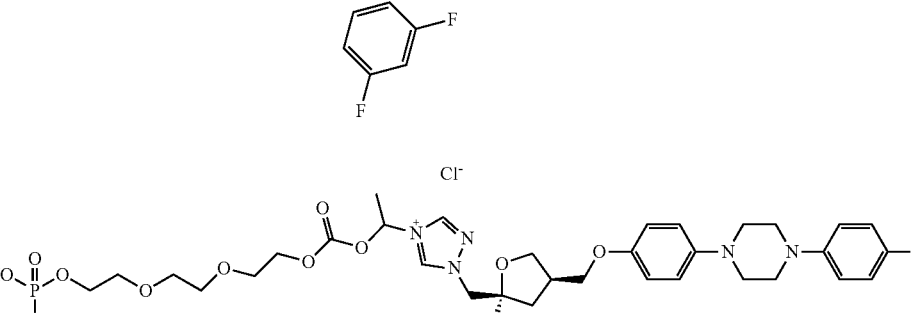 |
| 0044 | 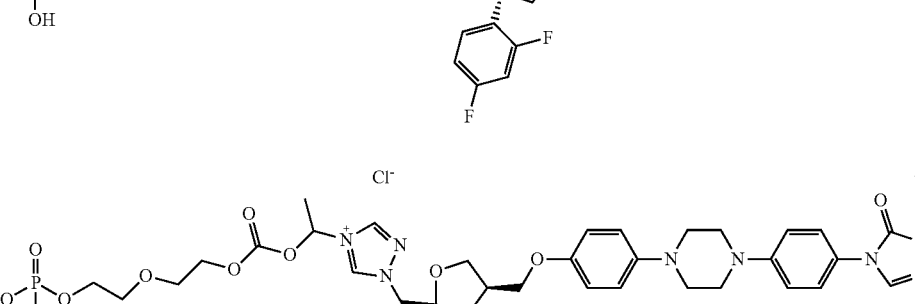 |

| No. | Structure |
|---|---|
| 0045 | 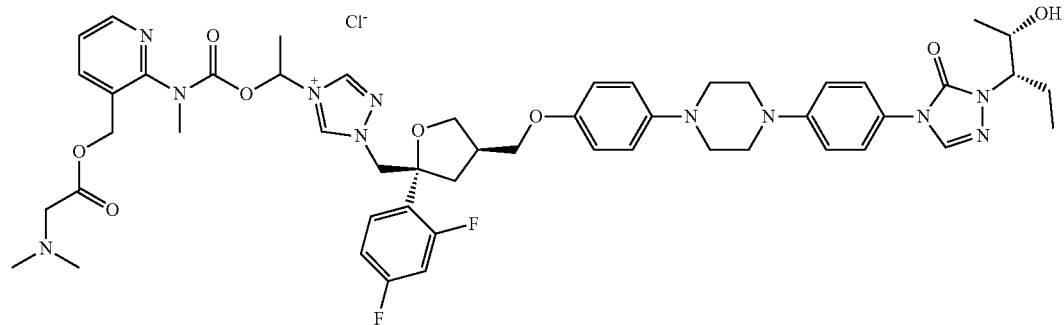 |
| 0046 | 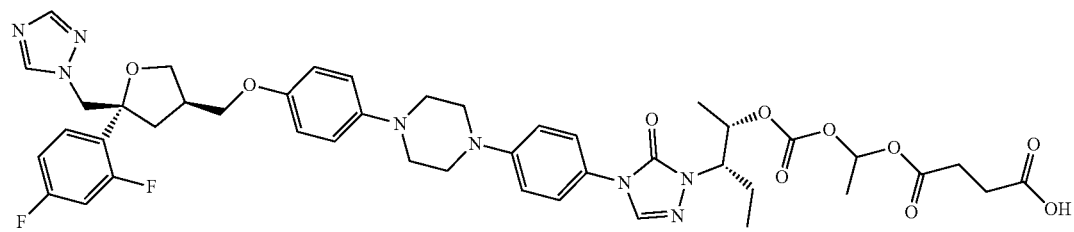 [SMILES: CC[C@@H]([C@H](C)OC(=O)OC(C)OC(=O)CCC(=O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0047 | 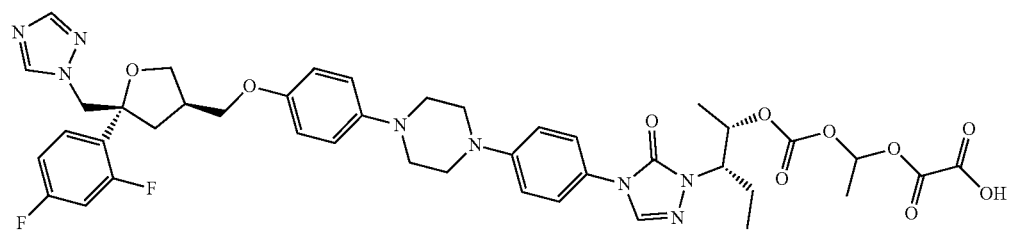 [SMILES: CC[C@@H]([C@H](C)OC(=O)OC(C)OC(=O)C(=O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0047 | 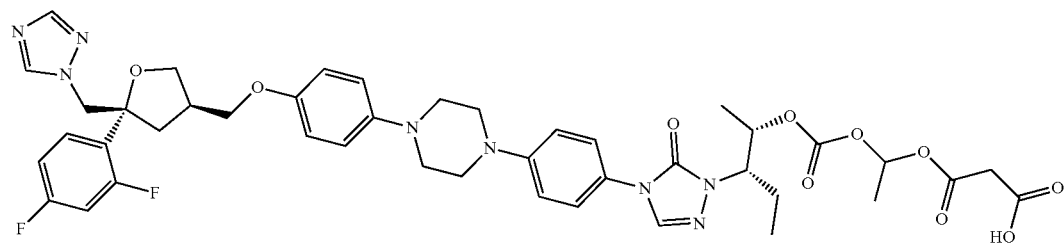 [SMILES: CC[C@@H]([C@H](C)OC(=O)OC(C)OC(=O)CC(=O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0049 | 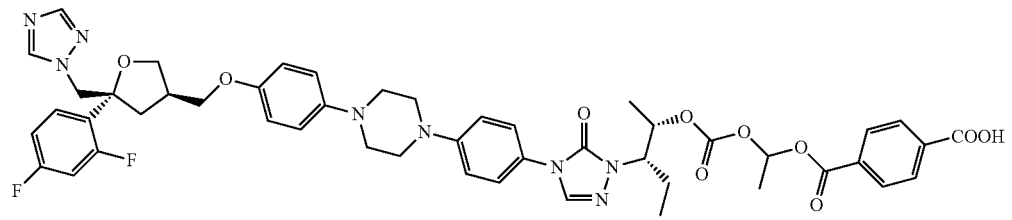 [SMILES: CC[C@@H]([C@H](C)OC(=O)OC(C)OC(=O)c1ccc(C(=O)O)cc1)n1ncn(-c2ccc(N3CCN(c4ccc(OC[C@@H]5CO[C@@](Cn6cncn6)(c6ccc(F)cc6F)C5)cc4)CC3)cc2)c1=O] |

| No. | Structure |
|---|---|
| 0051 | 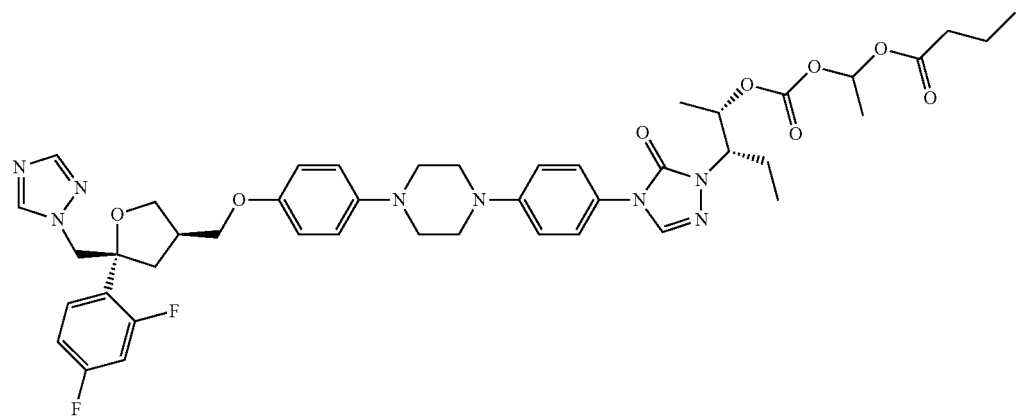 |
| 0052 | 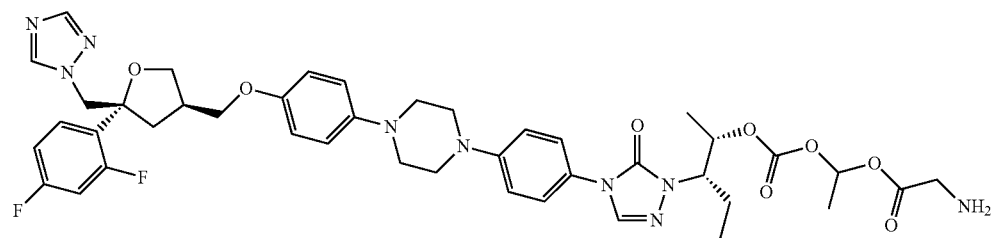 [SMILES: CC[C@@H]([C@H](C)OC(=O)OC(C)OC(=O)CN)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0053 | 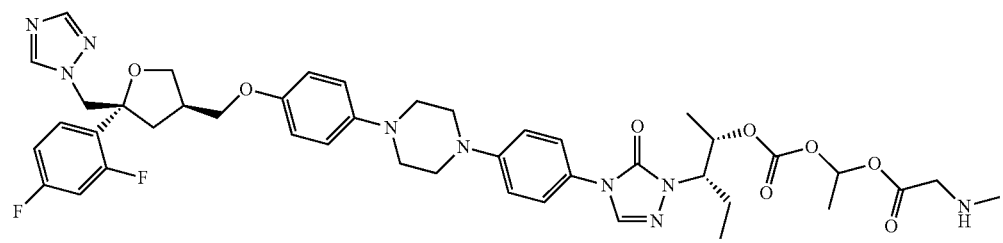 [SMILES: CC[C@@H]([C@H](C)OC(=O)OC(C)OC(=O)CNC)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0054 | 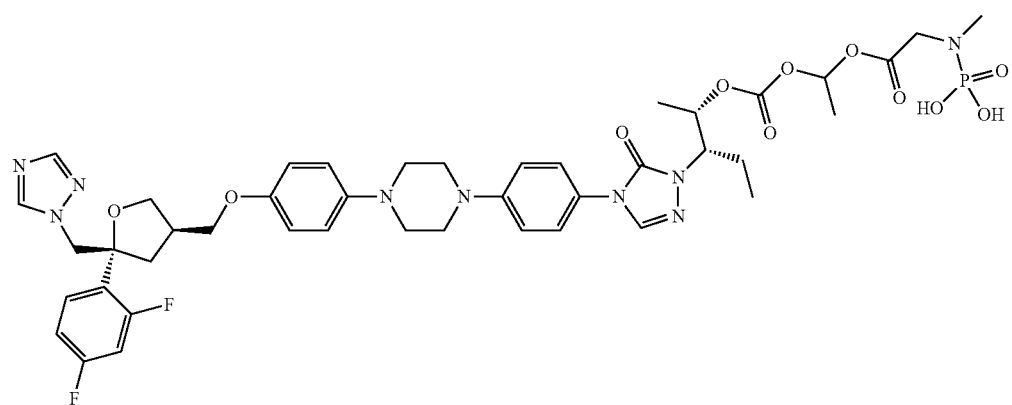 [SMILES: CC[C@@H]([C@H](C)OC(=O)OC(C)OC(=O)CN(C)P(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |

| No. | Structure |
|-----|-----------|
| 0055 | 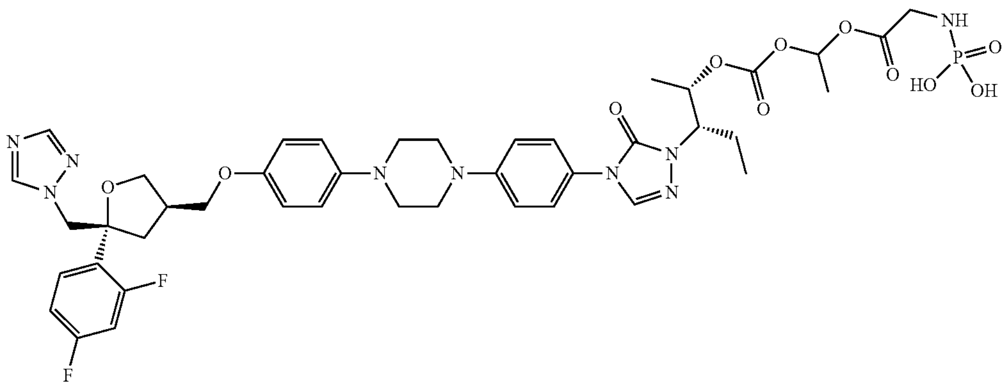 [SMILES: CC[C@@H]([C@H](C)OC(=O)OC(C)OC(=O)CNP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0056 | 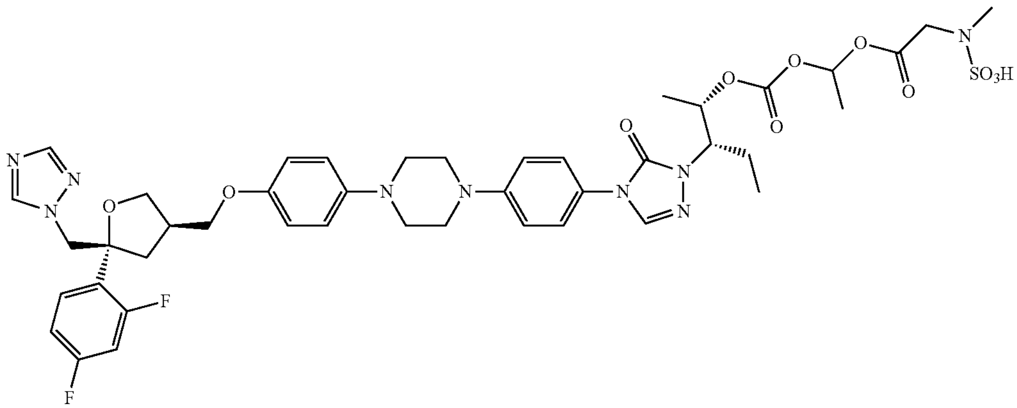 [SMILES: CC[C@@H]([C@H](C)OC(=O)OC(C)OC(=O)CN(C)S(=O)(=O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0057 | 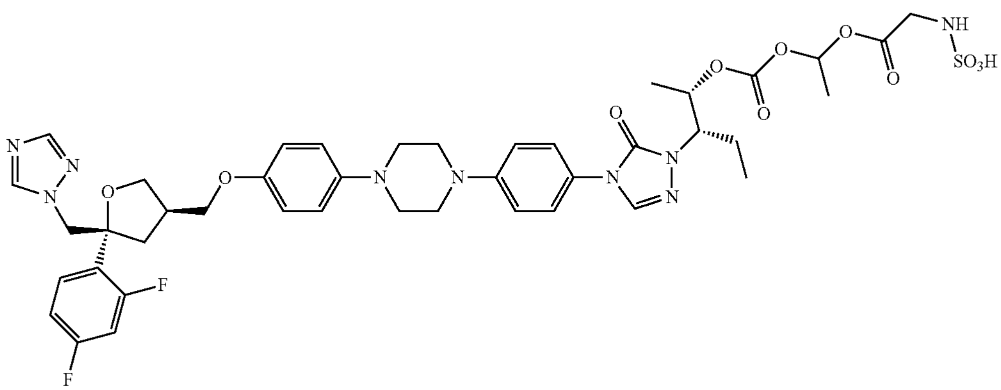 [SMILES: CC[C@@H]([C@H](C)OC(=O)OC(C)OC(=O)CNS(=O)(=O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0058 | 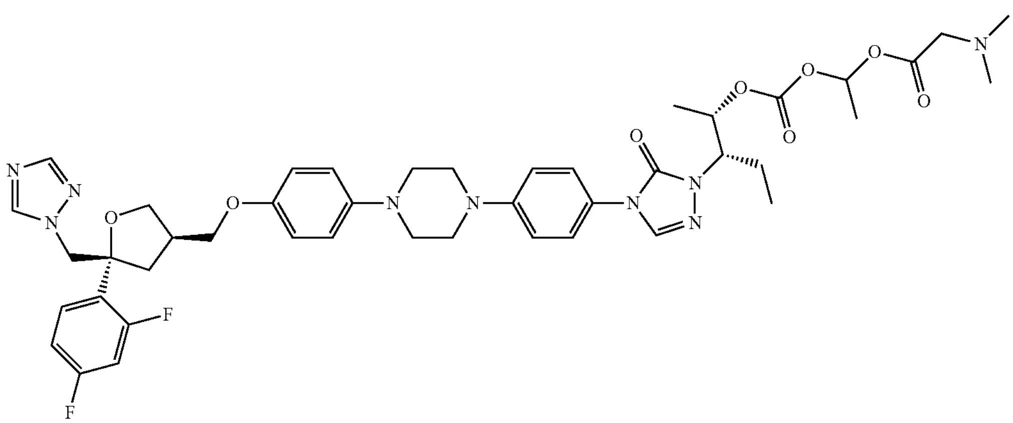 [SMILES: CC[C@@H]([C@H](C)OC(=O)OC(C)OC(=O)CN(C)C)n1ncn(-c2ccc(N3CCN(c4ccc(OC[C@@H]5CO[C@@](Cn6cncn6)(c6ccc(F)cc6F)C5)cc4)CC3)cc2)c1=O] |

| No. | Structure |
|---|---|
| 0062 | 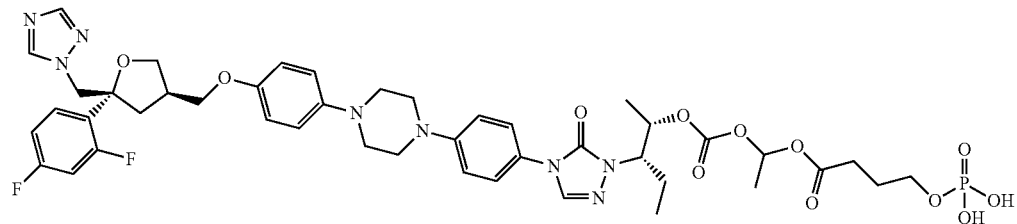 [SMILES: CC[C@@H]([C@H](C)OC(=O)OC(C)OC(=O)CCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0063 | 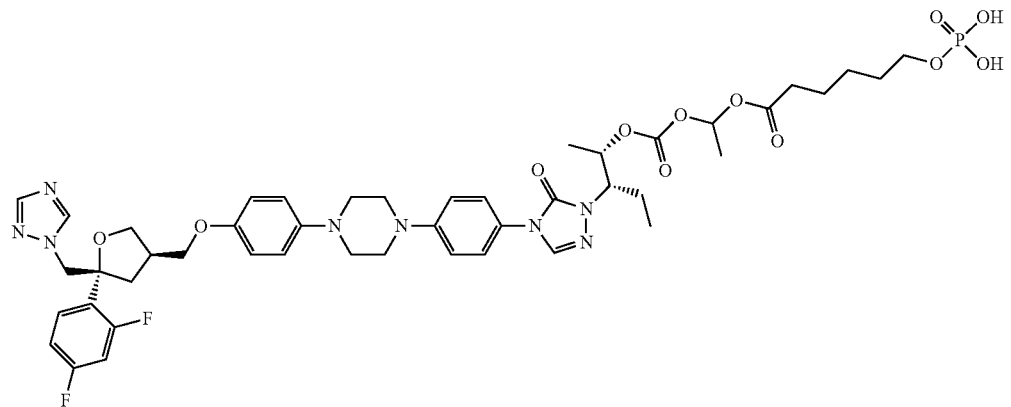 [SMILES: CC[C@@H]([C@H](C)OC(=O)OC(C)OC(=O)CCCCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0064 | 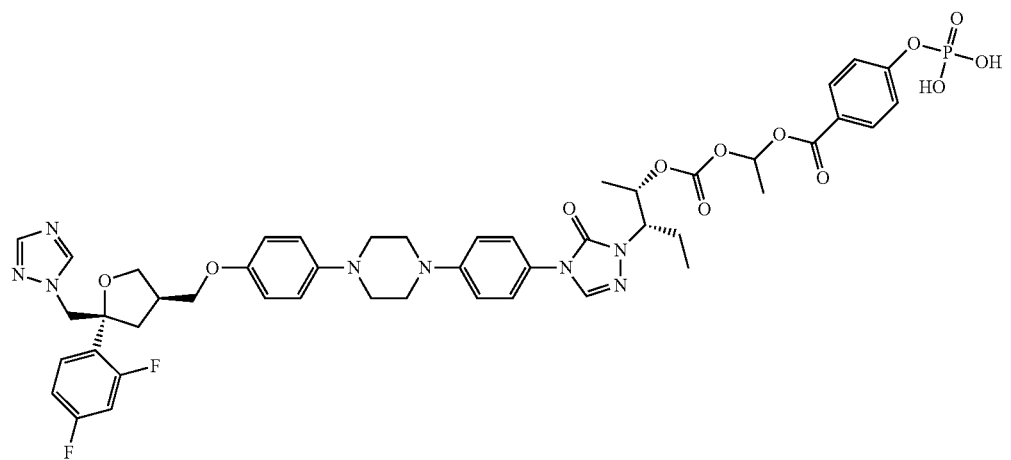 [SMILES: CC[C@@H]([C@H](C)OC(=O)OC(C)OC(=O)c1ccc(OP(=O)(O)O)cc1)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0065 | 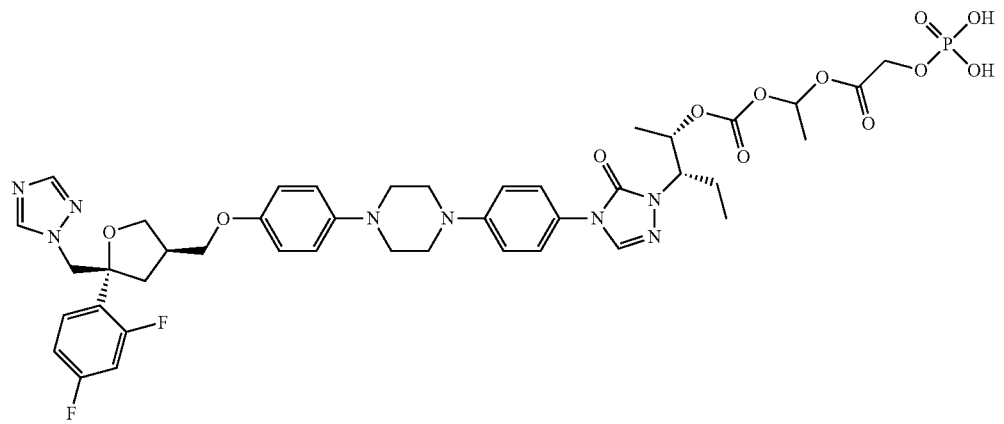 [SMILES: CC[C@@H]([C@H](C)OC(=O)OC(C)OC(=O)COP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |

| No. | Structure |
|---|---|
| 0066 | 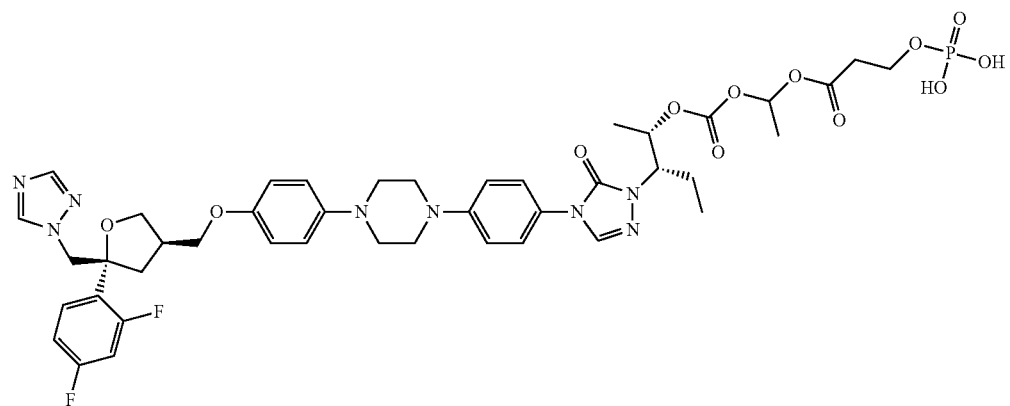 [SMILES: CC[C@@H]([C@H](C)OC(=O)OC(C)OC(=O)CCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0067 | 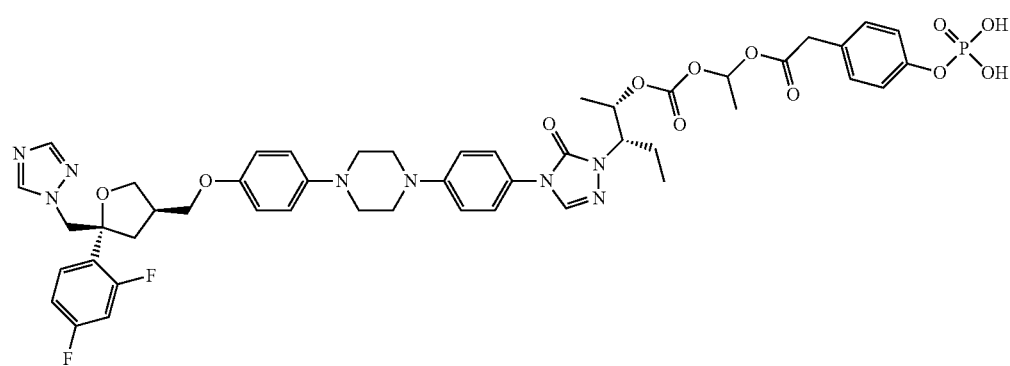 [SMILES: CC[C@@H]([C@H](C)OC(=O)OC(C)OC(=O)Cc1ccc(OP(=O)(O)O)cc1)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0068 | 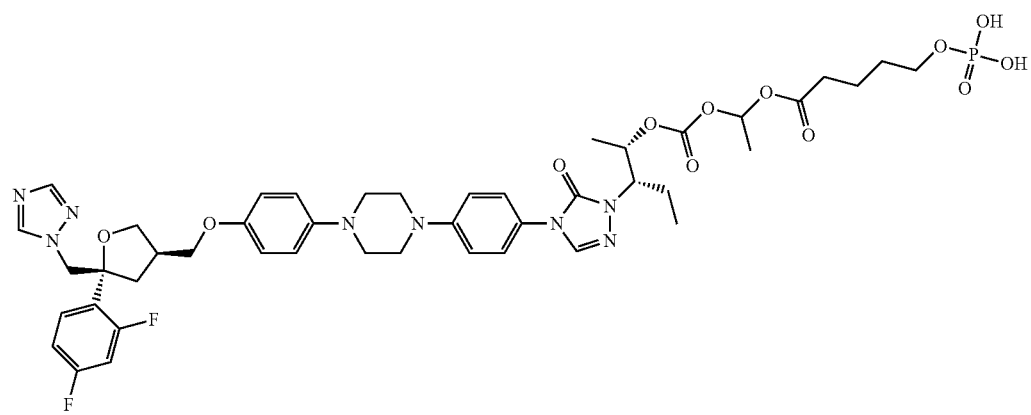 [SMILES: CC[C@@H]([C@H](C)OC(=O)OC(C)OC(=O)CCCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0069 | 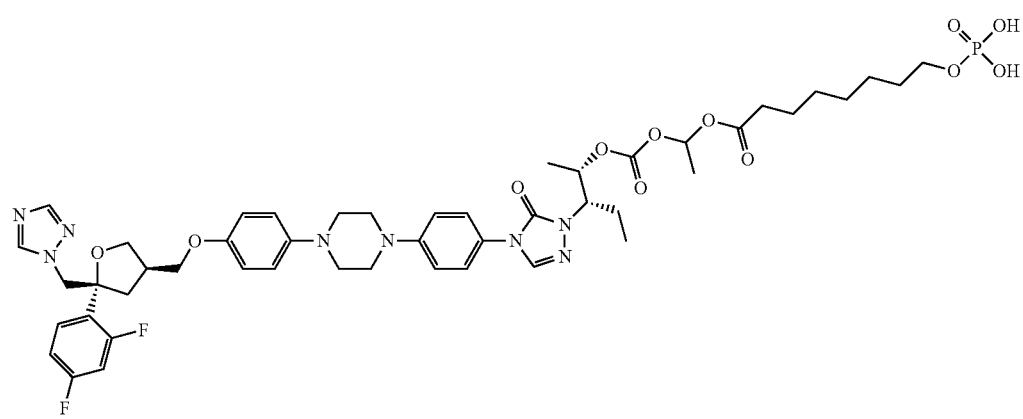 [SMILES: CC[C@@H]([C@H](C)OC(=O)OC(C)OC(=O)CCCCCCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |

-continued

| No. | Structure |
|---|---|
| 0070 | 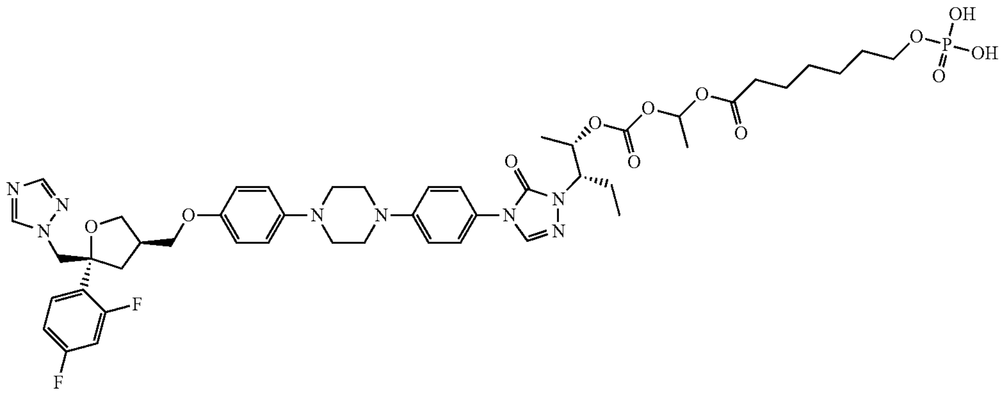 [SMILES: CC[C@@H]([C@H](C)OC(=O)OC(C)OC(=O)CCCCCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0071 | 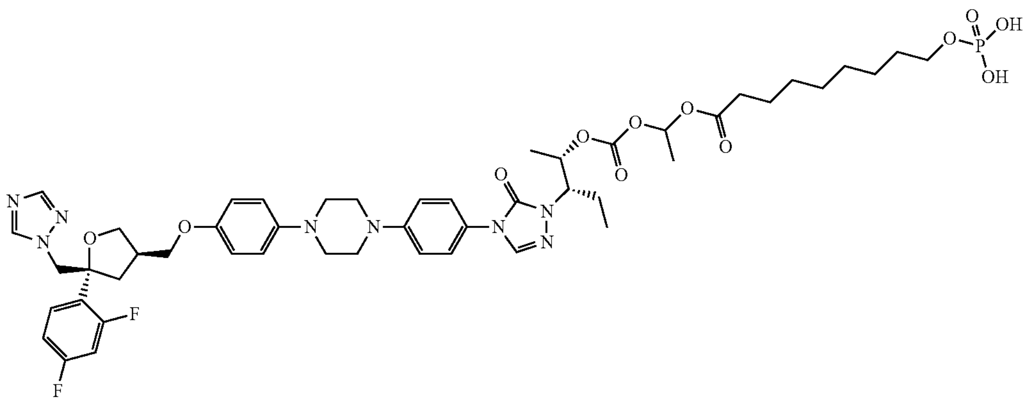 [SMILES: CC[C@@H]([C@H](C)OC(=O)OC(C)OC(=O)CCCCCCCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0072 | 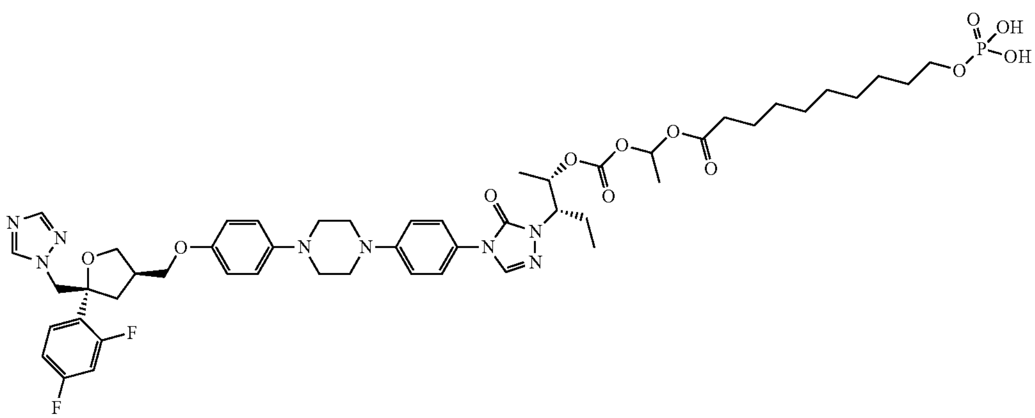 [SMILES: CC[C@@H]([C@H](C)OC(=O)OC(C)OC(=O)CCCCCCCCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0073 | 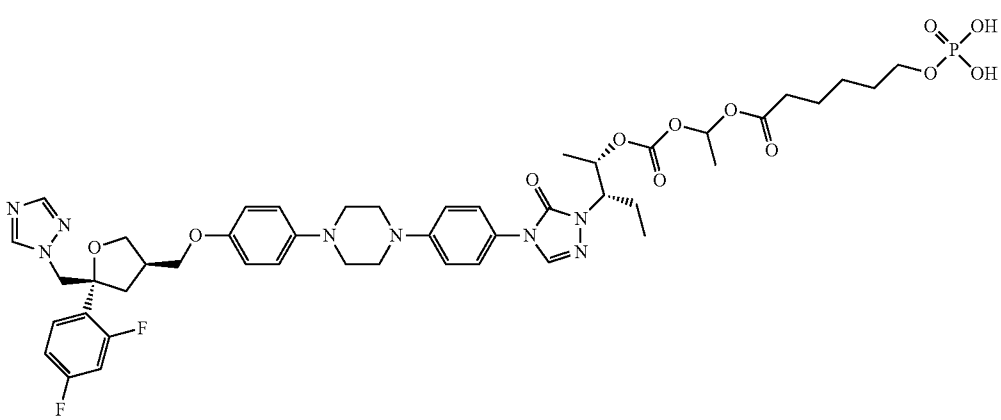 [SMILES: CC[C@@H]([C@H](C)OC(=O)OC(C)OC(=O)CCCCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |

| No. | Structure |
|---|---|
| 0074 | 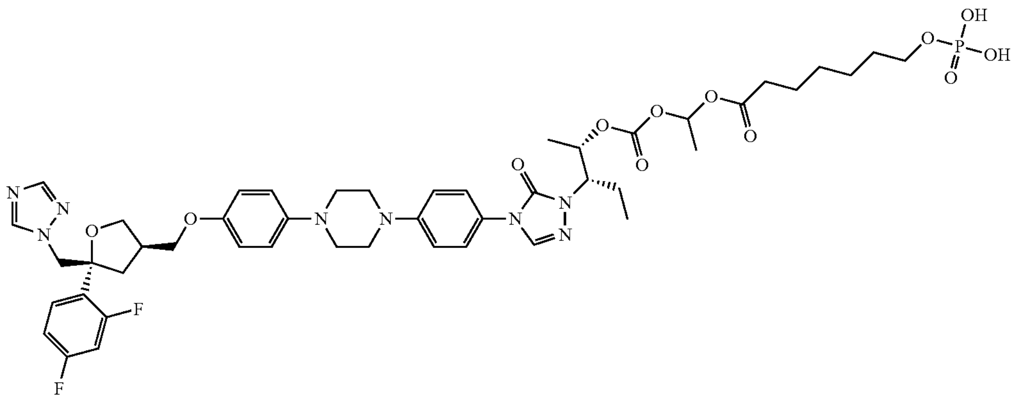 [SMILES: CC[C@@H]([C@H](C)OC(=O)OC(C)OC(=O)CCCCCCOP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0075 | 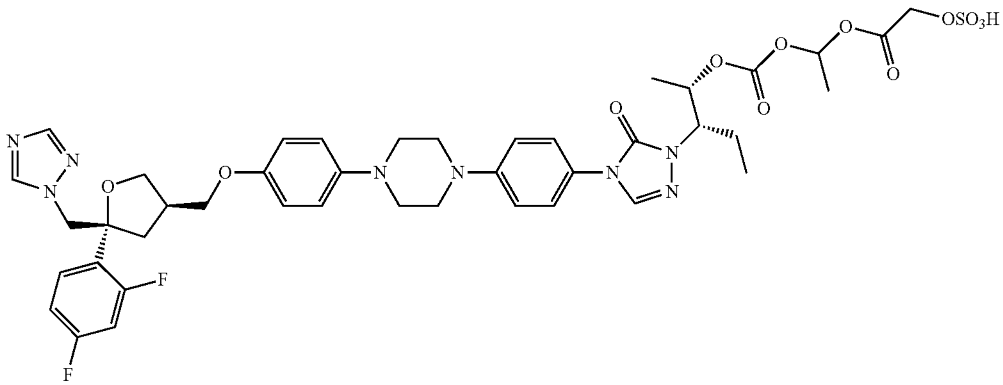 |
| 0076 | 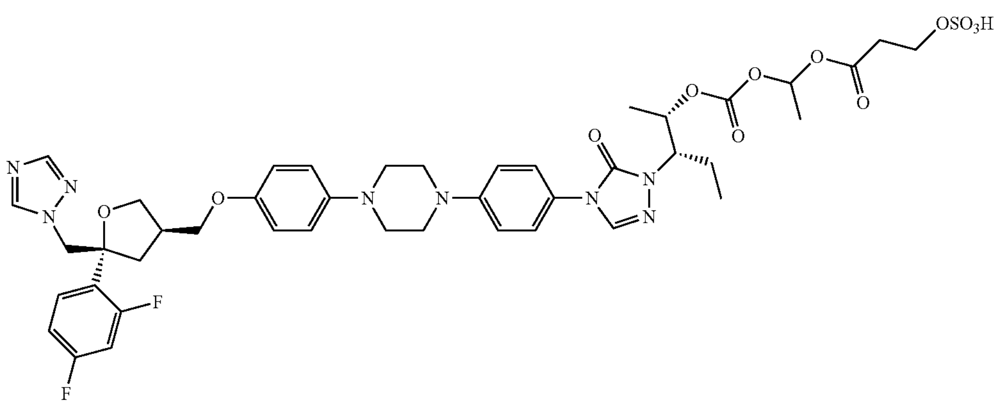 |
| 0077 | 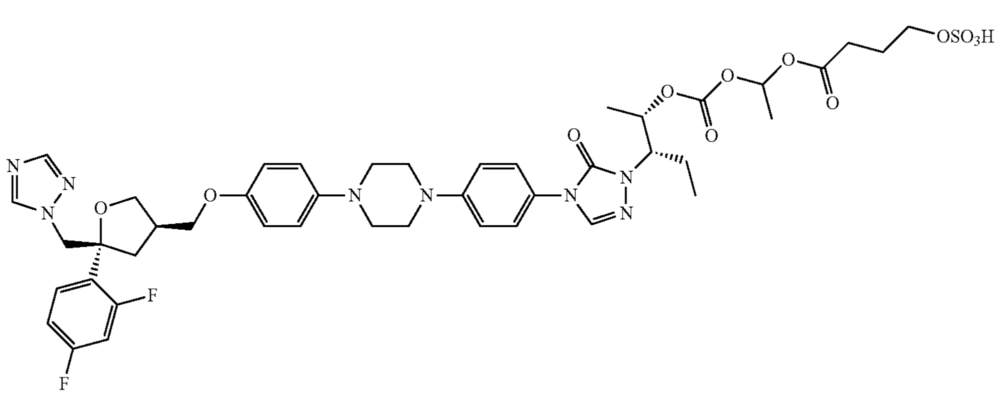 |

| No. | Structure |
|---|---|
| 0078 | 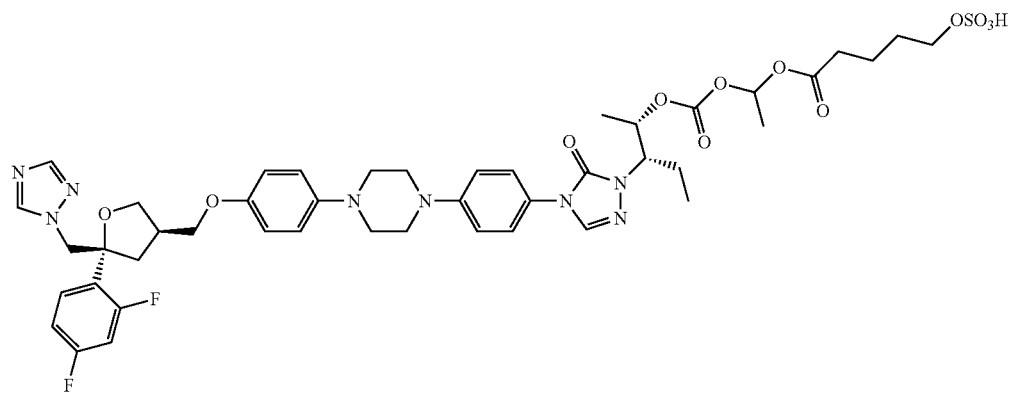 |
| 0079 | 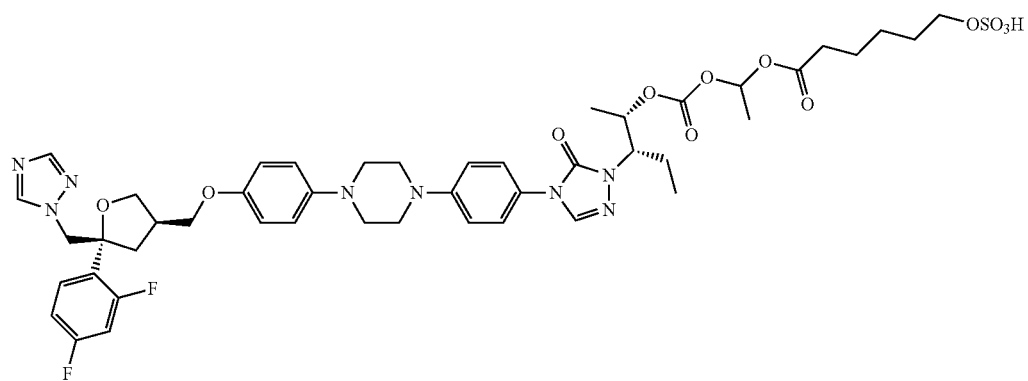 |
| 0080 | 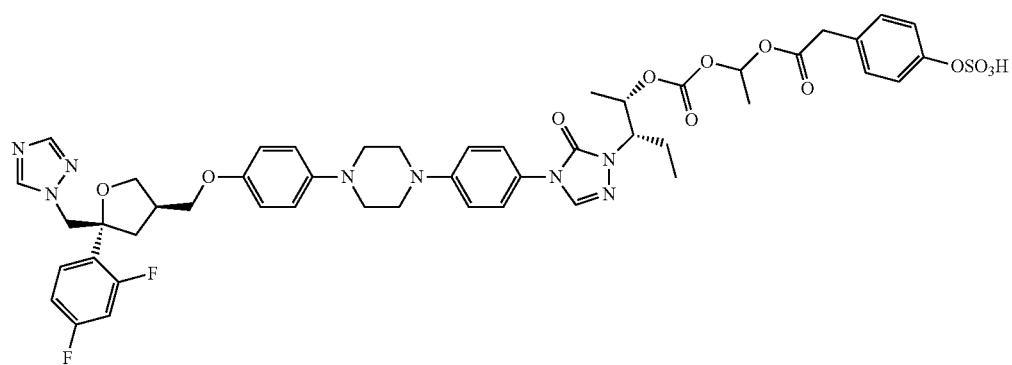 |
| 0081 | 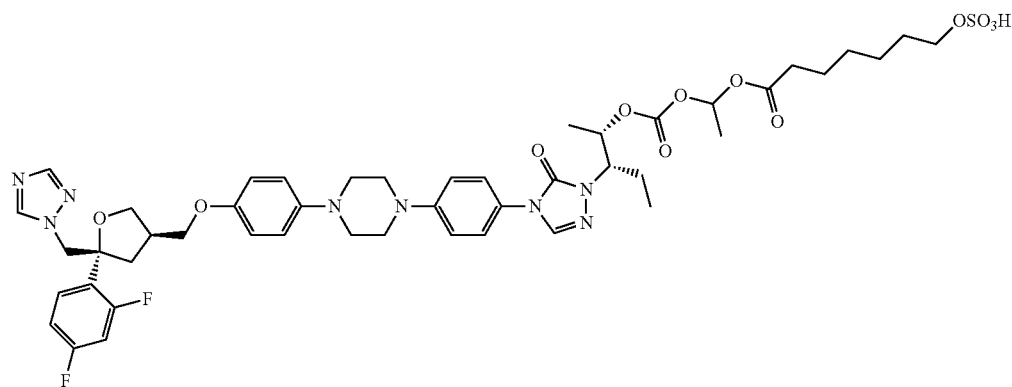 |

-continued
| No. | Structure |
|---|---|
| 0082 | 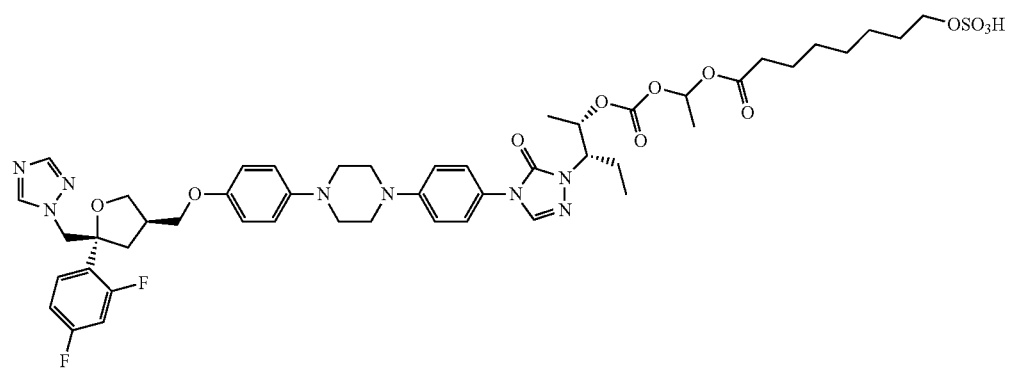 |
| 0083 | 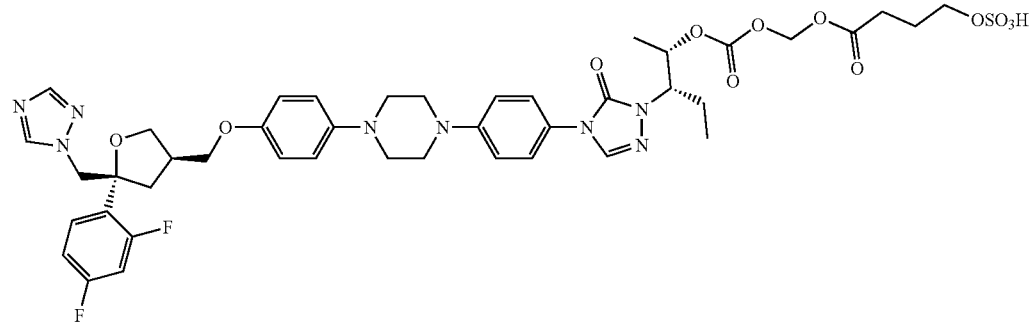 |
| 0084 | 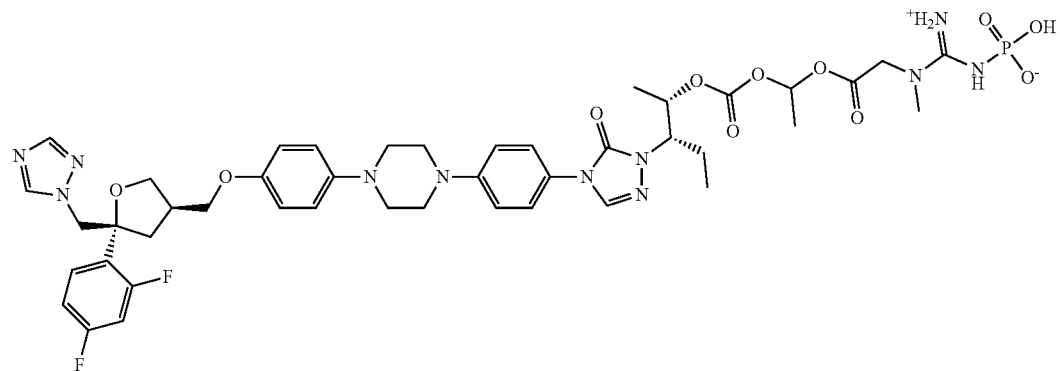 [SMILES: CC[C@@H]([C@H](C)OC(=O)OC(C)OC(=O)CN(C)C(=[NH2+])NP(=O)([O-])O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0085 | 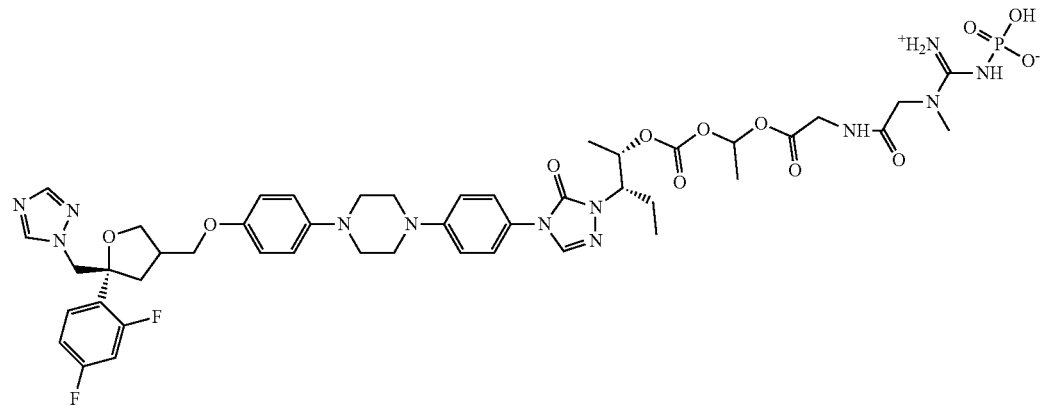 [SMILES: CC[C@@H]([C@H](C)OC(=O)OC(C)OC(=O)CNC(=O)CN(C)C(=[NH2+])NP(=O)([O-])O)n1ncn(-c2ccc(N3CCN(c4ccc(OCC5CO[C@@](Cn6cncn6)(c6ccc(F)cc6F)C5)cc4)CC3)cc2)c1=O] |

-continued
| No. | Structure |
|---|---|
| 0086 | 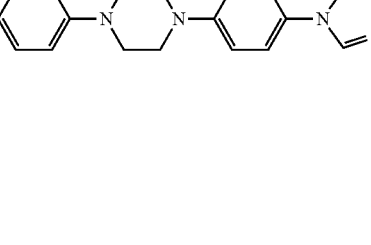 |
| 0087 | 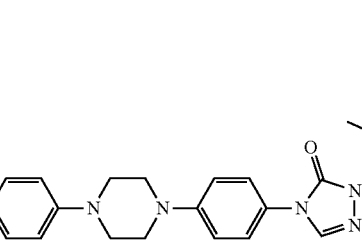 |
| 0088 | 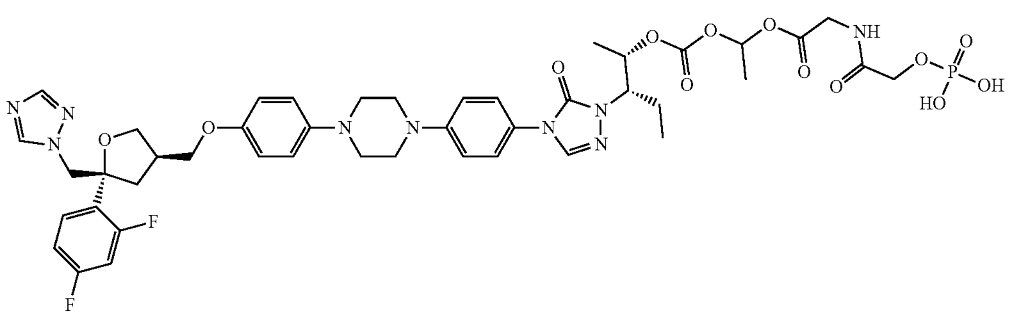 [SMILES: CC[C@@H]([C@H](C)OC(=O)OC(C)OC(=O)CNC(=O)COP(=O)(O)O)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0089 | 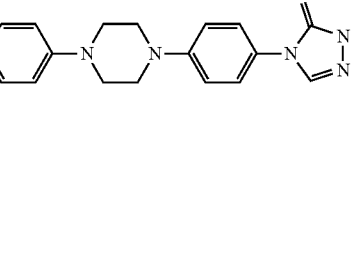 |

| No. | Structure |
| --- | --- |
| 0090 | 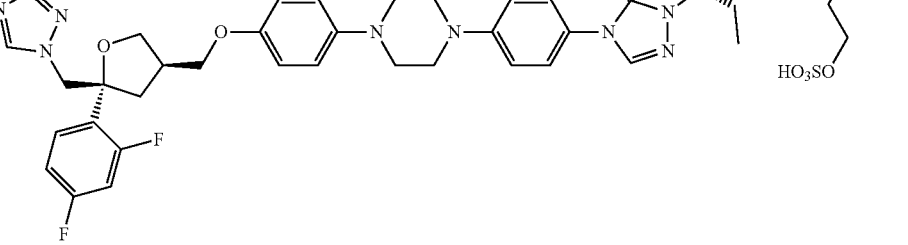 |
| 0091 | 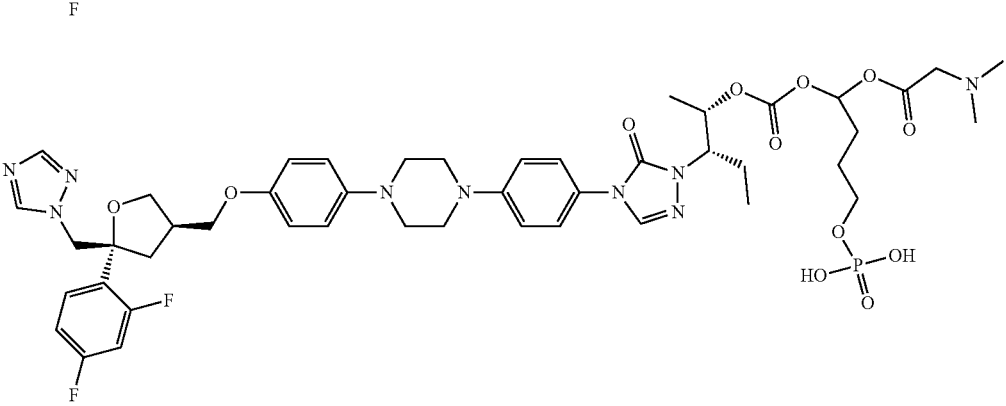 |
| 0092 | 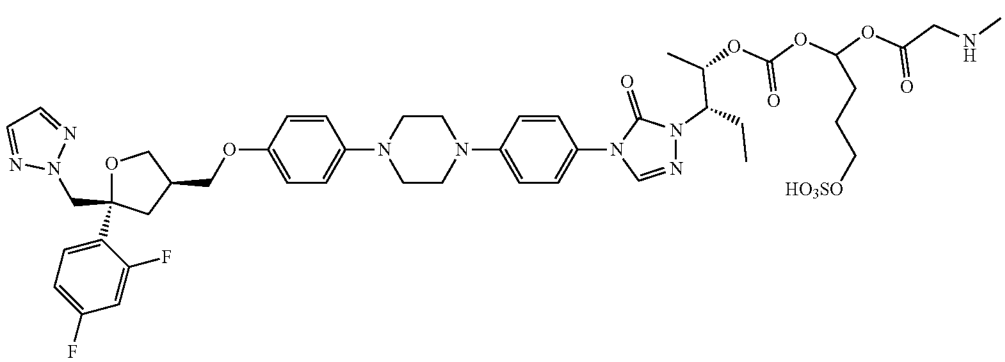 |
| | 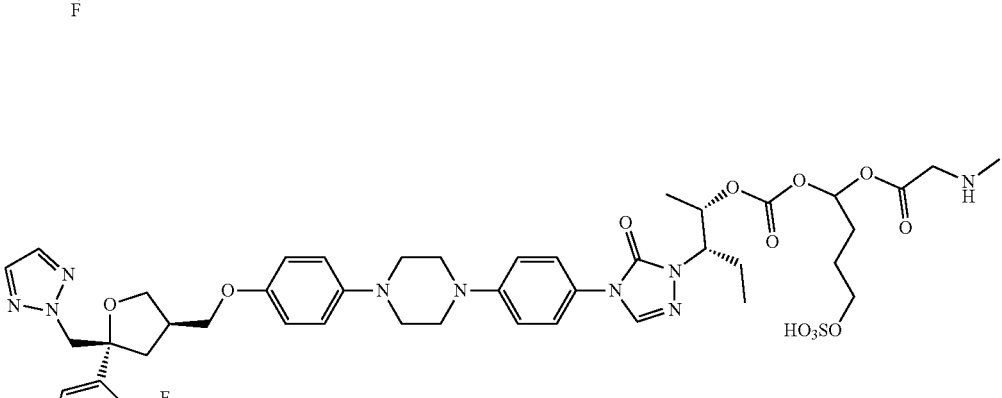 |
| 0096 | 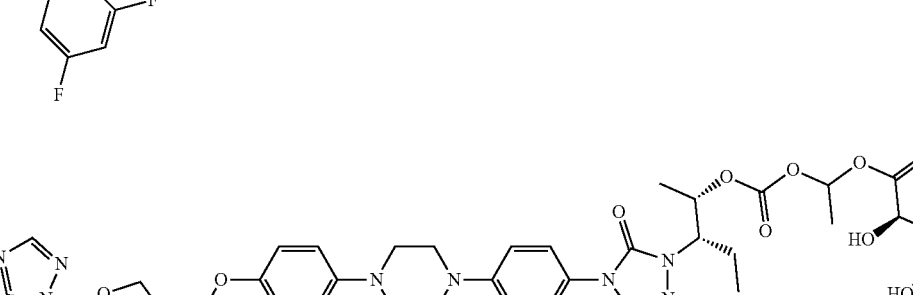 |

| No. | Structure |
|---|---|
| 0097 | 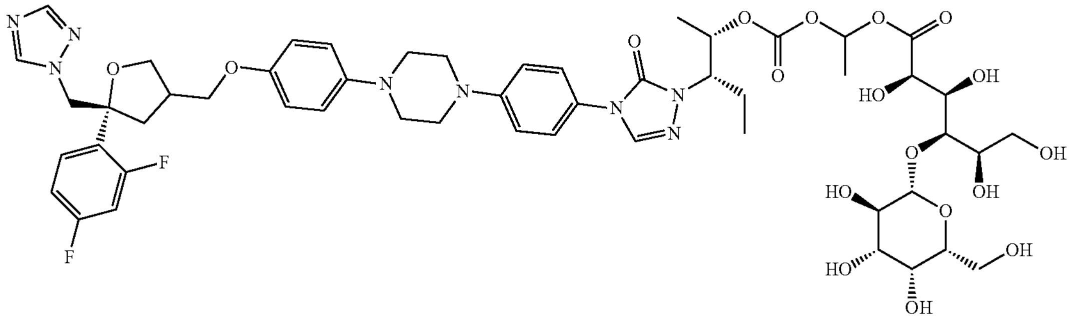 [SMILES: CC[C@@H]([C@H](C)OC(=O)OC(C)OC(=O)[C@H](O)[C@@H](O)[C@H](O[C@@H]1O[C@H](CO)[C@H](O)[C@H](O)[C@H]1O)[C@H](O)CO)n1ncn(-c2ccc(N3CCN(c4ccc(OCC5CO[C@@](Cn6cncn6)(c6ccc(F)cc6F)C5)cc4)CC3)cc2)c1=O] |
| 0098 | 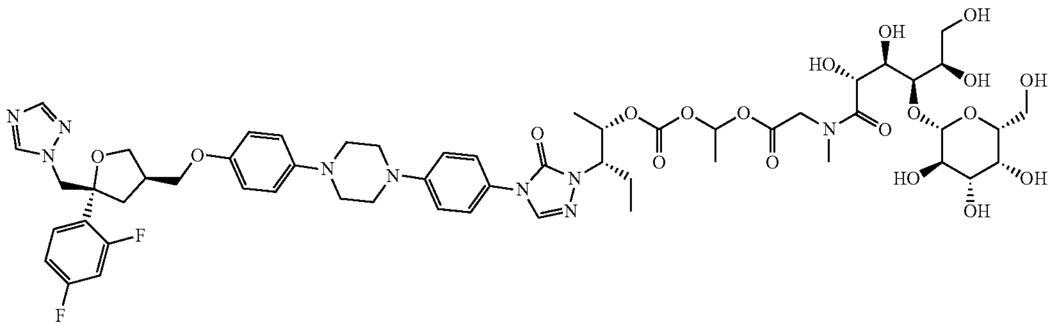 [SMILES: CC[C@@H]([C@H](C)OC(=O)OC(C)OC(=O)CN(C)C(=O)[C@H](O)[C@@H](O)[C@H](O[C@@H]1O[C@H](CO)[C@H](O)[C@H](O)[C@H]1O)[C@H](O)CO)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0099 | 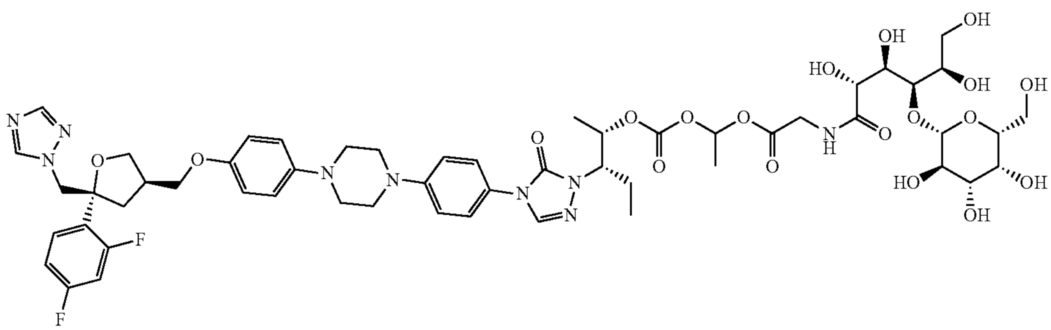 [SMILES: CC[C@@H]([C@H](C)OC(=O)OC(C)OC(=O)CNC(=O)[C@H](O)[C@@H](O)[C@H](O[C@@H]1O[C@H](CO)[C@H](O)[C@H](O)[C@H]1O)[C@H](O)CO)n1ncn(-c2ccc(N3CCN(c4ccc(OC[C@@H]5CO[C@@](Cn6cncn6)(c6ccc(F)cc6F)C5)cc4)CC3)cc2)c1=O] |
| 0100 | 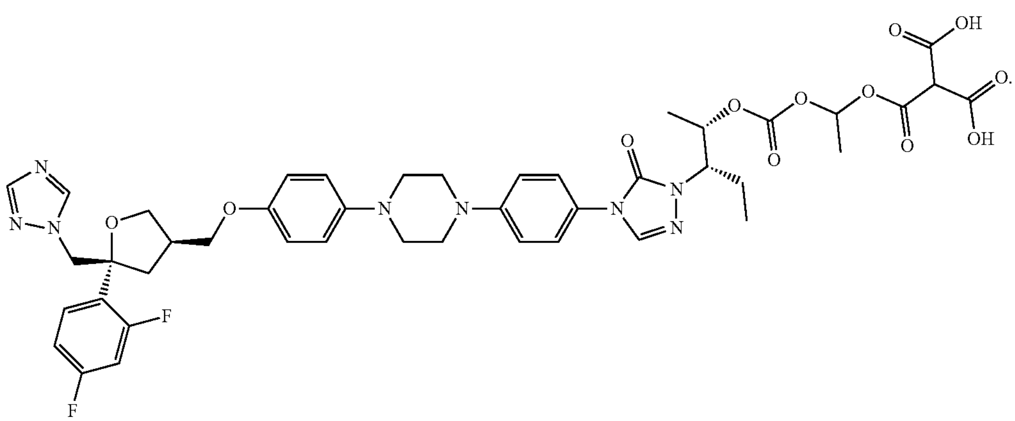 [SMILES: CC[C@@H]([C@H](C)OC(=O)OC(C)OC(=O)C(C(=O)O)C(=O)O)n1ncn(-c2ccc(N3CCN(c4ccc(OC[C@@H]5CO[C@@](Cn6cncn6)(c6ccc(F)cc6F)C5)cc4)CC3)cc2)c1=O] |

17. The compound, racemate, stereoisomer, tautomer or pharmaceutically acceptable salt thereof according to claim 1, wherein the pharmaceutically acceptable salts of the compound of formula (I) is one of the following salts:

| No. | Structure formula |
|---|---|
| ST0002 | 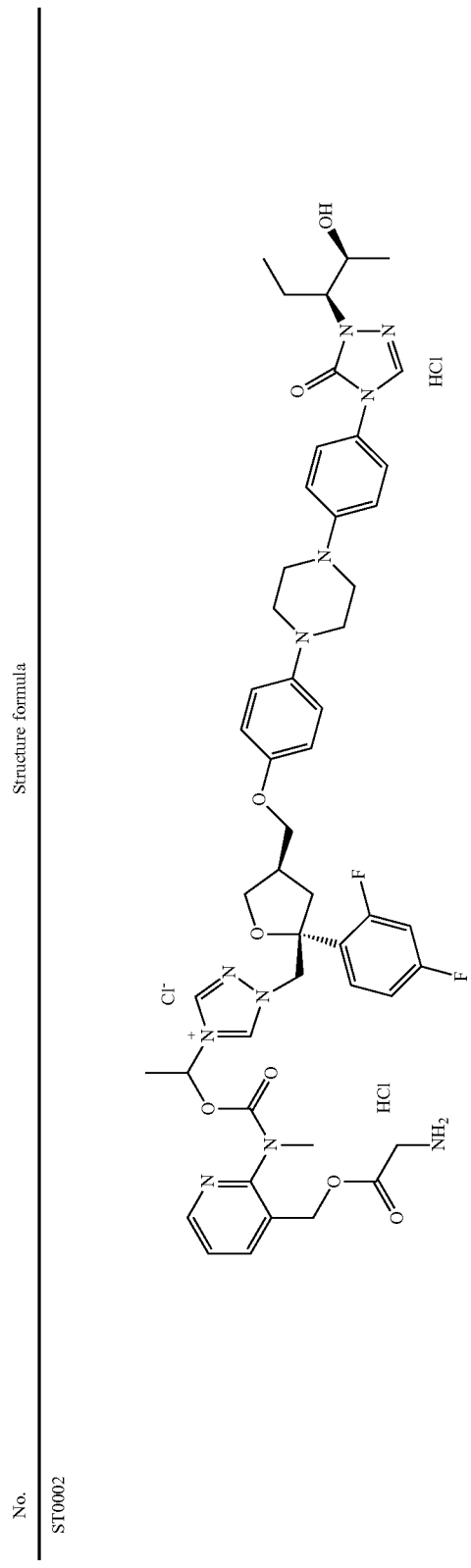 |
| ST0003 | 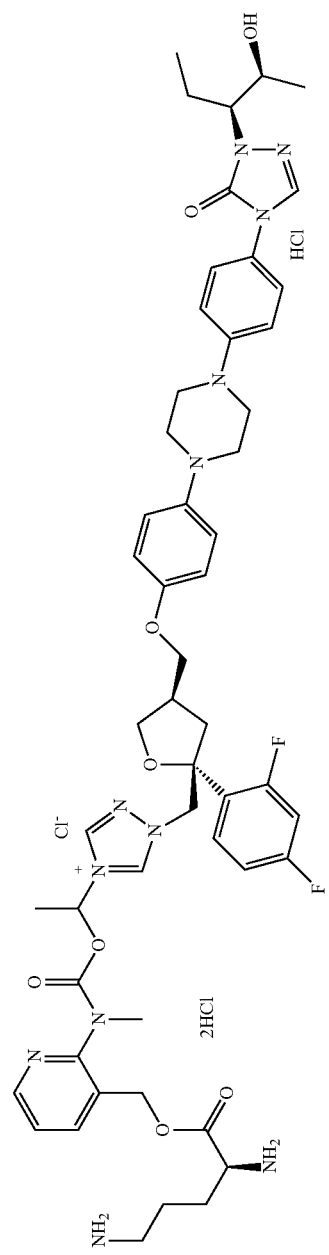 |

| No. | Structure formula |
|---|---|
| ST0004 | 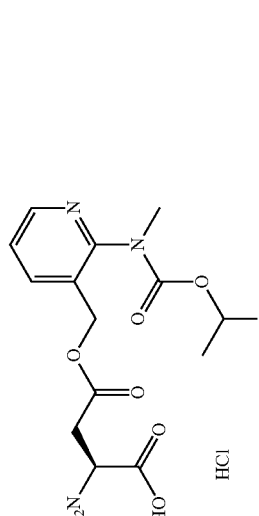 |
| ST0005 | 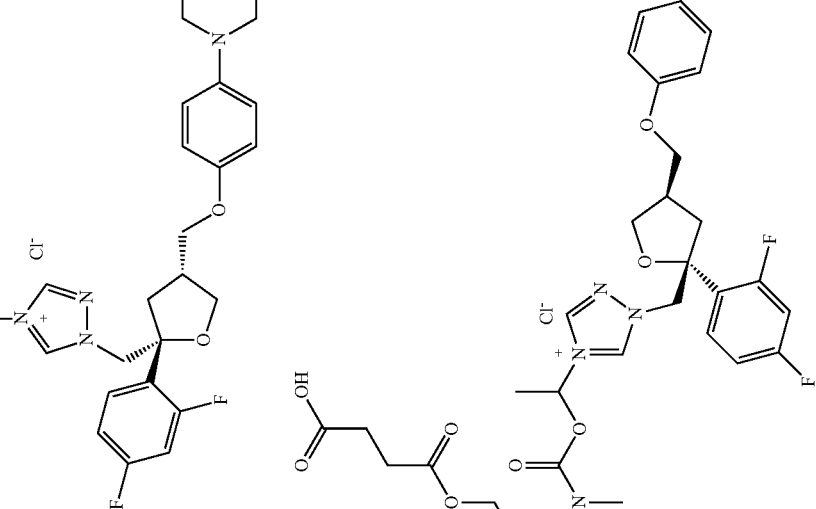 |

-continued
| No. | Structure formula |
|---|---|
| ST0006 | 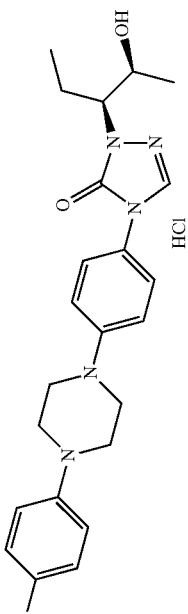 |
| ST0007 | 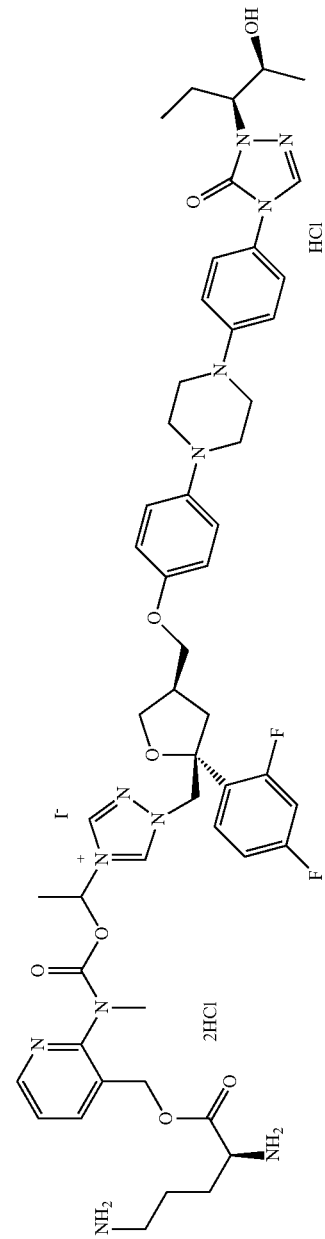 |

-continued
| No. | Structure formula |
|---|---|
| ST0008 | 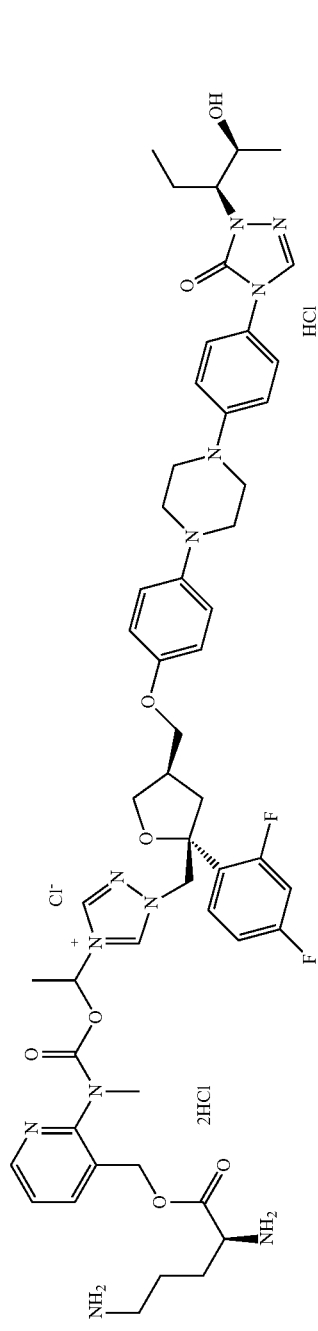 |
| ST0010 | 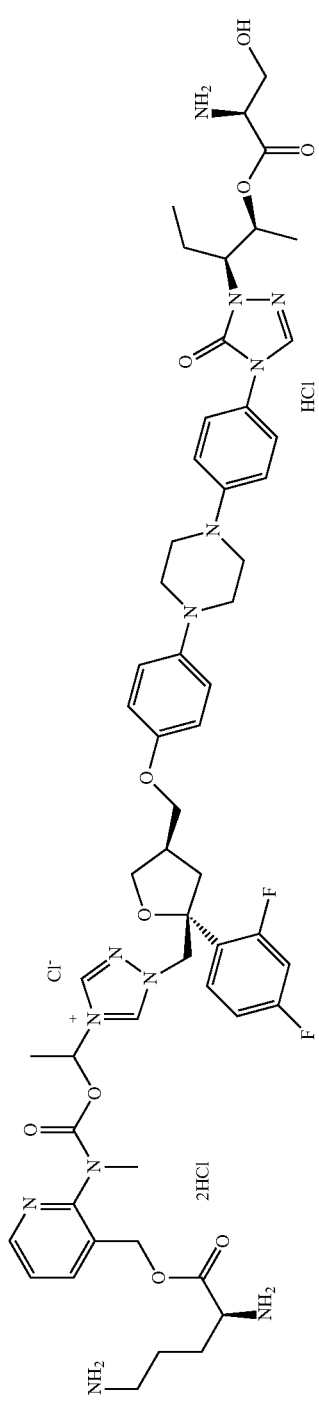 |
| ST0011 | 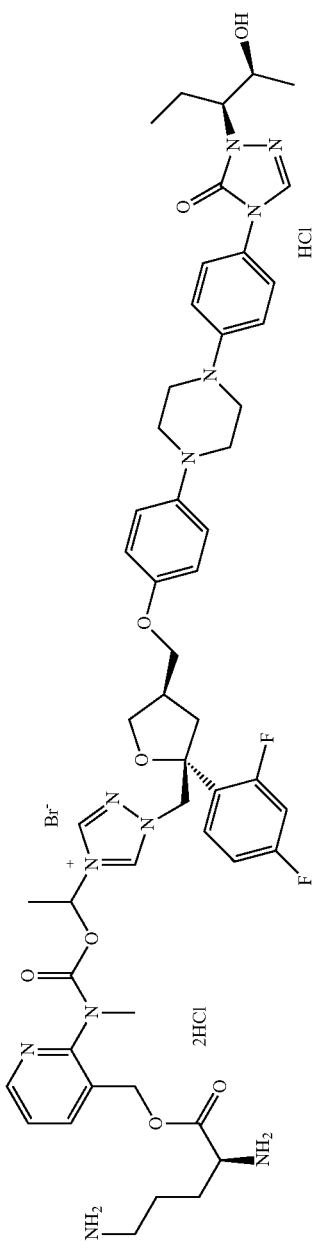 |

-continued
| No. | Structure formula |
|---|---|
| ST0012 |  |
| ST0013 | 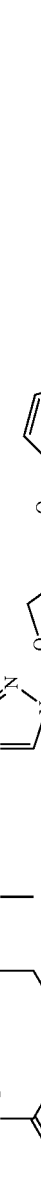 |
| ST0014 |  |

-continued
| No. | Structure formula |
|---|---|
| ST0015 | 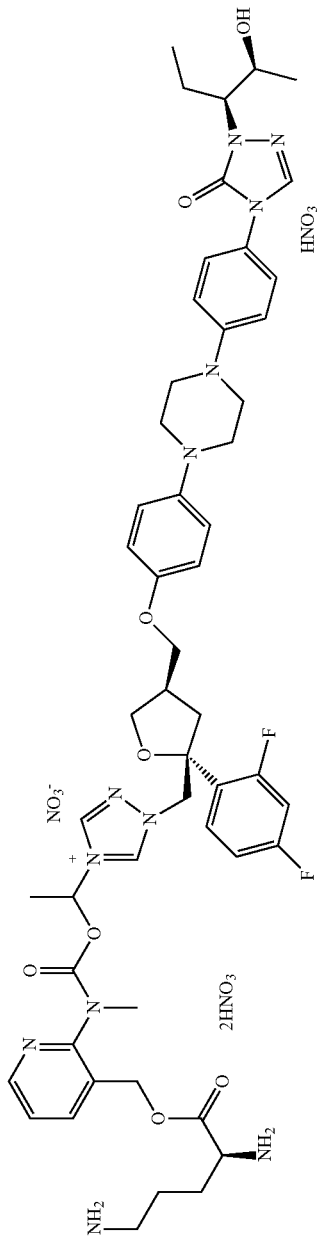 |
| ST0016 | 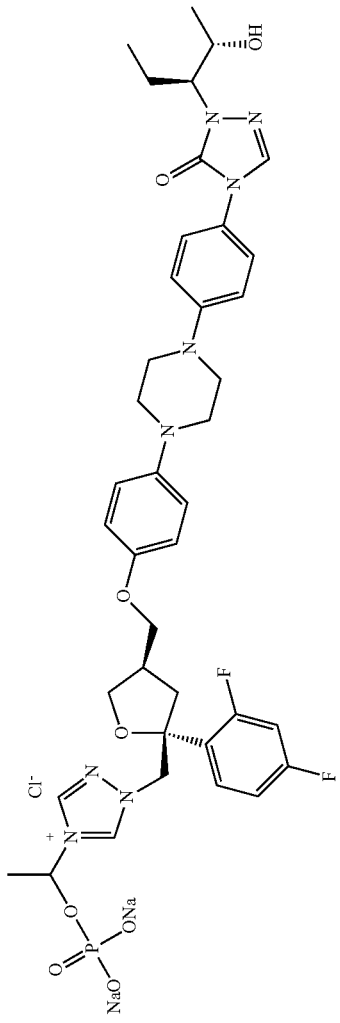 |
| ST0017 | 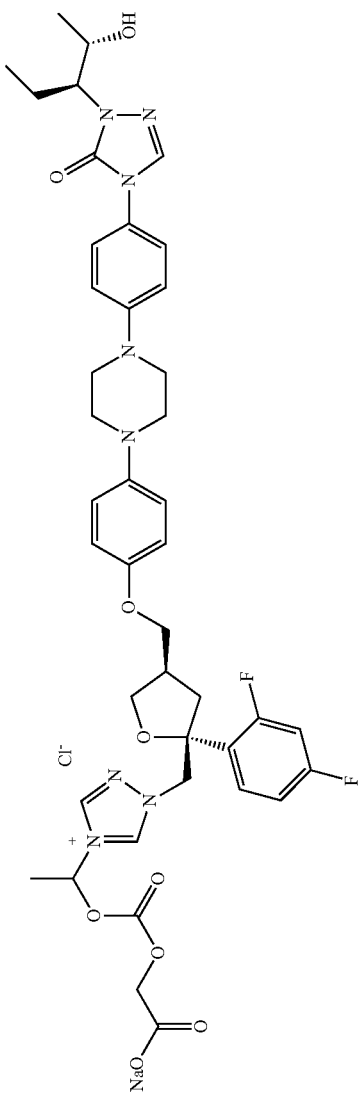 |

-continued
| No. | Structure formula |
|---|---|
| ST0018 | 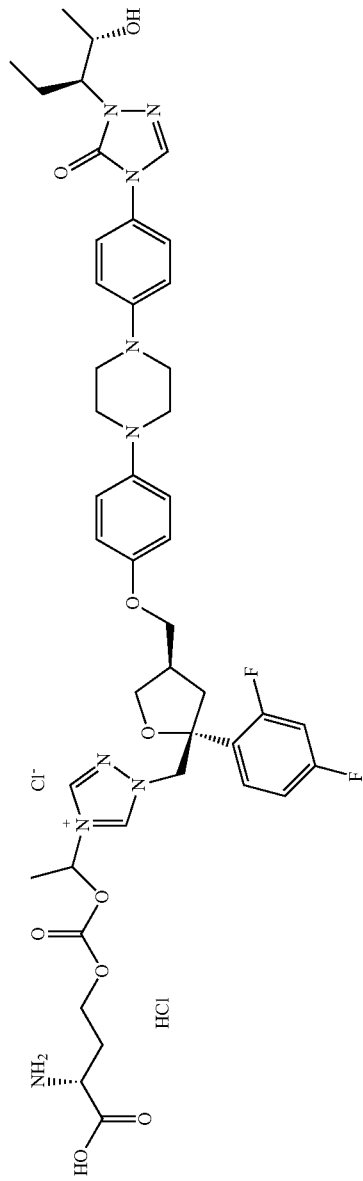 |
| ST0019 | 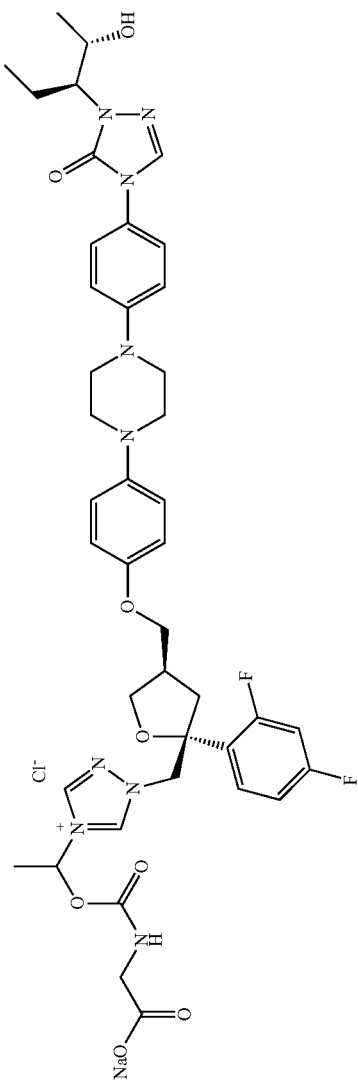 |

-continued
| No. | Structure formula |
|---|---|
| ST0020 | 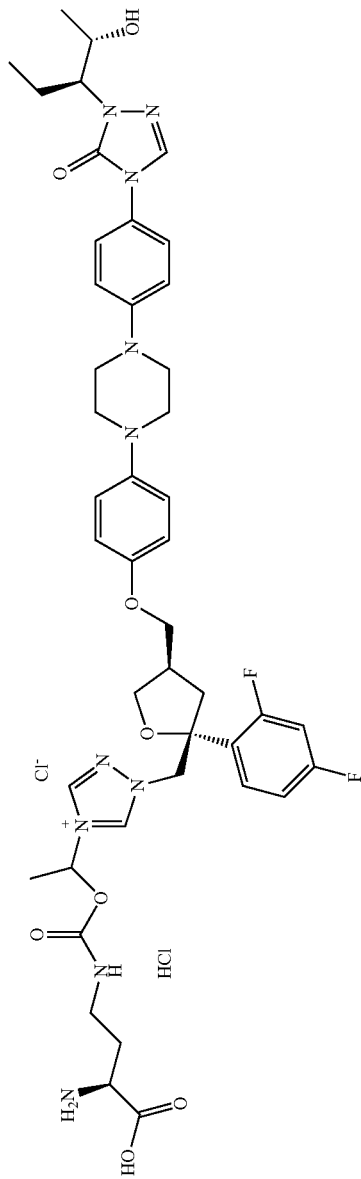 |
| ST0021 | 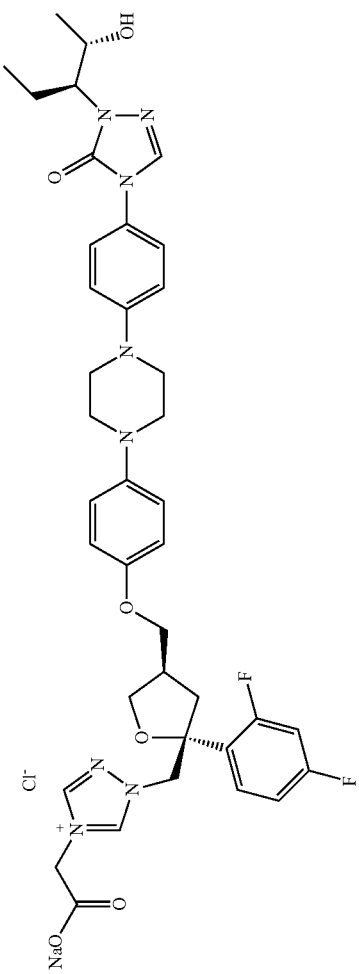 |

| No. | Structure formula |
|---|---|
| ST0022 | 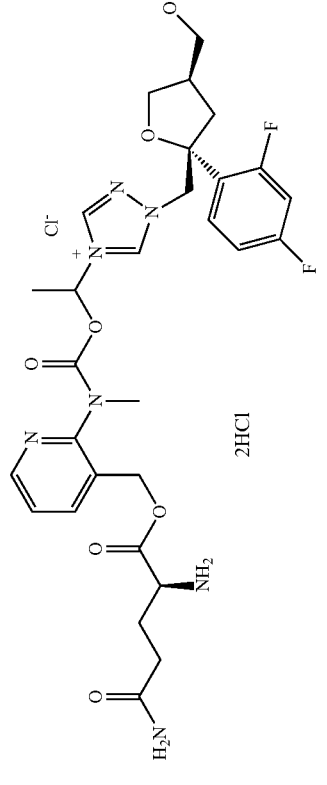 2HCl |
| ST0023 | 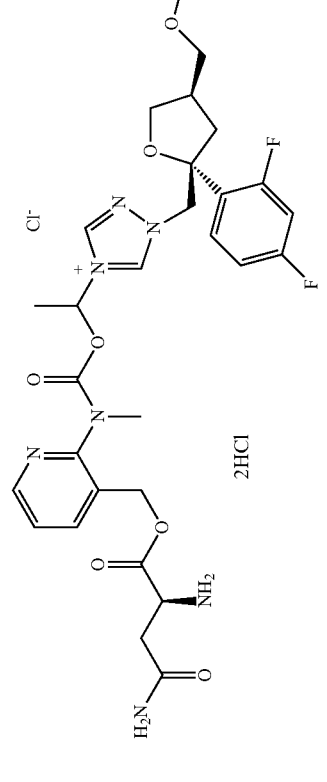 2HCl |
| ST0024 | 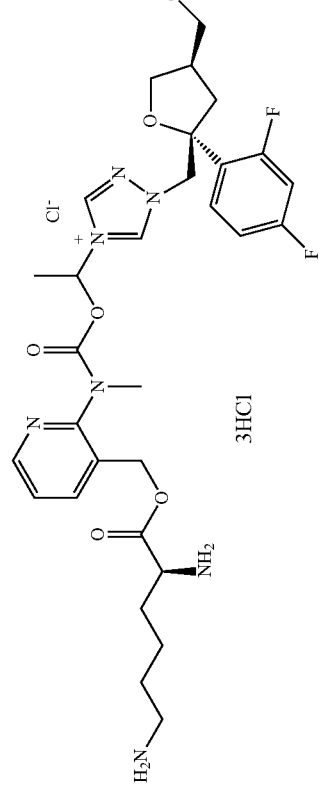 3HCl |

| No. | Structure formula |
|---|---|
| ST0025 | |
| ST0026 | |
| ST0027 | |

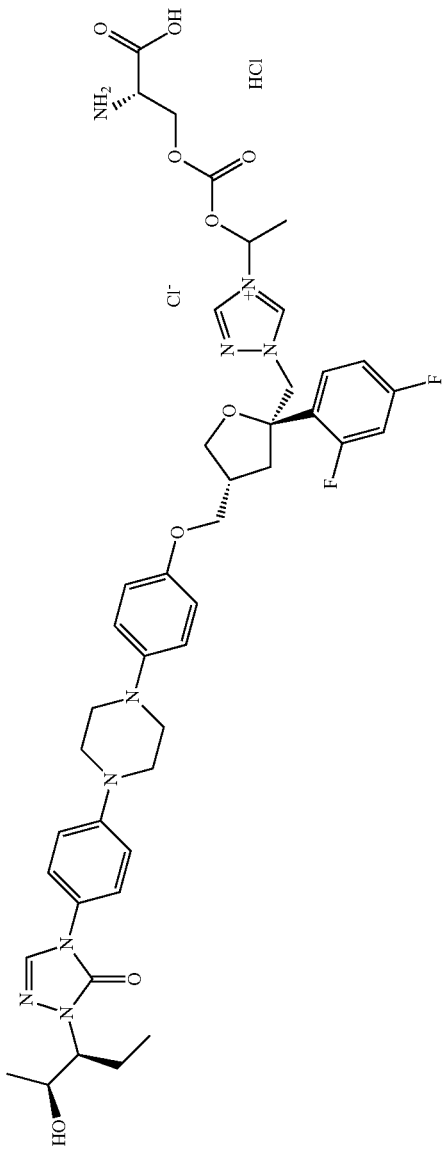

-continued
| No. | Structure formula |
|---|---|
| ST0030 | 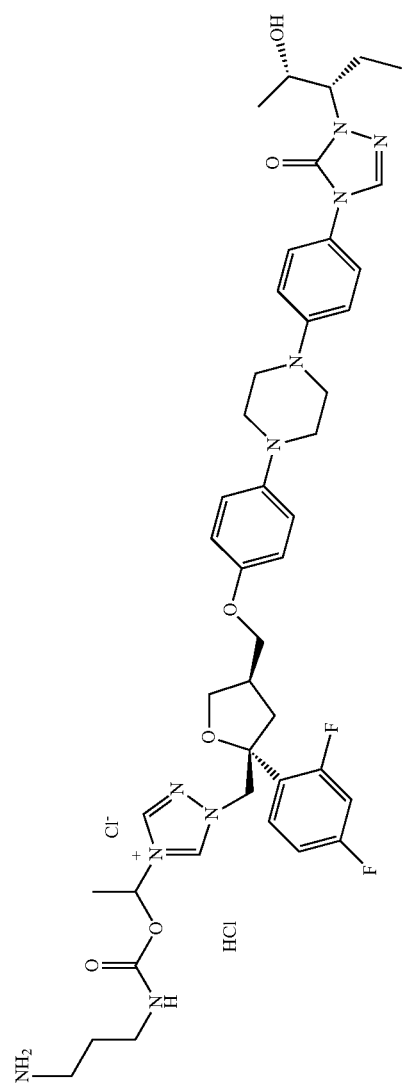 |
| ST0031 | |

-continued
| No. | Structure formula |
|---|---|
| ST0032 | 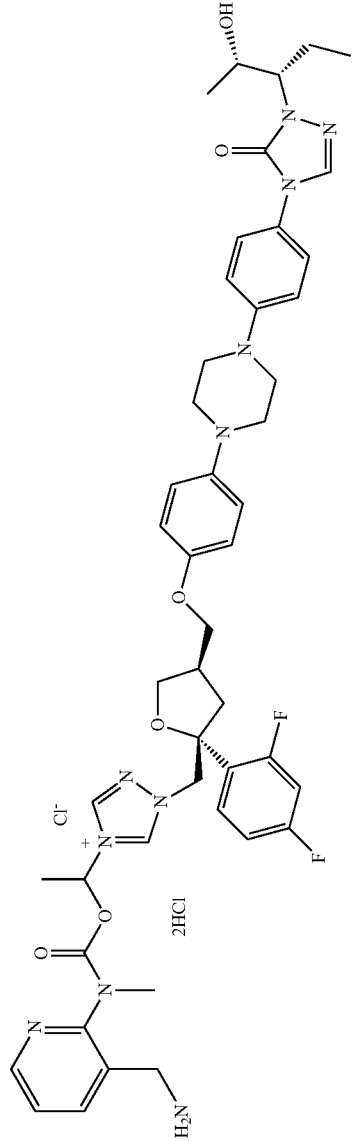 |
| ST0033 | 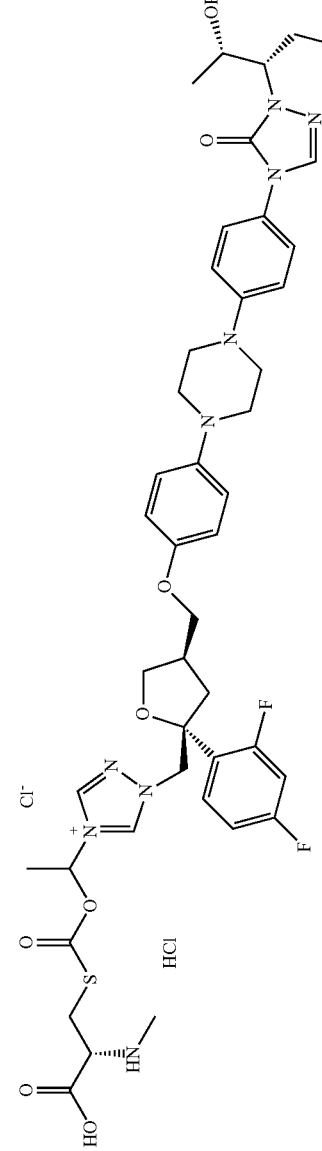 |
| ST0034 | 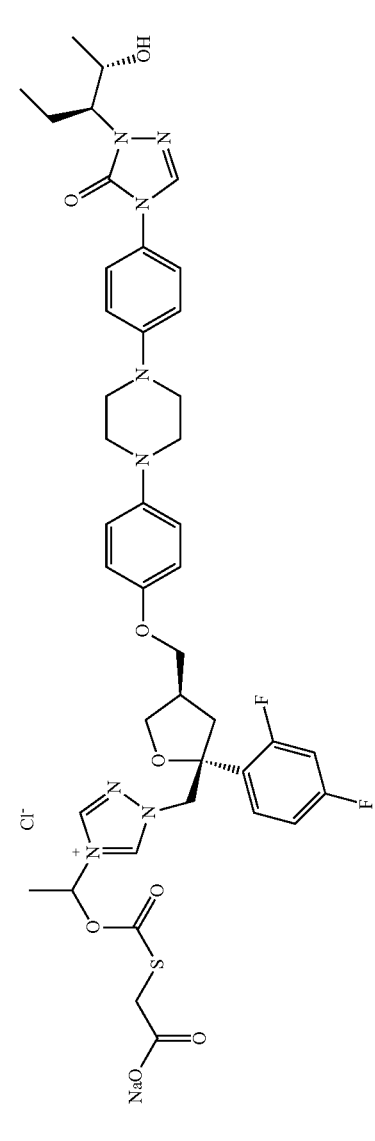 |

| No. | Structure formula |
|---|---|
| ST0037 | 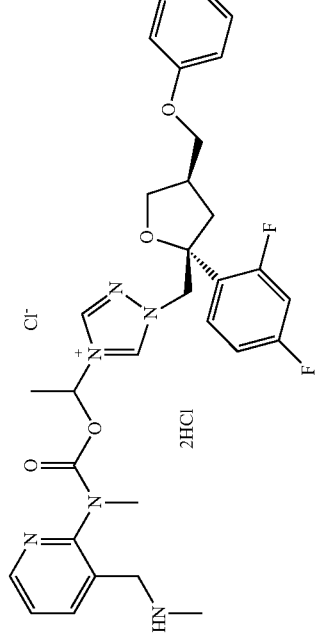 |
| ST0038 | 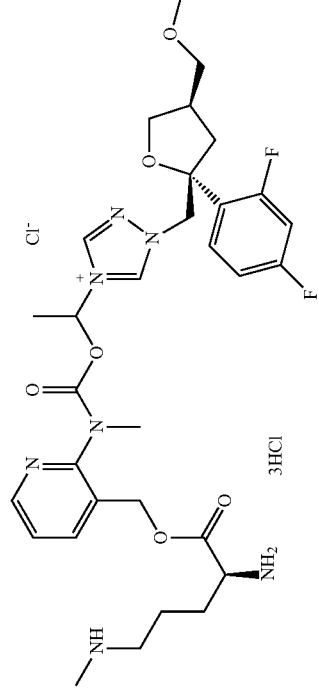 |
| ST0039 | 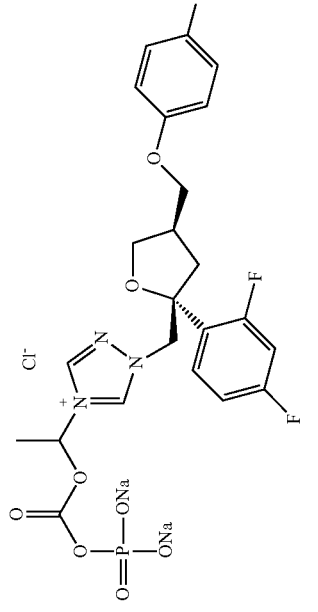 |

-continued

| No. | Structure formula |
|---|---|
| ST0040 | (structure, 3HCl) |
| ST0041 | (structure) |

-continued
| No. | Structure formula |
|---|---|
| ST0042 | 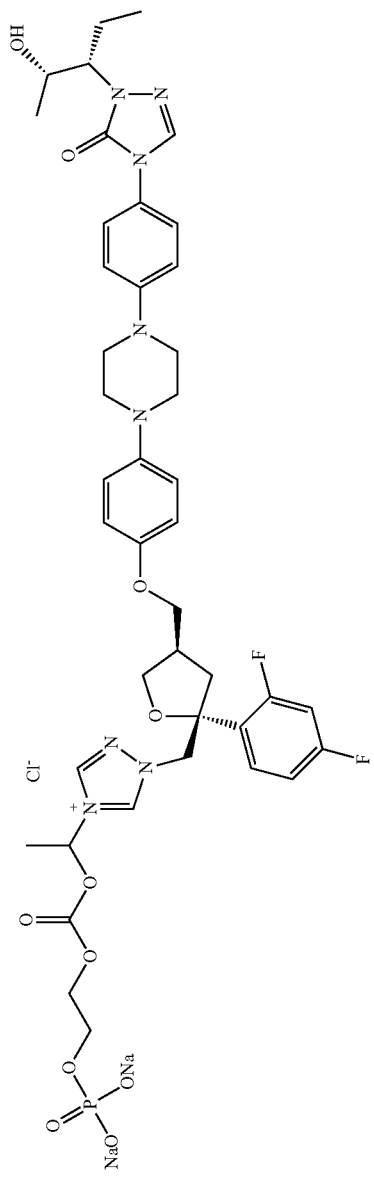 |
| ST0043 | 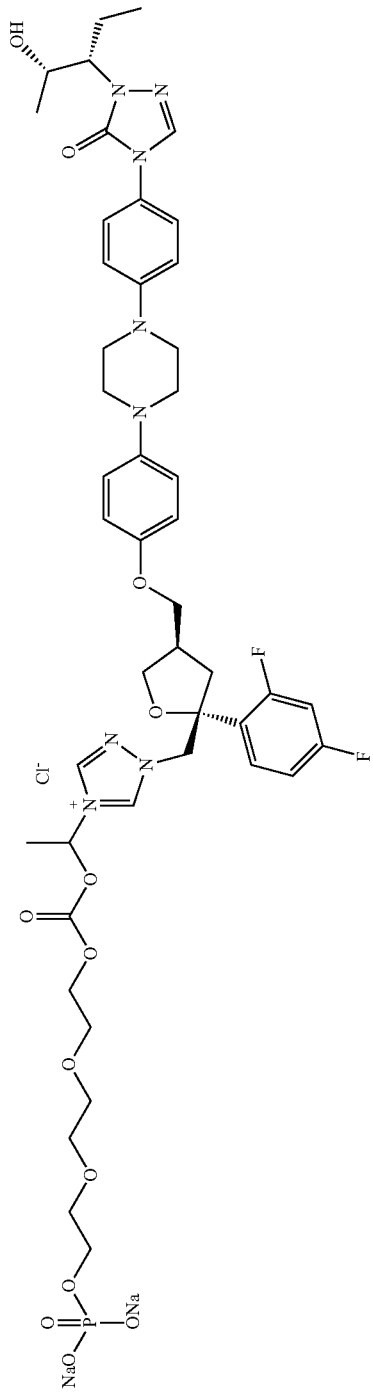 |

| No. | Structure formula |
|---|---|
| ST0044 | |
| ST0045 | |
| ST0046 | |

-continued
| No. | Structure formula |
|---|---|
| ST0047 | 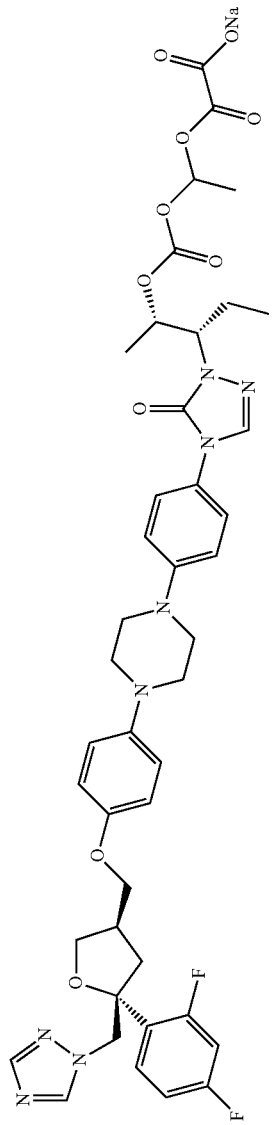 |
| ST0048 | 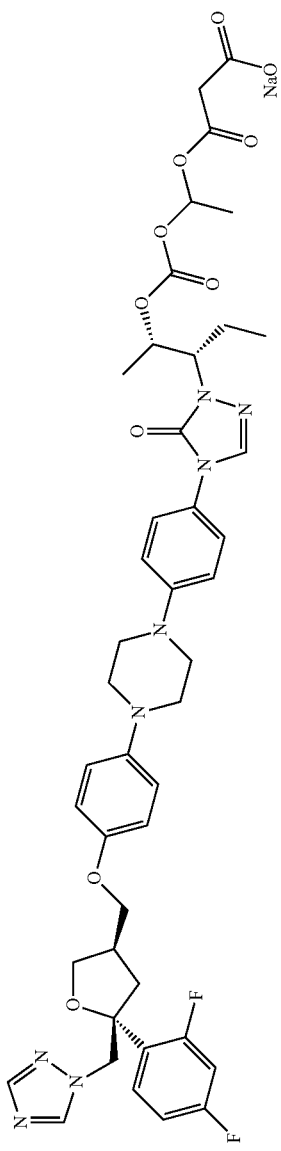 |
| ST0049 | 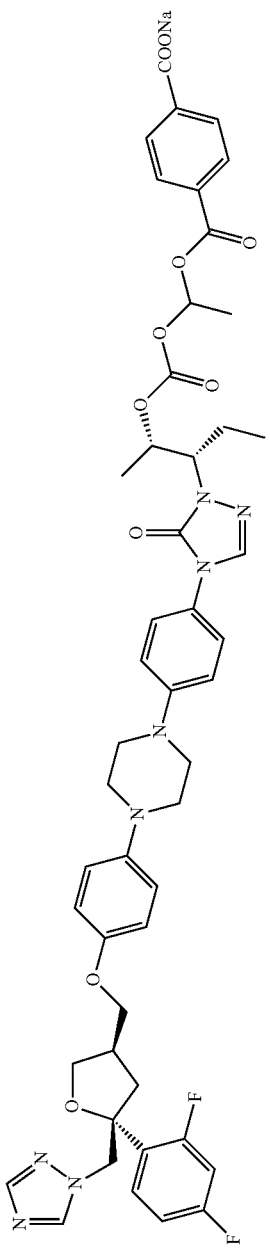 |

| No. | Structure formula |
|---|---|
| ST0052 | 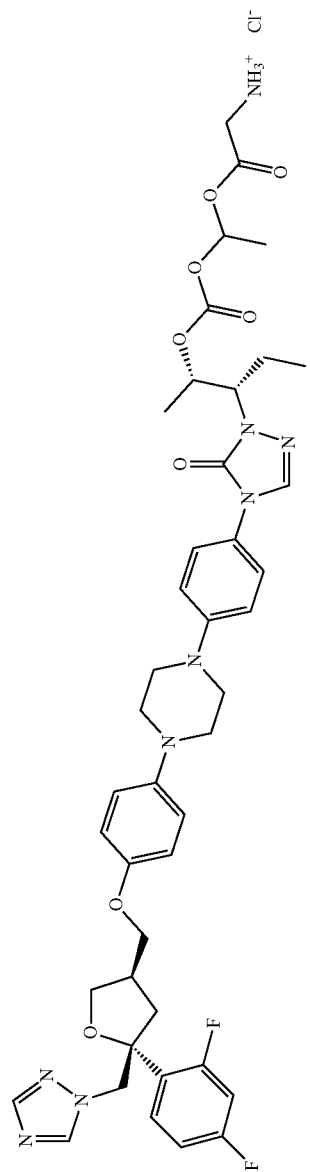 |
| ST0053 | 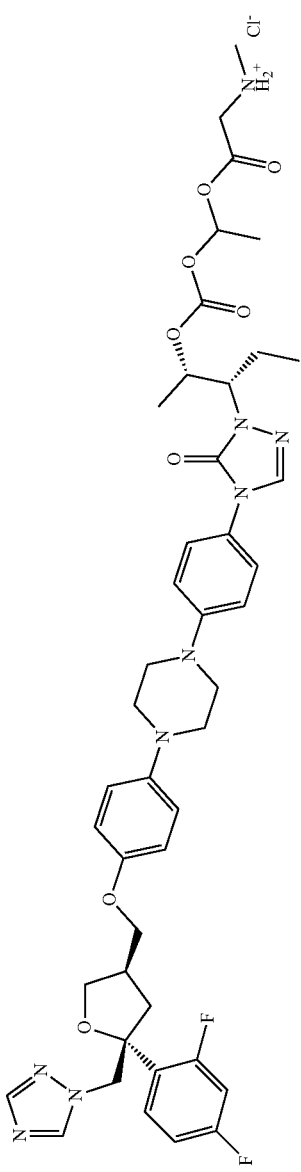 |
| ST0054 | 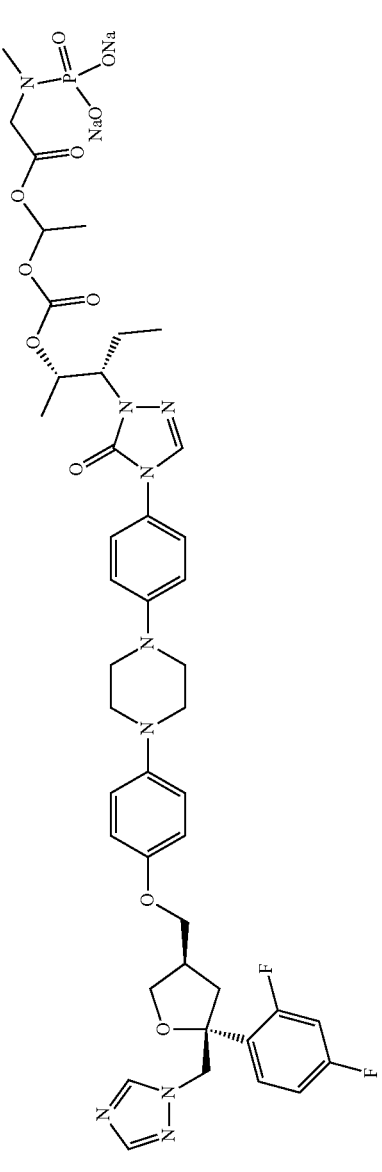 |

-continued
| No. | Structure formula |
|---|---|
| ST0055 | 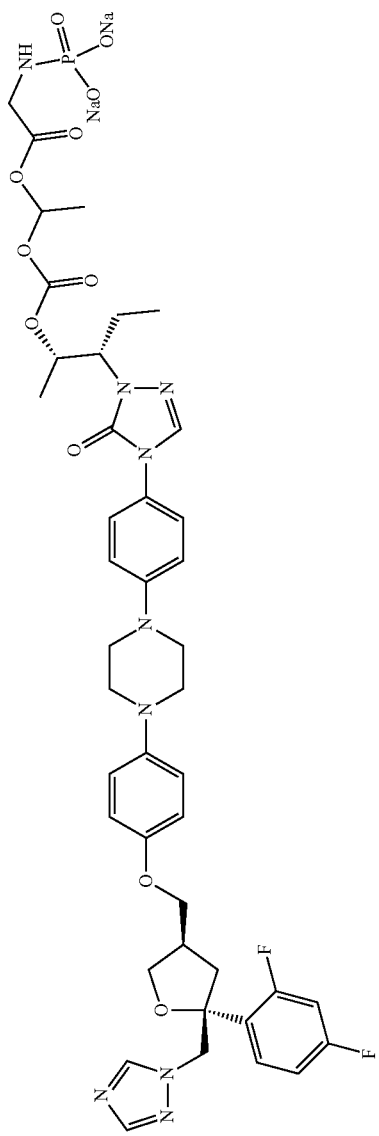 |
| ST0056 | 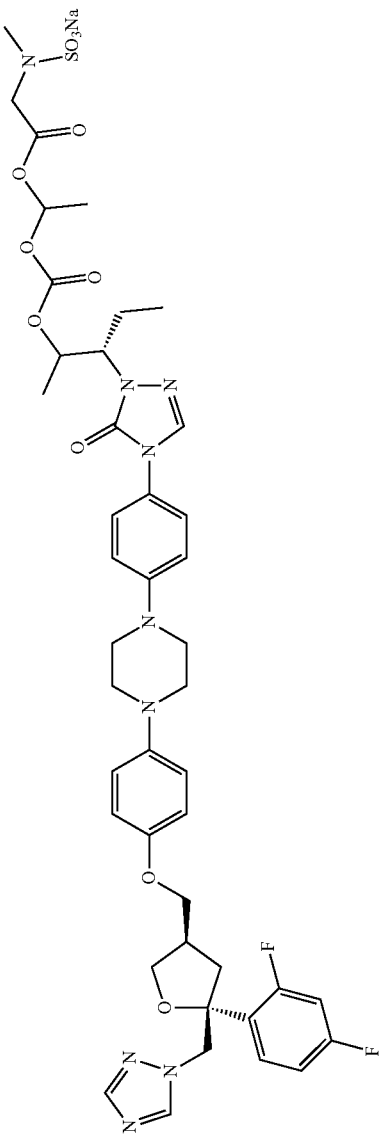 |

-continued
| No. | Structure formula |
|---|---|
| ST0057 | 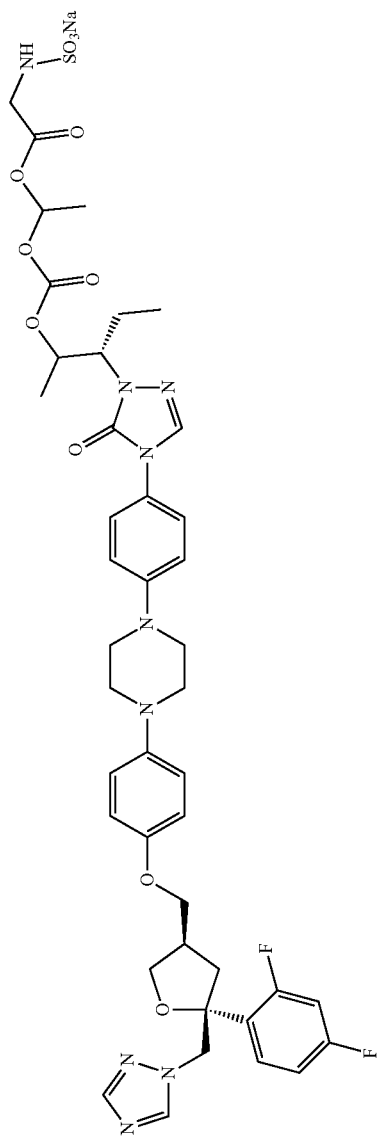 |
| ST0058 | |

-continued
| No. | Structure formula |
|---|---|
| ST0062 | 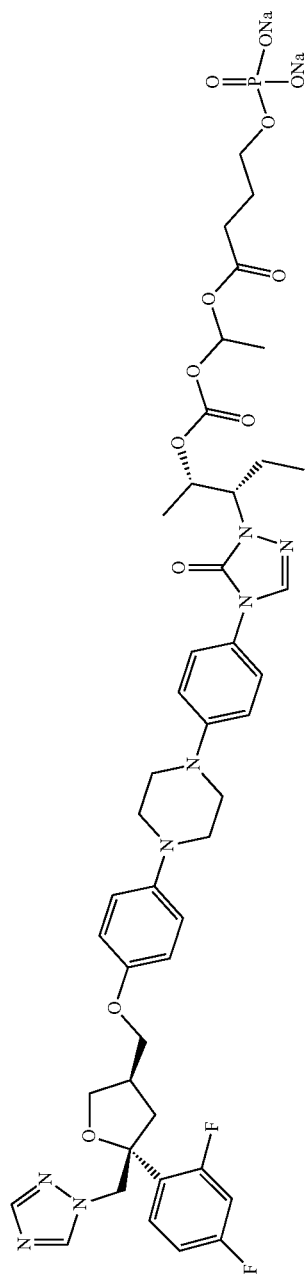 |
| ST0063 | 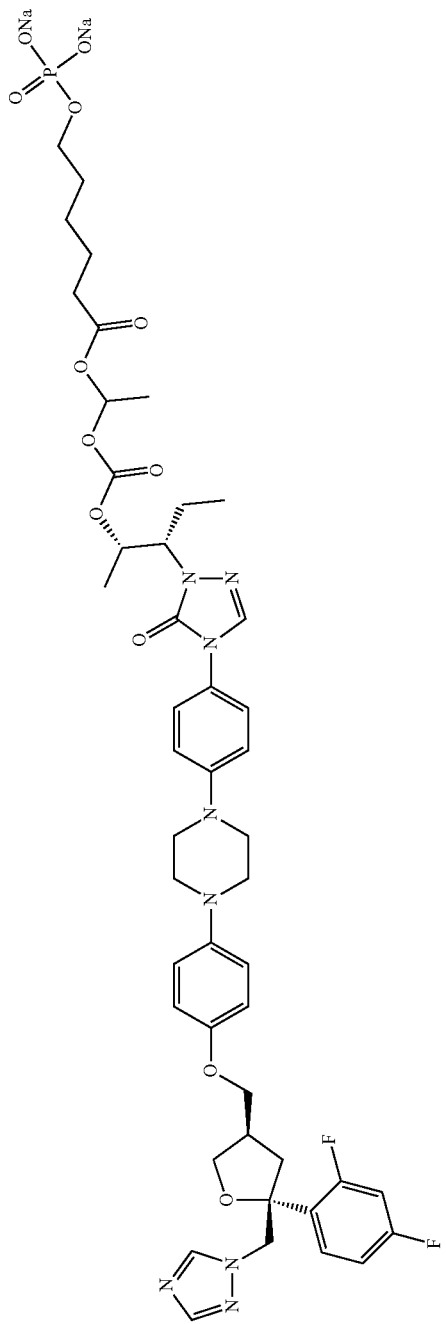 |

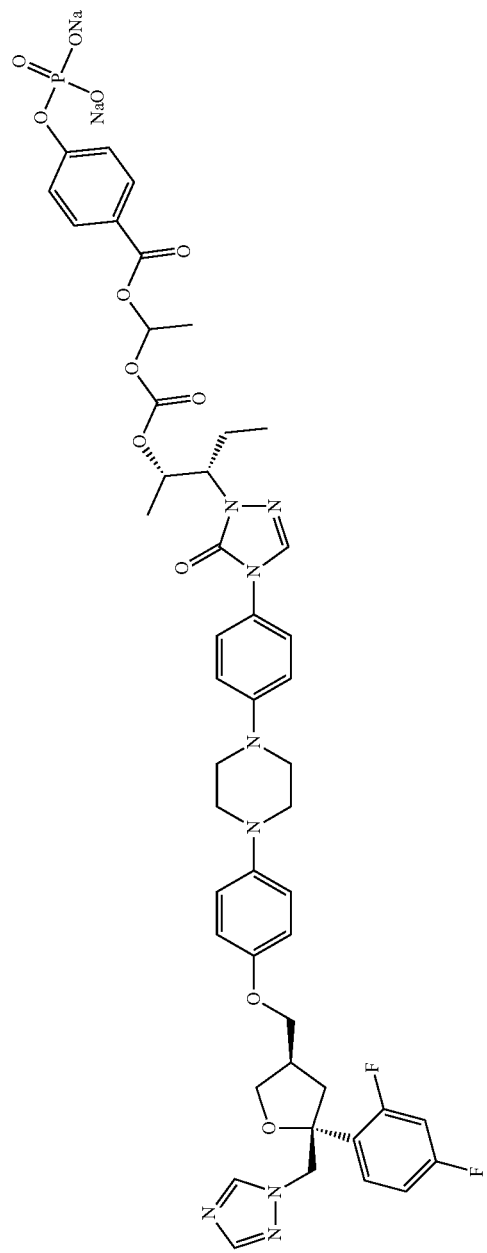

-continued
| No. | Structure formula |
|---|---|
| ST0066 | 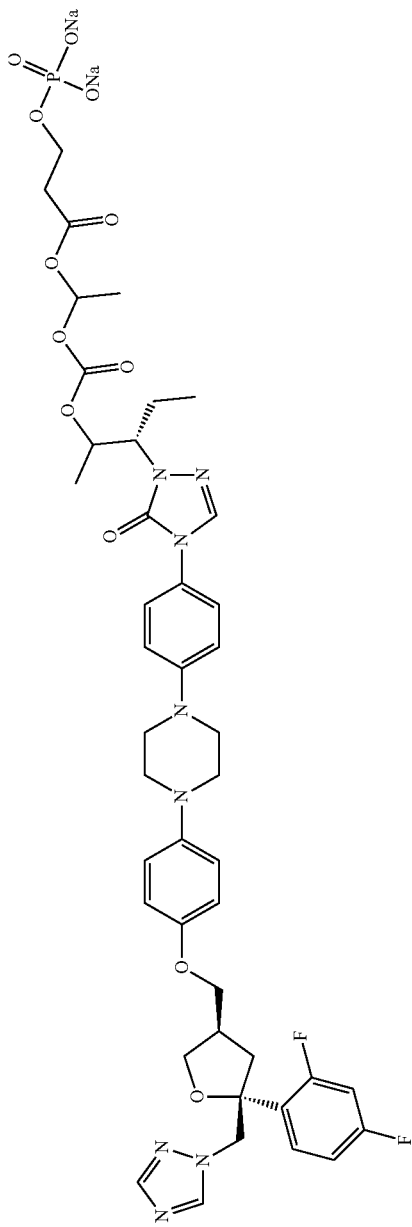 |
| ST0067 | 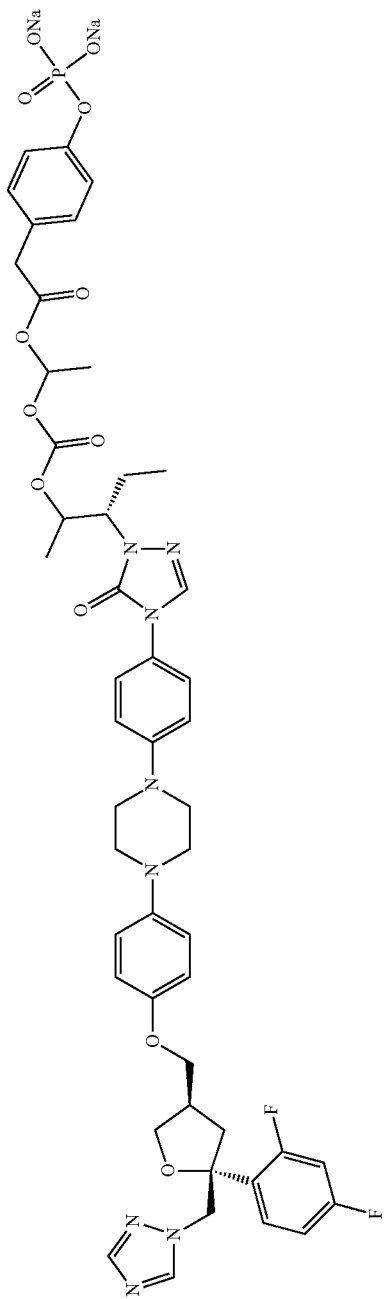 |

-continued
| No. | Structure formula |
|---|---|
| ST0068 | 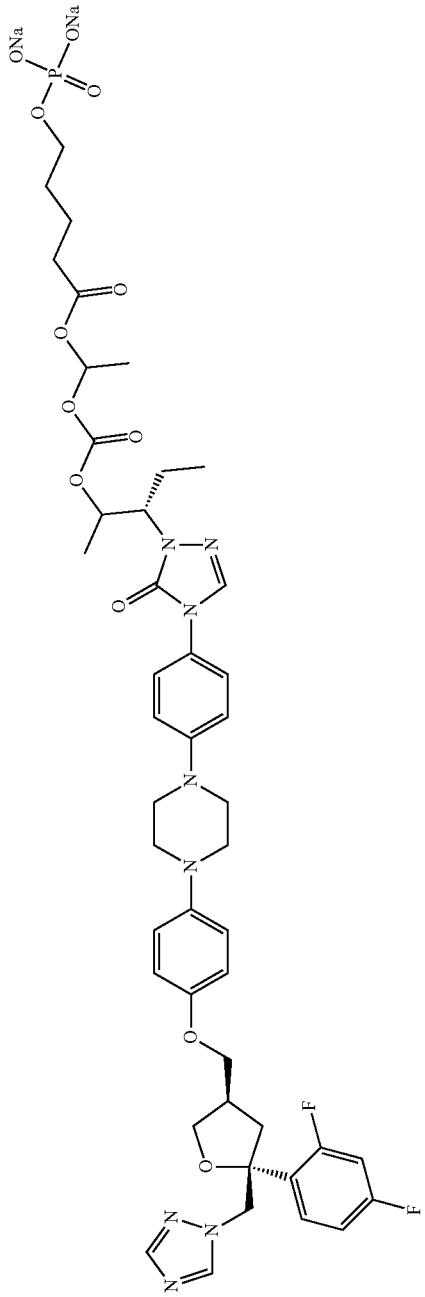 |
| ST0069 | 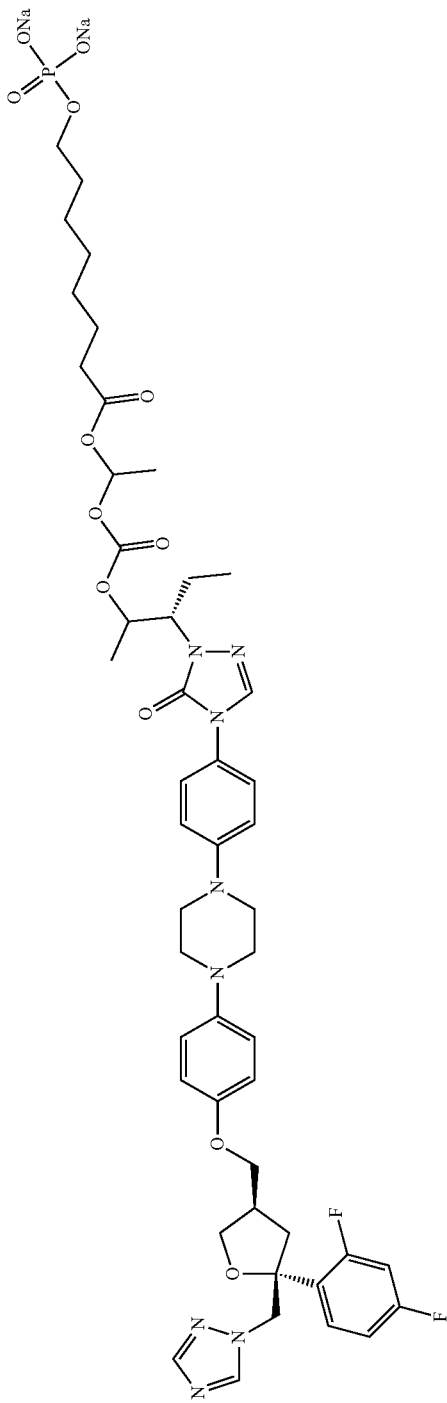 |

-continued

| No. | Structure formula |
|---|---|
| ST0070 | |
| ST0071 | |

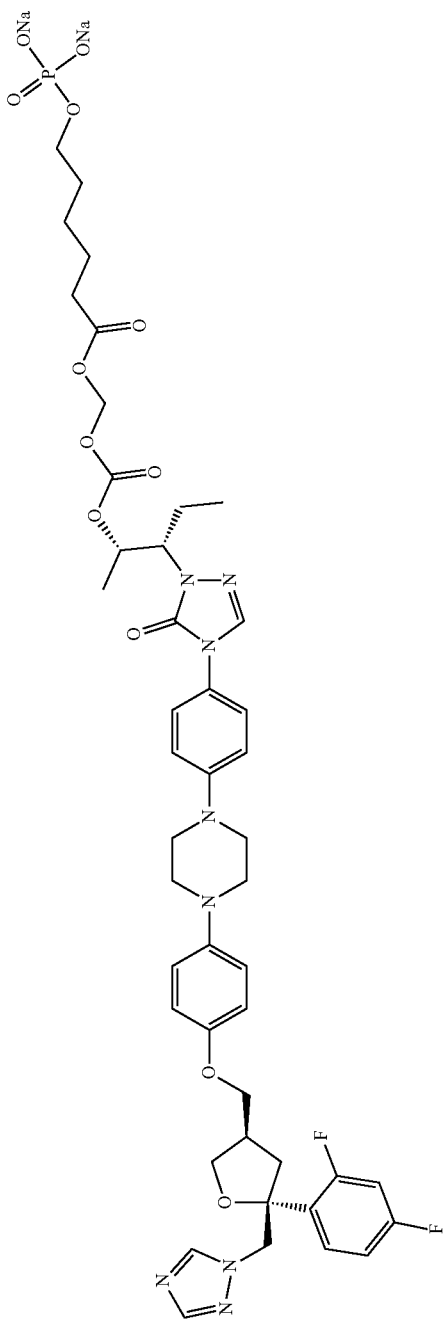

-continued
| No. | Structure formula |
|---|---|
| ST0074 | 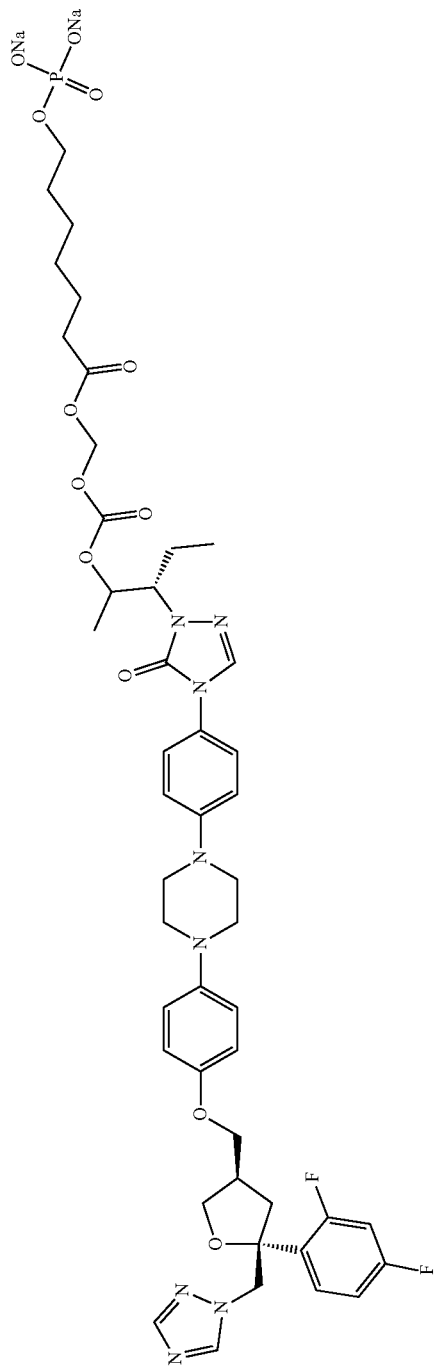 |
| ST0075 | 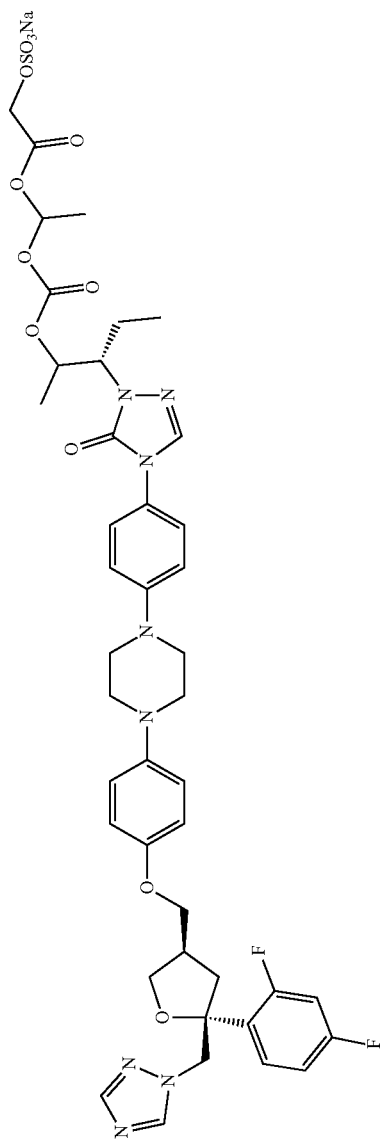 |

-continued
| No. | Structure formula |
|---|---|
| ST0076 | 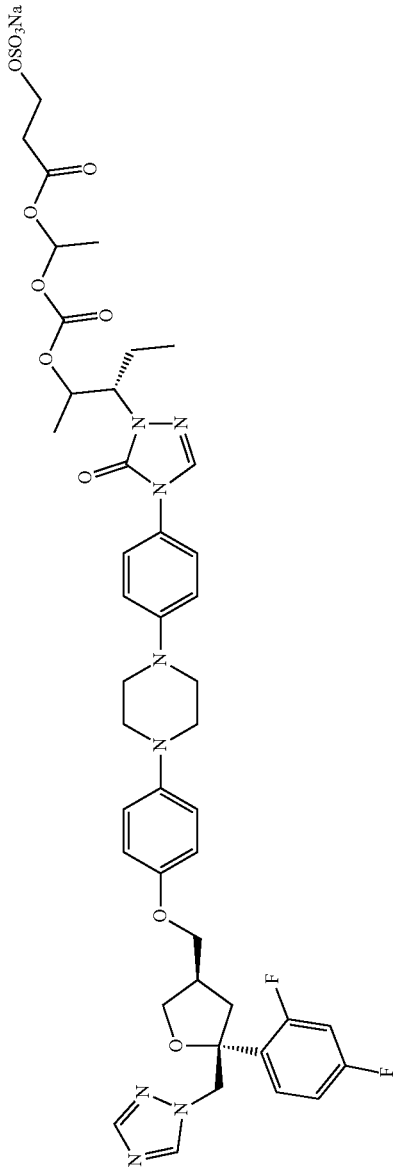 |
| ST0077 | 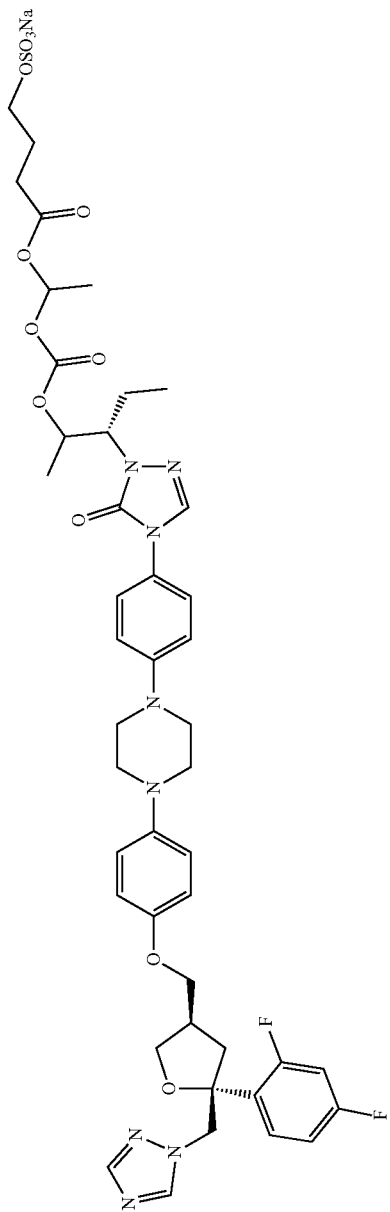 |

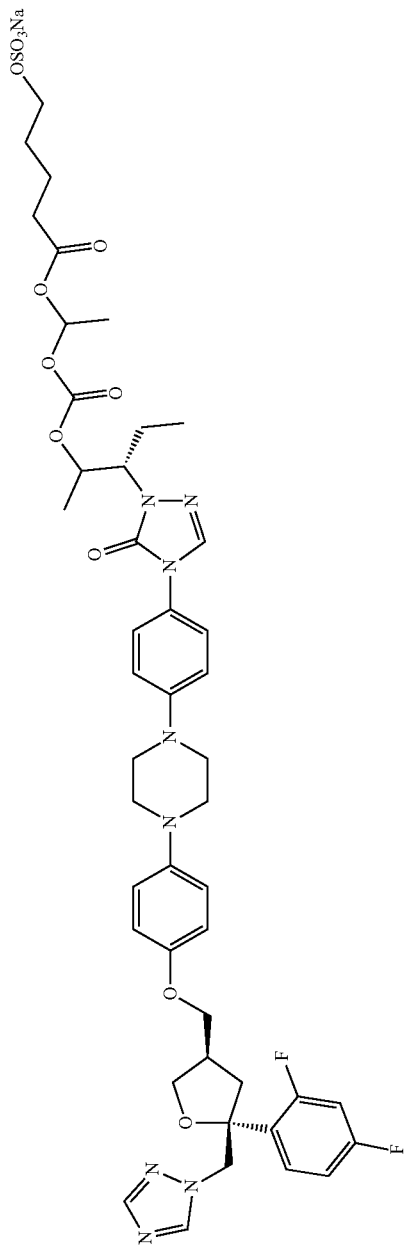

-continued
| No. | Structure formula |
|---|---|
| ST0080 | 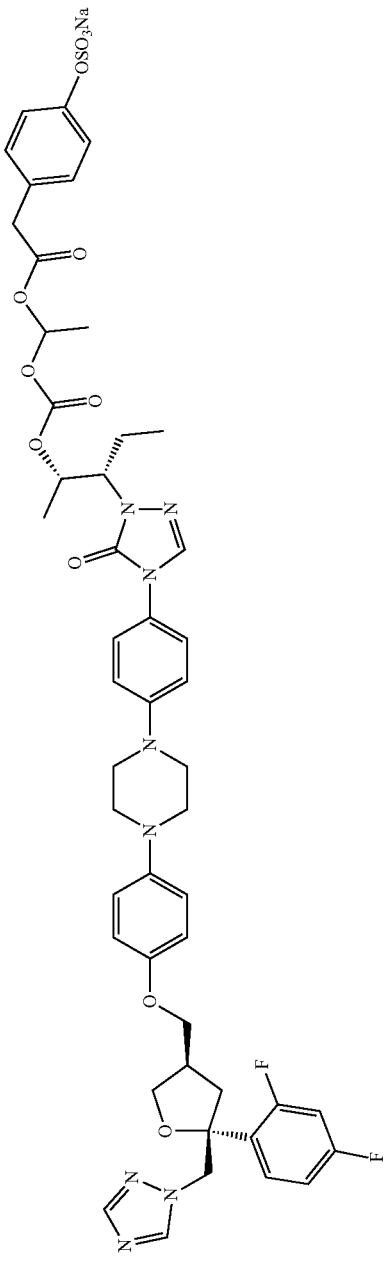 |
| ST0081 | 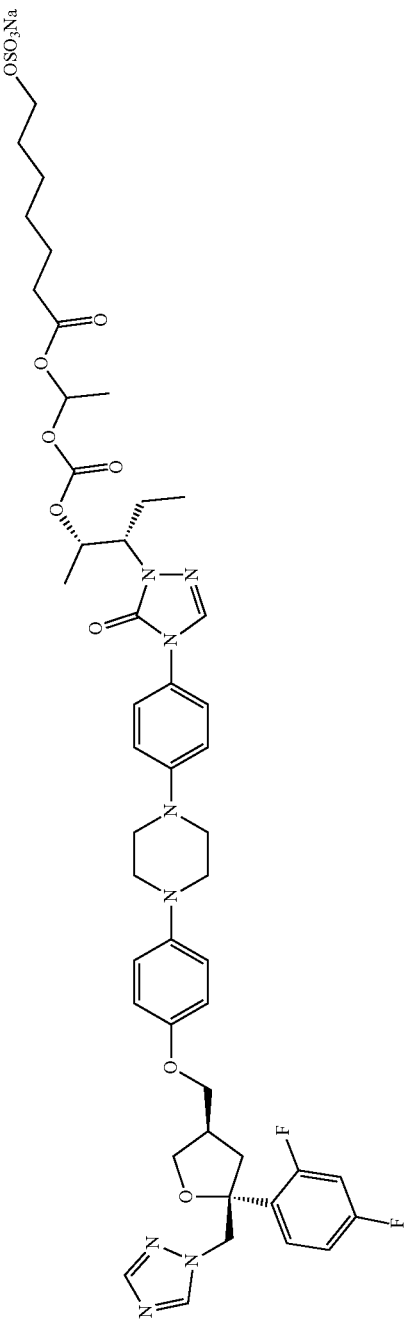 |

-continued
| No. | Structure formula |
|---|---|
| ST0082 | 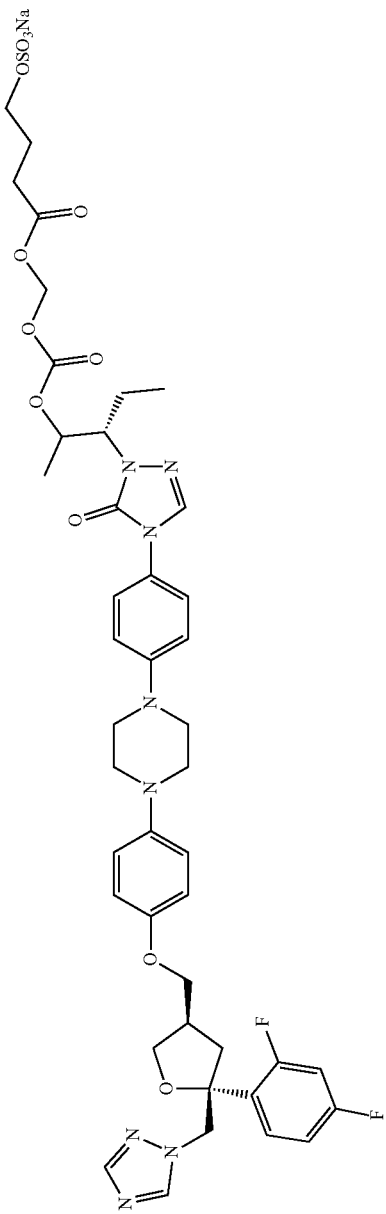 |
| ST0083 | |

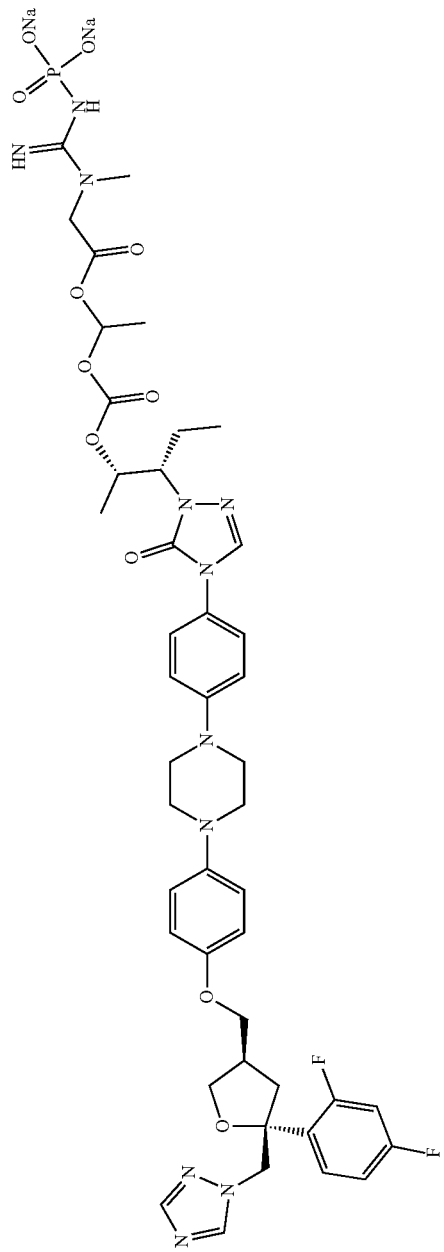

-continued
| No. | Structure formula |
|---|---|
| ST0086 | 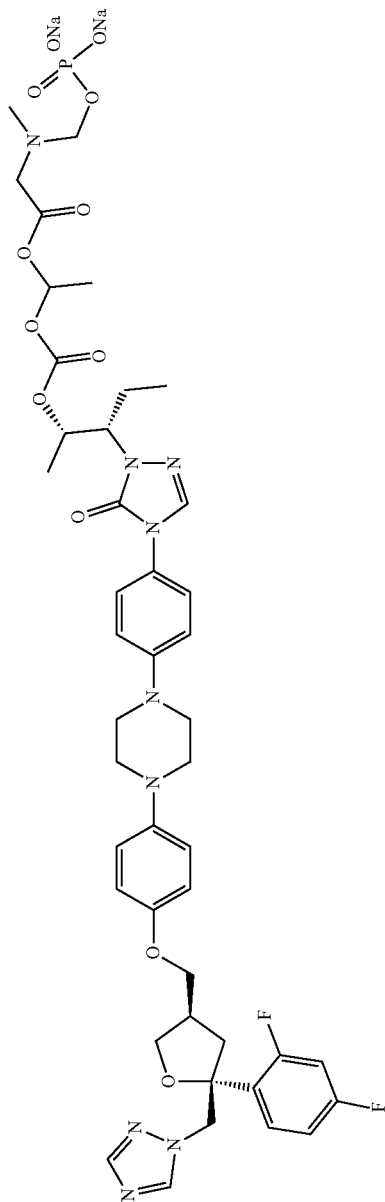 |
| ST0087 | 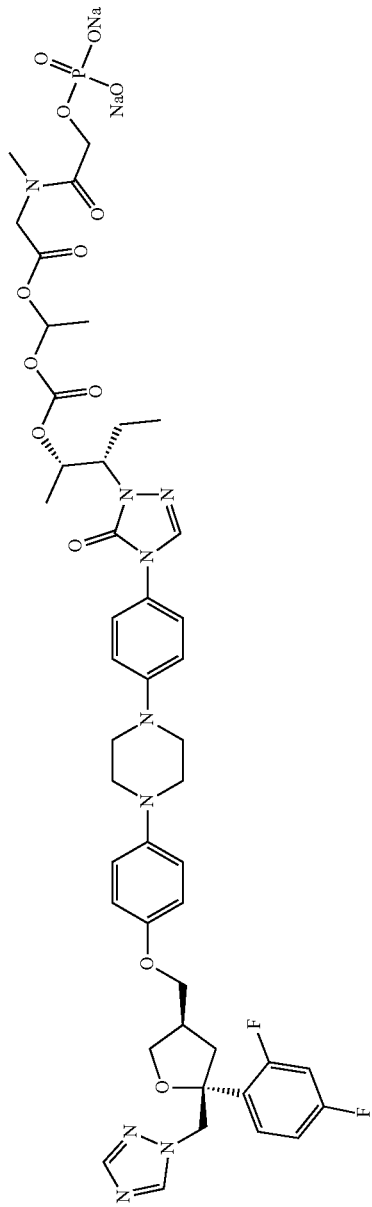 |

-continued
| No. | Structure formula |
|---|---|
| ST0088 | 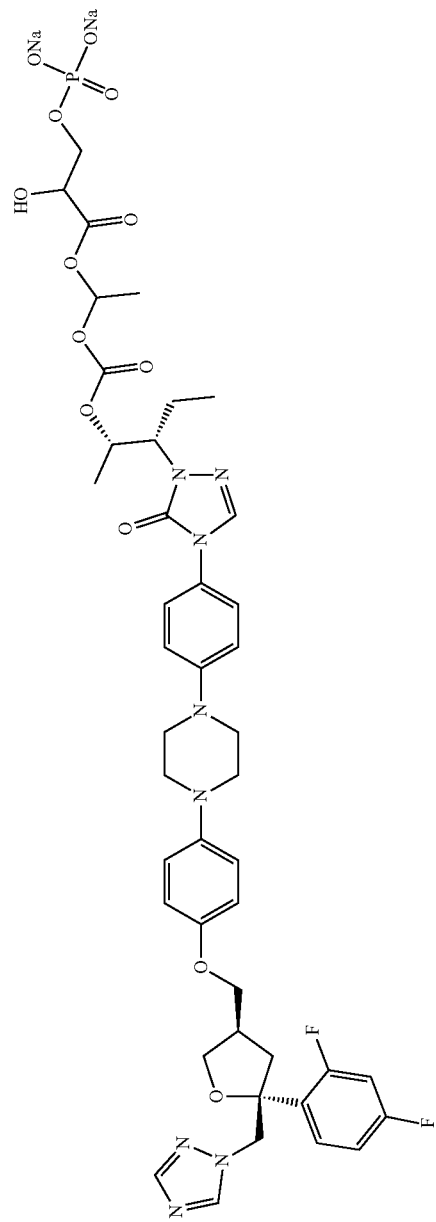 |
| ST0089 | |

-continued
| No. | Structure formula |
|---|---|
| ST0090 | 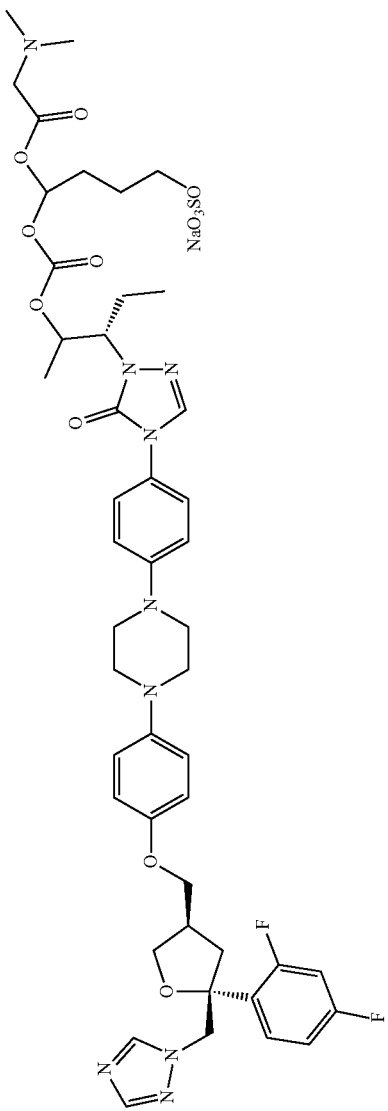 |
| ST0091 | 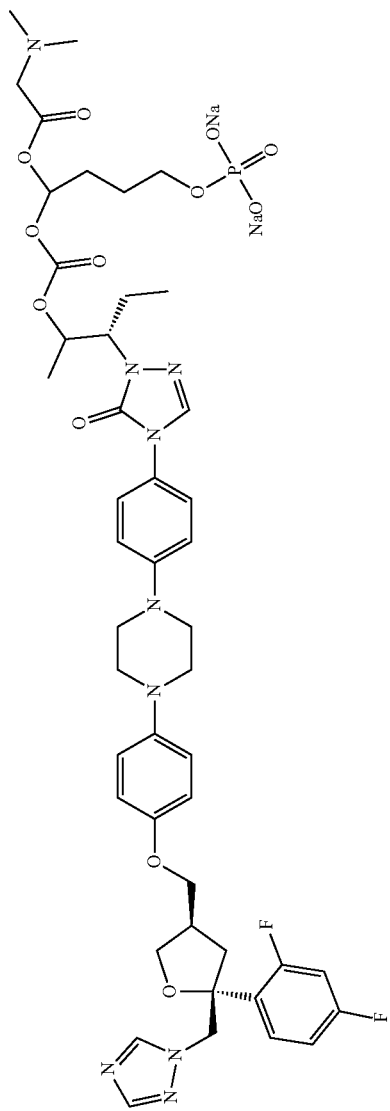 |

-continued
| No. | Structure formula |
|---|---|
| ST0092 | 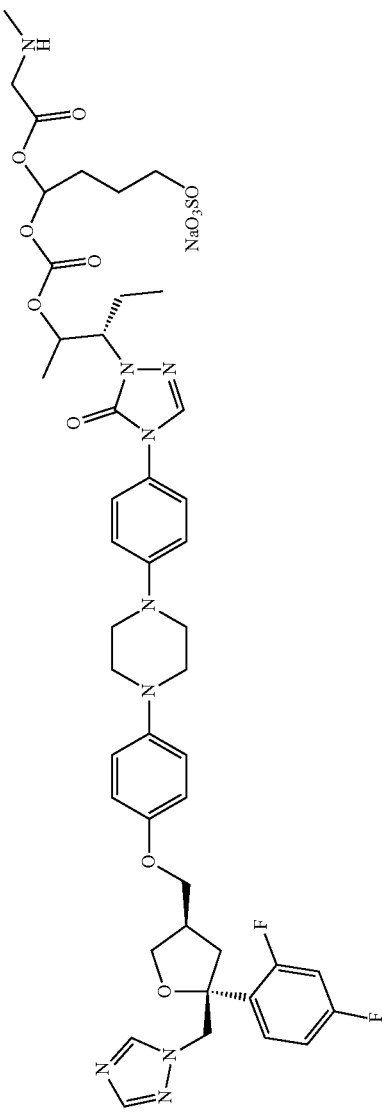 |
| ST0100 | 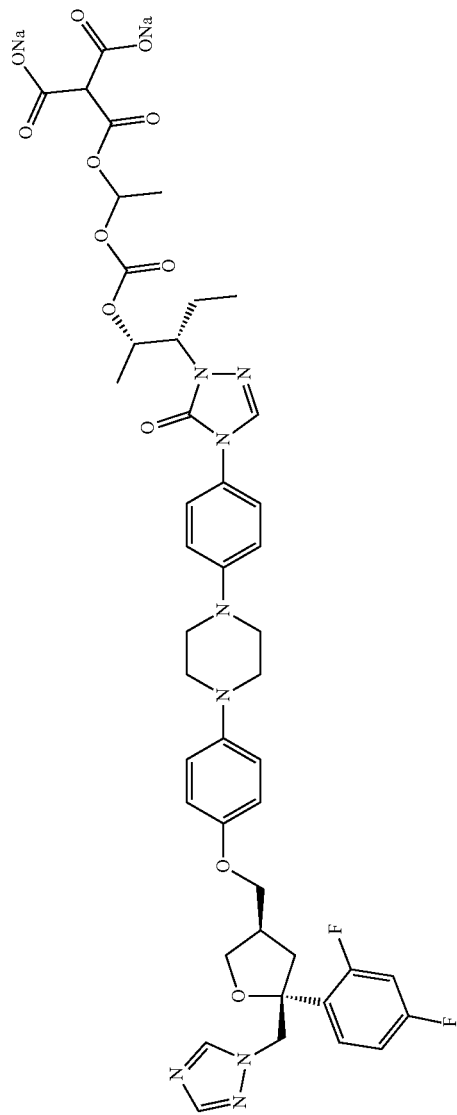 |

-continued
| No. | Structure formula |
|---|---|
| ST0101 | 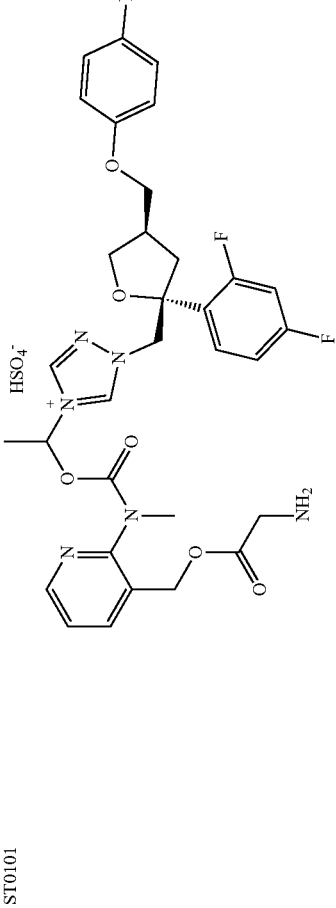 |
| ST0102 | 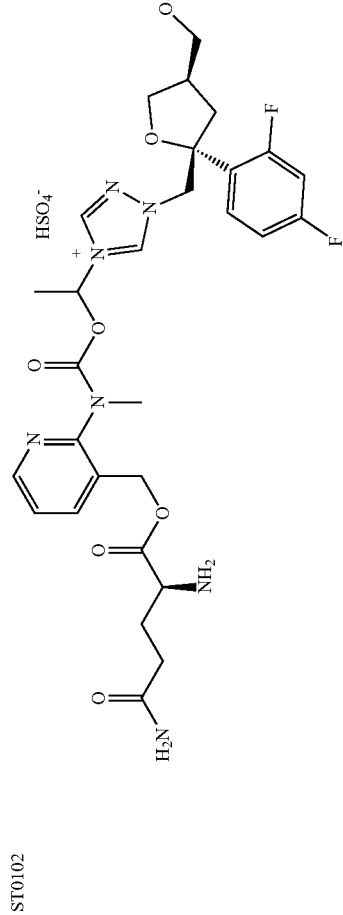 |
| ST0103 | 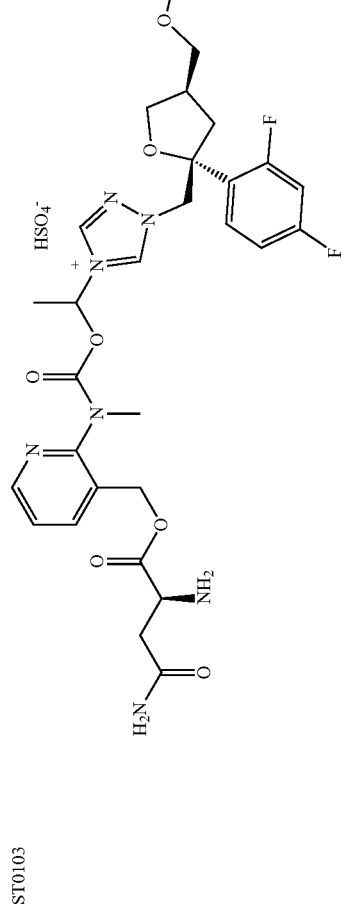 |

-continued
| No. | Structure formula |
|---|---|
| ST0104 | 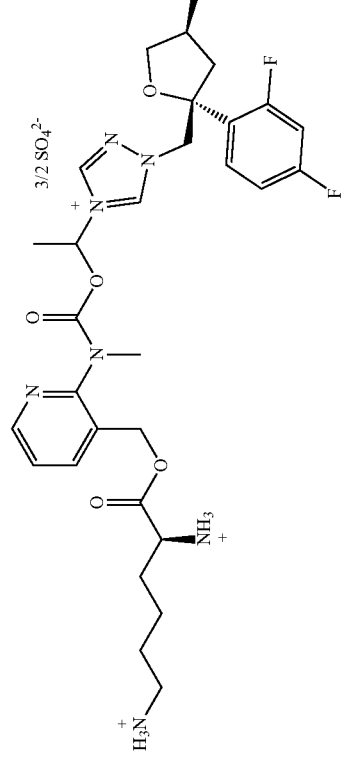 |
| ST0105 | 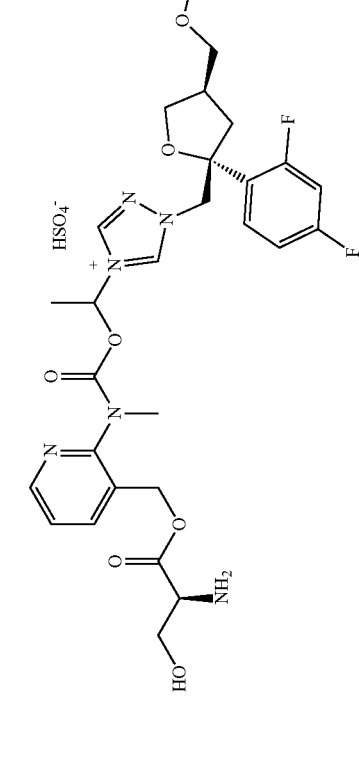 |
| ST0106 | 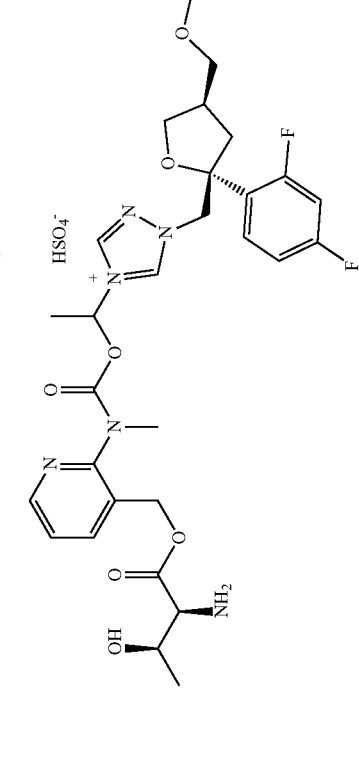 |

18. The method according to claim 5, wherein L is chosen from H, F, Br, Cl, I, mesylate ester group, or tosylate ester group, wherein the compound of formula (II) is first reacted with $R_h$-$L_1$ and the resulting compound is further reacted with $R_t$-$L_2$; or, the compound of formula (II) is first reacted with $R_t$-$L_2$, and the resulting compound is further reacted with $R_h$-$L_1$, wherein $L_1$ and $L_2$ are leaving groups independently chosen from H, F, Br, Cl, I, mesylate ester group, or tosylate ester group.

19. The method according to claim 8, wherein the fungus is *Candida albicans* or *Aspergillus fumigatus*.

* * * * *